(12) United States Patent
Shirvani et al.

(10) Patent No.: US 10,797,758 B2
(45) Date of Patent: Oct. 6, 2020

(54) ELECTROMAGNETIC SENSING AND DETECTION OF INGESTIBLE EVENT MARKERS

(71) Applicant: Proteus Digital Health, Inc., Redwood City, CA (US)

(72) Inventors: Alireza Shirvani, Menlo Park, CA (US); Mark Zdeblick, Portola Valley, CA (US); Jonathan Withrington, San Francisco, CA (US)

( * ) Notice: Subject to any disclaimer, the term of this patent is extended or adjusted under 35 U.S.C. 154(b) by 0 days.

(21) Appl. No.: 16/244,195

(22) Filed: Jan. 10, 2019

(65) Prior Publication Data

US 2019/0158151 A1    May 23, 2019

Related U.S. Application Data

(62) Division of application No. 15/657,608, filed on Jul. 24, 2017, now Pat. No. 10,187,121.

(Continued)

(51) Int. Cl.
  *H04B 5/00*  (2006.01)
  *A61B 5/00*  (2006.01)
  (Continued)

(52) U.S. Cl.
  CPC .......... *H04B 5/0075* (2013.01); *A61B 5/073* (2013.01); *A61B 5/4833* (2013.01);
  (Continued)

(58) Field of Classification Search
  CPC ........ H04B 5/0075; H04B 1/16; A61B 5/073; A61B 5/4833; A61B 5/4848;
  (Continued)

(56) References Cited

U.S. PATENT DOCUMENTS

| 1,548,459 A | 8/1925 | Hammer |
| 2,587,158 A | 2/1952 | Hofberg |

(Continued)

FOREIGN PATENT DOCUMENTS

| CA | 2953847 | 11/2006 |
| CN | 1588649 | 3/2005 |

(Continued)

OTHER PUBLICATIONS

"ASGE Technology Status Evaluation Report: wireless capsule endoscopy" American Soc. For Gastrointestinal Endoscopy (2006) vol. 63, No. 4; 7 pp.

(Continued)

*Primary Examiner* — Nguyen T Vo

(57) ABSTRACT

Provided is an electronic device having a control device, a driver circuit coupled to the control device. The driver circuit is configured to alter conductance. A partial power source is coupled to the control device and is configured to provide a voltage potential difference to the control device and the driver circuit as a result of the partial power source being in contact with a conductive fluid. The partial power source includes a first material electrically coupled to the control device and a second material electrically coupled to the control device and electrically isolated from the first material. An inductor is coupled to the driver circuit. The driver circuit is configured to develop a current through the inductor. The magnitude of the current developed through the inductor is varied to produce an encoded signal that is remotely detectable by a receiver. Receivers to receive and decode also are disclosed.

17 Claims, 89 Drawing Sheets

Related U.S. Application Data

(60) Provisional application No. 62/365,727, filed on Jul. 22, 2016.

(51) Int. Cl.
*H01Q 1/27* (2006.01)
*A61B 5/07* (2006.01)
*H01Q 7/00* (2006.01)
*H04B 1/16* (2006.01)
*H03K 3/02* (2006.01)

(52) U.S. Cl.
CPC .......... *A61B 5/4848* (2013.01); *A61B 5/6861* (2013.01); *A61B 5/7282* (2013.01); *H01Q 1/27* (2013.01); *H01Q 1/273* (2013.01); *H01Q 7/00* (2013.01); *H04B 1/16* (2013.01); *A61B 5/4238* (2013.01); *A61B 5/7203* (2013.01); *A61B 2560/0214* (2013.01); *A61B 2562/08* (2013.01); *H03K 3/02* (2013.01)

(58) Field of Classification Search
CPC ...... A61B 5/6861; A61B 5/7282; H01Q 1/27; H01Q 1/273; H01Q 7/00
See application file for complete search history.

(56) References Cited

U.S. PATENT DOCUMENTS

| | | |
|---|---|---|
| 2,973,555 A | 3/1961 | Schwepke |
| 3,048,526 A | 8/1962 | Boswell |
| 3,079,824 A | 3/1963 | Schott |
| 3,096,248 A | 7/1963 | Rudzki |
| 3,176,399 A | 4/1965 | Marino et al. |
| 3,218,638 A | 11/1965 | Honig |
| 3,345,989 A | 10/1967 | Reynolds |
| 3,353,539 A | 11/1967 | Preston |
| 3,409,721 A | 11/1968 | Applezweig |
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,129,125 A | 12/1978 | Lester |
| 4,133,730 A | 1/1979 | DuBois et al. |
| 4,139,589 A | 2/1979 | Beringer et al. |
| 4,141,349 A | 2/1979 | Ory et al. |
| 4,143,770 A | 3/1979 | Grimmell et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,775,536 A | 10/1988 | Patell |
| 4,784,162 A | 11/1988 | Ricks |
| 4,793,825 A | 12/1988 | Benjamin et al. |
| 4,809,705 A | 3/1989 | Ascher |
| 4,814,181 A | 3/1989 | Jordan et al. |
| 4,835,373 A | 5/1989 | Adams et al. |
| 4,844,076 A | 7/1989 | Lesho |
| 4,847,090 A | 7/1989 | Della Posta et al. |
| 4,871,974 A | 10/1989 | Davis et al. |
| 4,876,093 A | 10/1989 | Theeuwes et al. |
| 4,891,223 A | 1/1990 | Ambegaonakar et al. |
| 4,896,261 A | 1/1990 | Nolan |
| 4,900,552 A | 2/1990 | Sanvordeker et al. |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,018,335 A | 5/1991 | Yamamoto et al. |
| 5,079,006 A | 1/1992 | Urquhart |
| 5,110,441 A | 5/1992 | Kinlen et al. |
| 5,160,885 A | 11/1992 | Hannam et al. |
| 5,167,626 A | 12/1992 | Casper |
| 5,176,626 A | 1/1993 | Soehendra |
| 5,179,578 A | 1/1993 | Ishizu |
| 5,187,723 A | 2/1993 | Mueller |
| 5,213,738 A | 5/1993 | Hampton et al. |
| 5,218,343 A | 6/1993 | Stobbe et al. |
| 5,245,332 A | 9/1993 | Katzenstein et al. |
| 5,261,402 A | 11/1993 | DiSabito |
| 5,263,481 A | 11/1993 | Axelgaard et al. |
| 5,273,066 A | 12/1993 | Graham et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,310,301 A | 5/1994 | Aono |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,458,994 A | 10/1995 | Nesselbeck et al. |
| 5,468,222 A | 11/1995 | Altchuler |
| 5,485,841 A | 1/1996 | Watkin et al. |
| 5,506,248 A | 4/1996 | Nikfar et al. |
| 5,511,548 A | 4/1996 | Riazzi et al. |
| 5,538,007 A | 7/1996 | Gorman |
| 5,551,020 A | 8/1996 | Flax et al. |
| 5,551,953 A | 9/1996 | Lattin et al. |

(56) References Cited

U.S. PATENT DOCUMENTS

| | | |
|---|---|---|
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,603,363 A | 2/1997 | Nelson |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,659,247 A | 8/1997 | Clements |
| 5,703,463 A | 12/1997 | Smith |
| 5,705,189 A | 1/1998 | Lehmann et al. |
| 5,720,771 A | 2/1998 | Snell |
| 5,724,432 A | 3/1998 | Bouvet et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,842,324 A | 12/1998 | Grosskopf et al. |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,914,132 A | 6/1999 | Kelm et al. |
| 5,914,701 A | 6/1999 | Gersheneld et al. |
| 5,917,346 A | 6/1999 | Gord |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,018,229 A | 1/2000 | Mitchell et al. |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,068,465 A | 5/2000 | Wilson |
| 6,068,589 A | 5/2000 | Neukermans |
| 6,076,016 A | 6/2000 | Feierbach et al. |
| 6,081,734 A | 6/2000 | Batz |
| 6,083,248 A | 7/2000 | Thompson |
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,317,714 B1 | 11/2001 | Del Castillo |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,547,994 B1 | 4/2003 | Monkhouse et al. |
| 6,564,079 B1 | 5/2003 | Cory |
| 6,567,685 B2 | 5/2003 | Takamori et al. |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,602,518 B2 | 8/2003 | Seielstad et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,767,200 B2 | 7/2004 | Sowden et al. |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |

(56) References Cited

U.S. PATENT DOCUMENTS

| | | |
|---|---|---|
| 6,879,810 B2 | 4/2005 | Bouet |
| 6,882,881 B1 | 4/2005 | Lesser et al. |
| 6,888,337 B2 | 5/2005 | Sawyers |
| 6,889,165 B2 | 5/2005 | Lind et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,942,770 B2 | 9/2005 | Cai et al. |
| 6,946,156 B2 | 9/2005 | Bunick |
| 6,951,536 B2 | 10/2005 | Yokoi |
| 6,957,107 B2 | 10/2005 | Rogers et al. |
| 6,958,603 B2 | 10/2005 | Kondo |
| 6,959,929 B2 | 11/2005 | Pugnet et al. |
| 6,960,617 B2 | 11/2005 | Omidian et al. |
| 6,968,153 B1 | 11/2005 | Heinonen |
| 6,977,511 B2 | 12/2005 | Patel et al. |
| 6,982,094 B2 | 1/2006 | Sowden |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,061,236 B2 | 6/2006 | Britton |
| 7,062,308 B1 | 6/2006 | Jackson |
| 7,069,062 B2 | 6/2006 | Minotani et al. |
| 7,076,437 B1 | 7/2006 | Levy |
| 7,081,693 B2 | 7/2006 | Hamel et al. |
| 7,083,578 B2 | 8/2006 | Lewkowicz |
| 7,091,726 B2 | 8/2006 | Sano et al. |
| 7,116,252 B2 | 10/2006 | Teraguchi |
| 7,118,531 B2 | 10/2006 | Krill |
| 7,122,143 B2 | 10/2006 | Sowden et al. |
| 7,125,382 B2 | 10/2006 | Zhou et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,196,495 B1 | 3/2007 | Burcham |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,014 B2 | 11/2007 | Chung et al. |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,732 B1 | 2/2008 | Wiss |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,419,468 B2 | 9/2008 | Shimizu et al. |
| 7,424,268 B2 | 9/2008 | Diener |
| 7,424,319 B2 | 9/2008 | Muehlsteff |
| 7,427,266 B2 | 9/2008 | Ayer et al. |
| 7,433,731 B2 | 10/2008 | Matsumura et al. |
| 7,442,164 B2 | 10/2008 | Berrang et al. |
| 7,443,290 B2 | 10/2008 | Takiguchi |
| 7,449,262 B2 | 11/2008 | Christie et al. |
| 7,458,887 B2 | 12/2008 | Kurosawa |
| 7,462,150 B1 | 12/2008 | Bharmi |
| 7,469,838 B2 | 12/2008 | Brooks et al. |
| 7,471,665 B2 | 12/2008 | Perlman |
| 7,471,992 B2 | 12/2008 | Schmidt et al. |
| 7,485,093 B2 | 2/2009 | Glukhovsky |
| 7,485,095 B2 | 2/2009 | Shusterman |
| 7,492,128 B2 | 2/2009 | Shen |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,547,278 B2 | 6/2009 | Miyazaki et al. |

(56) References Cited

U.S. PATENT DOCUMENTS

| | | |
|---|---|---|
| 7,551,590 B2 | 6/2009 | Haller |
| 7,554,452 B2 | 6/2009 | Cole |
| 7,558,620 B2 | 7/2009 | Ishibashi |
| 7,558,622 B2 | 7/2009 | Tran |
| 7,558,965 B2 | 7/2009 | Wheeler et al. |
| 7,575,005 B2 | 8/2009 | Mumford |
| 7,614,743 B2 | 11/2009 | Geiger |
| 7,616,111 B2 | 11/2009 | Covannon |
| 7,616,710 B2 | 11/2009 | Kim et al. |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,683,761 B2 | 2/2010 | Burghard et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,689,437 B1 | 3/2010 | Teller et al. |
| 7,689,833 B2 | 3/2010 | Lange |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,747,454 B2 | 6/2010 | Bartfeld et al. |
| 7,756,587 B2 | 7/2010 | Penner et al. |
| 7,760,104 B2 | 7/2010 | Asp |
| 7,764,996 B2 | 7/2010 | Zhang et al. |
| 7,779,614 B1 | 8/2010 | McGonagle et al. |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,806,852 B1 | 10/2010 | Jursen |
| 7,809,399 B2 | 10/2010 | Lu |
| 7,811,231 B2 | 10/2010 | Jin et al. |
| 7,844,341 B2 | 11/2010 | Von Arx et al. |
| 7,857,766 B2 | 12/2010 | Lasater et al. |
| 7,860,731 B2 | 12/2010 | Jackson et al. |
| 7,871,734 B2 | 1/2011 | Hertz et al. |
| 7,881,799 B2 | 2/2011 | Greenberg et al. |
| 7,899,526 B2 | 3/2011 | Benditt et al. |
| 7,904,133 B2 | 3/2011 | Gehman et al. |
| D639,437 S | 6/2011 | Bishay et al. |
| 7,975,587 B2 | 7/2011 | Schneider |
| 7,978,064 B2 | 7/2011 | Zdeblick et al. |
| 7,983,189 B2 | 7/2011 | Bugenhagen |
| 8,025,149 B2 | 9/2011 | Sterry et al. |
| 8,036,731 B2 | 10/2011 | Kimchy et al. |
| 8,036,748 B2 | 10/2011 | Zdeblick et al. |
| 8,054,047 B2 | 11/2011 | Chen et al. |
| 8,054,140 B2 | 11/2011 | Fleming et al. |
| 8,055,334 B2 | 11/2011 | Savage et al. |
| 8,060,249 B2 | 11/2011 | Bear et al. |
| 8,073,707 B2 | 12/2011 | Teller et al. |
| 8,082,919 B2 | 12/2011 | Brunnberg et al. |
| 8,083,128 B2 | 12/2011 | Dembo et al. |
| 8,115,618 B2 | 2/2012 | Robertson et al. |
| 8,119,045 B2 | 2/2012 | Schmidt et al. |
| 8,123,576 B2 | 2/2012 | Kim |
| 8,131,376 B1 | 3/2012 | Faraji et al. |
| 8,135,596 B2 | 3/2012 | Jung et al. |
| 8,142,513 B2 | 3/2012 | Shalon et al. |
| 8,177,611 B2 | 5/2012 | Kang |
| 8,180,425 B2 | 5/2012 | Selvitelli et al. |
| 8,185,191 B1 | 5/2012 | Shapiro et al. |
| 8,185,646 B2 | 5/2012 | Headley |
| 8,200,320 B2 | 6/2012 | Kovacs |
| 8,207,731 B2 | 6/2012 | Moskalenko |
| 8,209,018 B2 | 6/2012 | Osorio et al. |
| 8,214,007 B2 | 7/2012 | Baker et al. |
| 8,224,596 B2 | 7/2012 | Agrawal et al. |
| 8,224,667 B1 | 7/2012 | Miller et al. |
| 8,238,998 B2 | 8/2012 | Park |
| 8,249,686 B2 | 8/2012 | Libbus et al. |
| 8,253,586 B1 | 8/2012 | Matak |
| 8,254,853 B2 | 8/2012 | Rofougaran |
| 8,258,962 B2 | 9/2012 | Robertson et al. |
| 8,262,394 B2 | 9/2012 | Walker et al. |
| 8,271,106 B2 | 9/2012 | Wehba et al. |
| 8,271,146 B2 | 9/2012 | Heber et al. |
| 8,285,356 B2 | 10/2012 | Bly et al. |
| 8,290,574 B2 | 10/2012 | Felid et al. |
| 8,298,574 B2 | 10/2012 | Tsabari et al. |
| 8,301,232 B2 | 10/2012 | Albert et al. |
| 8,308,640 B2 | 11/2012 | Baldus et al. |
| 8,314,619 B2 | 11/2012 | Takiguchi |
| 8,315,687 B2 | 11/2012 | Cross et al. |
| 8,343,068 B2 | 1/2013 | Najafi et al. |
| 8,369,936 B2 | 2/2013 | Farringdon et al. |
| 8,374,698 B2 | 2/2013 | Ok et al. |
| 8,386,009 B2 | 2/2013 | Lindberg et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,440,274 B2 | 5/2013 | Wang |
| 8,443,214 B2 | 5/2013 | Lee et al. |
| 8,454,528 B2 | 6/2013 | Yuen et al. |
| 8,454,561 B2 | 6/2013 | Uber, III et al. |
| 8,514,086 B2 | 8/2013 | Harper et al. |
| 8,532,776 B2 | 9/2013 | Greenberg et al. |
| 8,540,632 B2 | 9/2013 | Robertson et al. |
| 8,540,633 B2 | 9/2013 | Hafezi et al. |
| 8,540,664 B2 | 9/2013 | Robertson et al. |
| 8,542,123 B2 | 9/2013 | Robertson |
| 8,545,402 B2 | 10/2013 | Hafezi et al. |
| 8,547,248 B2 | 10/2013 | Zdeblick et al. |
| 8,558,563 B2 | 10/2013 | Zdeblick |
| 8,564,432 B2 | 10/2013 | Covannon et al. |
| 8,564,627 B2 | 10/2013 | Suzuki et al. |
| 8,583,227 B2 | 11/2013 | Savage et al. |
| 8,597,186 B2 | 12/2013 | Hafezi et al. |
| 8,634,838 B2 | 1/2014 | Hellwig et al. |
| 8,647,358 B2 | 2/2014 | Brister et al. |
| 8,660,645 B2 | 2/2014 | Stevenson et al. |
| 8,668,280 B2 | 3/2014 | Heller et al. |
| 8,668,643 B2 | 3/2014 | Kinast |
| 8,674,825 B2 | 3/2014 | Robertson et al. |
| 8,685,451 B2 | 4/2014 | Toneguzzo et al. |
| 8,697,057 B2 | 4/2014 | Van Epps et al. |
| 8,698,006 B2 | 4/2014 | Bealka et al. |
| 8,718,193 B2 | 5/2014 | Arne et al. |
| 8,721,540 B2 | 5/2014 | Hafezi et al. |
| 8,722,085 B2 | 5/2014 | McKinney et al. |
| 8,758,237 B2 | 6/2014 | Sherman et al. |
| 8,762,733 B2 | 6/2014 | Derchak et al. |
| 8,771,183 B2 | 7/2014 | Sloan |
| 8,784,308 B2 | 7/2014 | Duck et al. |
| 8,802,183 B2 | 8/2014 | Frank et al. |
| 8,810,260 B1 | 8/2014 | Zhou |
| 8,810,409 B2 | 8/2014 | Robertson et al. |
| 8,816,847 B2 | 8/2014 | Zdeblick et al. |
| 8,823,510 B2 | 9/2014 | Downey et al. |
| 8,836,513 B2 | 9/2014 | Hafezi et al. |
| 8,838,217 B2 | 9/2014 | Myr |
| 8,847,766 B2 | 9/2014 | Zdeblick et al. |
| 8,858,432 B2 | 10/2014 | Robertson |
| 8,868,453 B2 | 10/2014 | Zdeblick |
| 8,908,943 B2 | 12/2014 | Berry et al. |
| 8,912,908 B2 | 12/2014 | Berkman et al. |
| 8,926,509 B2 | 1/2015 | Magar et al. |
| 8,932,221 B2 | 1/2015 | Colliou et al. |
| 8,945,005 B2 | 2/2015 | Hafezi et al. |
| 8,951,234 B2 | 2/2015 | Hafezi et al. |
| 8,956,287 B2 | 2/2015 | Zdeblick et al. |
| 8,956,288 B2 | 2/2015 | Hafezi et al. |
| 8,961,412 B2 | 2/2015 | Hafezi et al. |

(56) References Cited

U.S. PATENT DOCUMENTS

| | | | |
|---|---|---|---|
| 8,966,973 B1 | 3/2015 | Milone |
| 8,989,837 B2 | 3/2015 | Weinstein et al. |
| 9,031,658 B2 | 5/2015 | Chiao et al. |
| 9,047,746 B1 | 6/2015 | Euliano et al. |
| 9,060,708 B2 | 6/2015 | Robertson et al. |
| 9,083,589 B2 | 7/2015 | Arne et al. |
| 9,088,168 B2 | 7/2015 | Mach et al. |
| 9,107,806 B2 | 8/2015 | Hafezi et al. |
| 9,119,554 B2 | 9/2015 | Robertson et al. |
| 9,119,918 B2 | 9/2015 | Robertson et al. |
| 9,125,868 B2 | 9/2015 | McKinney et al. |
| 9,149,423 B2 | 10/2015 | Duck et al. |
| 9,158,890 B2 | 10/2015 | Meredith et al. |
| 9,161,707 B2 | 10/2015 | Hafezi et al. |
| 9,189,941 B2 | 11/2015 | Eschelman et al. |
| 9,198,608 B2 | 12/2015 | Hafezi et al. |
| 9,226,663 B2 | 1/2016 | Fei |
| 9,226,679 B2 | 1/2016 | Balda |
| 9,235,683 B2 | 1/2016 | Robertson et al. |
| 9,258,035 B2 | 2/2016 | Robertson et al. |
| 9,268,909 B2 | 2/2016 | Jani et al. |
| 9,270,025 B2 | 2/2016 | Robertson et al. |
| 9,271,897 B2 | 3/2016 | Costello et al. |
| 9,277,864 B2 | 3/2016 | Yang et al. |
| 9,278,177 B2 | 3/2016 | Edwards et al. |
| 9,320,455 B2 | 4/2016 | Hafezi et al. |
| 9,415,010 B2 | 8/2016 | Hafezi et al. |
| 9,433,371 B2 | 9/2016 | Hafezi et al. |
| 9,439,582 B2 | 9/2016 | Berkman et al. |
| 9,439,599 B2 | 9/2016 | Thompson et al. |
| 9,444,503 B2 | 9/2016 | Arne et al. |
| 9,517,012 B2 | 12/2016 | Lane et al. |
| 9,597,010 B2 | 3/2017 | Thompson et al. |
| 9,597,487 B2 | 3/2017 | Robertson et al. |
| 9,599,679 B2 | 3/2017 | Taylor et al. |
| 9,603,550 B2 | 3/2017 | Behzadi |
| 9,649,066 B2 | 5/2017 | Zdeblick et al. |
| 9,681,842 B2 | 6/2017 | Zdeblick et al. |
| 9,741,975 B2 | 8/2017 | Laulicht et al. |
| 9,756,874 B2 | 9/2017 | Arne et al. |
| 9,796,576 B2 | 10/2017 | Thompson |
| 9,883,819 B2 | 2/2018 | Jensen et al. |
| 9,941,931 B2 | 4/2018 | Zdeblick |
| 9,962,107 B2 | 5/2018 | Frank et al. |
| 9,968,284 B2 | 5/2018 | Vidalis et al. |
| 1,017,537 A1 | 1/2019 | Schmidt et al. |
| 1,018,712 A1 | 1/2019 | Shirvani et al. |
| 1,020,709 A1 | 2/2019 | Robertson et al. |
| 1,022,390 A1 | 3/2019 | Zdeblick et al. |
| 1,023,860 A1 | 3/2019 | Hafezi et al. |
| 2001/0027331 A1 | 10/2001 | Thompson |
| 2001/0031071 A1 | 10/2001 | Nichols et al. |
| 2001/0039503 A1 | 11/2001 | Chan et al. |
| 2001/0044588 A1 | 11/2001 | Mault |
| 2001/0051766 A1 | 12/2001 | Gazdinski |
| 2001/0056262 A1 | 12/2001 | Cabin et al. |
| 2002/0002326 A1 | 1/2002 | Causey et al. |
| 2002/0019586 A1 | 2/2002 | Teller et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0067270 A1 | 6/2002 | Yarin et al. |
| 2002/0077620 A1 | 6/2002 | Sweeney et al. |
| 2002/0099423 A1 | 7/2002 | Berg et al. |
| 2002/0128934 A1 | 9/2002 | Shaer |
| 2002/0132226 A1 | 9/2002 | Nair |
| 2002/0136744 A1 | 9/2002 | McGlynn et al. |
| 2002/0138009 A1 | 9/2002 | Brockway et al. |
| 2002/0179921 A1 | 12/2002 | Cohn |
| 2002/0184415 A1 | 12/2002 | Naghavi et al. |
| 2002/0192159 A1 | 12/2002 | Reitberg |
| 2002/0193669 A1 | 12/2002 | Glukhovsky |
| 2002/0193846 A1 | 12/2002 | Pool et al. |
| 2002/0198470 A1 | 12/2002 | Imran et al. |
| 2003/0015672 A1* | 1/2003 | Gallagher ............ G01B 11/14 250/548 |
| 2003/0017826 A1 | 1/2003 | Fishman et al. |
| 2003/0023150 A1 | 1/2003 | Yokoi et al. |
| 2003/0028226 A1 | 2/2003 | Thompson |
| 2003/0037063 A1 | 2/2003 | Schwartz |
| 2003/0062551 A1 | 4/2003 | Chen et al. |
| 2003/0063522 A1 | 4/2003 | Sagar |
| 2003/0065536 A1 | 4/2003 | Hansen |
| 2003/0076179 A1 | 4/2003 | Branch et al. |
| 2003/0083559 A1 | 5/2003 | Thompson |
| 2003/0091625 A1 | 5/2003 | Hariharan et al. |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0181815 A1 | 9/2003 | Ebner et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0198619 A1 | 10/2003 | Dong et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0216793 A1 | 11/2003 | Karlsson et al. |
| 2003/0219484 A1 | 11/2003 | Sowden et al. |
| 2003/0229382 A1 | 12/2003 | Sun et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0019172 A1 | 1/2004 | Yang et al. |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0111011 A1 | 6/2004 | Uchiyama et al. |
| 2004/0115507 A1 | 6/2004 | Potter et al. |
| 2004/0115517 A1 | 6/2004 | Fukada et al. |
| 2004/0117062 A1 | 6/2004 | Bonney et al. |
| 2004/0121015 A1 | 6/2004 | Chidlaw et al. |
| 2004/0122296 A1 | 6/2004 | Hatlestad |
| 2004/0122297 A1 | 6/2004 | Stahmann et al. |
| 2004/0138558 A1 | 7/2004 | Dunki-Jacobs et al. |
| 2004/0147326 A1 | 7/2004 | Stiles |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167465 A1 | 8/2004 | Mihai et al. |
| 2004/0167801 A1 | 8/2004 | Say et al. |
| 2004/0171914 A1 | 9/2004 | Avni |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |

(56) References Cited

U.S. PATENT DOCUMENTS

| | | |
|---|---|---|
| 2004/0259899 A1 | 12/2004 | Sanghvi et al. |
| 2004/0260154 A1 | 12/2004 | Sidelnik |
| 2004/0267240 A1 | 12/2004 | Gross et al. |
| 2005/0003074 A1 | 1/2005 | Brown et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0021372 A1 | 1/2005 | Mikkelsen |
| 2005/0024198 A1 | 2/2005 | Ward |
| 2005/0027175 A1 | 2/2005 | Yang |
| 2005/0027205 A1 | 2/2005 | Tarassenko et al. |
| 2005/0038321 A1 | 2/2005 | Fujita et al. |
| 2005/0038680 A1 | 2/2005 | McMahon |
| 2005/0043583 A1 | 2/2005 | Killmann et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0159789 A1 | 7/2005 | Brockway |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122494 A1 | 6/2006 | Bouchoucha |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0204764 A1 | 9/2006 | Hirao et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0025739 A1* | 2/2007 | Moore .................. H04B 10/40 398/202 |
| 2007/0027386 A1 | 2/2007 | Such |
| 2007/0027388 A1 | 2/2007 | Chou |
| 2007/0029195 A1 | 2/2007 | Li et al. |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |

(56) References Cited

U.S. PATENT DOCUMENTS

| | | |
|---|---|---|
| 2007/0167495 A1 | 7/2007 | Brown et al. |
| 2007/0167848 A1 | 7/2007 | Kuo et al. |
| 2007/0172424 A1 | 7/2007 | Roser |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0000804 A1 | 1/2008 | Carey et al. |
| 2008/0004503 A1 | 1/2008 | Nisani et al. |
| 2008/0014866 A1 | 1/2008 | Lipowshi |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0240325 A1* | 10/2008 | Agazzi ............... H03M 1/0626 375/371 |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0284599 A1 | 11/2008 | Zdeblick et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0306362 A1 | 12/2008 | Davis |
| 2008/0311852 A1 | 12/2008 | Hansen |
| 2008/0312522 A1 | 12/2008 | Rowlandson |
| 2008/0316020 A1 | 12/2008 | Robertson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0010321 A1* | 1/2009 | Chalopin ........... H04B 1/71637 375/239 |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0047357 A1 | 2/2009 | Tomohira et al. |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0082645 A1 | 3/2009 | Hafezi et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |

(56) References Cited

U.S. PATENT DOCUMENTS

| | | |
|---|---|---|
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0194747 A1 | 8/2009 | Zou et al. |
| 2009/0197068 A1 | 8/2009 | Yamaguchi et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0019848 A1* | 1/2010 | Rossi .................... H03F 1/223 330/253 |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0082367 A1 | 4/2010 | Hairs et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1 | 5/2010 | Magent et al. |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0183199 A1 | 7/2010 | Smith et al. |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1 | 8/2010 | LeBoeuf et al. |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |

(56) References Cited

U.S. PATENT DOCUMENTS

| | | |
|---|---|---|
| 2011/0004079 A1 | 1/2011 | Al Ali et al. |
| 2011/0009715 A1 | 1/2011 | O'Reilly et al. |
| 2011/0021983 A1 | 1/2011 | Jurson |
| 2011/0029622 A1 | 2/2011 | Walker et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0134906 A1 | 6/2011 | Garudadri et al. |
| 2011/0144470 A1 | 6/2011 | Mazar et al. |
| 2011/0160549 A1 | 6/2011 | Saroka et al. |
| 2011/0212782 A1 | 9/2011 | Thompson et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |
| 2011/0270135 A1 | 11/2011 | Dooley et al. |
| 2011/0279963 A1 | 11/2011 | Kumar et al. |
| 2012/0004520 A1 | 1/2012 | Whitworth et al. |
| 2012/0011699 A1 | 1/2012 | Hafezi et al. |
| 2012/0016231 A1 | 1/2012 | Westmoreland |
| 2012/0024889 A1 | 2/2012 | Robertson et al. |
| 2012/0029309 A1 | 2/2012 | Paquet et al. |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0109112 A1 | 5/2012 | Strand et al. |
| 2012/0116184 A1 | 5/2012 | Shieh |
| 2012/0179004 A1 | 7/2012 | Roesicke et al. |
| 2012/0197144 A1 | 8/2012 | Christ et al. |
| 2012/0214140 A1 | 8/2012 | Brynelson et al. |
| 2012/0245043 A1 | 9/2012 | England |
| 2012/0265544 A1 | 10/2012 | Hwang et al. |
| 2012/0276451 A1 | 11/2012 | Lestriez et al. |
| 2012/0299723 A1 | 11/2012 | Hafezi et al. |
| 2012/0310070 A1 | 12/2012 | Kumar et al. |
| 2012/0316413 A1 | 12/2012 | Liu et al. |
| 2013/0002423 A1 | 1/2013 | Robertson et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2013/0073312 A1 | 3/2013 | Thompson et al. |
| 2013/0129869 A1 | 5/2013 | Hafezi et al. |
| 2013/0129872 A1 | 5/2013 | Kruger |
| 2013/0131283 A1 | 5/2013 | Wang et al. |
| 2013/0171596 A1 | 7/2013 | French |
| 2013/0172690 A1 | 7/2013 | Arne et al. |
| 2013/0185228 A1 | 7/2013 | Dresner |
| 2013/0196012 A1 | 8/2013 | Dill |
| 2013/0199662 A1 | 8/2013 | Gebbink |
| 2013/0209877 A1 | 8/2013 | Kren et al. |
| 2013/0223028 A1 | 8/2013 | Arne et al. |
| 2013/0275296 A1 | 10/2013 | Tietzen et al. |
| 2013/0328416 A1 | 12/2013 | Whitworth et al. |
| 2013/0338452 A1 | 12/2013 | Robertson et al. |
| 2014/0004492 A1 | 1/2014 | O'Reilly et al. |
| 2014/0039445 A1 | 2/2014 | Austin et al. |
| 2014/0051965 A1 | 2/2014 | Zdeblick et al. |
| 2014/0066734 A1 | 3/2014 | Zdeblick |
| 2014/0179221 A1 | 6/2014 | Whitworth et al. |
| 2014/0180202 A1 | 6/2014 | Zdeblick et al. |
| 2014/0203950 A1 | 7/2014 | Zdeblick et al. |
| 2014/0280125 A1 | 9/2014 | Bhardwaj et al. |
| 2014/0308930 A1 | 10/2014 | Tran |
| 2014/0315170 A1 | 10/2014 | Ionescu et al. |
| 2014/0349256 A1 | 11/2014 | Connor |
| 2014/0374276 A1 | 12/2014 | Guthrie et al. |
| 2015/0017486 A1 | 1/2015 | Lai |
| 2015/0051465 A1 | 2/2015 | Robertson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0112243 A1 | 4/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0150480 A1 | 6/2015 | Zdeblick et al. |
| 2015/0164746 A1 | 6/2015 | Costello et al. |
| 2015/0165313 A1 | 6/2015 | Thompson et al. |
| 2015/0193593 A1 | 7/2015 | Zdeblick et al. |
| 2015/0230728 A1 | 8/2015 | Hafezi et al. |
| 2015/0230729 A1 | 8/2015 | Zdeblick et al. |
| 2015/0248833 A1 | 9/2015 | Arne et al. |
| 2015/0352343 A1 | 12/2015 | Hafezi et al. |
| 2015/0361234 A1 | 12/2015 | Hafezi et al. |
| 2016/0106339 A1 | 4/2016 | Behzadi et al. |
| 2016/0155316 A1 | 6/2016 | Hafezi et al. |
| 2016/0345906 A1 | 12/2016 | Johnson et al. |
| 2016/0380708 A1 | 12/2016 | Dua et al. |
| 2017/0000179 A1 | 1/2017 | Cheng et al. |
| 2017/0014046 A1 | 1/2017 | Hafezi et al. |
| 2017/0020182 A1 | 1/2017 | Schmidt et al. |
| 2017/0215761 A1 | 8/2017 | Zdeblick |
| 2017/0216569 A1 | 8/2017 | Hafezi et al. |
| 2017/0265813 A1 | 9/2017 | Zdeblick et al. |
| 2017/0290513 A1 | 10/2017 | O'Reilly et al. |
| 2017/0296799 A1 | 10/2017 | Hafezi et al. |
| 2017/0303818 A1 | 10/2017 | Behzadi et al. |
| 2018/0110441 A1 | 4/2018 | Frank et al. |
| 2018/0184698 A1 | 7/2018 | Arne et al. |
| 2018/0214048 A1 | 8/2018 | Zdeblick et al. |
| 2018/0229996 A1 | 8/2018 | Thompson |
| 2018/0279910 A1 | 10/2018 | Jensen et al. |

FOREIGN PATENT DOCUMENTS

| | | |
|---|---|---|
| CN | 1650844 | 8/2005 |
| CN | 2748032 | 12/2005 |
| CN | 1991868 | 7/2007 |
| CN | 101005470 | 7/2007 |
| CN | 201076456 | 6/2008 |
| CN | 101524267 | 9/2009 |
| CN | 101795202 | 8/2010 |
| DE | 10313005 | 10/2004 |
| EP | 0344939 | 12/1989 |
| EP | 0526166 | 2/1993 |
| EP | 0981152 | 2/2000 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 1244308 | 12/2007 |
| EP | 2143369 | 1/2010 |
| GB | 775071 | 5/1957 |
| GB | 827762 | 2/1960 |
| GB | 2432862 | 6/2007 |
| IL | 172917 | 6/2010 |
| JP | S6117949 | 1/1986 |
| JP | 61072712 | 4/1986 |
| JP | S63280393 | 11/1988 |
| JP | H01285247 | 11/1989 |
| JP | 05228128 | 9/1993 |
| JP | H0884779 | 4/1996 |
| JP | 09330159 | 12/1997 |
| JP | 1014898 | 1/1998 |
| JP | H11195415 | 7/1999 |
| JP | 2000506410 | 5/2000 |
| JP | 2001078974 | 3/2001 |
| JP | 2002224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003050867 | 2/2003 |

(56) References Cited

FOREIGN PATENT DOCUMENTS

| | | |
|---|---|---|
| JP | 2003210395 | 7/2003 |
| JP | 3454525 | 10/2003 |
| JP | 2003325440 | 11/2003 |
| JP | 2004007187 | 1/2004 |
| JP | 2004507188 | 3/2004 |
| JP | 2004134384 | 4/2004 |
| JP | 2004274452 | 9/2004 |
| JP | 2004313242 | 11/2004 |
| JP | 2004318534 | 11/2004 |
| JP | 2004364016 | 12/2004 |
| JP | 2005031840 | 2/2005 |
| JP | 2005073886 | 3/2005 |
| JP | 2005087552 | 4/2005 |
| JP | 2005102959 | 4/2005 |
| JP | 2005124708 | 5/2005 |
| JP | 2005514966 | 5/2005 |
| JP | 2005148021 | 6/2005 |
| JP | 2005152037 | 6/2005 |
| JP | 2005287691 | 10/2005 |
| JP | 2005304880 | 11/2005 |
| JP | 2005532841 | 11/2005 |
| JP | 2005532849 | 11/2005 |
| JP | 2005343515 | 12/2005 |
| JP | 20055332328 | 12/2005 |
| JP | 2006006377 | 1/2006 |
| JP | 2006509574 | 3/2006 |
| JP | 2006177699 | 7/2006 |
| JP | 2006187611 | 7/2006 |
| JP | 2006278091 | 10/2006 |
| JP | 2006346000 | 12/2006 |
| JP | 3876573 | 1/2007 |
| JP | 2007151809 | 6/2007 |
| JP | 2007159631 | 6/2007 |
| JP | 2007200739 | 8/2007 |
| JP | 2007313340 | 12/2007 |
| JP | 2007330677 | 12/2007 |
| JP | 2008011865 | 1/2008 |
| JP | 2008501415 | 1/2008 |
| JP | 2008176434 | 7/2008 |
| JP | 2008191955 | 8/2008 |
| JP | 2008289724 | 12/2008 |
| JP | 2009034345 | 2/2009 |
| JP | 2009050541 | 3/2009 |
| JP | 2009061236 | 3/2009 |
| JP | 2009065726 | 3/2009 |
| JP | 2009514870 | 4/2009 |
| JP | 2009528909 | 8/2009 |
| JP | 2011015817 | 1/2011 |
| JP | 2011519583 | 7/2011 |
| KR | 20020015907 | 3/2002 |
| KR | 20020061744 | 7/2002 |
| KR | 200600977523 | 7/2006 |
| KR | 100927471 | 11/2009 |
| KR | 20110137001 | 12/2011 |
| KR | 10-2012-099995 | 9/2012 |
| TW | 200301864 | 7/2003 |
| TW | 553735 | 9/2003 |
| TW | 200406192 | 5/2004 |
| TW | 200724094 | 7/2007 |
| TW | 200812556 | 3/2008 |
| TW | 200916136 | 4/2009 |
| TW | 201120673 | 6/2011 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO9516393 | 6/1995 |
| WO | WO1997014112 | 4/1997 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2000032474 | 6/2000 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001058236 | 8/2001 |
| WO | WO2001074011 | 10/2001 |
| WO | WO2001080731 | 11/2001 |
| WO | WO2002000920 | 1/2002 |
| WO | WO200235997 | 5/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075032 | 9/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041438 | 5/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2005123569 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006123346 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |

(56) References Cited

FOREIGN PATENT DOCUMENTS

| | | |
|---|---|---|
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009031149 | 3/2009 |
| WO | WO2009032381 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010129288 | 11/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012112561 | 8/2012 |
| WO | WO2012158190 | 11/2012 |
| WO | WO2013012869 | 1/2013 |
| WO | WO2015112603 | 7/2015 |
| WO | WO2015112604 | 7/2015 |
| WO | WO2015119911 | 8/2015 |

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.

Aronson, J., "Meyer's Side Effects of Cardiovascular Drugs," Elsevier, Mar. 2, 2009, Medical , 840 pages. (Not Attached).

Arshak et al., A Review and Adaptation of Methods of Object Tracking to Telemetry Capsules IC-Med (2007) vol. 1, No. 1, Issue 1, 12pp.

Au-Yeung, K., et al., "A Networked System for Self-Management of Drug Therapy and Wellness", Wireless Health '10, Oct. 5-7, 2010, San Diego, 9 pages.

Aydin et al., "Design and implementation considerations for an advanced wireless interface in miniaturized integrated sensor Microsystems" Sch. of Eng. & Electron., Edinburgh Univ., UK; (2003); abstract (1 page).

Barrie, Heidelberg pH capsule gastric analysis. Texbook of Natural Medicine, (1992), Pizzorno, Murray & Barrie (4 pages).

Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf (14 pages).

Browne, S.H., et al., "Let visuals tell the story: Medication adherence in patients with type II diabetes captured by a novel ingestion sensor platform," JMIR Mhealth Uhealth; 3(4): e108; 2015; 27 pages.

Carlson et al., "Evaluation of a non-invasive respiratory monitoring system for sleeping subjects" Physiological Measurement (1999) 20(1): 53.

Chan, Adrian D.C., et al.,; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.

Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.

Coury, L. "Conductance Measurement Part 1: Theory"; Current Separations, 18:3 (1999) p. 91-96.

Delvaux et al., "Capsule endoscopy: Technique and indications" Clinical Gastroenterology (2008) vol. 22, Issue 5, pp. 813-837.

Description of ePatch Technology Platform for ECG and EMG, located it http://www.madebydelta.com/imported/images/DELTA_Web/documents/ME/ePatch_ECG_EMG.pdf, Dated Sep. 2, 2010; 1 page.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Evanczuk, S., "PIC MCU software library uses human body for secure communications link"; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pp.

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf (5 pages).

Ferguson et al., "Dielectric Constant Studies III Aqueous Gelatin Solutions" J. Chem. Phys. 2, 94 (1934) p. 94-98.

Ferguson et al., "Wireless communication with implanted medical devices using the conductive properties of the body," Expert Rev Med Devices, Jul. 2011, 8(4): 427-433.

Frias, J. et al., "Effectiveness of Digital Medicines to Improve Clinical Outcomes in Patients with Uncontrolled Hypertension and

(56) References Cited

OTHER PUBLICATIONS

Type 2 Diabetes: Prospective, Open-Label, Cluster-Randomized Pilot Clinical Trial," J Med Internet Res, 2017;19(7):e246; p. 15 (16 pages).
Furse C. M., "Dipole Antennas" J. Webster (ed). Wiley Encyclopedia of Electrical and Electronics Engineering (1999) p. 575-581.
Gaglani S. "Put Your Phone, or Skin, on Vibrate" MedGadget (2012) http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12): 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html (1 page).
Greene, "Medicaid Efforts to Incentivize Healthy Behaviours", Center for Health Care Strategies, Inc., Resource Paper, Jul. 2007 (20 pages).
Halthion Medical Technologies "Providing Ambulatory Medical Devices Which Monitor, Measure and Record" webpage. Online website: http://www.halthion.com/; downloaded May 30, 2012; 2 pp.
Herbig, S.M., "Asymmetric-membrane tablet coatings for osmotic drug delivery", Journal of Controlled Release 35 (1995) 127-136.
Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider (2010) http://www.e-health-insider.com/news/5910/new_'smart_pill'_monitors_medicines (1 page).
Hoover et al., "Rx for health: Engineers design pill that signals it has been swallowed" University of Florida News (2010) 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
Intromedic, MicroCam Innovative Capsule Endoscope Pamphlet. (2006) 8 pp (http://www.intromedic.com/ene/product/productinfo.asp) (8 pages).
ISFET—Ion Sensitive Field-Effect Transistor; Microsens S.A. pdf document. Office Action dated Jun. 13, 2011 for U.S. Appl. No. 12/238,345; 4pp.
Jimbo et al., "Gastric-fluid-utilized micro battery for micro medical devices" The Sixth International Workshop on Micro and Nanotechnology for Power Geneartion and Energy Conservation Applications, (2006) pp. 97-100.
Jung, S. "Dissolvable 'Transient Electronics' Will Be Good for Your Body and the Environment" MedGadget; Oct. 1, 2012; Conine website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).

Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.
Lin et al., "Do Physiological Data Relate to Traditional Usability Indexes?" Proceedings of OZCHI 2005, Canberra, Australia (2005) 10 pp.
Mackay et al., "Endoradiosonde" Nature, (1957) 1239-1240, 179 Nature Publishing Group.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-06/04/0004; 2 pp.
McDermott-Wells, P., "What is Bluetooth?", IEEE Potentials, IEEE, New York, NY, vol. 23, No. 5, Dec. 1, 2004, pp. 33-35.
McKenzie et al., "Validation of a new telemetric core temperature monitor" J. Therm. Biol. (2004) 29(7-8):605-11.
Medtronic "The New MiniMed Paradigm® REAL-Time Revel™ System" (2010) http://www.medtronicdiabetes.com/products/index.html; 2 pp.
Medtronic, "CareLink Therapy Management Software for Diabetes" (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic, "MINI MED Paradigm® Revel™ Insulin Pump" (2010) http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget (2008); http://www.engadget.com/2008/07/29/walkers-swallow-rfid-pills-for-science/ (1 page).
Mini Mitter Co, Inc. 510(k) Premarket Notification for VitalSense. Apr. 22, 2004 (11 pages).
Mini Mitter Co, Inc. 510(k) Premarket Notification Mini-Logger for Diagnostic Spirometer. 9-21 (1999) (9 pages).
Minimitter Co. Inc. "Actiheart" Traditional 510(k) Summary. Sep. 27, 2005 (8 pages).
Minimitter Co. Inc. Noninvasive technology to help your studies succeed. Mini Mitter.com Mar. 31, 2009 (4 pages).
Minimitter Co. Inc. VitalSense Integrated Physiological Monitoring System. Product Description. (2005) (4 pages).
Minimitter Co. Inc. VitalSense Wireless Vital Signs Monitoring. Temperatures.com Mar. 31, 2009 (3 pages).
Mojaverian et al., "Estimation of gastric residence time of the Heidelberg capsule in humans: effect of varying food composition" Gastroenterology (1985) 89:(2): 392-7.
Noble et al., "Medication adherence and activity patterns underlying uncontrolled hypertension: Assessment and recommendations by practicing pharmacists using digital health care," JAPHA; 56 (2016) pp. 310-315 (6 pages).
O'Brien et al., "The Production and Characterization of Chemically Reactive Porous Coatings of Zirconium Via Unbalanced Magnetron Sputtering" Surface and Coatings Technology (1996) 86-87; 200-206.
Owano, N., "Study proposes smart sutures with sensors for wounds" phys.org. Aug. 2012. http://phys.org/news/2012-08-smart-sutures-sensors-wounds.html; 2pp.

(56) References Cited

OTHER PUBLICATIONS

"PALO Bluetooth Baseband" PALO Bluetooth Resource Center; Retrieved from internet Dec. 12, 2012 at URL:http://palowireless.com/bluearticles/baseband.asp; first cited in Office Action dated Jan. 17, 2013 for EP08853901.0 (2013); 6pp.
Park, "Medtronic to Buy MiniMed for $3.7 Billion" (2001) HomeCare; http://homecaremag.com/mag/medical_medtronic_buy_minimed/; 2 pp.
Philips Respironics Products, Noninvasive Technology to Help Your Studies Succeed. 510 (k) Permanent Notification for Vital Sense. Apr. 22, 2004; http/minimitter.com/products.cfm.
Platt, D., "Modulation and Deviation" AE6EO, Foothills Amateur Radio Society; Oct. 26, 2007; 61 pp.
Radio Antennae, http://www.erikdeman.de/html/sail018h.htm; (2008) 5 pages.
"RFID "pill" monitors marchers" RFID News (2008) http://www.rfidnews.org/2008/07/23/rfid-pill-monitors-marchers/ (4 pages).
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sammoura, F. et al., "Water-activated disposable and long shelf life microbatteries", Sensors and Actuators A 111 (2004) 79-86.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
Savage, G., "Predictive Analytics: Advancing Precision and Population Medicine," Harvard Health Policy Review, 2015; vol. 14; Issue 2; 4 pages.
"SensiVida minimally invasive clinical systems" Investor Presentation Oct. 2009 28pp; http://www.sensividamedtech.com/SensiVidaGeneralOctober09.pdf; pp. 1-28.
Sharma, et al., "The Future is Wireless: Advances in Wireless Diagnostic and Therapeutic Technologies in Gastoenterology," Gastroenterology, Elesevier, Philadelphia, PA, vol. 137, No. 2, Aug. 1, 2009, pp. 434-439.
Shawgo, R.S. et al. "BioMEMS from drug delivery", Current Opinion in Solid State and Material Science 6 (2002), p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010); pp. 11-12.
"Smartlife awarded patent for knitted transducer" Innovation in Textiles News: http://www.innovationintextiles.com/articles/208.php; 2pp. (2009).
"The SmartPill Wireless Motility Capsule" Smartpill, The Measure of GI Health; (2010) http://www.smartpillcorp.com/index.cfm?pagepath=Products/The_SmartPill_Capsule&id=17814 (1 page).
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal 2010 Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Target Innovations, Tablet Metal Detector, https://web.arch ive.org/web/20 130215063351 /http://www. metaldetectorindia.com/tablet -metal-detector. html, Feb. 15, 2013.
TargetPharmaceutical Metal Detector, Feb. 15, 2013 downloaded from Target Innovations, Tablet Metal Detector, Feb. 15, 2013.
Tatbul et al., "Confidence-based data management for personal area sensor networks" ACM International Conference Proceeding Series (2004) 72; 3 pages.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Trutag Technologies, Inc., Spectral Microtags for Authentication and Anti-Counterfeiting; "Product Authentication and Brand Protection Solutions"; http://www.trutags.com/; downloaded Feb. 12, 2013; 1 pp.
Van der Biest, O., et al., "Electrophoretic deposition of materials," Annu. Rev. Mater. Sci. 1999, 29: pp. 327-352.
VonStetten, F. et al., "Biofuel cells as power generation for implantable devices", Pore. Eurosensors XX, (2006), pp. 222-225.
Walkey, "MOSFET Structure and Processing"; 97.398* Physical Electronics Lecture 20; 24 pages, Office Action dated Jun. 13, 2011 for U.S. Appl. No. 12/238,345.
Wang, X. et al "Resistance to Tracking and Erosion of Silicone Rubber Material under Various Types of Precipitation", Jpn. J. Appl. Phys. vol. 38 (1999) pp. 5170-5175.
Watson, et al., "Determination of the relationship between the pH and conductivity of gastric juice" Physiol Meas. 17 (1996) pp. 21-27.
Winter, J. et al. "The material properties of gelatin gels"; USA Ballistic Research Laboratories, Mar. 1975, p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3. 2006; pp. 6249-6252.
Youtube video Pharmaceutical Metal Detector/Tablet Metal Detector/ Capsule Metal Detector/ Dry Fruits; https://www.youtube.com/watch?v=I0126txam_s, May 12, 2012.
Zhang, Y-T. et al., "Wireless Biomedical Sensing," Wiley Encyclopedia of Biomedical Engineering, 2006, pp. 1-9.
Zimmerman, "Personal Area Networks: Near-field intrabody communication" IBM Systems Journal (1996) 35 (3-4):609-17.
Zworykin, "A Radio Pill" Nature, (1957) 898, 179 Nature Publishing Group.

\* cited by examiner

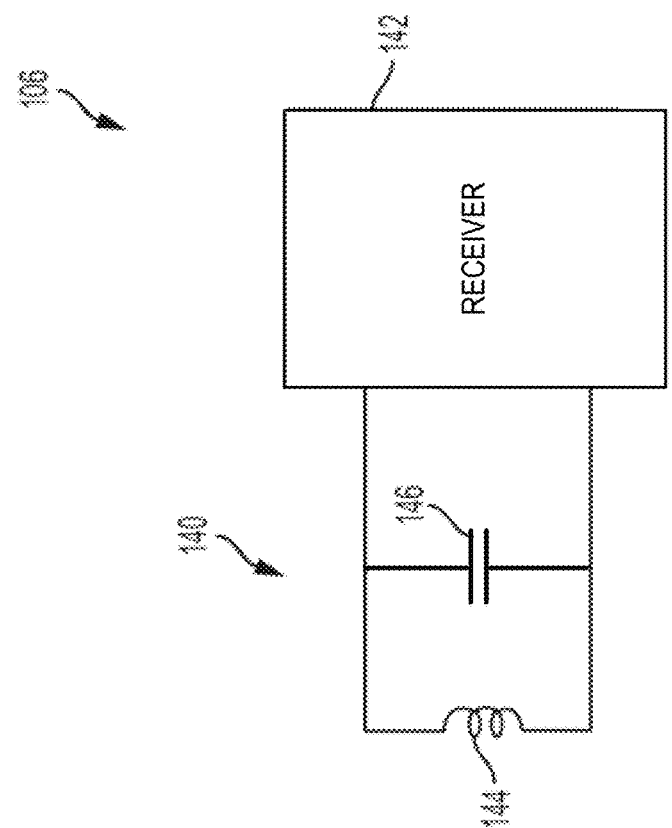
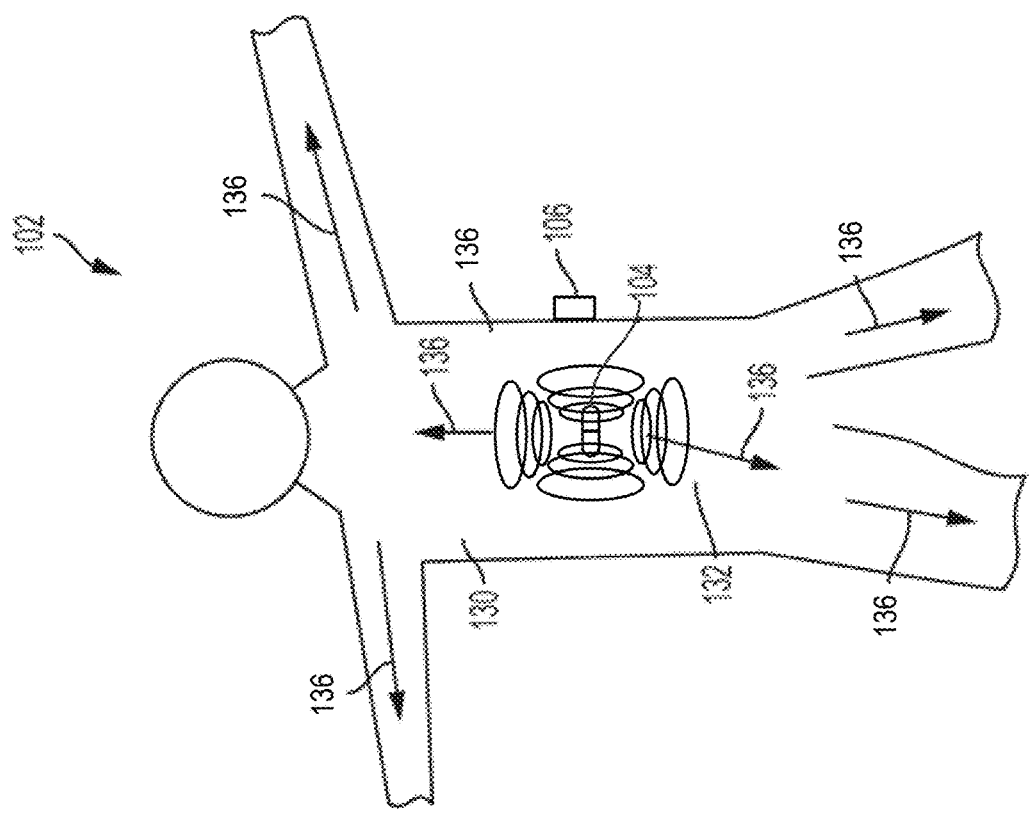
FIG. 3
FIG. 2

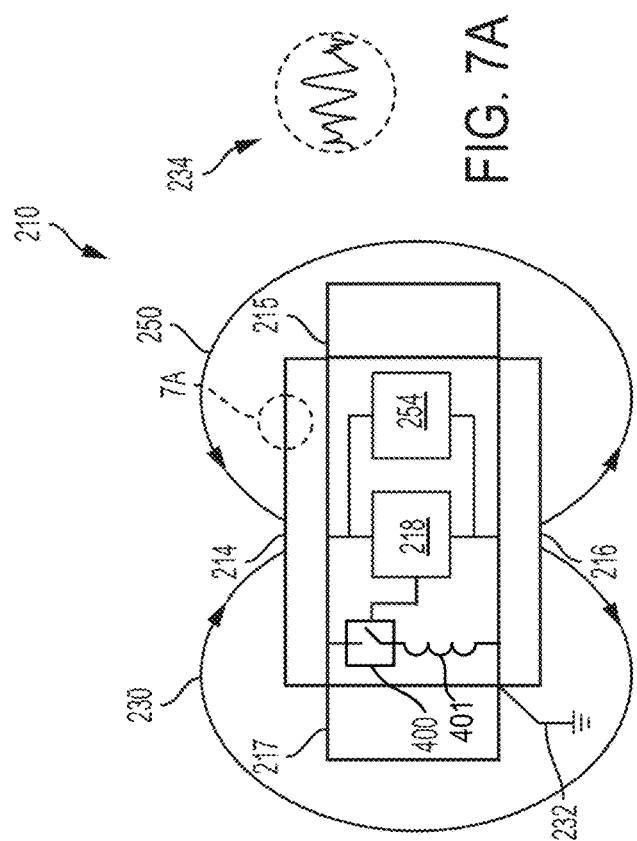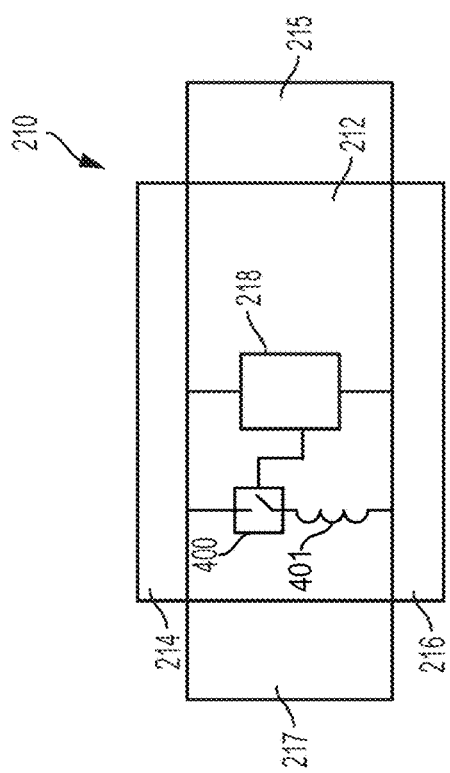

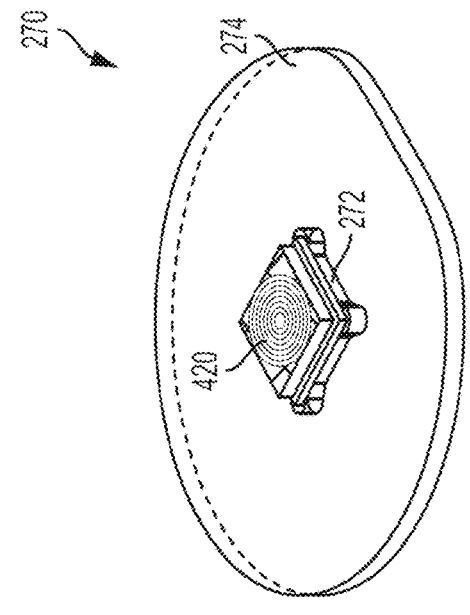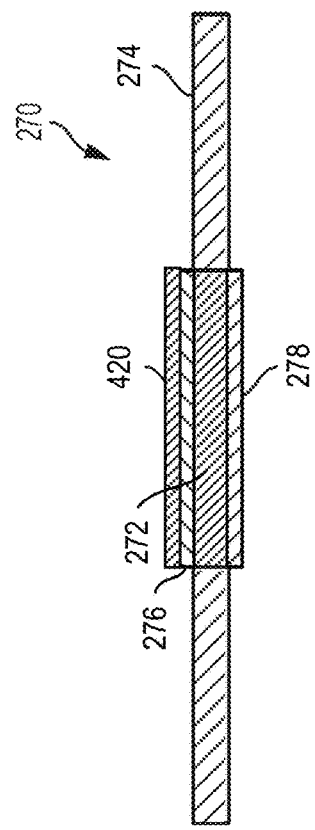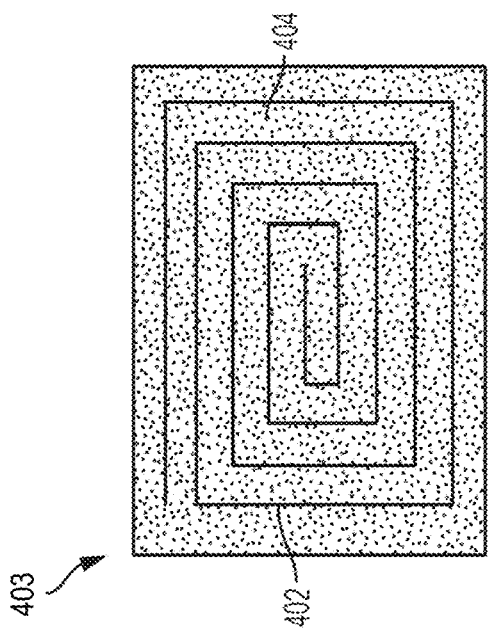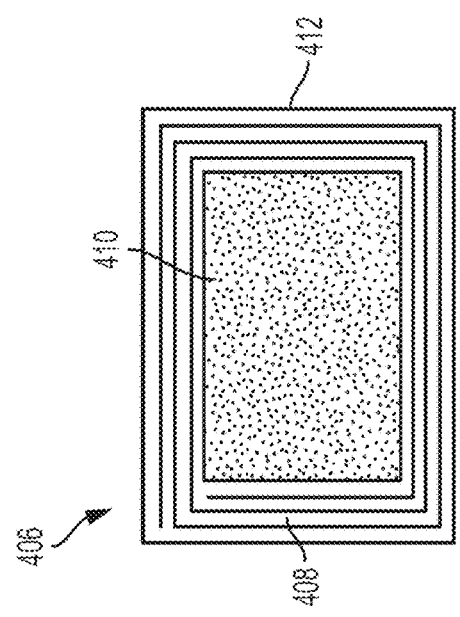
FIG. 12
FIG. 13
FIG. 10
FIG. 11

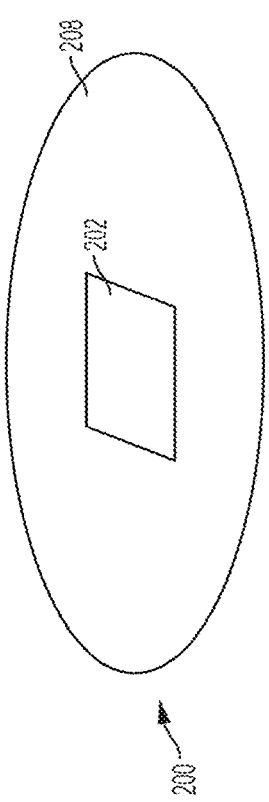
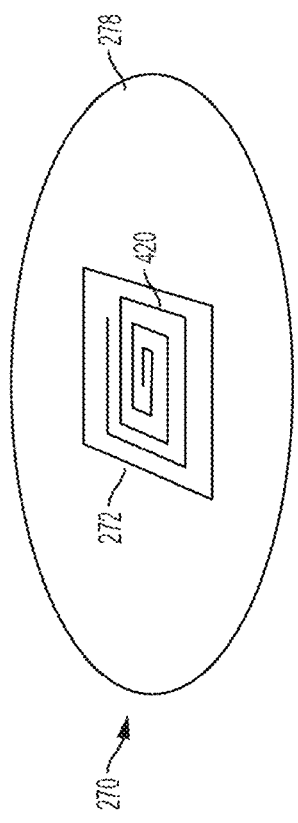
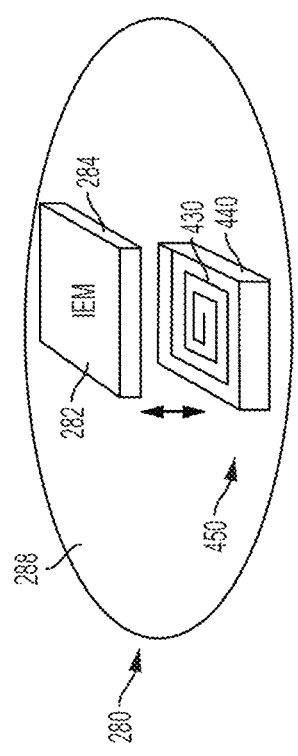
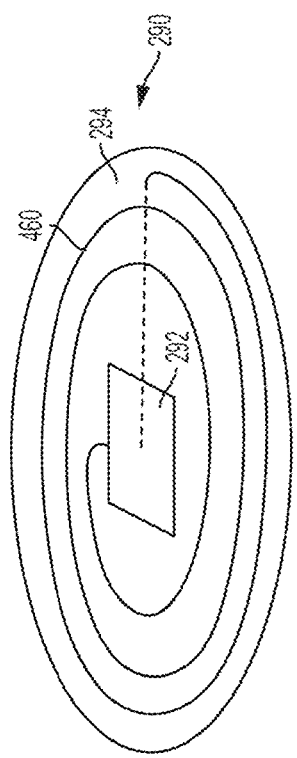
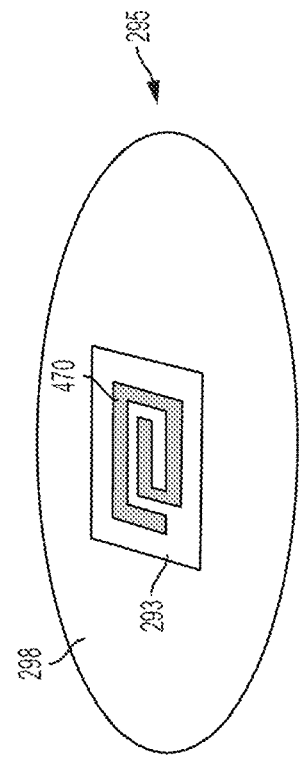

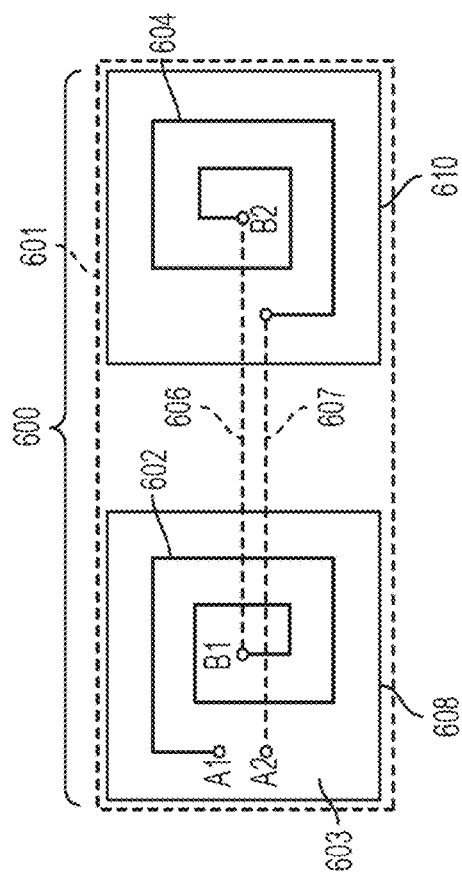
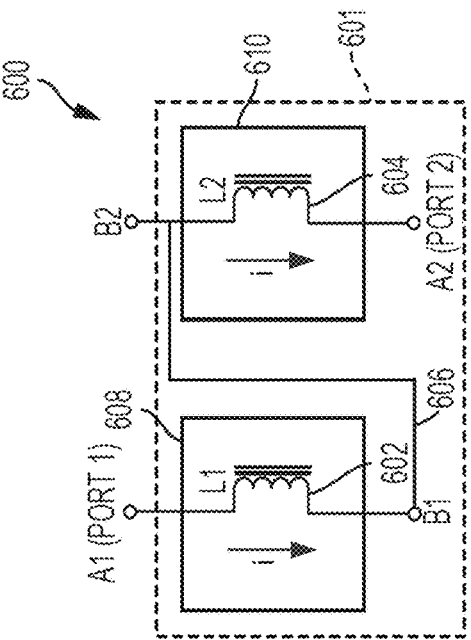
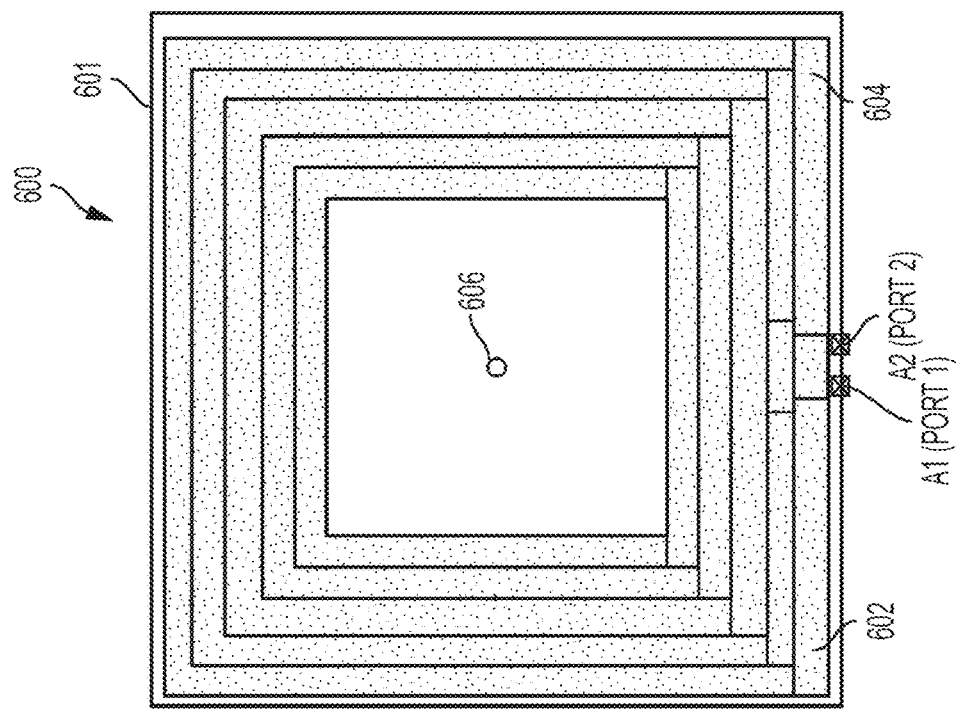
FIG. 25
FIG. 26
FIG. 27

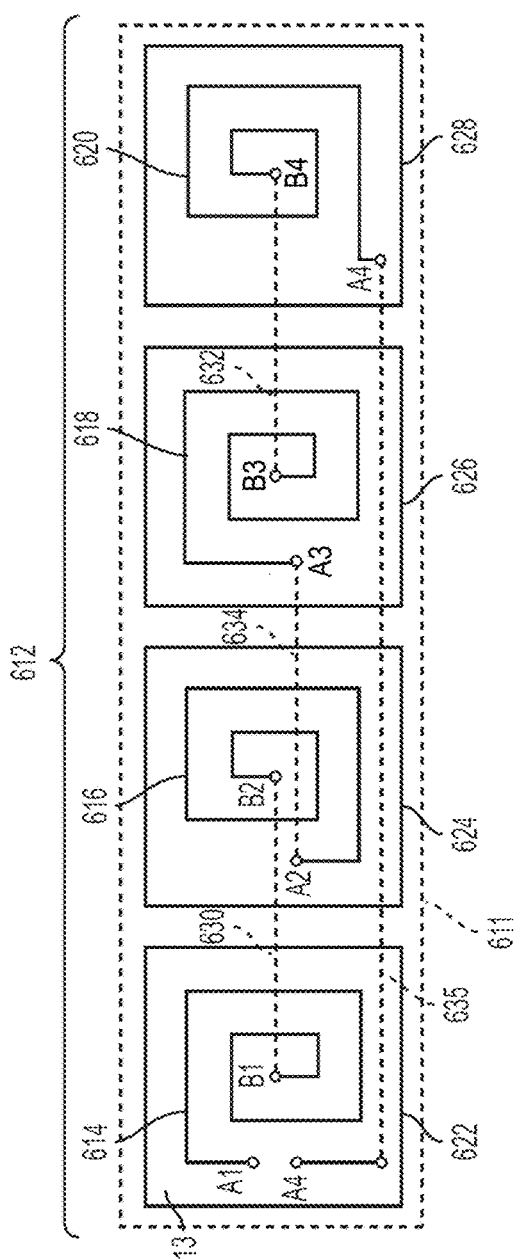
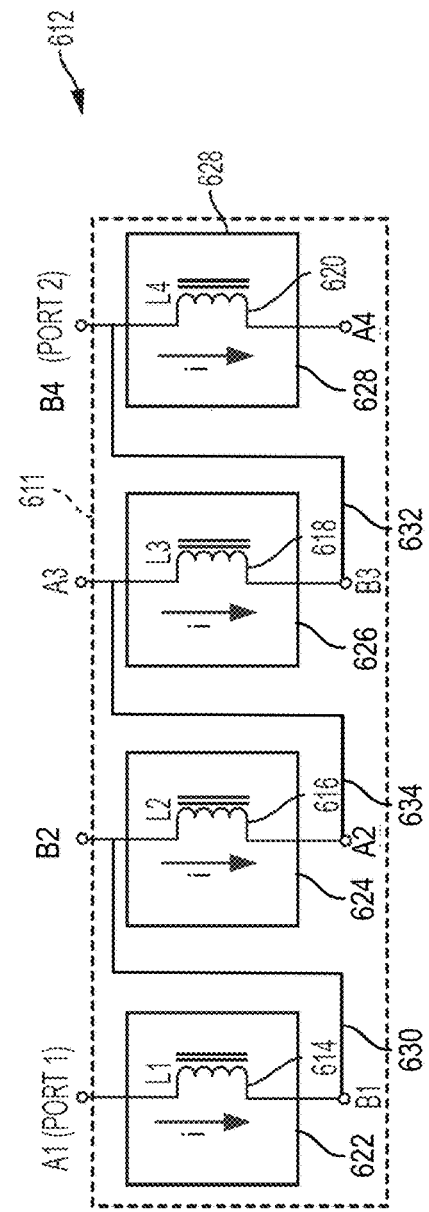
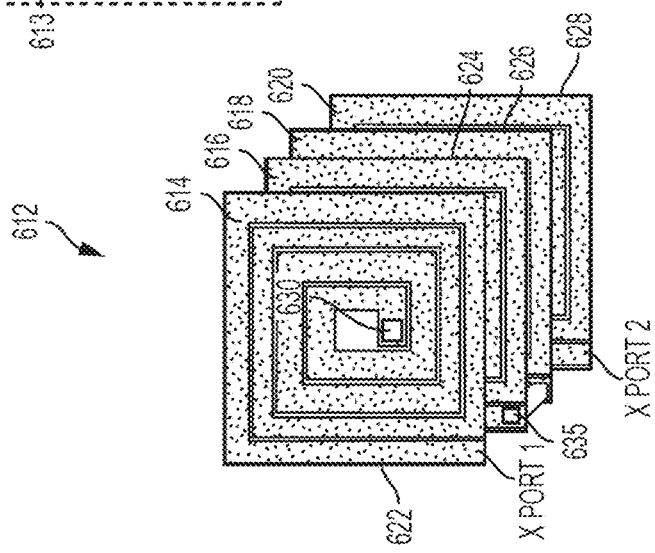
FIG. 29
FIG. 30
FIG. 28

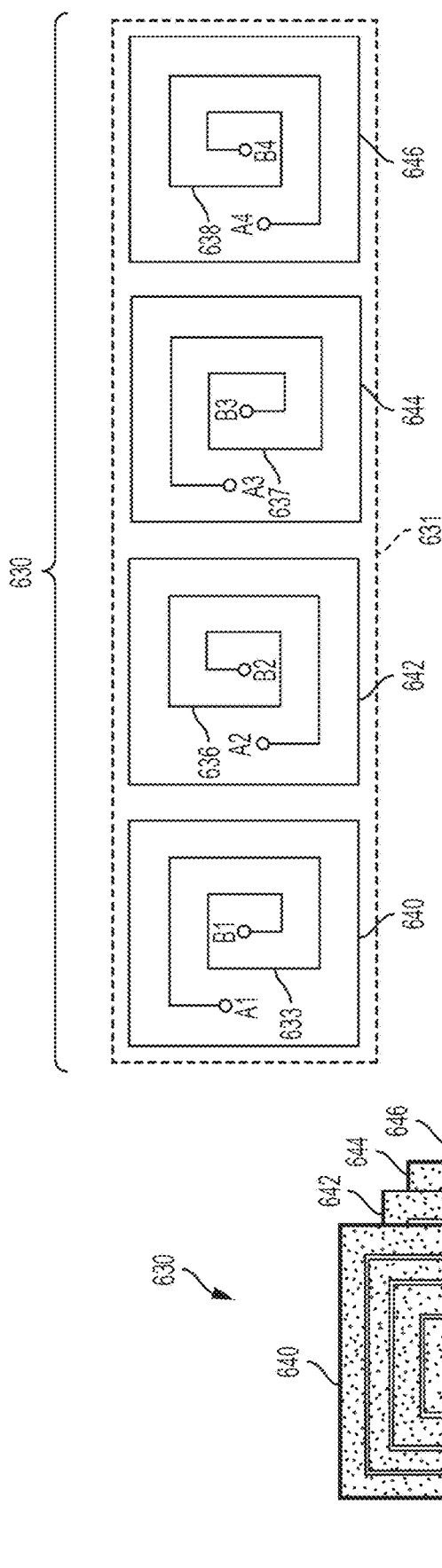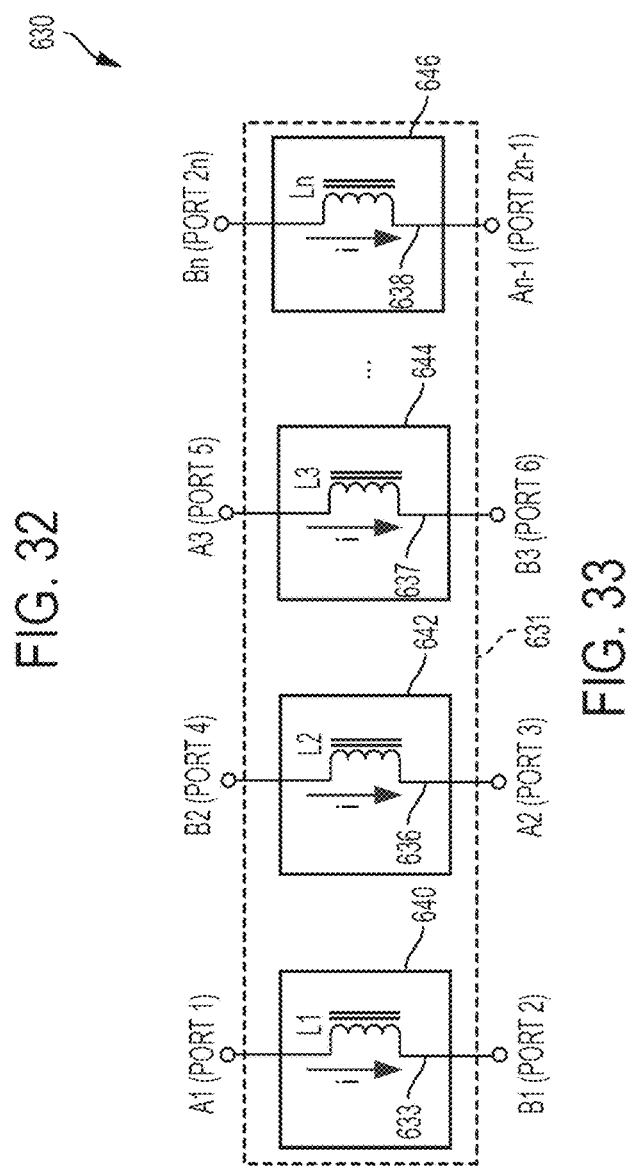
FIG. 32
FIG. 33
FIG. 31

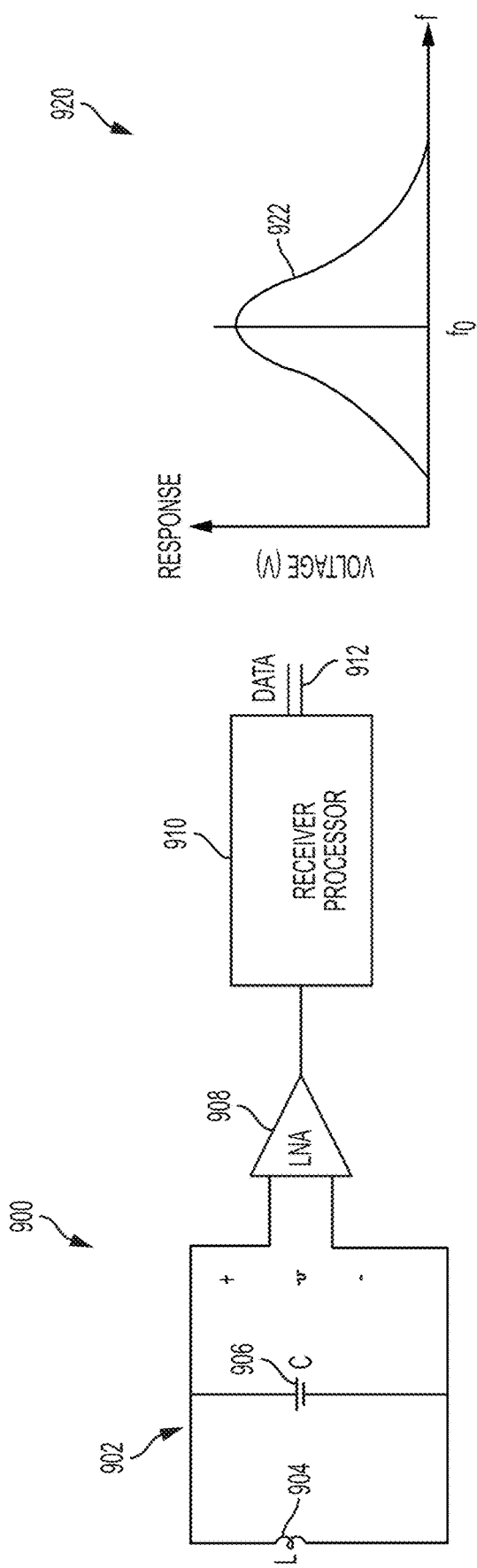
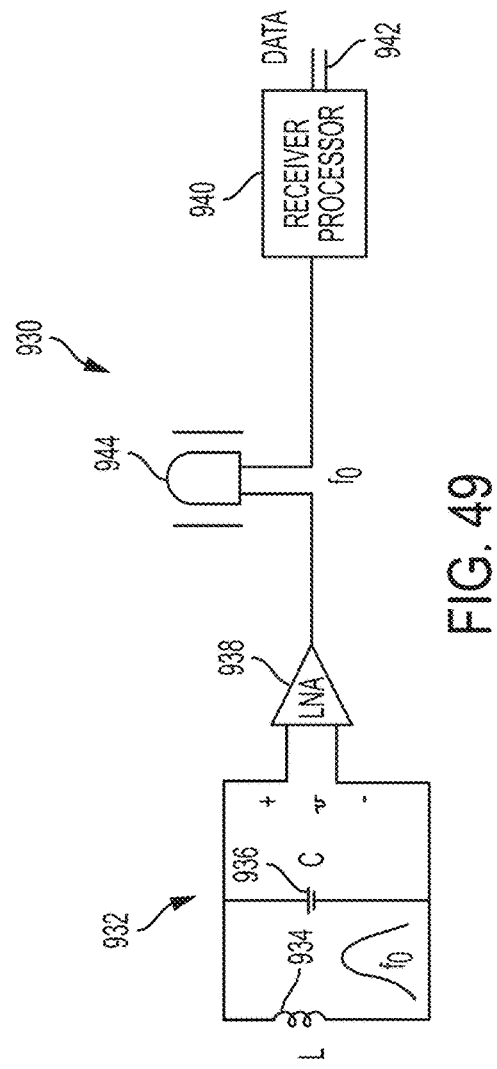
FIG. 47
FIG. 48
FIG. 49

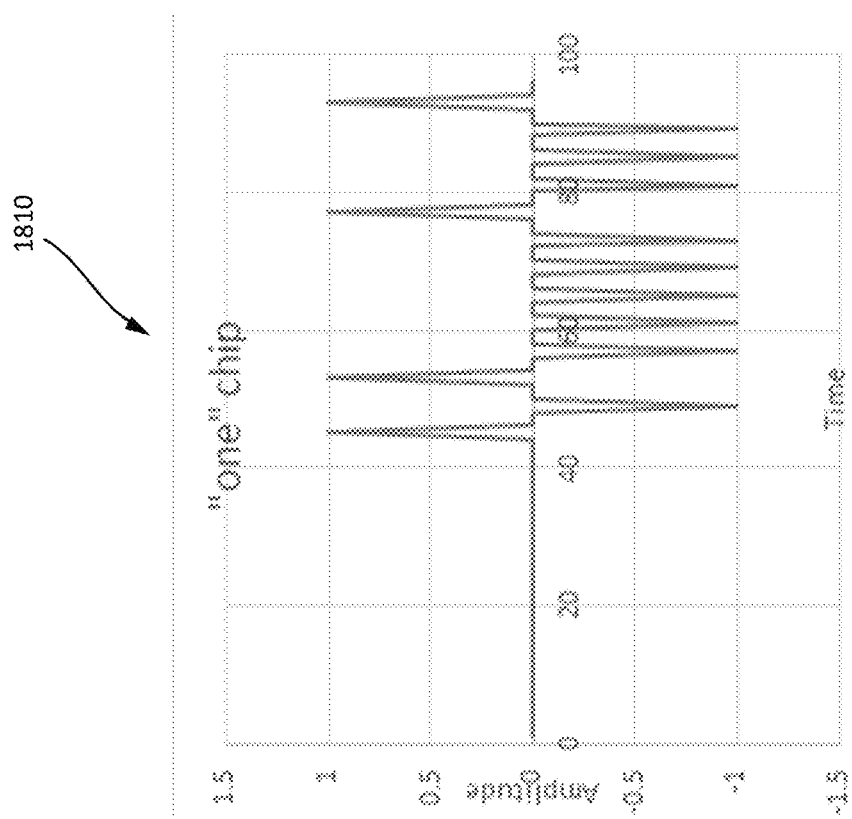
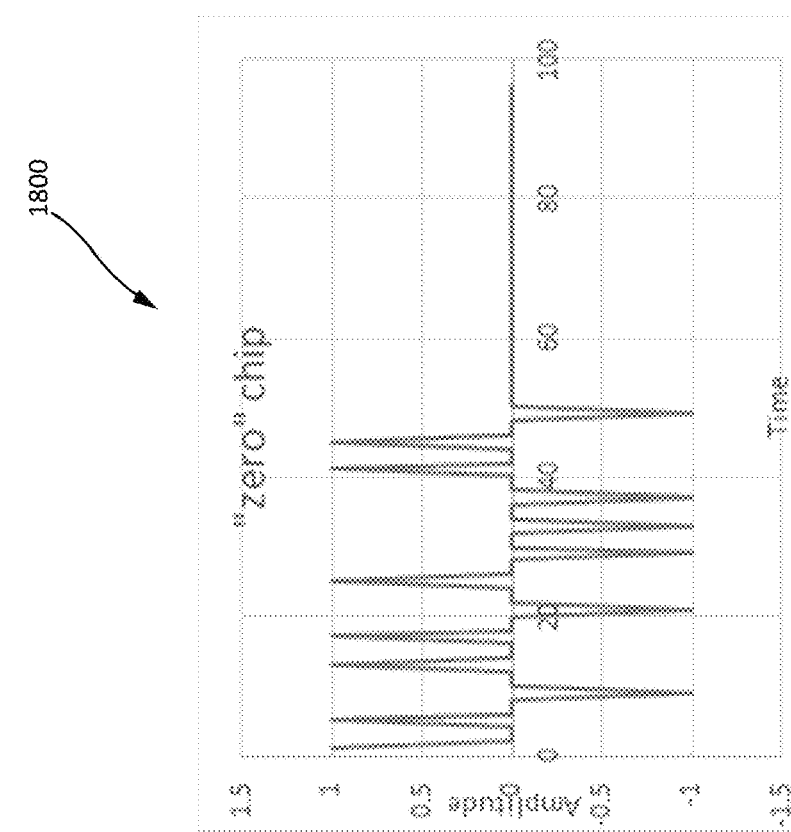
FIG. 62

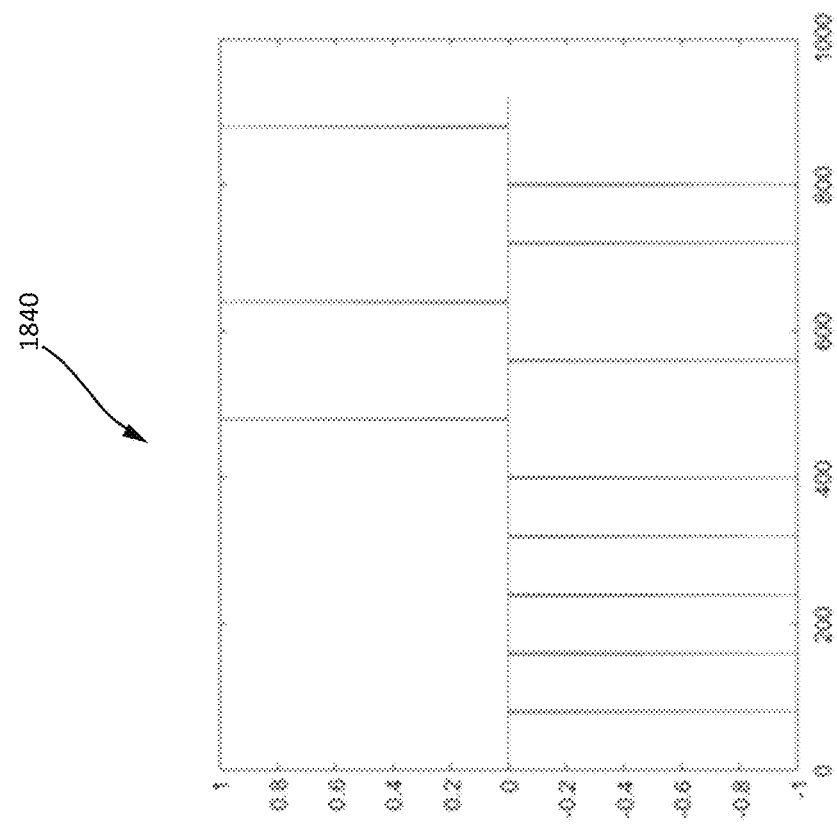
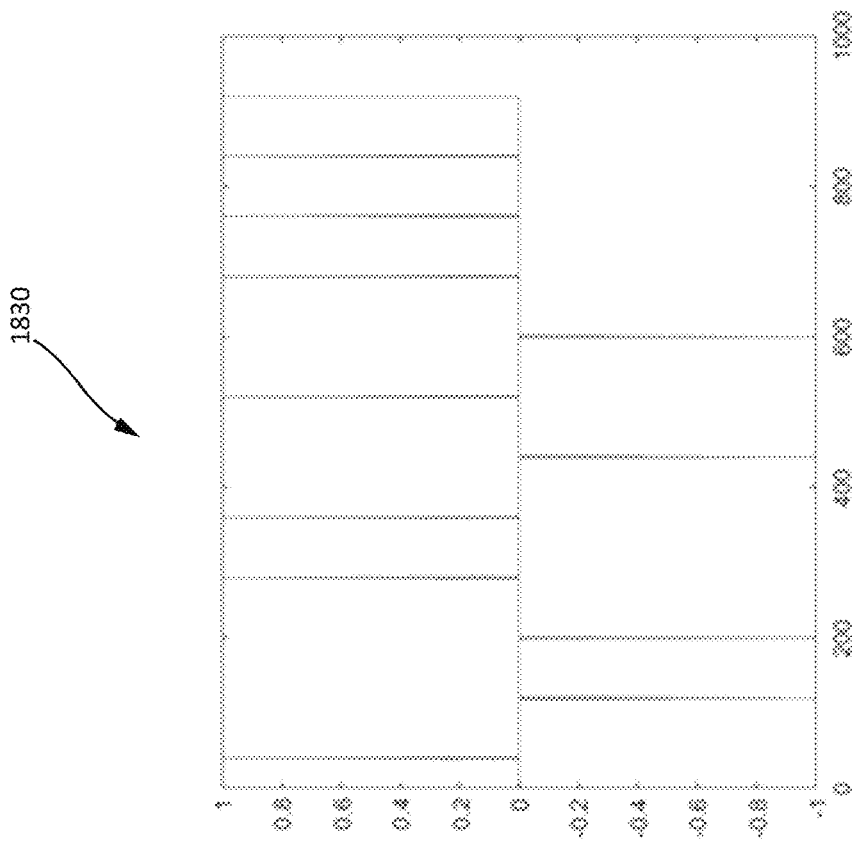
FIG. 64

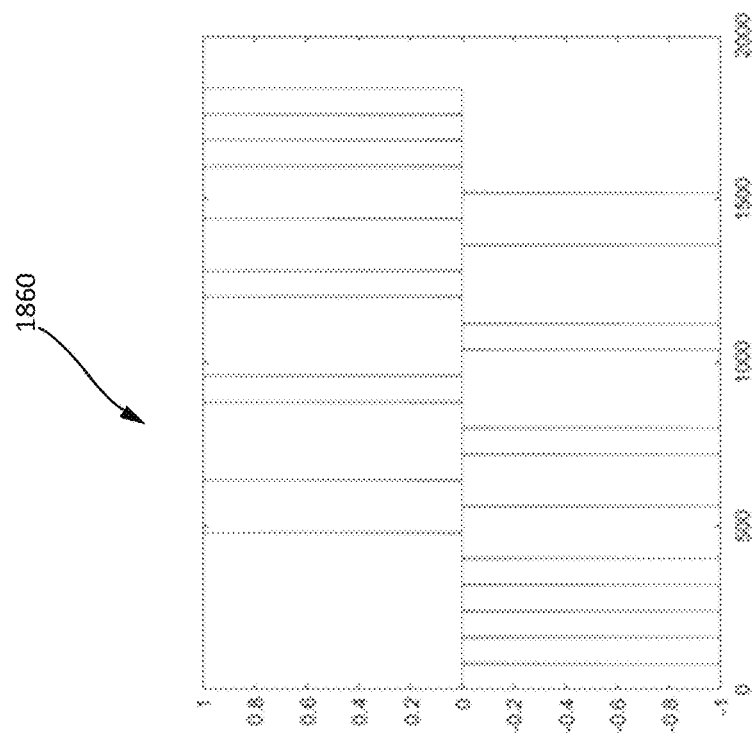
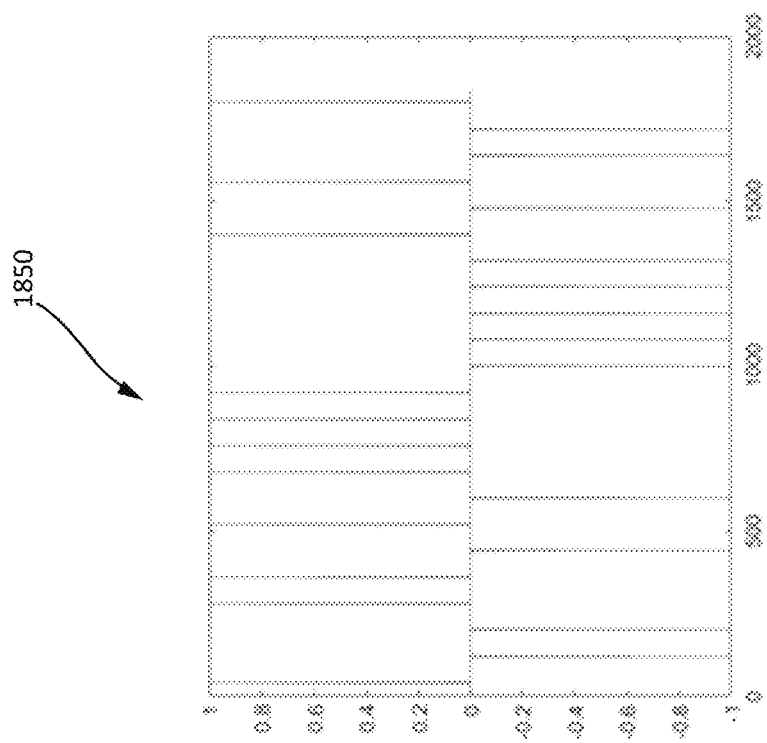
FIG. 65

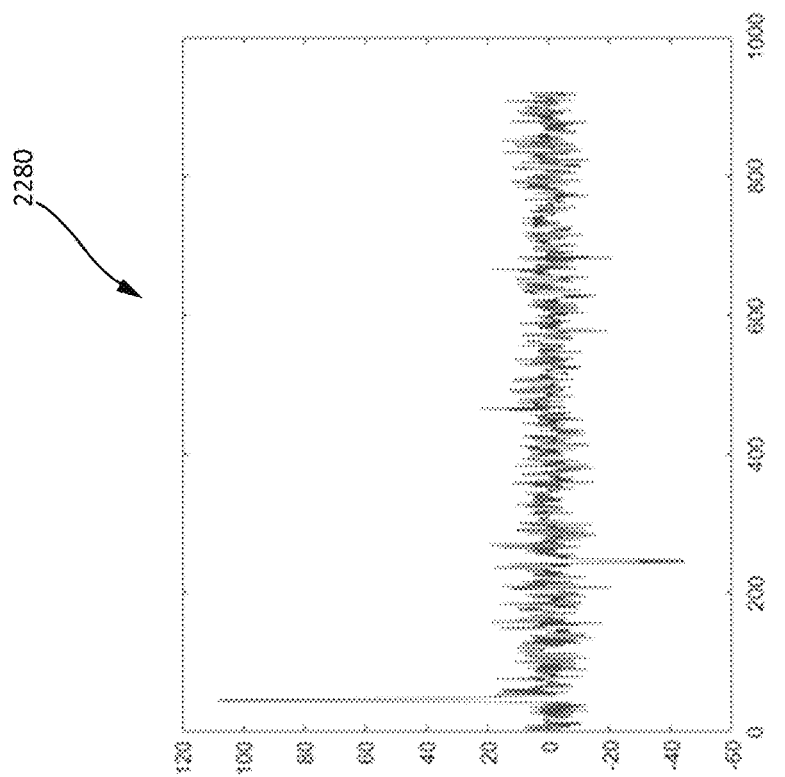
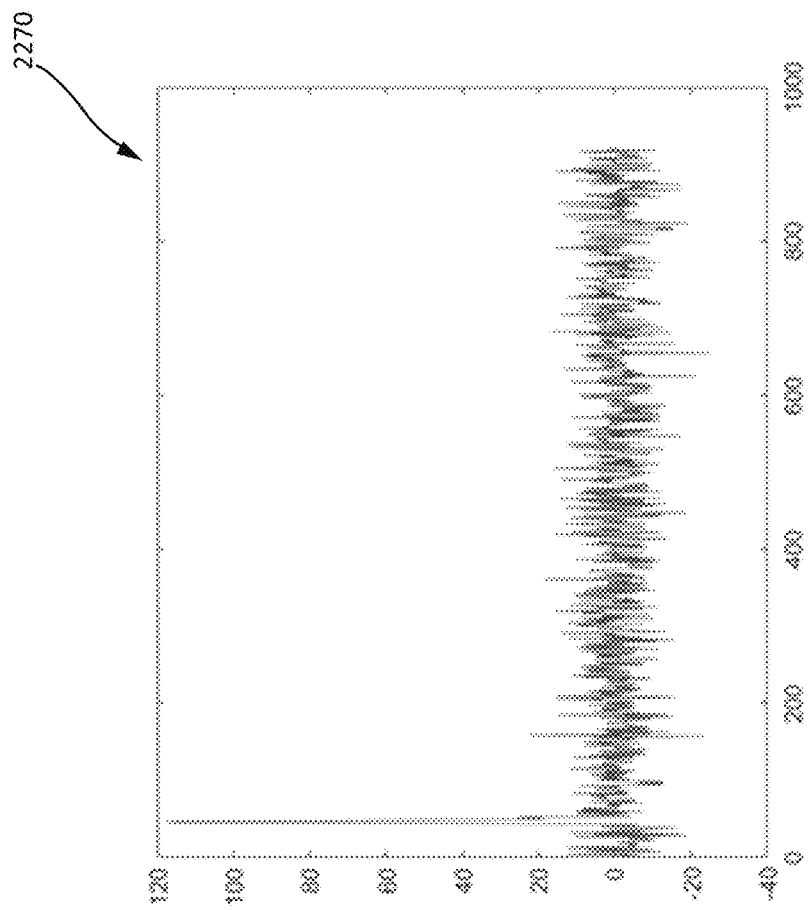
FIG. 90

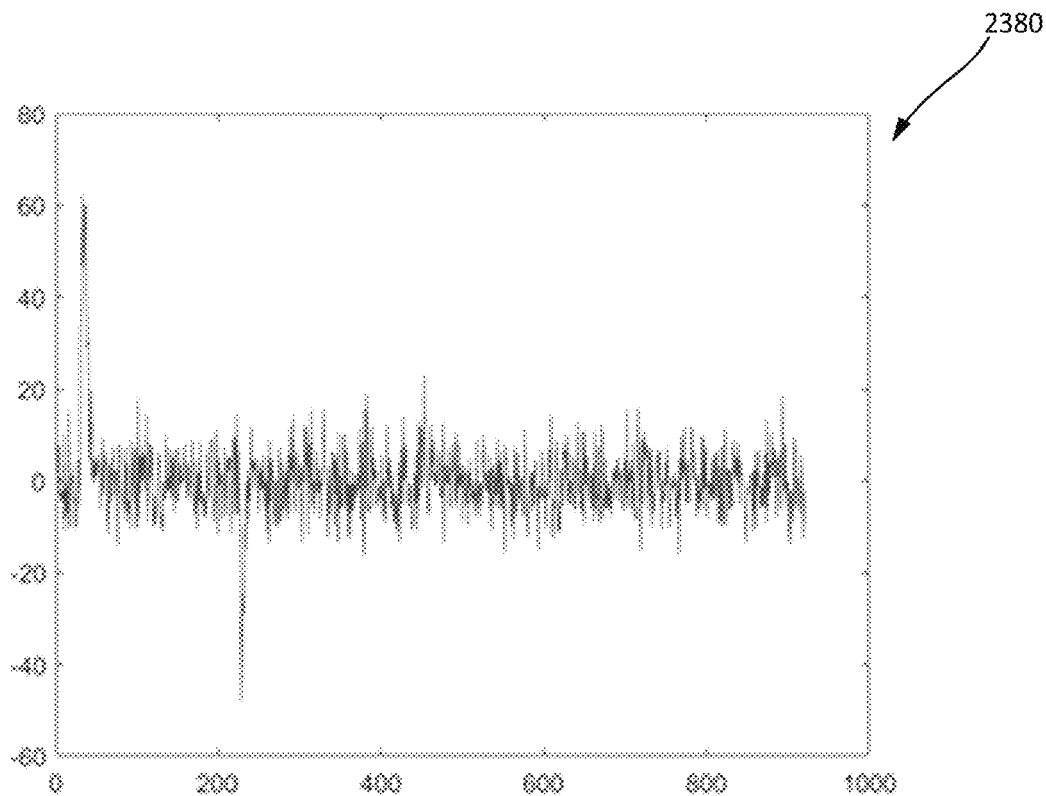
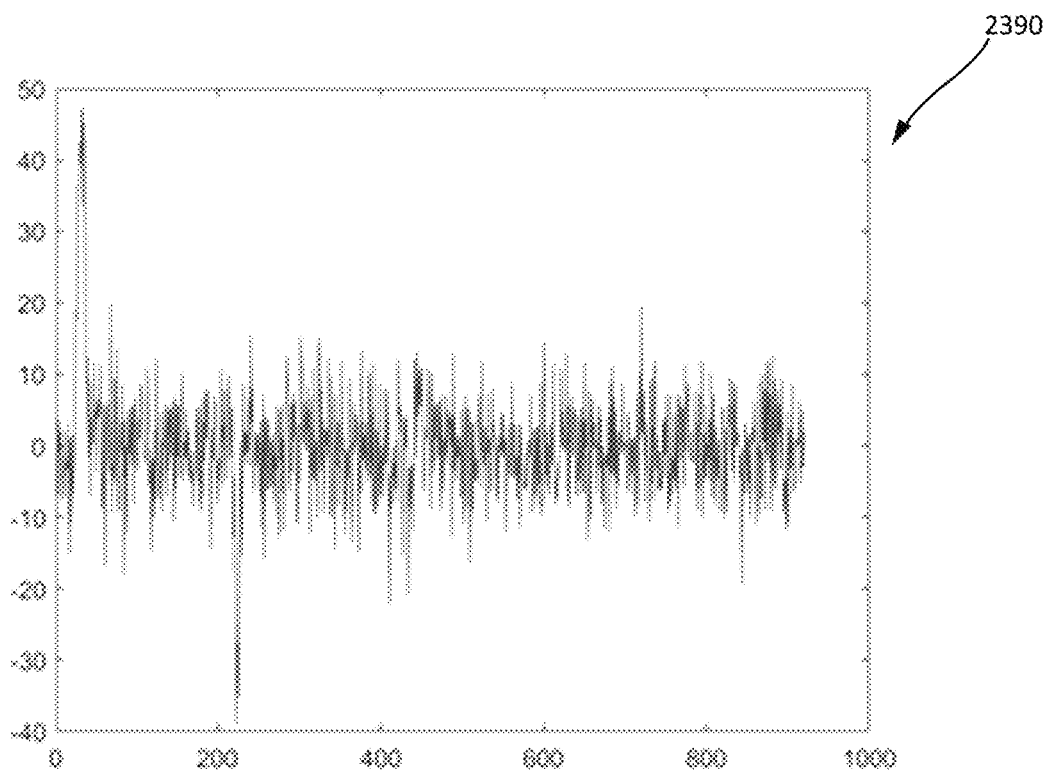
FIG. 99

ELECTROMAGNETIC SENSING AND DETECTION OF INGESTIBLE EVENT MARKERS

CROSS REFERENCES TO RELATED APPLICATIONS

The present application is a divisional application claiming priority under 35 U.S.C. § 121 to U.S. patent application Ser. No. 15/657,608, titled ELECTROMAGNETIC SENSING AND DETECTION OF INGESTIBLE EVENT MARKERS, filed Jul. 24, 2017, and which application claims the benefit under 35 USC § 119(e) of U.S. Provisional Application 62/365,727, filed Jul. 22, 2016, titled ELECTROMAGNETIC SENSING AND DETECTION OF INGESTIBLE EVENT MARKERS, the disclosures of which are hereby incorporated herein in their entireties and for all purposes.

BACKGROUND

The present disclosure is related generally to various devices and techniques for sensing and detecting an event. More particularly, the present disclosure is related to ingestible identifiers that employ electromagnetic energy to transmit a signal representative of a sensing or detection event.

Ingestible event markers that include electronic circuitry have been proposed for use in a variety of different medical applications, including both diagnostic and therapeutic applications. State of the art techniques for detecting an ingestible identifier includes making wet contact to two points on the skin and measuring the voltage difference induced by the ingestible identifier activation. Weak signal levels and strong background noise limit these conventional techniques, making detecting and decoding signals from the ingestible identifier difficult and computationally intensive. Two other limitations make communication between an ingestible sensor and an external detector unusual. First is that due to the very small amount of power available on an ingestible sensor and the small size of the ingestible sensor, communication is only one way. There are no aknowledgements returned to sender, as is typical of virtually all duplex communication systems that are prevalent throughout the world. Second, is that due to the small size, limited list of safe materials that may be ingested, and very low manufacturing cost required of this application, it is not commercially feasible—and perhaps not technically feasible but at least would be extremely difficult—to add a crystal oscillator to the circuit. Thus, an inherent distinguishing feature of this communication situation is the uncertainty of the transmitted frequency. Whereas most commercial communication systems operate in an environment where the frequency is known to tens of parts per million, an ingestion sensor powered by a partial power source and stomach fluids is challenged to produce a center frequency with a +/−1% range. Thus, an important contribution of aspects of the present disclosure is the realization of a communication protocol for RF systems where the transmitting power is very low compared to the background noise of the detector and the transmitting frequency uncertainty is large compared to typical modern systems. Compared to other RF systems, ingestible sensors have extremely limited size available for both the coils that transmit the signals and any capacitors that might be used to store energy between communications. In addition, health concerns and opinions of regulatory agencies such as the FDA limit the amount of certain metals that may be digested by a patient, thus placing a cap on the total available power for both sensing and communication. These communication protocols effectively improve the signal levels available for external detection and decoding. There is incentive to increase the signal levels received from ingestible identifiers such that the ingestible identifier can be detected more readily, and by receivers placed on various parts of the body, or worn by a patient.

SUMMARY

In one aspect, an electronic device is provided. The electronic device comprises a control device, a driver circuit coupled to the control device, a partial power source coupled to the control device, the partial power source is configured to provide a voltage potential difference to the control device and the driver circuit as a result of the partial power source being in contact with a conductive fluid. The partial power source comprises a first material electrically coupled to the control device and a second material electrically coupled to the control device and electrically isolated from the first material. An inductor is coupled to the driver circuit, wherein the driver circuit is configured to develop a current through the inductor, and wherein a magnitude of the current developed through the inductor is varied to produce an encoded signal that is remotely detectable by a receiver.

In another aspect, a receiver circuit is provided. The receiver circuit comprises a resonant circuit, a low noise voltage amplifier coupled to the resonant circuit, and a receiver processor circuit coupled to an output of the low noise voltage amplifier, the receiver processor configured to receive an analog signal representative of an impulse communication signal, convert the analog signal to a digital signal, and decode the digital signal to reproduce data transmitted as the impulse communication signal. In addition, the receiver is intended to be worn by a patient on a daily basis for extended periods of time. Therefore, its size and power consumption are both limited.

In yet another aspect, a receiver circuit is provided. The receiver circuit comprises a receiving inductor, a transimpedance amplifier coupled to the receiving coil, an amplifier coupled to an output of the transimpedance amplifier, and a receiver processor circuit coupled to an output of the amplifier, the receiver processor configured to receive an analog signal representative of an impulse communication signal, convert the analog signal to a digital signal, and decode the digital signal to reproduce data transmitted as the impulse communication signal.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing summary is illustrative only and is not intended to be in any way limiting with regard to the scope of the appended claims. In addition to the illustrative aspects and features described above, further aspects and features will become apparent by reference to the drawings and the following detailed description.

FIGURES

The novel features of the aspects described herein are set forth with particularity in the appended claims. The aspects, however, both as to organization and methods of operation may be better understood by reference to the following description, taken in conjunction with the accompanying drawings as follows.

FIG. 2 illustrates an individual having swallowed an ingestible identifier, according to one aspect of the present disclosure.

FIG. 3 illustrates a receiver for detecting an electromagnetic field generated by an ingestible identifier, according to one aspect of the present disclosure.

FIG. 5 illustrates a block diagram of one aspect of an ingestible identifier with dissimilar metals positioned on opposite ends, according to one aspect of the present disclosure.

FIG. 6 illustrates a block diagram of another aspect of the ingestible identifier with dissimilar metals positioned on the same end and separated by a non-conducting material, according to one aspect of the present disclosure.

FIG. 7 illustrates ionic transfer or the current path through a electrically conductive fluid when the ingestible identifier of FIG. 9 is in contact with conducting liquid and in an active state, according to one aspect of the present disclosure.

FIG. 7A illustrates an exploded view of the surface of dissimilar materials of FIG. 7, according to one aspect of the present disclosure.

FIG. 10 illustrates a first inductor component, according to one aspect of the present disclosure.

FIG. 11 illustrates a second inductor component, according to one aspect of the present disclosure.

FIG. 12 illustrates an ingestible identifier that includes a conductive communication component and an inductor component, according to one aspect of the present disclosure.

FIG. 13 illustrates a side sectional view of the ingestible identifier shown in FIG. 12, according to one aspect of the present disclosure.

FIG. 14 illustrates one aspect of the ingestible identifier shown in FIGS. 4A and 4B, according to one aspect of the present disclosure.

FIG. 15 illustrates one aspect of the ingestible identifier shown in FIGS. 12-13, according to one aspect of the present disclosure.

FIG. 16 illustrates an ingestible identifier comprising an integrated circuit and a separate inductor component formed on a separate substrate, according to one aspect of the present disclosure.

FIG. 17 illustrates an ingestible identifier comprising an inductor formed on a nonconductive membrane, according to one aspect of the present disclosure.

FIG. 18 illustrates an ingestible identifier comprising an inductor formed on one or both of the dissimilar materials shown in FIG. 13 after the dissimilar materials are deposited on the integrated circuit, according to one aspect of the present disclosure.

FIG. 25 illustrates a two-layer two-port inductor configuration, according to one aspect of the present disclosure.

FIG. 26 is a diagram of the two-layer two-port inductor shown in FIG. 25, according to one aspect of the present disclosure.

FIG. 27 is a schematic representation of the two-layer two-port inductor shown in FIGS. 25 and 26, according to one aspect of the present disclosure.

FIG. 28 illustrates a four-layer two-port inductor configuration, according to one aspect of the present disclosure.

FIG. 29 is a diagram of the four-layer two-port inductor 612 shown in FIG. 28, according to one aspect of the present disclosure.

FIG. 30 is a schematic representation of the four-layer two-port inductor shown in FIGS. 28 and 29, according to one aspect of the present disclosure.

FIG. 31 illustrate an n-layer n-port inductor configuration, according to one aspect of the present disclosure.

FIG. 32 is a diagram of the n-layer n-port inductor shown in FIG. 31, according to one aspect of the present disclosure.

FIG. 33 is a schematic representation of the n-layer n-port inductor shown in FIGS. 31 and 30, according to one aspect of the present disclosure.

FIG. 47 illustrates a voltage mode receiver for detecting an electromagnetic field generated by an ingestible identifier, according to one aspect of the present disclosure.

FIG. 48 is a graphical representation of an impulse response from a receiving inductor, according to one aspect of the present disclosure.

FIG. 49 illustrates a voltage mode receiver for detecting an electromagnetic field generated by an ingestible identifier, according to one aspect of the present disclosure.

FIG. 62 is a plot showing an example of the "zero" chip sequence of pulses, and a plot showing an example of the "one" chip sequence of pulses.

FIG. 64 shows graphical representations of the the "A" subchip and the "B" subchip in previous plots.

FIG. 65 is a plot showing how combining subchips A and B according to the above descriptions produces the "Zero" chip=[A B] and the "One" chip=[B A].

FIG. 90 shows two plots of the same first slice and second slice sum, in the presence of noise, in the two shown plots, respectively.

FIG. 99 show the second slice of the symbol-length slice, with SNR=7 dB, but the frequency is at 551 units instead of 501.

DETAILED DESCRIPTION

Figure 1:
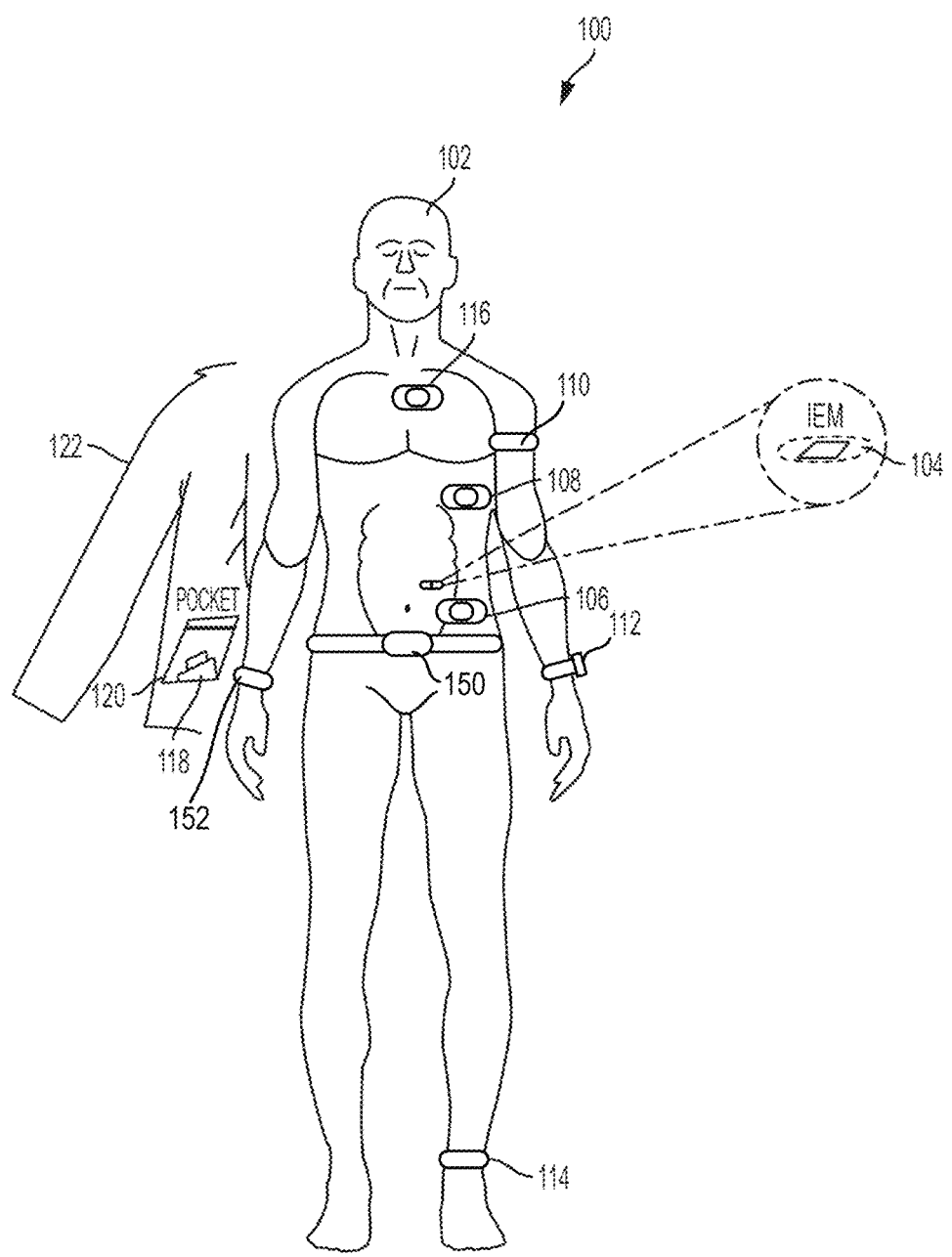
FIG. 1 illustrates an electromagnetic field based sensing and detection system, according to one aspect of the present disclosure.

In the following detailed description, reference is made to the accompanying drawings, which form a part hereof. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the spirit or scope of the subject matter presented here.

Before explaining the various aspects of sensing and detecting ingestible identifiers using electromagnetic signals in detail, it should be noted that the various aspects disclosed herein are not limited in their application or use to the details of construction and arrangement of parts illustrated in the accompanying drawings and description. Rather, the disclosed aspects may be positioned or incorporated in other aspects, variations and modifications thereof, and may be practiced or carried out in various ways. Accordingly, aspects of sensing and detecting ingestible identifiers using electromagnetic signals disclosed herein are illustrative in nature and are not meant to limit the scope or application thereof. Furthermore, unless otherwise indicated, the terms and expressions employed herein have been chosen for the purpose of describing the aspects for the convenience of the reader and are not to limit the scope thereof. In addition, it should be understood that any one or more of the disclosed aspects, expressions of aspects, and/or examples thereof, can be combined with any one or more of the other disclosed aspects, expressions of aspects, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various aspects will be described in more detail with reference to the drawings.

As previously described, conventional means of detecting an ingestible identifier includes making wet contact to two points on the skin and measuring the voltage difference induced by conductive electrical currents flowing through the body of the patient after activating the ingestible identifier. Weak signal levels and strong background noise may limit the conductive current technique and may make detecting and decoding signals from the ingestible identifier difficult and computationally intensive. In addition, in conventional sensing and detecting techniques the signal fades as the receiver is moved away from the abdomen to locations such as the neck, thorax or chest, arm, wrist, thigh, or leg, for example.

General Overview

In various aspects, an electromagnetic coil in the form of an electrical conductor such as a wire in the shape of a coil, spiral or helix may be employed to generate electromagnetic signals. Electric currents generated in electromagnetic coils interact with magnetic fields in devices such as inductors and sensor coils. Either an electric current is passed through the wire of the coil to generate a magnetic field, or conversely an external time-varying magnetic field through the interior of the coil generates an EMF (voltage) in the conductor. As described in more detail hereinbelow, an electromagnetic signal may be generated by an inductor formed on a semiconductor substrate comprising active device regions. The conductive elements of the inductor can be formed on a dielectric layer overlying a semiconductor substrate or a glass substrate, for example. The conductive elements may be patterned and etched into a desired shape such as a planar spiral, for example. A region of the substrate below the inductor may be removed to lower the inductive Q factor. The current revolution in wireless communications and the need for smaller wireless communications devices have spawned significant efforts directed to the optimization and miniaturization of radio communications electronic devices. Passive components (such as inductors, capacitors and transformers), play a necessary role in the operation of these devices and thus efforts have been directed toward reducing the size and improving the performance and fabrication efficiency of such passive components.

Discrete inductors and capacitors are passive electromagnetic components employed in alternating current and radio frequency applications, such as oscillators, amplifiers and signal filters, to provide frequency dependent effects. Specifically, the voltage across the inductor is a function of the product of the inductance and the time derivative of the current through the inductor. A conventional inductor comprises a plurality of windings enclosing a core constructed of a ferromagnetic or an insulating material. Although an inductor core is not required, use of a ferromagnetic core, for example, increases the inductance value. The inductance is also a function of the number of coil turns (specifically, the inductance is proportional to the square of the number of turns) and the core area. Conventional discrete inductors are formed as a helix (also referred to as a solenoidal shape) or a toroid. The core is typically formed of iron, cobalt or nickel (or a ferromagnetic alloy) comprising a plurality of magnetic domains. The current supplied to the inductor induces a magnetic field in the core material, causing domain alignment and a resulting increase in the material permeability, which in turn increases the inductance.

Developments in the semiconductor industry have over the years been directed at fabricating higher performance devices of decreasing size. One challenge of semiconductor circuit design and fabrication is the integration of high performance capacitors and inductors into the semiconductor device. Ideally, these components are formed on a relatively small surface area of a semiconductor substrate, using methods and procedures that are conventional in the semiconductor fabrication art. However, compared with the feature sizes and line widths of active devices, inductors and capacitors are large and not easily integrated into semiconductor devices that typically have feature sizes in the sub-micron range. It will be appreciated that the inductors may be formed on a glass substrate rather than a semiconductor substrate, for example.

Most inductors formed on a semiconductor or glass substrate surface have a spiral shape, where the plane of the spiral is parallel to the substrate surface. Many techniques are known for forming a spiral inductor, such as masking, patterning, and etching a layer of conductive material formed on the substrate surface. Multiple interconnected spiral inductors can also be formed to provide the desired inductive properties and/or to simplify the fabrication process. See for example, U.S. Pat. No. 6,429,504 describing a multi-layer spiral inductor and U.S. Pat. No. 5,610,433 disclosing a high value inductor with a high Q factor formed from a plurality of layers with each layer comprising two or more. The coils in the various layers are interconnected in series such that current flows through the inductors in the same direction, for example.

The Q (or quality factor), an important inductor figure of merit, is defined as the ratio of inductive reactance to resistance. High-Q inductors (e.g., having a low resistance) present a narrow Q peak as a function of the input signal frequency, where the peak occurs at the inductor resonant frequency. High-Q inductors are especially important for use in frequency-dependent circuits operating with narrow bandwidths. For example, increasing the Q for an inductor operating in an oscillator decreases the oscillator phase noise, and confines the oscillator frequency to a narrower band of frequencies. Because the Q value is an inverse function of inductor resistance, minimizing the resistance increases the Q. One known technique for minimizing the resistance increases the cross-sectional area of the conductive material forming the inductor.

Various aspects of the present disclosure leverage alternative physical phenomena to conventional conductive current based ingestible identifier detection techniques. In one aspect, for example, the present disclosure provides techniques for sensing and detecting ingestible identifiers employing the generation of electromagnetic fields by the electrical currents induced in the stomach fluid by the ingestible identifier, which travel more readily in and on the surface of the body. A receiving apparatus, namely an antenna, such as an inductor, may be employed to receive the electromagnetic field and convert it to a voltage. Such voltage then can be received by any suitable means, such as discrete or integrated electronics. See Wang, Jianqing, Qiong Wang, Body Area Communications: Channel Modeling, Communication Systems, and EMC. Singapore: John Wiley & Sons Singapore Pte. Ltd., 2013, for example, for a discussion of body area communication techniques.

For directionality, such that the electromagnetic field receiver does not pick up signals from adjacent patients, a magnetic shield can be placed atop the receiving antenna (e.g., inductor). By confining the antenna between the shield and the body, the receiver will only receive fields traveling in the body. As an enhancement, the shield can be made a parabolic surface, with the antenna (inductor) placed in the focal point to enhance the signal strength as is done in satellite dish antennae.

FIG. 1 illustrates an electromagnetic field based sensing and detection system 100, according to one aspect of the present disclosure. FIG. 1 shows an individual 102 who has recently swallowed an ingestible identifier 104. The ingestible identifier 104, as described in more detail hereinbelow, generates an encoded electromagnetic signal when it comes into contact with the gastrointestinal fluids in the stomach of the individual 102. Although the encoded electromagnetic signal may be configured to represent many variables, in one aspect, the encoded electromagnetic signal represents an ingestible event. In one aspect, an ingestible event may be associated with the individual 102 taking a medication dosage, type of medication, or dosage amount, or combinations thereof, among other variables.

The system 100 implementation may include many variations. For example, in one aspect, an ingestible identifier, as described in connection with FIGS. 4-9, may be employed. In this implementation, the ingestible identifier is powered when it comes into contact with an electrically conductive fluid and then generates an electromagnetic field that can be detected by an inductor antenna, for example. This technique is advantageous because an electromagnetic field tends to propagate better on the surface of the skin of a patient as compared to electrical current conduction on the surface of the skin. The electromagnetic field on the surface of the skin can be tapped with an inductor antenna having N windings, where N is an integer, and optionally a ferrite core to increase sensitivity. Since the body of the individual 102 assists the propagation of the electromagnetic field, the system 100 provides added flexibility in the location and placement of the inductor antenna of the ingestible identifier 104 and/or the receiver 106, 108, 110, 112, 114, 116, 118, 150, 152, for example.

In another aspect, the ingestible identifier may include an amplifier to amplify the signal generated by the ingestible identifier circuit. The inductor winding may be provided on the same integrated circuit of the ingestible identifier. In another aspect, the inductor windings may be printed on a nonconductive membrane interposed between the electrodes made of dissimilar materials located on the ingestible identifier (e.g., a skirt). In other aspects, the inductor antenna may be printed using a conductive digestible material either on the nonconductive membrane or the integrated circuit. In another aspect, an inductor winding may be added as a separate integrated circuit and coupled to the ingestible identifier circuitry. Furthermore, the system 100 may operate at various frequencies such as, for example, 100 kHz to 1 MHz, which may provide opportunities for reducing the size of the transmitter inductor and the receiver inductor antenna. The upper frequency limit may be detected by the threshold at which the body of the individual 102 begins to absorb the electromagnetic energy. Such upper frequency threshold may approximately 400 MHz, without limitation. In other implementations, the operating frequency may be selected from 10 Mhz to 1 GHz, for example.

In various aspects, an inductor having N turns may be positioned on two sides of the ingestible identifier integrated circuit. Excitation would be positive on one side and negative on the other side to boost or double the signal strength. The ingestible identifier may be configured to transmit at multiple frequencies, rather than a single frequency, by the addition of multiple transmitters and multiple inductors, or a single transmitter coupled to multiple inductors via a multiplexer, or a single transmitter and single inductor coupled to multiple tuning elements, such as two or more capacitors, via a multiplexer. In other aspects, magnetic materials, such as a ferrite inductor, for example, may be deposited or added to the ingestible identifier integrated circuit to increase the inductance of the transmission inductor. In other aspects, the ingestible identifier electrodes can be formed in the shape of an inductor.

In other aspects, the ingestible identifier can be configured to communicate directly to a mobile telecommunication device such as mobile telephone, cellular telephone, or smart-phone provided availability of increased signal strength and data security consideration.

The electromagnetic signal emitted by the ingestible identifier 104 can be detected by a receiver associated with the individual 102. In various aspects, the ingestible identifier 104 and any of the receivers 106, 108, 110, 112, 114, 116, 118, 150, 152 can be configured for one-way, and in some cases, two-way communication. The receivers 106, 108, 110, 112, 114, 116, 118, 150, 152 may be configured to sense and detect the ingestible identifier 104 and may be located on or off the body of the individual 102. Thus, the receivers 106, 108, 110, 112, 114, 116, 118, 150, 152 may be located on the body of the individual 102, partially or wholly implanted in the individual 102, or may be located off the individual 102 but proximal to the individual 102 such that a receiver can readily detect a relatively weak electromagnetic signal.

In one aspect, a receiver 106 may be located in a patch and adhered to the abdomen of the individual 102 or anywhere on the lower body of the individual 102 to sense and detect the ingestible identifier 104 after the ingestible identifier is ingested by the individual 102. In another aspect, a receiver 108 may be located in a patch and adhered to the thorax, breast, or upper body portions of the individual 102. In yet another aspect, a receiver 116 may be located on a patch or necklace and worn near or around the neck or throat, or other place on or proximal the head, of the individual 102. In another aspect, a receiver 110 may be located in an arm band and worn around the upper arm of the individual 102 near the shoulder, for example. In another aspect, a receiver 112 may be located in a watch and worn around the wrist of the individual 102. In yet another aspect, a receiver 152 may be located in a wrist band and worn around the wrist of the individual 102. In yet another aspect, a receiver 150 may be located in a belt and worn around the waist of the individual 102. In another aspect, a receiver 114 may be located in ankle band and worn around the ankle of the individual 102 or other locations on the leg of the individual 102. In various other aspects, a receiver may be located anywhere on or proximal to the individual 102. In another aspect, a receiver 118 may be located off the body but proximal the individual 102. For example, the receiver 118 may be located inside the pocket 120 of a garment 122 worn by the individual 102.

The receivers 106, 108, 116 that are coupled directly to the body of the individual 102, may be attached by an adhesive applied to the skin contacting surface of the receiver 106, 108, 116. The receivers 110, 112, 152 that are placed around arm or wrist of the individual may include a band or strap to hold the receiver 110, 112, 152 in place. In one aspect, the receiver 112 may have a form factor similar to a wristwatch. The receiver 118 may be loosely positioned within the pocket 120 of the garment 122 worn by the individual 102. The receiver 150 may be worn around the waist like a belt.

In present implementations of systems for sensing and detecting ingestible identifiers, low energy electromagnetic signals may be required to limit the propagation of the field beyond the body of the individual 102 to maintain privacy of the information carried by the electromagnetic signals.

In various aspects, an electromagnetic shield or "can" can be positioned over the receiver inductor antenna to shield the receiver from electromagnetic waves from sources external to the body of the individual 102. In some aspects, the shield may be shaped as a parabolic reflector to focus the electromagnetic field from the body of the individual into the receiver inductor antenna. In other aspects, two inductors can be positioned in a perpendicular or orthogonal orientation relative to each other on the ingestible identifier to provide a more non-homogenous reception of the electromagnetic signal. Other forms of antennas such as dipole or patch antennas may be employed in the receiver technique in addition to the inductor antenna.

FIG. 2 illustrates an individual 102 having swallowed an ingestible identifier 104, according to one aspect of the present disclosure. When the ingestible identifier 104 is immersed in electrolytic fluids typically found in the stomach 132, an internal partial battery is activated to energize the electrical circuits of the ingestible identifier 104. As shown, the ingestible identifier 104 is transmitting an electromagnetic field 136 in the body 130 of the individual 102. The ingestible identifier 104 includes an inductor in a resonant circuit to set the frequency of the electromagnetic field 136. The electromagnetic field 136 propagates throughout the body 134 and propagates on the surface of the body 130 where it can be detected by a receiver 106 located near the abdomen of the body 130. The receiver 106 comprises an inductor antenna to detect the electromagnetic field 134. The ingestible identifier 104 includes circuitry to encode the electromagnetic field 134 with information programmed in the ingestible identifier 104.

FIG. 3 illustrates a receiver 106 for detecting an electromagnetic field generated by an ingestible identifier, according to one aspect of the present disclosure, such as the ingestible identifier 104 discussed in connection with FIGS. 1 and 2. The receiver 106 comprises a resonant circuit 140 and receiver electronics 142 to process the encoded electromagnetic signal received from the ingestible identifier. The resonant circuit 140 may comprise an inductor antenna 144 and a tuning capacitor 146 to resonate at the frequency of operation.

Transmission by Ingestible Identifier

Figure 4A:
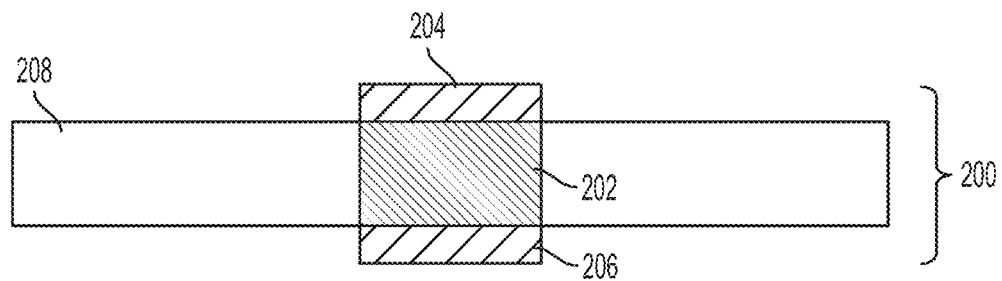
FIG. 4A illustrates a side view of an ingestible identifier comprising an electrically insulative element according to one aspect of the present disclosure.
Figure 4B:
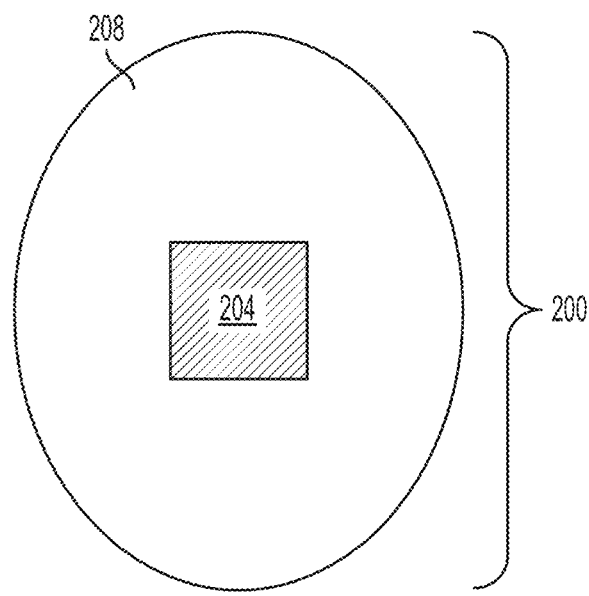
FIG. 4B illustrates a top view of an ingestible identifier comprising an electrically insulative element according to one aspect of the present disclosure.

FIGS. 4A and 4B illustrate various views of an ingestible identifier 200 comprising an electrically insulative element 208, according to one aspect of the present disclosure. The electrically insulative element 208 extends beyond the outer edges of the integrated circuit 202. FIG. 4B is a plan view of the identifier 200 shown in FIG. 4A. As shown in FIG. 4A, the integrated circuit 202 comprises an upper electrode 204 composed of a first material and a lower electrode 206 composed of a second material, where the first and second materials are dissimilar and have a different electrochemical potential. A shown in FIG. 4B, the electrically insulative element 208 has a disc shape. With reference to FIGS. 4A and 4B, the upper and lower electrodes 204, 206 and the integrated circuit 202 are positioned in or close to the center of the disc shaped electrically insulative element 208. The distance from the edge of the electrically insulative element 208 to the perimeter of the integrated circuit 202 and the electrodes 204, 206 may vary, and in certain aspects is ~0.05 mm or more, e.g., ~0.1 mm or more, including ~1.0 mm or more, such as ~5.0 mm or more and including ~10 mm or more, where the distance may not exceed ~100 mm in certain aspects. An inductor or inductive elements may be disposed on the electrically insulative element 208 taking advantage of the larger available surface area relative to the surface area available on the integrated circuit 202.

In the example shown in FIGS. 4A to 4B, the upper and lower electrodes 204, 206 have a planar configuration. In other aspects, however, the electrodes 204, 206 may have any convenient shape, e.g., square, disc, etc., planar or otherwise. The disc shaped electrically insulative element 208 has a planar disc structure, where the edge of the electrically insulative element 208 extends beyond the edge of the planar upper and lower electrodes 204, 206 and the integrated circuit 202. In the depicted example, the radius of the electrically insulative element 208 is greater than the radius of the upper and lower electrodes 204, 206, e.g., by ~1 mm or more, such as by ~10 mm or more.

It is noted that in any given example, the electrically insulative element 208 may or may not extend beyond the edge of the electrodes 204, 206 or the integrated circuit 202. For example, as shown in FIGS. 4A to 4B, the electrically insulative element 208 extends beyond the edge of the upper and lower electrodes 204, 206 as well as the integrated circuit. However, in other examples, the electrically insulative element 208 may define an edge commensurate with the edge of one of the electrodes, e.g., the bottom electrode 206, such that it does not extend beyond the edge of both electrodes 204, 206 or the integrated circuit 202, where the electrically insulative element 208 may include an edge that extends beyond the edge of top electrode 204 but not beyond the edge of the bottom electrode 206.

FIGS. 5-9 illustrate various aspects of ingestible identifier systems 210, 220, 260 in accordance with various aspects of the present disclosure. The ingestible identifier systems 210, 220, 260 shown in FIGS. 5-9 comprise a solid state semiconductor switch 400 coupled to an inductor 401. The solid state semiconductor switch 400 switches power (AC or DC current) to the inductor 401 under control of an electronic control device 218 (FIGS. 5, 7, 8), 228 (FIG. 6). It will be appreciated that FIGS. 5-8 are simplified block diagram circuits and are intended for illustrative purposes only. Accordingly, the solid state semiconductor switch 400 and/or the inductor 401 may include additional circuits or sub-circuits.

With reference to FIGS. 5 and 7, the ingestible identifier system 210 comprise a first material 214 (metal 1) and a second material 216 (metal 2) applied to the framework 212 of a control device 218. The output of the control device 218 is coupled to the solid state semiconductor switch 400 which controls current flow through the inductor 401 to generate an electromagnetic field. This configuration provides a battery created by the first material 214 (metal 1) and the second material 216 (metal 2) when exposed to an ionic solution. Thus, when the system 210 is in contact with and/or partially in contact with an electrically conductive liquid, a current path 230, 250, as shown in FIG. 7 by way of example, is formed through the conductive liquid between the first and second dissimilar materials 214, 216. The battery drives the control device 218, which creates an oscillating frequency by controlling the current switched into the inductor 401. The oscillating current flows through the inductor 401 when the switch 400 is closed and generates a RF electromagnetic signal. The RF electromagnetic signal is propagated through the body of the individual and can be detected by an external or internal receiver device that has an electromagnetic-signal detection mechanism. If a broadcast is provided at a high enough energy, a pager-like device that is worn by the patient will detect whenever a pill is ingested.

With reference to FIG. 5, the first and second dissimilar materials 214, 216 (metal 1 and metal 2) are positioned on opposite ends thereof. The ingestible identifier system 210 can be used in association with any pharmaceutical product, as mentioned above, to determine when a patient takes the pharmaceutical product. As indicated above, the scope of the present disclosure is not limited by the environment and the product that is used with the system 210. For example, the system 210 may be placed within a capsule and the capsule is placed within the conducting liquid. The capsule would then dissolve over a period of time and release the system 210 into the conducting liquid. Thus, in one aspect, the capsule would contain the system 210 and no product. Such a capsule may then be used in any environment where an electrically conductive liquid is present and with any product. For example, the capsule may be dropped into a container filled with jet fuel, salt water, tomato sauce, motor oil, or any similar product. Additionally, the capsule containing the system 210 may be ingested at the same time that any pharmaceutical product is ingested in order to record the occurrence of the event, such as when the product was taken.

In the specific example of the system 210 shown in FIG. 5 combined with a pharmaceutical product, as the product or pill is ingested, the system 210 is activated. In one aspect, the system 210 generates an electromagnetic signal by controlling current driven into the inductor 401 by the control device 400 to produce a unique electromagnetic signal that is detectable with receivers described herein, thereby signifying that the pharmaceutical product has been taken. The framework 212 is a chassis for the system 210 and multiple components are attached to, deposited upon, or secured to the framework 212. In this aspect of the system 210, a first digestible material 214 is physically associated with the framework 212. The first material 214 may be chemically deposited on, evaporated onto, secured to, or built-up on the framework all of which may be referred to herein as "deposit" with respect to the framework 212. The first material 214 is deposited on one side of the framework 212. The materials of interest that can be used as the first material 214 include, but are not limited to: Cu or CuCl. The first material 214 is deposited by physical vapor deposition, electrodeposition, or plasma deposition, among other protocols. The first material 214 may be from about ~0.05 to about ~500 µm thick, such as from about ~5 to about ~100 µm thick. The shape is controlled by shadow mask deposition, or photolithography and etching. Additionally, even though only one region is shown for depositing the material, each of the systems 210 may contain two or more electrically unique regions where the material 214 may be deposited, as desired.

At a different side, which is the opposite side as shown in FIG. 5, another, second, digestible material 216 is deposited, such that the first and second materials 214, 216 are dissimilar. Although not shown, the different side selected may be the side next to the side selected for the first material 214. The scope of the present disclosure is not limited by the side selected and the term "different side" can mean any of the multiple sides that are different from the first selected side. Furthermore, even though the shape of the system is shown as a square, the shape maybe any geometrically suitable shape. The first and second dissimilar materials 214, 216 are selected such that they produce a voltage potential difference when the system 210 is in contact with an electrically conductive liquid, such as body fluids. The materials of interest for material 216 include, but are not limited to: Mg, Zn, or other electronegative metals. As indicated above with respect to the first material 214, the second material 216 may be chemically deposited on, evaporated onto, secured to, or built-up on the framework. Also, an adhesion layer may be necessary to help the second material 216 (as well as the first material 214 when needed) to adhere to the framework 212. Typical adhesion layers for the material 216 are Ti, TiW, Cr or similar material. Anode material and the adhesion layer may be deposited by physical vapor deposition, electrodeposition or plasma deposition. The second material 216 may be from about ~0.05 to about ~500 µm thick, such as from about ~5 to about ~100 µm thick. The scope of the present disclosure, however, is not limited by the thickness of any of the materials nor by the type of process used to deposit or secure the materials to the framework 212.

Thus, when the system 210 is in contact with an electrically conductive liquid, a current path, an example is shown in FIG. 7, is formed through the conducting liquid between the first and second materials 214, 216. The control device 218 is secured to the framework 212 and electrically coupled to the first and second materials 214, 216. The control device 218 includes electronic circuitry, for example control logic that is capable of controlling and altering the conductance between the first and second materials 214, 216 as well as electronic circuitry for driving current through the inductor 401 to generate a unique electromagnetic signal that is encoded to provide a unique identifier corresponding to the system 210 and/or the product that the system 210 is attached to or combined with.

The voltage potential created between the first and second materials 214, 216 provides the power for operating the system 210 including the control device 218 and the inductor 401. In one aspect, the system 210 operates in direct current (DC) mode. In an alternative aspect, the system 210 controls the direction of the current so that the direction of current is reversed in a cyclic manner, similar to alternating current (AC) mode. As the system reaches the electrically conductive fluid or the electrolyte, where the fluid or electrolyte component is provided by a physiologic fluid, e.g., stomach acid, the path for current flow between the first and second materials 214, 216 is completed external to the system 210; the current path through the system 210 is controlled by the control device 218. Completion of the current path allows for the current to flow and in turn a receiver, not shown, can detect the presence of the current and recognize that the system 210 has been activate and the desired event is occurring or has occurred.

In one aspect, the two materials 214, 216 are similar in function to the two electrodes needed for a direct current (DC) power source, such as a battery. The electrically conductive liquid acts as the electrolyte needed to complete the power source. The completed power source described is defined by the physical chemical reaction between the first and second materials 214, 216 of the system 210 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the electrically conductive fluid may be salt water or a metallic based paint.

In certain aspects, the two materials 214, 216 can be shielded from the surrounding environment by an additional layer of material. Accordingly, when the shield is dissolved and the two dissimilar materials are exposed to the target site, a voltage potential is generated.

Referring still to FIG. 5, the first and second materials 214, 216 provide the voltage potential to activate the control device 218. Once the control device 218 is activated or powered up, the control device 218 can alter current conductance through inductor 401 in a unique manner to produce a unique electromagnetic signal. By altering the current flow though the inductor 401, the control device 218 is configured to control the magnitude, phase, or direction of the current through the inductor 401. This produces a unique electromagnetic signature that can be detected and measured by a receiver (not shown), which can be positioned internal, external, partially internal, or partially external to the body of a patient.

In addition, electrically insulative elements 215, 217 may be disposed between the first and second materials 214, 216 and may be associated with, e.g., secured to, the framework 212. Various shapes and configurations for the electrically insulative elements 215, 217 are contemplated as within the scope of the present disclosure. For example, the system 210 may be surrounded entirely or partially by the electrically insulative elements 215, 217 and the electrically insulative elements 215, 217 may be positioned along a central axis of the system 210 or off-center relative to a central axis. Thus, the scope of the present disclosure as claimed herein is not limited by the shape or size of the nonconductive membrane 215, 217. Furthermore, in other aspects, the first and second dissimilar materials 214, 216 may be separated by one membrane that is positioned in any defined region between the first and second materials 214, 216.

In various aspects, the inductor 401 may include a predetermined number of windings and may be integrated circuit with the framework 212 or the control device 218. The windings of the inductor 401 may be formed either on the substrate of the framework 212 or the control device 218 or may be printed on the electrically insulative elements 215, 217 interposed between the first and second materials 214, 216 located on the ingestible identifier 210. In other aspects, the inductor 401 may be printed using a conductive digestible material either on the electrically insulative elements 215, 217 or the integrated control device 218. In another aspect, an inductor winding may be added as a separate integrated circuit coupled to the ingestible identifier control device 218.

Figure 21:
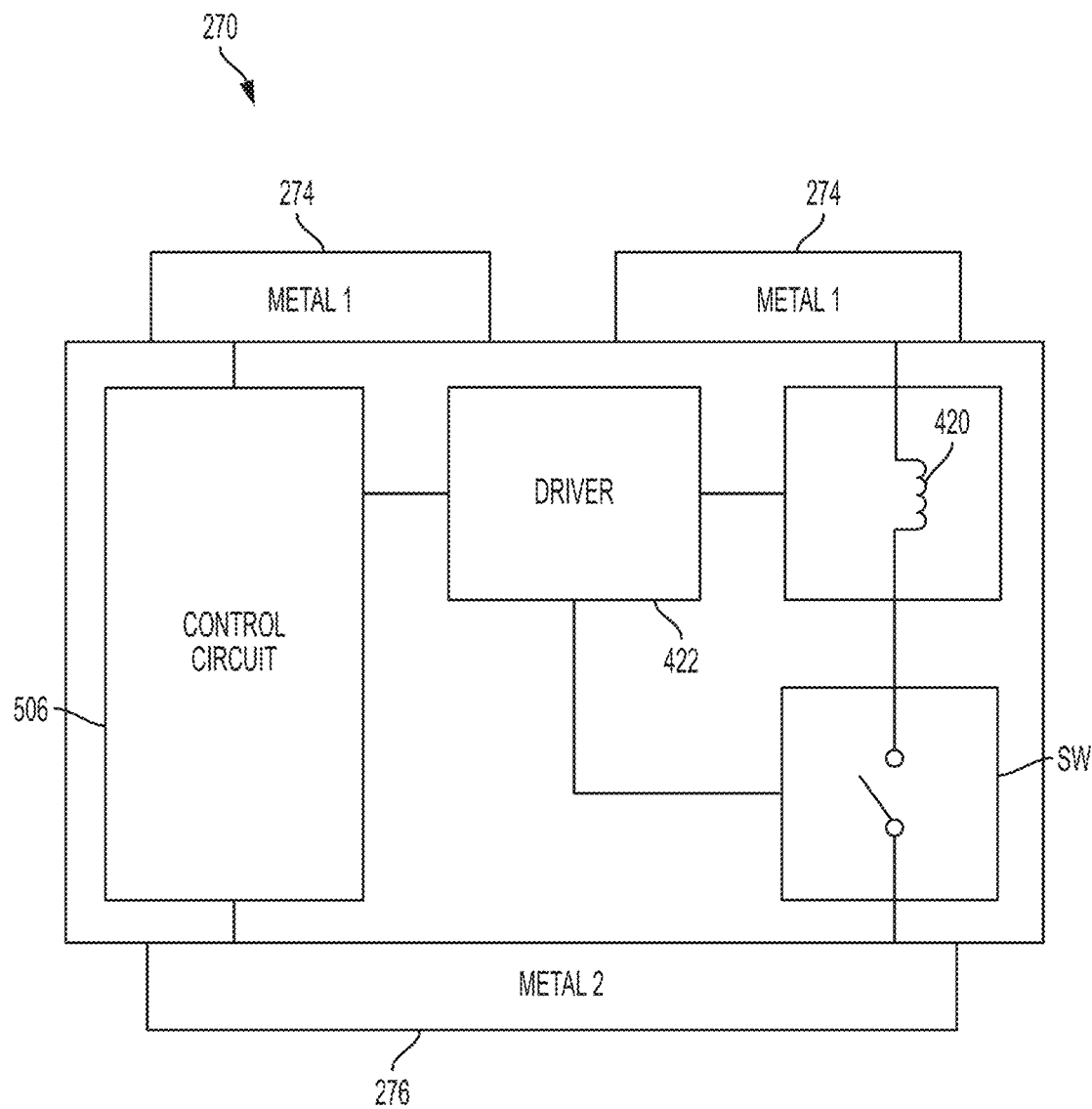
FIG. 21 is a schematic representation of an ingestible identifier comprising an inductor and a single ended inductor driver circuit where a first metal layer is divided into two regions and a second metal layer is provided in a single region, according to one aspect of the present disclosure.
Figure 21A:
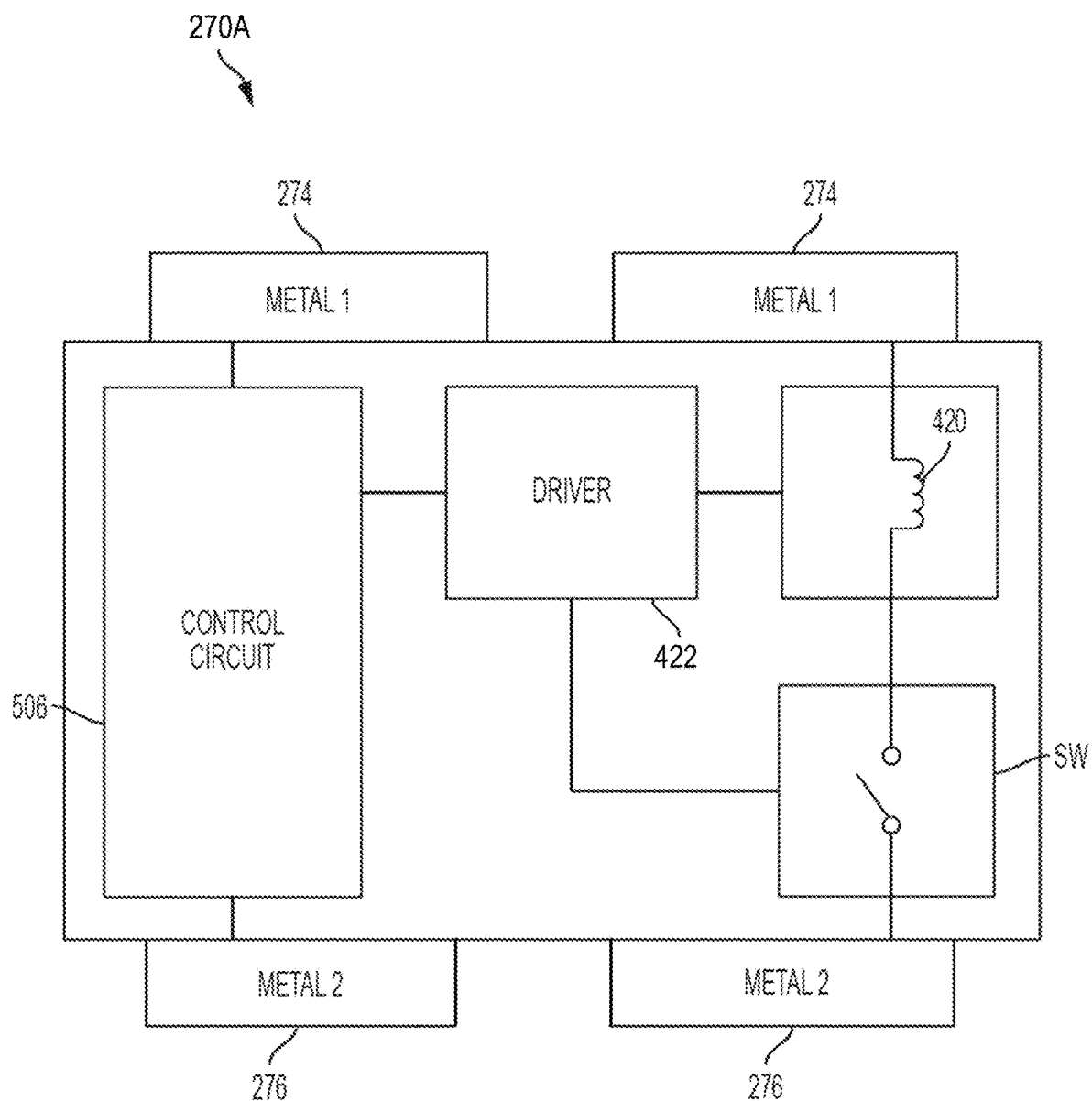
FIG. 21A is a schematic representation of an ingestible identifier comprising an inductor and a single ended inductor driver circuit where a first metal layer is divided into two regions and a second metal layer is divided into two regions, according to one aspect of the present disclosure.
Figure 22:
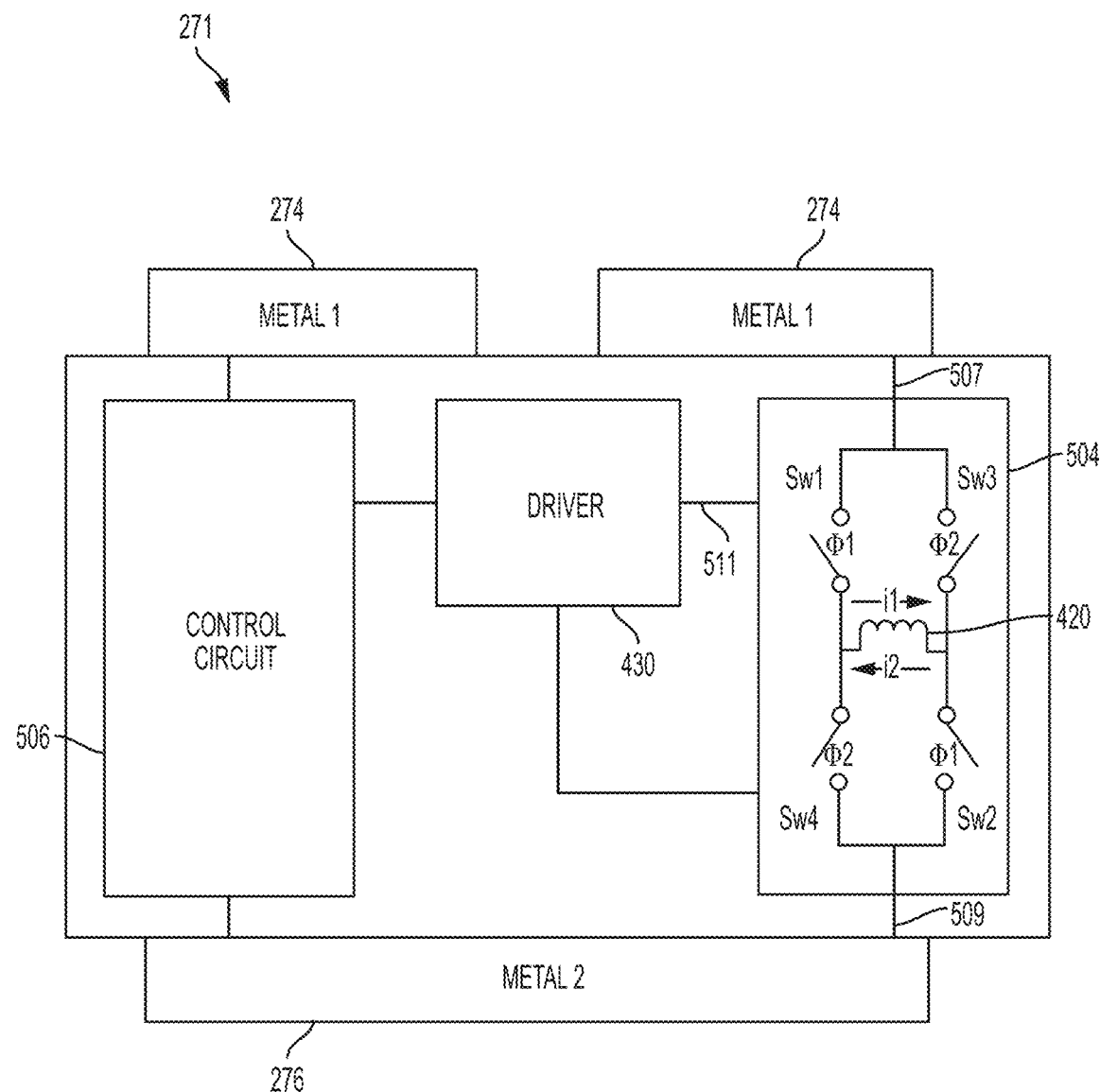
FIG. 22 is a schematic representation of an ingestible identifier comprising an inductor and a push-pull H-bridge type inductor driver circuit where a first metal layer is divided into two regions and a second metal layer is provided in a single region, according to one aspect of the present disclosure.
Figure 22A:
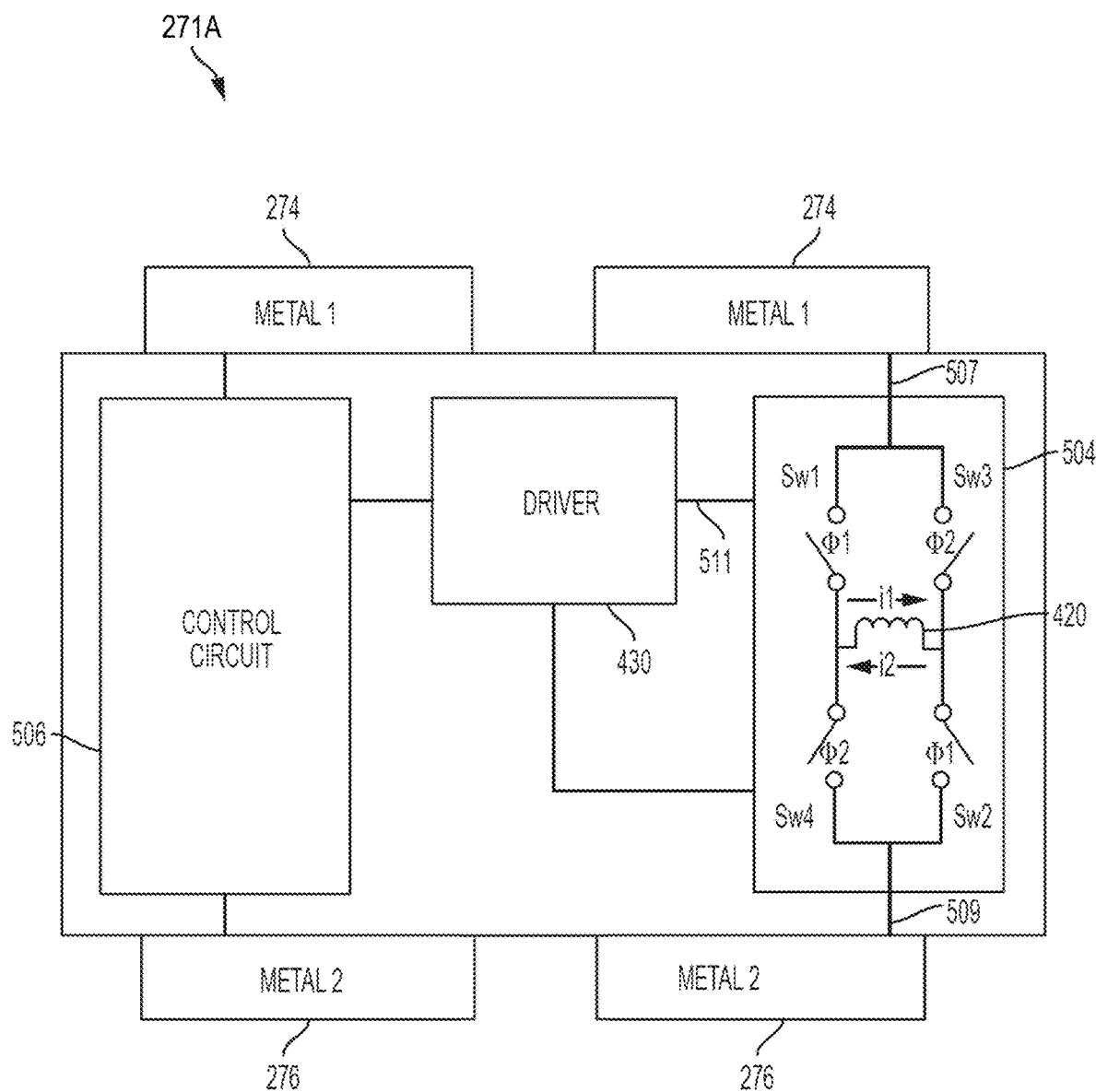
FIG. 22A is a schematic representation of an ingestible identifier comprising an inductor and a push-pull H-bridge type inductor driver circuit where a first metal layer is divided into two regions and a second metal layer is divided into two regions, according to one aspect of the present disclosure.

The conductive current generated by the ingestible identifier 210 may be routed through the inductor 401 by the switch 400 by way of a switch or switching matrix, as shown in FIGS. 21, 21A showing a single ended inductor 420 and driver circuit 500 arrangement and FIGS. 22, 22A showing a push-pull H-bridge inductor 504 and driver circuit arrangement 502, for example. With reference back to FIG. 5, the system 210 may be configured to operate at various frequencies such as, for example, about 100 kHz to about 1 MHz, which may provide opportunities for reducing the size of the transmitter inductor and the receiver inductor antenna. The upper frequency limit may be detected by the threshold at which the body of the individual 102 (FIG. 1) begins to absorb the electromagnetic energy. Such upper frequency threshold may approximately 400 MHz, without limitation.

FIG. 6 depicts an ingestible identifier 220 comprising a first material 224 (metal 1) and a second material 226 (metal 2) applied to the framework 222 of an electronic control device 228. The output of the control device 228 is coupled to the solid state semiconductor switch 400 which controls current flow through the inductor 401 to generate an electromagnetic field. This configuration provides a battery created by the first material 224 (metal 1) and the second material 226 (metal 2) when exposed to an ionic solution. The battery drives the control device 228, which creates an oscillating frequency by controlling the current switched into the inductor 401. The oscillating current flows through the inductor 401 when the switch 400 is closed and generates a RF electromagnetic signal. The RF electromagnetic signal is propagated through the body of the individual and can be detected by an external or internal receiver device that has an electromagnetic-signal detection mechanism. If a broadcast is provided at a high enough energy, a pager-like device that is worn by the patient will detect whenever a pill is ingested.

The framework 222 of the system 220 illustrated in FIG. 6 is similar to the framework 212 of the system 210 shown in FIG. 5. In this aspect of the system 220, a digestible or dissolvable material 224 is deposited on a portion of one side of the framework 222. At a different portion of the same side of the framework 222, another digestible or dissolvable material 226 is deposited, such that the two materials 224, 226 are dissimilar. More specifically, the first and second material 224, 226 are selected such that they generate a voltage potential difference when in contact with an electrically conductive liquid, such as body fluids.

The control device 228 is secured to the framework 222 and electrically coupled to the dissimilar materials 224, 226. The control device 228 includes electronic circuitry that is capable of controlling part of the conductance path between the materials 224, 226. The dissimilar materials 224, 226 are separated by a nonconductive (electrically insulative) element 229. Various examples of the electrically insulative element 229 are disclosed in U.S. Pat. No. 8,545,402 filed on Apr. 27, 2010 and entitled "HIGHLY RELIABLE INGESTIBLE EVENT MARKERS AND METHODS OF USING SAME" and U.S. Pat. No. 8,961,412 filed Sep. 25, 2008 entitled "IN-BODY DEVICE WITH VIRTUAL DIPOLE SIGNAL AMPLIFICATION"; the entire disclosure of each is incorporated herein by reference.

Once the control device 228 is activated or powered up, the control device 228 can alter conductance between the dissimilar materials 224, 226. Thus, the control device 228 is capable of controlling the magnitude of the current through the electrically conductive liquid that surrounds the system 220. As indicated above with respect to system 210, a unique current signature that is associated with the system 220 can be detected by a receiver (not shown) to mark the activation of the system 220. In order to increase the "length" of the current path the size of the electrically insulative membrane 229 is altered. The longer the current path, the easier it may be for the receiver to detect the current.

In various aspects, as described in more detail hereinbelow, the system 220 may comprise a transmission inductor 401 to generate an electromagnetic field. The inductor 401 may include a predetermined number of windings and may be integrated with the control device 228 of the ingestible identifier 210. In another aspect, the inductor windings may be printed on the electrically insulative membrane 229 interposed between the electrodes 224, 226. The inductor 401 may be printed using a conductive digestible material either on the electrically insulative membrane 229 or may be integrated with the control device 228. In another aspect, an inductor winding may be added as a separate integrated circuit coupled to the ingestible identifier control device 228. The conductive current generated by the ingestible identifier 220 may be routed through the inductor 401 by the switch 400 before the current is routed to the battery circuitry of the system 220. The system 220 may be configured to operate at various frequencies such as, for example, about 100 kHz to about 1 MHz, which may provide opportunities for reducing the size of the transmitter inductor 401 and the receiver inductor antenna. The upper frequency limit may be detected by the threshold at which the body of the individual 102 (FIG. 1) begins to absorb the electromagnetic energy. Such upper frequency threshold may approximately 400 MHz, without limitation.

FIG. 7 illustrates the system 210 shown in FIG. 5 in an activated state and in contact with an electrically conductive liquid, according to one aspect of the present disclosure. The system 210 is grounded through a ground contact 232. The system 210 also includes a sensor component 254, which is described in greater detail with respect to FIG. 9. Ion or current paths 230 are established between the first material 214 and the second material 216 through the electrically conductive fluid in contact with the system 210. The voltage potential created between the first and second dissimilar materials 214, 216 is created through chemical reactions between the first and second dissimilar materials 214, 216 and the electrically conductive fluid.

FIG. 7A shows an exploded view of the surface of the first material 214, according to one aspect of the present disclosure. The surface of the first material 214 is not planar, but rather has an irregular surface 234 as shown. The irregular surface 234 increases the surface area of the material and, hence, the area that comes in contact with the electrically conductive fluid. It will be appreciated that second material 216 shown in FIG. 7 also may have an irregular surface.

In one aspect, at the surface of the first material 214, there is a chemical reaction between the first material 214 and the surrounding electrically conductive fluid such that mass is released into the electrically conductive fluid. The term "mass" as used herein refers to protons and neutrons that form a substance. One example includes the instant where the material is CuC; and when in contact with the electrically conductive fluid, CuCl becomes Cu (solid) and Cl— in solution. The flow of ions into the conduction fluid is depicted by the ion paths 230. In a similar manner, there is a chemical reaction between the second material 216 and the surrounding electrically conductive fluid and ions are captured by the second material 216. The release of ions at the second material 214 and capture of ion by the second material 216 is collectively referred to as the ionic exchange. The rate of ionic exchange and, hence the ionic emission rate or flow, is controlled by the control device 218. The control device 218 can increase or decrease the rate of ion flow by altering the conductance, which alters the impedance, between the first and second dissimilar materials 214, 216. Through controlling the ion exchange, the system 210 can encode information in the ionic exchange process. Thus, the system 210 uses ionic emission to encode information in the ionic exchange.

The control device 218 can vary the duration of a fixed ionic exchange rate or current flow magnitude while keeping the rate or magnitude near constant, similar to when the frequency is modulated and the amplitude is constant. Also, the control device 218 can vary the level of the ionic exchange rate or the magnitude of the current flow while keeping the duration near constant. Thus, using various combinations of changes in duration and altering the rate or magnitude, the control device 218 encodes information in the current flow or the ionic exchange. For example, the control device 218 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 210, 220 of FIGS. 5 and 6, respectively, include electronic components as part of the control device 218 of the system 210 or the control device 228 of the system 220. Components that may be present include but are not limited to: logic and/or memory elements, an integrated circuit, an inductor, a resistor, sensors for measuring various parameters, inductors 400, resonant circuits, and driver circuits to drive the inductor and/or the resonant circuits. Each component may be secured to the framework and/or to another component. The components on the surface of the support may be laid out in any convenient configuration. Where two or more components are present on the surface of the solid support, interconnects may be provided.

Figure 8:
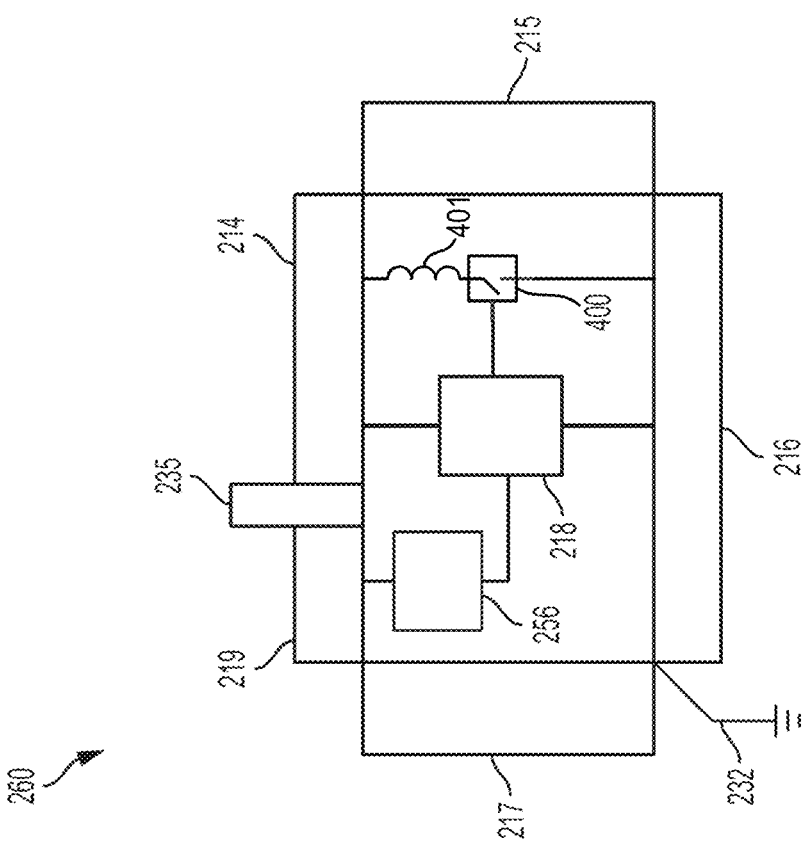
FIG. 8 illustrates the ingestible identifier of FIG. 5 with a pH sensor unit, according to one aspect of the present disclosure.

Referring now to FIG. 8, the system 260 includes a pH sensor component 256 connected to a third material 219, which is selected in accordance with the specific type of sensing function being performed, according to one aspect of the present disclosure. The pH sensor component 256 is also is connected to the control device 218. The third material 219 is electrically isolated from the first material 214 by a nonconductive barrier 235. In one aspect, the third material 219 is platinum. In operation, the pH sensor component 256 uses the voltage potential difference between the first and second dissimilar materials 214, 216. The pH sensor component 256 measures the voltage potential difference between the first material 214 and the third material 219 and records that value for later comparison. The pH sensor component 256 also measures the voltage potential difference between the third material 219 and the second material 216 and records that value for later comparison. The pH sensor component 256 calculates the pH level of the surrounding environment using the voltage potential values. The pH sensor component 256 provides that information to the control device 218. The control device 218 is coupled to the switch 400 and controls the current flow through the inductor 401 to generate an electromagnetic field. In one aspect, the electromagnetic field may encode the information relevant to the pH level in the ionic transfer, which can be detected by a receiver (not shown). Thus, the system 260 can determine and provide information related to the pH level to a source external to the environment.

Figure 9:
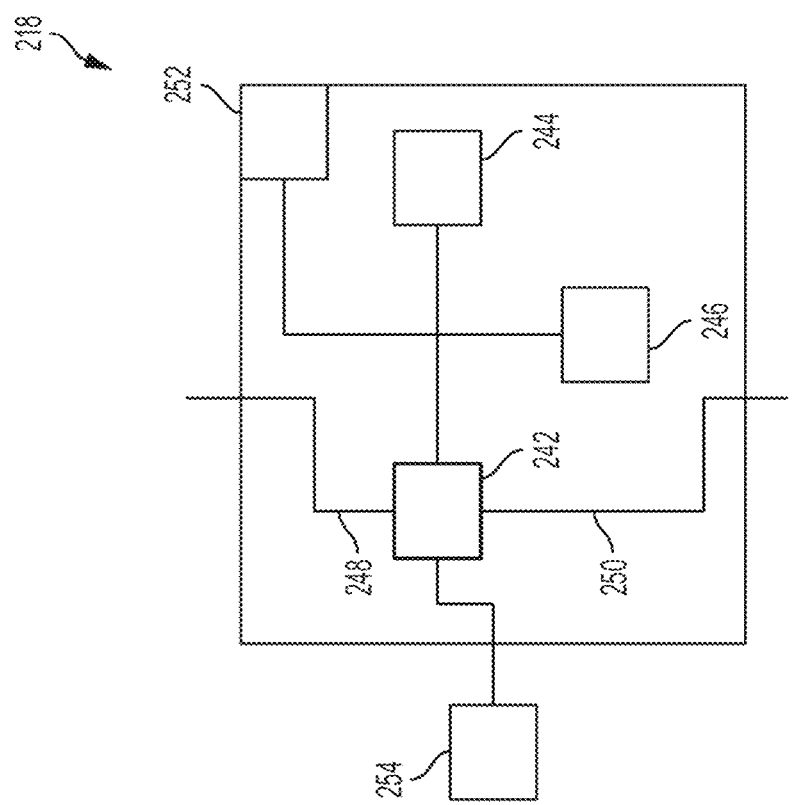
FIG. 9 is a block diagram illustration of one aspect of the control device used in the system of FIGS. 5 and 6, according to one aspect of the present disclosure.

FIG. 9 illustrates a block diagram representation of the control device 218, according to one aspect of the present disclosure. The control device 218 includes a control component 242, a counter or clock 244, and a memory 246. Additionally, the control device 218 is shown to include a sensor component 252 as well as the sensor component 254, which was initially referenced in FIG. 7. The control component 242 has an input 248 electrically coupled to the first material 214 and an output 250 electrically coupled to the second material 216. The control component 242, the clock 244, the memory 246, and the sensor components 252/254 also have power inputs (some not shown). The power for each of these components is supplied by the voltage potential produced by the chemical reaction between the first and second materials 214, 216 and the electrically conductive fluid, when the system 210 (FIGS. 1 and 7) is in contact with the electrically conductive fluid. The control component 242 controls the conductance through logic that alters the overall impedance of the system 210. The control component 242 is electrically coupled to the clock 244. The clock 244 provides a clock cycle to the control component 242. Based upon the programmed characteristics of the control component 242, when a set number of clock cycles have passed, the control component 242 alters the conductance of the switch 400 (FIGS. 5, 7, 8) to control the current flow through the inductor 401 (FIGS. 5, 7, 8) to encode information in an electromagnetic field. This cycle is repeated and thereby the control device 218 produces a unique current signature characteristic. The control component 242 is also electrically coupled to the memory 246. Both the clock 244 and the memory 246 are powered by the voltage potential created between the first and second materials 214, 216.

The control component 242 is also electrically coupled to and in communication with the first and second sensor components 252, 254. In the aspect shown, the first sensor component 252 is part of the control device 218 and the second sensor component 254 is a separate component. In alternative aspects, either one of the first and second sensor components 252, 254 can be used without other and the scope of the present disclosure is not limited by the structural or functional location of the sensor components 252 or 254. Additionally, any component of the system 210 may be functionally or structurally moved, combined, or repositioned without limiting the scope of the present disclosure as claimed. Thus, it is possible to have one single structure, for example a processor, which is designed to perform the functions of all of the following components: the control component 242, the clock 244, the memory 246, and the sensor component 252 or 254. On the other hand, it is also within the scope of the present disclosure to have each of these functional components located in independent structures that are linked electrically and able to communicate.

Referring again to FIG. 9, the sensor components 252, 254 can include any of the following sensors: temperature, pressure, pH level, and conductivity. An additional node may be configured as a reference electrode to allow measurement of anode and cathode independently. In one aspect, the sensor components 252, 254 gather information from the environment and communicate the analog information to the control component 242. The control component then converts the analog information to digital information and the digital information is encoded in the electromagnetic field. In another aspect, the sensor components 252, 254 gather information from the environment and convert the analog information to digital information and then communicate the digital information to control component 242. In the aspect shown in FIG. 9, the sensor component 254 is shown as being electrically coupled to the first and second dissimilar materials 214, 216 as well as the control device 218. In another aspect, as shown in FIG. 9, the sensor component 254 is electrically coupled to the control device 218 at a different connection point that acts as both a source for power supply to the sensor component 254 and a communication channel between the sensor component 254 and the control device 218.

As indicated above, the control device 218 can be programmed in advance to output a pre-defined electromagnetic encoded signal. In another aspect, the system can include a receiver system that can receive programming information when the system is activated. In another aspect, not shown, the switch 244 and the memory 246 can be combined into one device.

In addition to the above components, the system 210 (FIGS. 5 and 7) also may include one or other electrical or electronic components. Electrical or electronic components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, inductor, etc.; a passive element, e.g., an inductor, resistor, etc.

FIG. 10 illustrates a first component 403 comprising an inductor 402, according to one aspect of the present disclosure. The first component 403 is configured in association with an integrated circuit 404 having a cathode layer (not shown) on top of the integrated circuit 404. The integrated circuit 404 component is associated with an ingestible identifier, such as an ingestible identifier 270 shown in FIGS. 12 and 13, for example. Returning to FIG. 10, The integrated circuit 404 component is, for example, between 10 micrometers and 10 millimeters on a side, such as 100 micrometers to 5 millimeters, e.g. one millimeter on a side, having a cathode on a first side (not shown) and an anode on a second side (not shown). The inductor 402 may be formed by depositing, etching, or printing a patterned layer of metal on the integrated circuit 404. The inductor 402 may comprise a dense pattern of metal defining a multi-turn, spiral-patterned design. The metal layer has slits cut therein, such as single spiral slit cut. In other aspects, the inductor 402 may be a solenoid or a solenoid with a ferrite, without limitation. The inductor 402 is a component of a resonant circuit coupled to a driver circuit to generate an electrical signal that oscillates inside the inductor 402.

FIG. 11 illustrates a second component 406 comprising an inductor 408, according to one aspect of the present disclosure. The second component 406 is configured in association with an integrated circuit 410 (integrated circuit or flexible electrode). The integrated circuit 410 component is, for example, between 10 micrometers and 10 millimeters on a side, such as 100 micrometers to 5 millimeters, e.g. one millimeter on a side, having a cathode on a first side (not shown) and an anode on a second side (not shown). The integrated circuit 410 is embedded in a nonconductive membrane 412 by which conductive transmission is generated by modulating current. The inductor 408 runs along, i.e., is associated with, the perimeter of the integrated circuit 410. The inductor 408 includes, for example, a multi-turn/multi-layer coli. In one aspect, the inductor 408 is relatively small. In various aspects, an insulating layer (not shown) is introduced over the inductor 408 to extend range. For example, the insulting layer includes several hundred microns of plastic over the inductor 408.

With reference to FIGS. 10 and 11, in various aspects, the inductor 4502, 408 may be configured according to any pattern and/or location respective to the lifecycle pharma informatics system. Patterns include, for example, spirals, squiggles, curves, multi-turned, straight, curved, single layer, multi-layer, and other designs and combinations of designs.

FIG. 12 illustrates an ingestible identifier 270 that includes an inductor 420, according to one aspect of the present disclosure. In FIG. 12, the ingestible identifier 270 includes an integrated circuit 272 and a nonconductive membrane 274 (e.g., skirt, electrically insulative element). The integrated circuit 272 includes both a conductive communication component and an inductor 420.

FIG. 13 is a side sectional view of the ingestible identifier 270 shown in FIG. 12. The ingestible identifier 270 an integrated circuit 272 (also referred to herein as the identifier) as well as upper and lower electrodes 276, 278, where the upper and lower electrodes 276, 278 are fabricated from dissimilar materials and are configured such that upon contact with stomach fluid current runs through the integrated circuit 272 to cause one or more functional blocks in the circuit to emit a detectable signal. The ingestible identifier 270 includes a nonconductive membrane 274 (sometimes referred to herein as a "skirt" or electrically insulative element), as previously discussed. The ingestible identifier 270 includes an inductor 420 element formed above one of the electrodes 276, as shown.

The ingestible identifier 270 may be used in conjunction with receivers configured to receive the electromagnetic field generated by the inductor 420 component. One example of an attachable medical device is a transmitter/receiver, permanently associated with a body (such as implanted in a body) or removably attachable to an external portion of a body. The ingestible identifier 270 can be communicably associated with a transmitting and/or receiving device. The transmitting/receiving device includes in-body devices, external devices removably or permanently attachable to the body, and remote devices, i.e., devices not physically associated with the body, but capable of communication with the Ingestible Event Marker. Receivers of interest are discussed in more detail hereinbelow in connection with FIGS. 3, 47, 49, and 50-55, for example.

Various aspects of the devices and systems, including communication-enabled pills and packaging, enable identification of the ingestible identifier 270 and any medication thereof (if present). "Pill" as used below is representative of any communication-enabled medication. Ingestible identifier 270 packaging includes, for example, a "blister" pack capable of housing an individual ingestible identifier (such as a pill or a limited number of pills or capsules). The ingestible identifier 270 packaging further includes containers, boxes, wrappings, IV bags, and so forth associated with the medication.

In various aspects, the communication components can be sovereign to the pill. In other aspects, the communication components can be distributed, e.g., physically associated with the packaging as well as with the ingestible component, such as a pill or capsule.

Once the ingestible identifier 270 reaches the patient environment, information associated with the ingestible identifier 270 can be used for a variety of purposes. For example, the ingestible identifier 270 may interoperate with a container of the ingestible identifier 270 and with a receiver to ensure that the person attempting to open the ingestible identifier container is actually the person for whom it is prescribed. Further communication activities include an information control system, in which medication information associated with the ingestible identifier 270 is compared against patient data received from one or multiple sources to determine, for example, if a medication is contraindicated, subject to appropriate dosage amounts and times, or other events and/or conditions.

After patient ingestion, information stored by the ingestible identifier 270 may be recovered from one or more of the communications components. For example, communication capabilities can be performed after ingestion via the electromagnetic field communication components, for example, using the receiver. Data can be stored in the ingestible identifier 270 and reprogrammed with secure digital signature at each transaction.

When patient expulsion of an ingestible identifier 270 has taken place, various aspects permit communication with a device such as a sensor to determine, for example, data related to the patient or the medication, or transit time through the body. Alternatively, in various aspects, the data is erased (or various components/subcomponents associated with the data are destroyed or separated from the system) to protect privacy concerns after expulsion.

Having described the electromagnetic ingestible identifier sensing and detection system at a general level in connection with FIGS. 1-13, the disclosure now turns to specific implementations of an electromagnetic ingestible identifier sensing and detection system including (1) an ingestible identifier impulse circuit and driver circuit comprising a low impedance inductor, (2) the combined ingestible identifier and inductor resonant circuit, (3) an impulse communication system and protocol, and (4) various receiver configurations to receive the electromagnetic signal transmitted by the ingestible identifier.

FIGS. 14-18 illustrate various configurations of an electromagnetic ingestible identifier sensing and detection system, according to various aspects of the present disclosure. Each of the ingestible identifiers illustrated in FIGS. 14-18 can be employed as the transmission component of the electromagnetic ingestible identifier sensing and detection system, according to various aspects of the present disclosure.

FIG. 14 illustrates one aspect of the ingestible identifier 200 shown in FIGS. 4A and 4B, according to one aspect of the present disclosure. The ingestible identifier 200 comprises an integrated circuit 202 and a nonconductive membrane 208 positioned between the dissimilar materials 204, 206 (FIG. 4A) provided on the integrated circuit 202. As described herein, the dissimilar materials 204, 206 generate a voltage potential to power when the ingestible identifier 200 is immersed in an electrically conductive fluid. In one aspect, the ingestible identifier 200 shown in FIG. 14 may be configured in the manner described in connection with FIGS. 5-9. In other words, the ingestible identifier 200 can be employed in the electromagnetic field based sensing and detection system as described herein by generating an encoded signal within the body of the individual shown in FIGS. 1 and 2.

FIG. 15 illustrates one aspect of the ingestible identifier 270 shown in FIGS. 12-13, according to one aspect of the present disclosure. The ingestible identifier 270 comprises an integrated circuit 272, a nonconductive membrane 274, and an inductor 420 provided on the integrated circuit 272. As described herein, the dissimilar materials 274, 276 (FIG. 13) generate a voltage potential to power the integrated circuit 272 when the ingestible identifier 270 is immersed in a conductive fluid. In one aspect, the ingestible identifier 272 may be configured in the manner described in connection with FIGS. 12-13.

With reference back to FIG. 15, the inductor 420 may be patterned as shown in FIGS. 10 and 11, for example, without limitation. The inductor 420 is a component of a resonant circuit and is driven by a driver circuit component of the integrated circuit 272. The driven resonant circuit generates an electromagnetic signal that can be detected by a receiver external to the individual.

In one aspect, the ingestible identifier 270 is generally composed of a single piece of Si material formed in a single semiconductor manufacturing process. Accordingly, the metals employed in the semiconductor fabrication process used to make the integrated circuit 272 can be employed to make the ingestible identifier 270 and the inductor 420. Thus, the resonant circuit comprising the inductor 420 and a capacitor can be formed on the integrated circuit 272 during the semiconductor fabrication process.

The inductor 420 can be formed on the integrated circuit 272 of the ingestible identifier 270 using a variety of techniques. In one aspect, the inductor 420 can be formed as (1) a spiral from the bottom of the integrated circuit 272 to the top of the integrated circuit 272 where the different layers are interconnected through vias. In another aspect, the inductor 420 can be formed as (2) a first layer of metal on one side of the integrated circuit 272 from an outer portion of the integrated circuit 272 to an inner portion and a second layer of metal is formed on top of the first layer of metal. The inductor 420 may comprise four stacked layers of inductors and eight different nodes for driving the inductor 420. In another aspect, the inductor 420 can be formed as (3) two separate inductors with a center tap to match any parasitic degradations in the signal.

FIG. 16 illustrates an ingestible identifier 280 comprising an integrated circuit 282 and a separate inductor 430 component formed on a separate substrate 440, according to one aspect of the present disclosure. Accordingly, the ingestible identifier 280 can be fabricated in two separate processes as two separate substrates that are later interconnected. In one aspect, the ingestible identifier 280 comprises an integrated circuit 282, an integrated passive device (IPD) component 450, and optionally a nonconductive membrane 288. The IPD component 450 is a passive device that is integrated with the integrated circuit 282. The integrated circuit 282 comprises dissimilar materials provided thereon to generate a voltage potential when in contact with an electrically conductive fluid, where the voltage potential powers up the integrated circuit 282, as described in connection with FIGS. 4A-4B and 5-9. The nonconductive membrane 288 may be interposed between the dissimilar materials to extend the path of the electrical current flow between the dissimilar materials. The inductor 430 on the IPD component 450 is formed on a separate substrate 440 and is electrically coupled to the output of the integrated circuit 282.

The integrated circuit 282 may be fabricated using a first complementary metal oxide semiconductor (CMOS) process on a single Si wafer substrate 284. The inductor 430 and a capacitor may be fabricated using a second process on a second wafer substrate 440 to produce the IPD component 450. The IPD component 450 can employ high quality metals for building the inductor 430 on a secondary integrated circuit (IC) die substrate 440. The integrated circuit 282 portion of the ingestible identifier 280 and the IPD component 450 can then be stacked together with additional processing such as deposition, drilling, etc., if necessary. The process would yield a single semiconductor (e.g., Si) from two separate wafer substrates 284, 440. The two separate semiconductor substrates 284, 440 can be combined or bonded using various techniques such as molecular bonding, for example. If the optional nonconductive membrane 288 is employed, the integrated circuit 282 can be located on the nonconductive membrane 288 (e.g., skirt). In another aspect, a ReDistribution Layer (RDL) may be employed to implement the inductor 430. In another aspect, the inductor may be formed on a glass substrate rather than a semiconductor substrate.

FIG. 17 illustrates an ingestible identifier 290 comprising an inductor 460 formed on a nonconductive membrane 294, according to one aspect of the present disclosure. The ingestible identifier 290 comprises an integrated circuit 292, a nonconductive membrane 294, and an inductor 460 formed on the nonconductive membrane 294. The integrated circuit 292 comprises dissimilar materials formed thereon to generate a voltage potential when in contact with an electrically conductive fluid and to generate a conductive current in the fluid, as described in connection with FIGS. 4A-4B and 5-9. The nonconductive membrane 294 is interposed between the dissimilar materials to extend the path of the electrical current flow. The inductor 460 may be fabricated on the nonconductive membrane 294 using various processes such as deposition, printing, and the like. The inductor 460 is electrically coupled to the integrated circuit 292.

FIG. 18 illustrates an ingestible identifier 295 comprising an inductor 470 formed on one or both of the dissimilar materials 274, 276 (FIG. 13) after the dissimilar materials 274, 276 are deposited on the integrated circuit 272, according to one aspect of the present disclosure. The capacitor portion of the resonant circuit can be formed either during the semiconductor fabrication process or afterwards. In one aspect, the separate semiconductor wafers can be bonded together and connected to the dissimilar materials of the ingestible identifier (e.g., Mg and CuCl) through a Si via process and filled with copper (Cu) metal. The process can be performed on one side or both sides of the die and then singulated to produce individual components.

Figure 19:
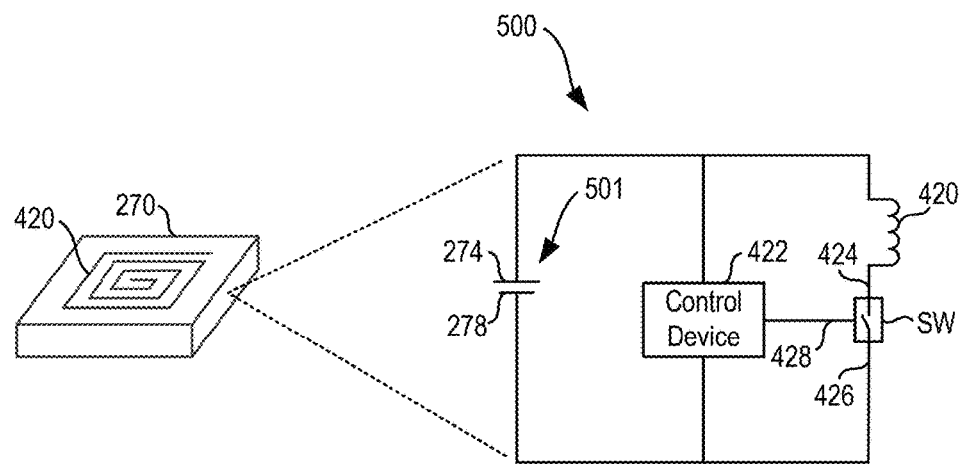
FIG. 19 is a schematic representation of an ingestible identifier comprising an inductor and a single ended inductor driver circuit, according to one aspect of the present disclosure.

FIG. 19 is a schematic representation of an ingestible identifier 270 comprising an inductor 420 and a single ended inductor driver circuit 500, according to one aspect of the present disclosure. The single ended driver circuit 500 is configured to drive the inductor 420. The driver circuit 500 is powered by the partial battery 501 formed by the dissimilar materials 274, 276, as previously discussed herein in connection with FIGS. 12-13, immersed in an electrically conductive fluid. A control device 422 controls the switch SW, which connected in series with the inductor 420. The switch SW comprises an input terminal 424, an output terminal 426, and a control terminal 428. The control device 422 is coupled to the control terminal 428 of the switch SW to control the operation of the switch SW. For example, the control device 422 can be configured to open and close the switch SW to generate an RF oscillating current through the inductor 420, which generates a RF electromagnetic signal. The switch SW can be opened and closed in a predefined manner to generate an encoded RF electromagnetic signal. The RF electromagnetic signal can be transmitted through body tissues. The RF electromagnetic signal can be detected by an external or internal receiver device that has a magnetic-signal detection mechanism.

Figure 20:
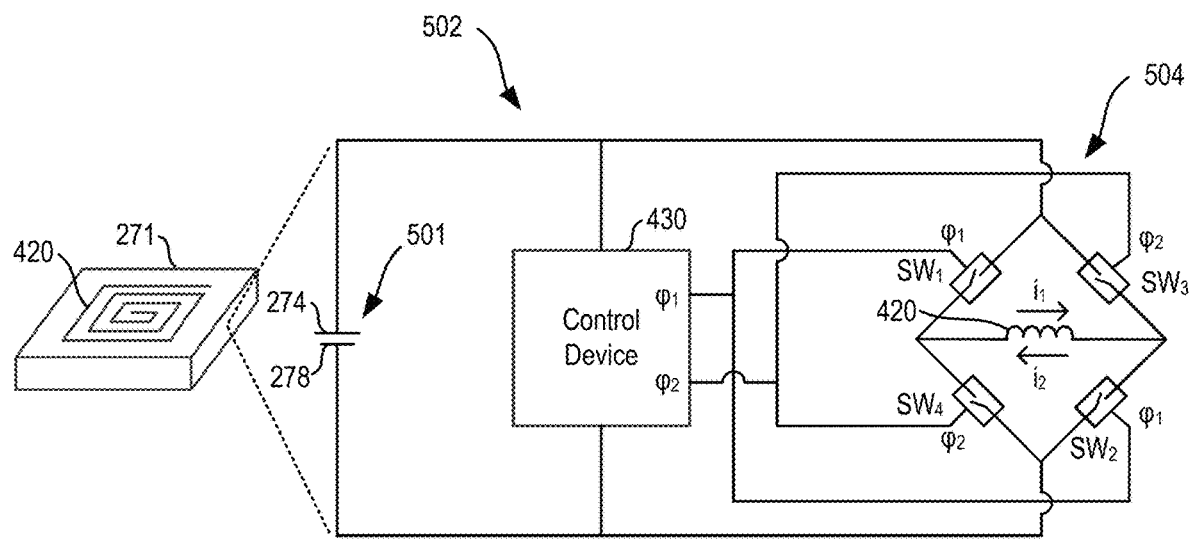
FIG. 20 is a schematic representation of an ingestible identifier comprising an inductor and a push-pull H-bridge type inductor driver circuit, according to one aspect of the present disclosure.

FIG. 20 is a schematic representation of an ingestible identifier 271 comprising an inductor 420 and a push-pull H-bridge 504 type inductor driver circuit 502, according to one aspect of the present disclosure. The push-pull bridge 504 type inductor driver circuit 502 is configured to drive the inductor 420. The driver circuit 502 is powered by the partial battery 501 formed by the dissimilar materials 274, 276, previously discussed in connection with FIGS. 12-13, immersed in an electrically conductive fluid. The inductor 420 is connected between two nodes of the H-bridge 504 comprising at least four switches SW1, SW2, SW3, SW4 in a floating configuration. Each of the switches SW1, SW2, SW3, SW4 comprises an input terminal, an output terminal, and a control terminal. A control device 430 is coupled to the control terminal of each of the switches SW1, SW2, SW3, SW4 to control the conductance of the switches SW1, SW2, SW3, SW4. For example, the control device is configured to open and close the switches SW1, SW2, SW3, SW4 in a predefined manner to generate an oscillating current through the inductor 420, which generates an encoded RF magnetic signal. In one aspect, two of the switches SW1, SW2 in the H-bridge 504 are closed at one time to conduct current $(i)_1$ through the inductor 420 while the other two switches SW3, SW4 remain open. Then, two of the switches SW3, SW4 in the H-bridge 504 are closed at one time to conduct current $(i)_2$ through the inductor 420 while the other two switches SW1, SW2 remain open. The pair of switches (SW1, SW2) and (SW3, SW4) are alternately connect the inductor 420 between the positive and return terminals of the partial battery 501 to alternately conduct current $(i)_1$ and $i_2$ through the inductor 420.

The control device 430 operates the switches SW1, SW2, SW3, SW4 to connect two of the switches in series with the inductor 420 for a half cycle. Thus the control device 430 drives the inductor 420 twice per cycle to double the signal while placing a constant load on the battery 501. For example, in one aspect, the control device operates two of the switches SW1, SW2 at a first phase $\phi_1$ and the other two switches SW3, SW4 at a second phase $\phi_2$, where the first phase $\phi_1$ is 180° out of phase with the second phase $\phi_2$. Accordingly, during the first half of the cycle, switches SW1 and SW2 are closed and switches SW3 and SW4 are open to generate a first current $(i)_1$ through the inductor 420. During the second half of the cycle, switches SW3 and SW4 are closed and switches SW1 and SW2 are open to generate a second current $(i)_2$ through the inductor 420 in an opposite direction of the first current $(i)_1$. In one cycle, the inductor 420 is driven by $i_1$ and $i_2$ to double the output signal. Accordingly, as the pair of switches SW1, SW4 and SW2, SW3 are cycled on and off by the control device, an encoded oscillating current through the inductor 420 is generated, which in turn generates a RF electromagnetic signal that can be transmitted through the body tissues. The RF electromagnetic signal can be detected by an external or internal receiver device that has a magnetic-signal detection mechanism.

FIG. 21 is a schematic representation of an ingestible identifier 270 comprising an inductor 420 and a single ended inductor driver circuit 422, according to one aspect of the present disclosure. The single ended driver circuit 422 is configured to drive the inductor 420. The driver circuit 422 is powered by a partial battery formed by electrically coupling the dissimilar materials 274, 276 immersed in an electrically conductive fluid, as previously discussed in connection with FIGS. 12-13. As shown FIG. 21, the battery portion of the ingestible identifier 270 is split such that the power applied to the control device 506 is isolated from the power applied to the inductor 420. The switch SW comprises an input terminal 507, an output terminal 509, and a control terminal 511. A control device 506 is coupled to the single ended driver circuit 422, which is coupled to the control terminal 511 of the switch SW to control the conductance of the switch SW. Under control of the control device 506, the single ended driver circuit 422 operates the switch SW connected in series with the inductor 420. The switch SW is opened and closed by the control device 506 to generate an encoded oscillating current through the inductor 420, which generates a RF electromagnetic signal. The RF electromagnetic signal can be transmitted through body tissues with little or no attenuation. The RF magnetic signal can be detected by an external or internal receiver device that has a magnetic-signal detection mechanism.

FIG. 21A is a schematic representation of an ingestible identifier 270A comprising an inductor 420 and a single ended inductor driver circuit 422 where a first metal layer 274 is divided into two regions and a second metal layer 276 is divided into two regions, according to one aspect of the present disclosure.

FIG. 22 is a schematic representation of an ingestible identifier 271 comprising an inductor 420 and a push-pull H-bridge 504 type inductor driver circuit 502, according to one aspect of the present disclosure. The push-pull bridge 504 type inductor driver circuit 430 is configured to drive the inductor 420. The driver circuit 430 is powered by the partial battery formed by the dissimilar materials 274, 276 immersed in an electrically conductive fluid, as previously discussed in connection with FIGS. 12-13. As shown FIG. 22, the battery portion of the ingestible identifier 270 is split such that the power applied to the control device 506 is isolated from the power applied to the inductor 420. The inductor 420 is connected between two nodes of the H-bridge 504 comprising at least four switches SW1, SW2, SW3, SW4 in a floating configuration. In one aspect, two of the switches in the H-bridge 504 are closed at one time to enable current to flow through the inductor 420 while the other two switches remain open alternately connecting the inductor 420 between the positive and return terminals of the battery. Each of the switches SW1, SW2, SW3, SW4 comprises an input terminal, an output terminal, and a control terminal. A control device 506 is coupled to the push-pull bridge 504 type inductor driver circuit 502, which is coupled to the control terminals of the switches SW1, SW2, SW3, SW4 to control the conductance of the switches SW1, SW2, SW3, SW4.

Under control of the control device 506, the push-pull bridge 504 type inductor driver circuit 430 operates the switches SW1, SW2, SW3, SW4 to connect two of the switches in series with the inductor 420 for a half cycle. Thus the inductor 420 is driven twice per cycle to double the signal while placing a constant load on the battery 501. For example, in one aspect, the driver circuit 430 operates two of the switches SW1, SW2 at a first phase $\phi_1$ and the other two switches SW3, SW4 at a second phase $\phi_2$, where the first phase $\phi_1$ is 180° out of phase with the second phase $\phi_2$. Accordingly, during the first half of the cycle, switches SW1 and SW2 are closed and switches SW3 and SW4 are open to generate a first current $(i)_1$ through the inductor 420. During the second half of the cycle, switches SW3 and SW4 are closed and switches SW1 and SW2 are open to generate a second current $(i)_2$ through the inductor 420 in an opposite direction of the first current $(i)_1$. Thus in one cycle, the inductor 420 is driven by and $i_2$ to double the output signal. Accordingly, as the pair of switches (SW1, SW2) and (SW3, SW4) are cycled on and off by the control device 430, an encoded oscillating current through the inductor 420 is generated, which in turn generates a RF electromagnetic signal that can be transmitted through body tissues with little or no attenuation. The RF magnetic signal can be detected by an external or internal receiver device that has a magnetic-signal detection mechanism.

The switches SW, SW1, SW2, SW3, SW4 described in connection with FIGS. 19-22 may be implemented as solid state electronic switching elements such as a semiconductor switching elements including, for example, transistors, field effect transistors (FET), metal-oxide semiconductor FETs (MOSFET), bipolar junction transistors, and any suitable equivalents thereof.

FIG. 22A is a schematic representation of an ingestible identifier 271A comprising an inductor 420 and a push-pull H-bridge type inductor driver circuit 430 where a first metal layer 274 is divided into two regions and a second metal layer 276 is divided into two regions, according to one aspect of the present disclosure.

Figure 23:
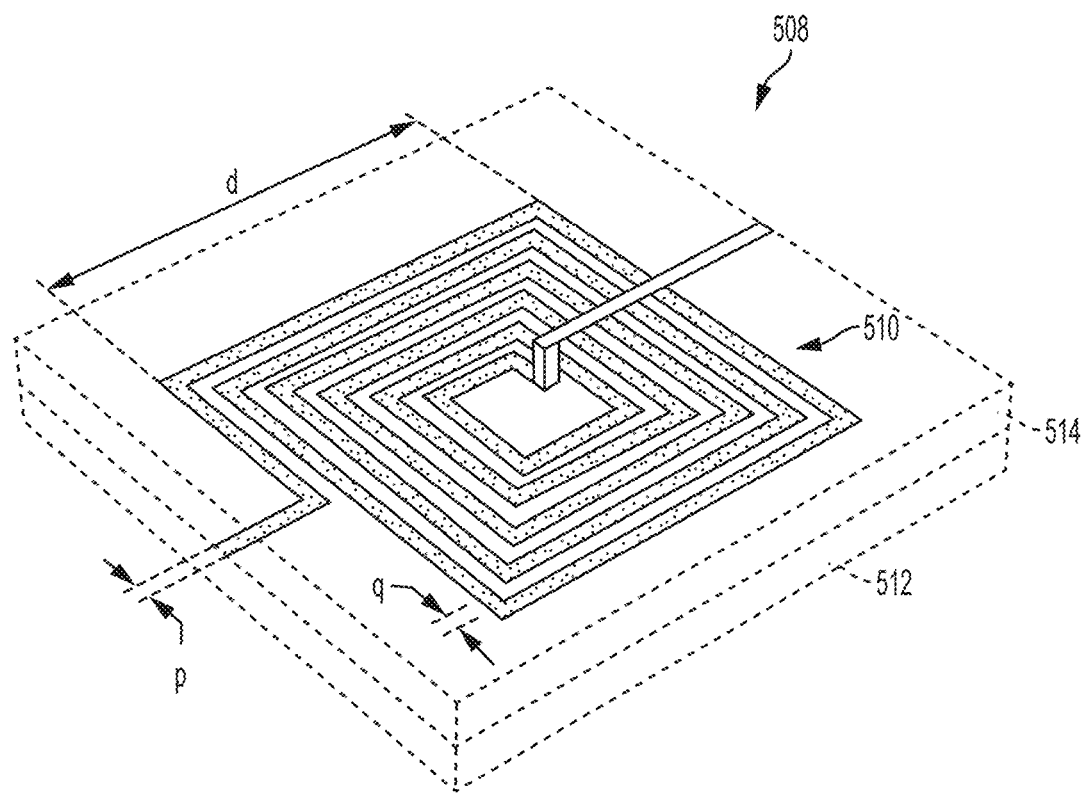
FIG. 23 illustrates an inductive element or inductor structure formed on an insulating substructure, which may be employed as the inductive element in an ingestible identifier integrated circuit, according to one aspect of the present disclosure.

FIG. 23 illustrates an inductive element 508 or inductor structure formed on an insulating substructure 514, which may be employed as the inductive element in an ingestible identifier integrated circuit, according to one aspect of the present disclosure. For example, a planar-type inductor 508 formed over a semiconductor substrate 512. As shown in FIG. 23, such a planar-type inductor structure 508 typically has a spiral configuration which includes a ribbon or spiral of conductive metal 510 formed over a semiconductor substrate 512 through an insulating layer 514 on the substrate. The inductance value of the conventional square shaped inductor shown in FIG. 23 can be expressed as the following equation (1):

$$L = \frac{0.27(d)^{\frac{8}{3}}}{p^{\frac{5}{3}}\left(1+\frac{1}{r}\right)^{\frac{5}{3}}}$$

Where L is the inductance (nH), d is a length (mm) of the most outer dimension of the spiral shaped inductor metallization layer 510, p is a width (mm) of the spiral-shaped inductor metallization layer 510, q is the spacing (mm) between two neighboring regions of the spiral-shaped metallization layer 510, and r is ratio of p/q, i.e. (p/q). When p=q, the above equation is simplified to the following equation (2):

$$L = \frac{0.085(d)^{\frac{8}{3}}}{p^{\frac{5}{3}}}$$

For example, if p=q=0.05 mm and d=0.5 mm, the inductance L is calculated from the above equation (1) or (2) as approximately 2 nH.

The planar inductor 508 construction described above increases the level of integration for the circuit by reducing the number of circuit elements located off the chip along with attendant need for complex interconnections. Recently, however, to decrease the size and fabrication cost of semiconductor integrated circuit devices, not only active components (e.g., transistors) but also passive components (e.g., inductors and capacitors) have been required to be miniaturized more and more. Accordingly, for the above planar-type inductors, attempts have been made to address the miniaturization requirement by decreasing the size of the spiral-shaped conductor layer 510. That is, by reducing the size of the width p and the interval q.

For example, if p=0.006 mm, q=0.006 mm and d=0.15 mm, the inductance L is calculated from the above equation (1) to be approximately 2.5 nH. If the spiral-shaped metallization layer or conductor layer 510 having this dimension is formed on a GaAs substrate, the inter-line capacitance C of the conductor layer 510 is equal to approximately 0.06 pF. This value is obtained by an approximation of the two neighboring regions of the spiral-shaped conductor layer 510 as coplanar strip lines. The resonance frequency $f_o$ in this case is approximately equal to 12.5 GHz, where $f_o$ is defined as the following equation (3):

$$f_o = \frac{1}{\left[2\pi(LC)^{\frac{1}{2}}\right]}$$

To reduce the plan size of the spiral-shaped inductor metallization or conductor layer 510 to, say, 70% of its original size, if the above parameters are designed as p=0.0024 mm and q=0.001 mm, the inductance L can be maintained at approximately 2.5 nH. However, the inter-line capacitance C of the conductor 510 increases up to approximately 0.28 pF and, as a result, the resonance frequency $f_o$ will decrease to approximately 6.0 GHz, which is lower than the case of the original size by approximately 6.5 GHz. Accordingly, with the inductor 508 shown in FIG. 23, when the interval q of the neighboring regions of the spiral-shaped conductor layer 510 is decreased for miniaturization, the inter-line capacitance C will increase and the resonance frequency $f_o$ will decrease and, consequently, the maximum operable frequency is lowered.

Figure 24:
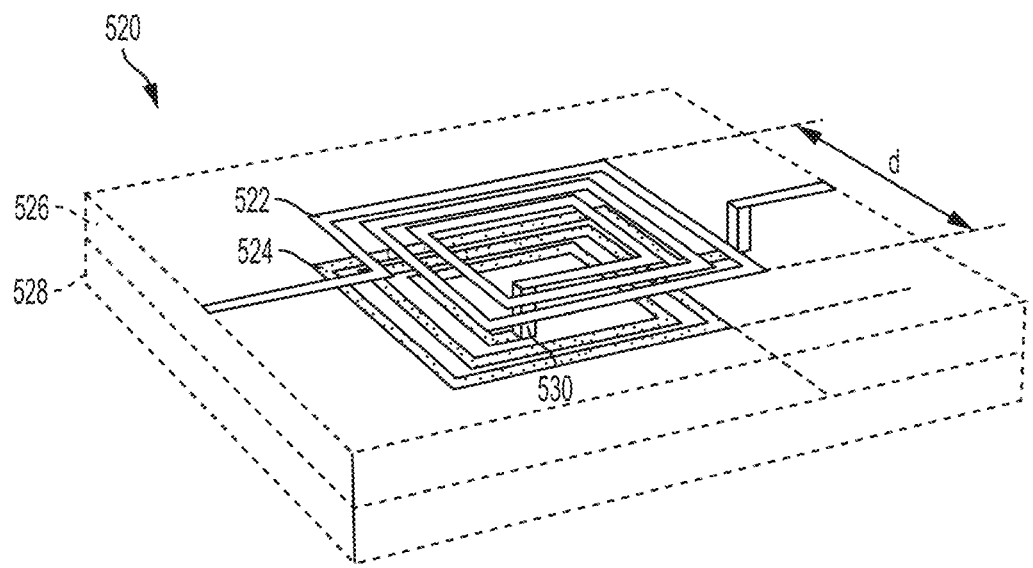
FIG. 24 illustrates a multi-layer inductive element or inductor structure formed on an insulating substructure, which may be employed as the inductive element in an ingestible identifier integrated circuit, according to one aspect of the present disclosure.

FIG. 24 illustrates a multi-layer inductive element 520 or inductor structure formed on an insulating substructure 526, 528, which may be employed as the inductive element in an ingestible identifier integrated circuit, according to one aspect of the present disclosure. One example of a multilayer inductor configuration is illustrated in FIG. 24. As seen in FIG. 24, the multilayer inductor structure 520 is fabricated with first and second levels of metallization constituting respective spiral inductor sections 522, 524. Each inductor section 522, 524 is formed on a corresponding insulating layer 526, 528, and is connected end to end by a centrally locating conductive via 530. In comparison to the planar structure 508 depicted in FIG. 23, the multilayer arrangement of FIG. 24 does provide a substantial increase in inductance per unit area, as well as a reduction in the dimension d.

FIGS. 25-27 illustrate a two-layer two-port inductor 600 configuration, according to one aspect of the present disclosure. The two-layer two-port inductor 600 configuration illustrated in FIG. 25 comprises two inductor sections 602, 604 formed on two corresponding insulating layers 608, 610 of a semiconductor integrated circuit 601 and are connected end to end by a first centrally located conductive via 606. Two ports A1 (Port 1), A2 (Port 2) for connecting the inductor 600 to other circuit elements are located on a top layer 603 of the semiconductor integrated circuit 601. The second port A2 of the second inductor section 604 is connected to the top layer 603 of the semiconductor integrated circuit 601 by a second off-center located conductive via 607. Although FIGS. 25-27 show a two-layer two-port inductor 600, the present disclosure contemplates an n-layer n-port inductor comprising a plurality of n inductor sections formed on corresponding n insulating layers of a semiconductor integrated circuit interconnected in series, parallel, or any suitable combination thereof, by one or more conductive vias, where n is any integer greater than 2. An example of a multilayer inductor with more than two layers is shown in FIGS. 28-30, which disclose a four-layer two-port inductor comprising inductor sections 614, 616, 618, 620 formed on corresponding insulating layers 622, 624, 626, 628 of a semiconductor integrated circuit and interconnected end to end by a centrally located conductive via.

FIG. 26 is a diagram of the two-layer two-port inductor 600 shown in FIG. 25, according to one aspect of the present disclosure. The two-layer two-port inductor 600 is shown as two separate inductor sections 602, 604 for clarity of illustration. The first inductor section 602 is formed on a first insulating layer 608 and a second inductor section 604 is formed on a second insulating layer 610 of a semiconductor integrated circuit 601. The first and second inductor sections 602, 604 are connected in series through a conductive via 606 shown in dashed line. Connections to the two ports A1 (Port 1), A2 (Port 2) are provided on a top layer 603 of the semiconductor integrated circuit 601. The connection to the second port A2 is provided through a conductive via 607.

FIG. 27 is a schematic representation of the two-layer two-port inductor 600 shown in FIGS. 25 and 26, according to one aspect of the present disclosure. The first inductor section 602 is designated as L1 and the second inductor section 604 is designated as L2. Ends B1, B2 of the inductor sections L1, L2 are connected in series through a conductive via 606. The inductor 600 may be coupled to a circuit element through the two ports A1 (Port 1), A2 (Port 2). Because the inductor sections 602, 604 (L1, L2) are formed as coils on adjacent insulating layers 608, 610 of a semiconductor integrated circuit 601, current (i) flowing in one inductor section 602 induces a voltage in an adjacent inductor section 604 by way of mutual inductance. As shown in FIG. 27, the current (i) flows in the same direction through the first and second inductor sections 602, 604.

FIGS. 28-30 illustrate a four-layer two-port inductor 612 configuration, according to one aspect of the present disclosure. The four-layer two-port inductor 612 configuration illustrated in FIG. 28 comprises four inductor sections 614, 616, 618, 620 formed on four corresponding insulating layers 622, 624, 626, 628 of a semiconductor integrated circuit 611 and are connected end to end through conductive vias 630, 632, 634, 635, according to one aspect of the present disclosure. Two-ports A1 (Port 1), A4 (Port 2) are provided on a top layer 613 of the semiconductor integrated circuit 611 for connecting the inductor 612 to other circuit elements. The second port A4 is coupled to the fourth inductor section 620 and is connected to the top layer 613 of the semiconductor integrated circuit 611 by a conductive via 634.

FIG. 29 is a diagram of the four-layer two-port inductor 612 shown in FIG. 28, according to one aspect of the present disclosure. The four-layer two-port inductor 612 is shown as four separate inductor sections 614, 616, 618, 620 for clarity of illustration. Each of the inductor sections 614, 616, 618, 620 is formed on a separate insulating layer 622, 624, 626, 628 and is connected in series through conductive vias 630, 632, 634, 635. A connection between A4 (Port 2) to the top layer 613 of the semiconductor integrated circuit 611 is provided through a conductive via 635. Connections to ports A1 (Port 1) and A4 (Port 2) are provided on a top layer 613 of the semiconductor integrated circuit 611.

FIG. 30 is a schematic representation of the four-layer two-port inductor 612 shown in FIGS. 28 and 29, according to one aspect of the present disclosure. The first inductor section 614 is designated as L1, the second inductor section 616 is designated as L2, the third inductor section 618 is designated as L3, and the fourth inductor section 620 is designated as L4. The inductor sections L1-L4 are connected end to end in series through conductive vias 630, 632, 634. The inductor 612 may be coupled to a circuit element through the two ports A1 (Port 1), A4 (Port 2). Because the inductor sections 614, 616, 618, 620 (L1-L4) are formed as coils on adjacent layers 622, 624, 626, 628 of a semiconductor integrated circuit 611, current (i) flowing in one inductor section 614 induces a voltage in an adjacent inductor section 616, and so forth, by way of mutual inductance. As shown in FIG. 30, the current (i) flows in the same direction through the first, second, third, and fourth inductor sections 614, 616, 618, 620 (L1-L4).

FIGS. 31-33 illustrate an n-layer n-port inductor 630 configuration, according to one aspect of the present disclosure. The n-layer n-port inductor 630 configuration illustrated in FIG. 31 comprises n inductor sections 633, 636, 637, 638 formed on n corresponding insulating layers 640, 642, 644, 646 of a semiconductor integrated circuit 631, according to one aspect of the present disclosure. Each of the n inductor sections 633, 636, 637, 638 formed on the n separate corresponding insulating layers 640, 642, 644, 646 is a mirror image of the one above it. As shown in FIG. 31, the n inductor sections 633, 636, 637, 638 are not interconnected, but rather are arranged as n individual inductor sections 633, 636, 637, 638. The n inductor sections 633, 636, 637, 638 may be interconnected to each other and other circuits in any suitable manner by 2n-ports A1 (Port 1), B1 (Port 2), A2 (Port 3), B2 (Port 4), A3 (Port 5), B3 (Port 6), An (Port (2n−1)), Bn (Port 2n).

FIG. 32 is a diagram of the n-layer n-port inductor 630 shown in FIG. 31, according to one aspect of the present disclosure. The n-layer n-port inductor 630 is shown as n separate inductor sections 633, 636, 637, 638 for clarity of illustration. The first inductor section 633 is formed on a first insulating layer 640, the second inductor section 636 is formed on a second insulating layer 642, the third inductor section 637 is formed on a third insulating layer 644, and the n-th inductor section 638 is formed on a n-th insulating layer 646. Each of the inductor sections defines a coil that is a mirror image of a coil above it. The n-inductor sections 633, 636, 637, 638 are not connected, but rather are individually formed. The n-port pairs (A1 (Port 1), B1 (Port 2)), (A2 (Port 3), B2 (Port 4)), (A3 (Port 5), B3 (Port 6)), (An (Port (2n−1)), Bn (Port 2n)) may be provided on n-separate insulating layers for connecting the individual inductor sections 630 to a circuit in any predetermined configuration.

FIG. 33 is a schematic representation of the n-layer n-port inductor 630 shown in FIGS. 31 and 30, according to one aspect of the present disclosure. The first inductor section 633 is designated as L1, the second inductor section 636 is designated as L2, the third inductor section 637 is designated as L3, and the n-th inductor section 638 is designated as Ln. As shown in FIG. 33, the inductor sections L1-Ln are not interconnected and can be individually coupled to a circuit element through the n-port pairs (A1 (Port 1), B1 (Port 2)), (A2 (Port 3), B2 (Port 4)), (A3 (Port 5), B3 (Port 6)), (An (Port (2n−1)), Bn (Port 2n)) in any predetermined configuration. Because the inductor sections 633, 636, 637, 638 (L1-Ln) are formed as individual coils adjacent insulating layers 640, 642, 644, 646 of a semiconductor integrated circuit 631, current flowing in one inductor section 633 induces a voltage in an adjacent inductor section 636, and so forth, by way of mutual inductance.

Figure 35:
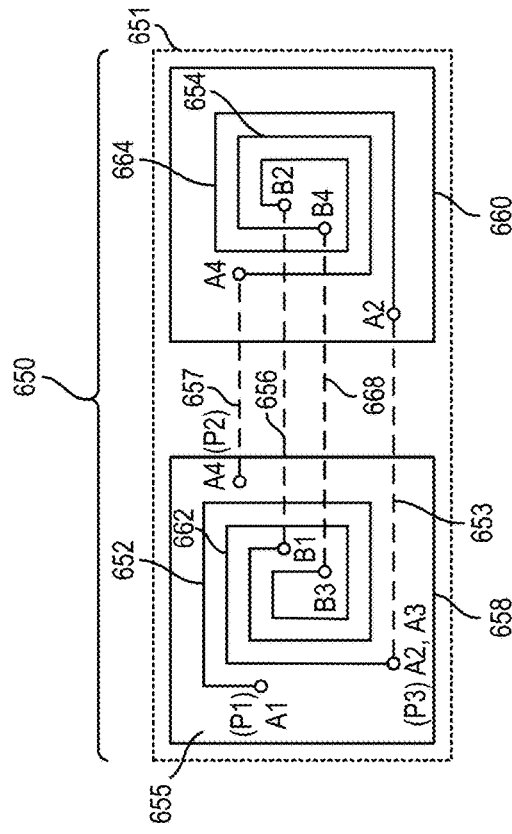
FIG. 35 is a diagram of the symmetrical two-layer three-port inductor with a center tap connection shown in FIG. 34, according to one aspect of the present disclosure.
Figure 36:
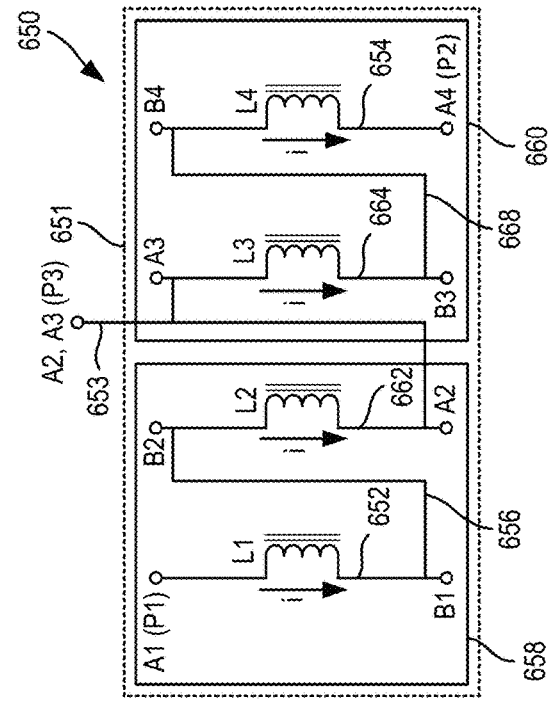
FIG. 36 is a schematic representation of the inductor shown in FIGS. 34 and 35, according to one aspect of the present disclosure.
Figure 34:
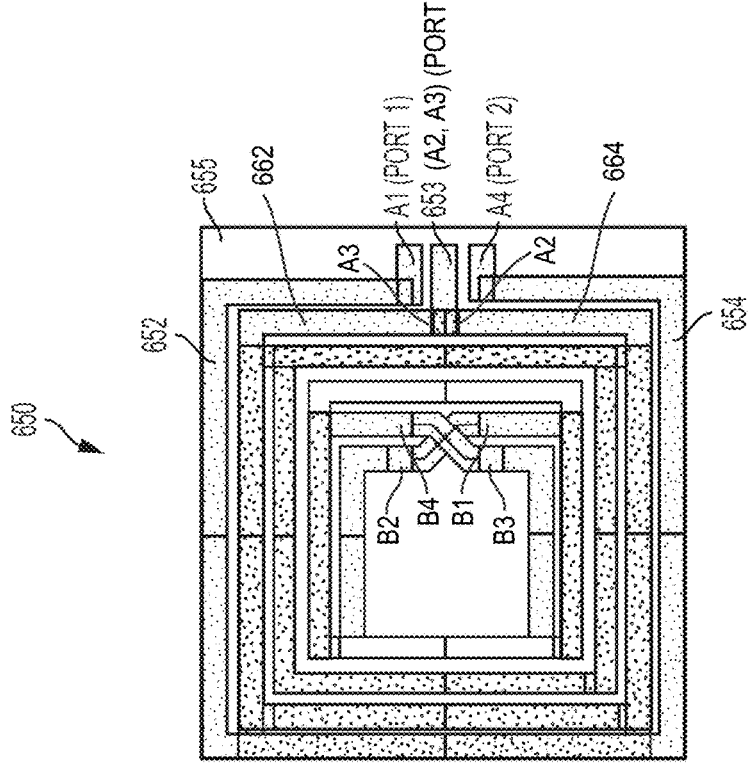
FIG. 34 illustrates a symmetrical two-layer three-port inductor with a center tap connection configuration, according to one aspect of the present disclosure.

FIGS. 34-36 illustrate a two-layer three-port inductor 650 with a center tap connection 653 configuration, according to one aspect of the present disclosure. The two-layer three-port inductor 650 with a center tap connection 653 configuration illustrated in FIG. 34 comprises four inductor sections 652, 662, 664, 654, formed on two corresponding insulating layers 658, 660 of a semiconductor integrated circuit 651 and are connected end to end through conductive vias 653, 656, 657, 668. Three-ports A1 (Port 1), A4 (Port 2), A2/A3 (Port 3) for connecting the inductor 650 to other circuit elements are located on a top layer 655 of the semiconductor integrated circuit 651. This geometry enables the construction of two layers of symmetric coils with two layers of metal whereas traditional symmetric, center tapped coils require two layers per coil. Accordingly, the present geometry provides more turns in the same die area.

FIG. 35 is a diagram of the two-layer three-port inductor 650 with a center tap connection 653 shown in FIG. 34, according to one aspect of the present disclosure. The two-layer three-port inductor 650 with a center tap connection 653 is shown as four separate inductor sections 652, 662, 664, 654 for clarity of illustration. The first and second inductor sections 652, 662 are formed on a first insulating layer 658 and the third and fourth inductor sections 664, 654 are formed on a second insulating layer 660. The second inductor section 654 is a mirror image of the first inductor section 652. The first, second, third, and fourth inductor sections 652, 662, 664, 654 are connected in series through conductive vias 653, 656, 657, 668 shown in dashed line. Connections to the three-ports A1 (Port 1), A4 (Port 2), A2/A3 (Port 3) may be provided on a top layer 655 of the semiconductor integrated circuit 651.

FIG. 36 is a schematic representation of the inductor 650 shown in FIGS. 34 and 35, according to one aspect of the present disclosure. In the schematic diagram, the first inductor section 652 of two-layer two-port inductor 650 is referenced as L1, the second inductor section 654 is referenced as L2, the third inductor section 664 is referenced as L3, and the fourth inductor section 654 is referenced as L4. The inductors L1, L2, L3, L4 are connected in series through connections 656, 657, 668. Because the inductors L1, L2, L3, L4 are formed as coils 652, 654 on adjacent layers 658, 660 of a semiconductor integrated circuit 651, current flowing in one coil 652 induces a voltage in the adjacent coil 654 by way of mutual inductance. As shown, current (i) flows through each of the inductors L1, L2, L3, L4 in the same direction.

Figure 37:
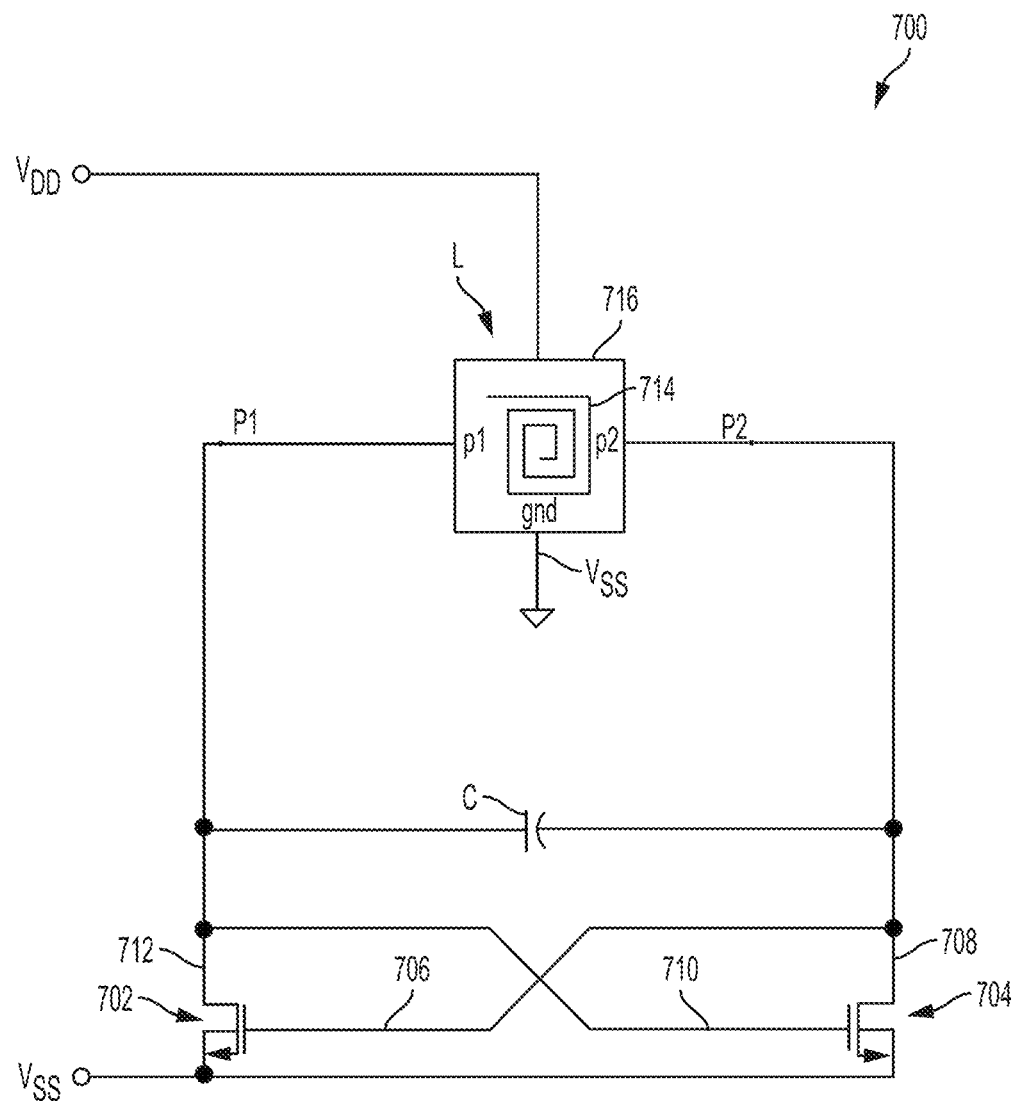
FIG. 37 is schematic diagram of a resonant (oscillatory) inductor driver circuit, according to one aspect of the present disclosure.

FIG. 37 is schematic diagram of a resonant (oscillatory) inductor driver circuit 700, according to one aspect of the present disclosure. The inductor driver circuit 700 adds a negative resistance (−R) using cross-coupled MOSFET transistors 702, 704 that manifests itself as a negative resistance (−R) which provides self-oscillatory behavior. The gate of the first MOSFET transistor 706 is coupled to the drain 708 of the second MOSFET transistor 704. Likewise, the gate 710 of the second MOSFET transistor 704 is coupled to the drain 712 of the first MOSFET transistor 702. An inductor L comprises an inductor section 714 similar to the inductor sections described herein. A supply voltage $V_{DD}$ is coupled to the inductor L and the substrate 716 is coupled to $V_{SS}$. The inductor L comprises two ports P1 and P2 to connect the inductor L to other circuit elements such as the cross-coupled MOSFET transistors 702, 704. In the example of FIG. 37, the inductor L is coupled across the drains 712, 712 of the first and second MOSFET transistors 702, 704, where Port 1 (P1) of the inductor L is coupled to the drain 712 of the first MOSFET transistor 702 and Port 2 (P2) of the inductor L is coupled to the drain 708 of the second MOSFET transistor 704. A capacitor C is coupled across the drains 712, 712 of the first and second MOSFET transistors 702, 704 to set the oscillation frequency of the inductor driver circuit 700. Alternatively, the parasitic capacitance of the inductor L may be used to set the oscillation frequency. The cross-coupled MOSFET transistors 702, 704 provide a current that oscillates inside the inductor L. This provides a reasonable Q, defined as the power loss in a power cycle compared to the energy instituted in the inductor L in a cycle. A high-enough Q provides adequate energy stored in the inductor L and provides higher current to make a more efficient system. It will be appreciated that other types of negative-resistance circuits may be employed other than the one illustrated in FIG. 37.

Figure 38:
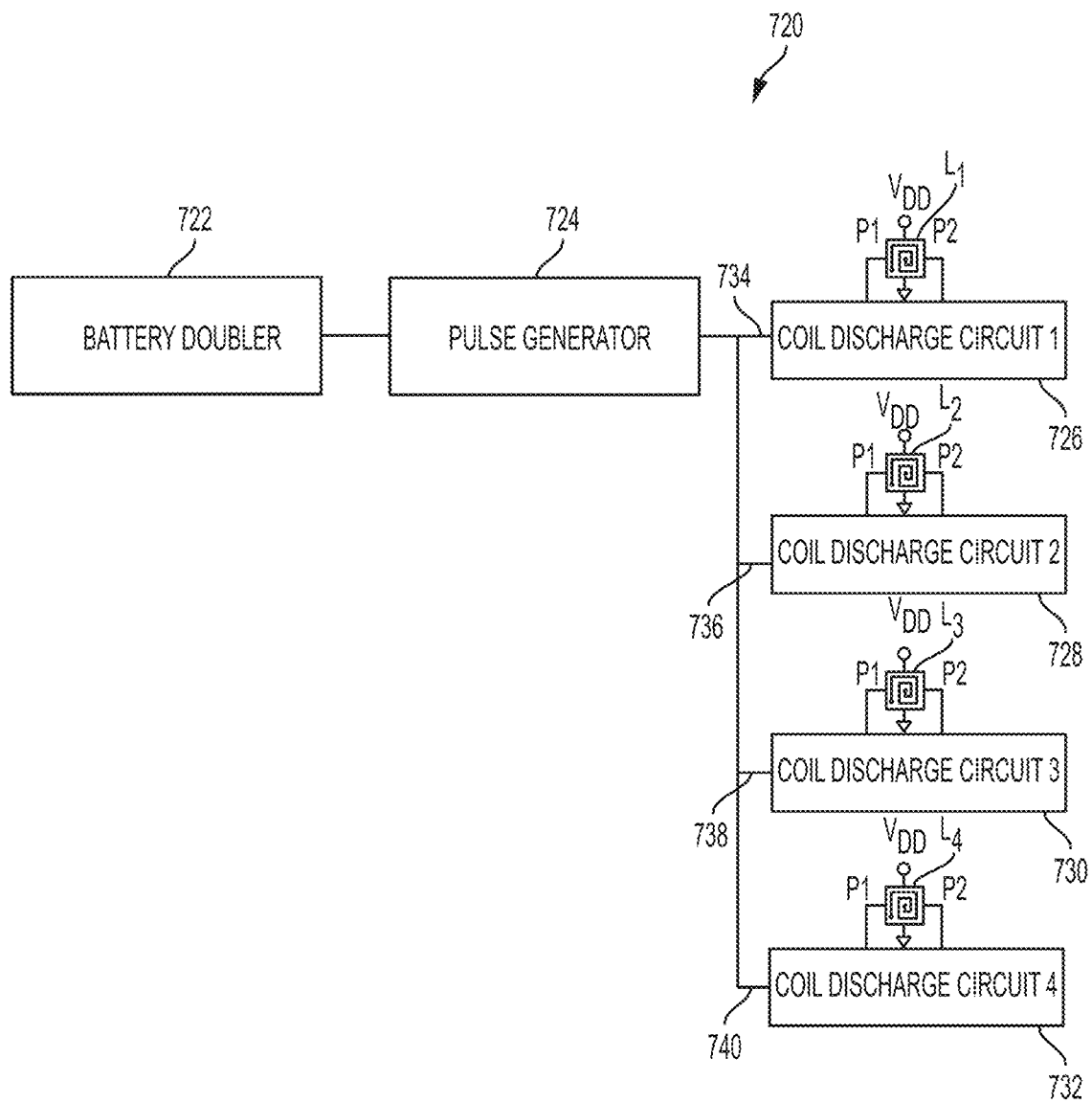
FIG. 38 is a block diagram of an impulse inductor driver circuit, according to one aspect of the present disclosure.

FIG. 38 is a block diagram of an impulse inductor driver circuit 720, according to one aspect of the present disclosure. The inductor driver circuit 720 is employed to push a signal through the inductor sections L1, L2, L3, L4 provided on individual layers of a semiconductor integrated circuit. Rather than coupling the inductor sections L1, L2, L3, L4 to an oscillator, an impulse of current is created that decays exponentially with time. Charge can be stored in a capacitor and can be discharged. As shown in FIG. 38, the impulse inductor driver circuit 720 comprises a battery voltage doubler section 722 coupled to a pulse generator circuit 724, which is coupled to a coil discharge circuit 726. In the example illustrated in FIG. 38, the pulse generator circuit 724 is coupled to four inductor discharge circuits 726, 728, 730, 732. It will be appreciated, however, that up to n-inductor discharge circuits can be coupled to the pulse generator circuit 724 without departing from the scope of the present disclosure. As discusses herein, the inductor driver circuit 720 pumps charge into a capacitor and then discharges the capacitor into the inductor sections L1, L2, L3, L4 over a very short discharge cycle relative to duty cycle.

The inductor discharge circuits 726, 728, 730, 732 are coupled to the pulse generator circuit 724 in parallel. In this "charge pump" configuration, the inductor discharge circuits 726, 728, 730, 732 structures are provided in parallel branches 734, 736, 738, 740 to provide four times the current rather than stacking them to provide four times the voltage. N-layers of inductors can be configured to provide N-capacitors. The inductor sections L1, L2, L3, L4 can be connected to be mono-phasic rather than alternating current (AC). As described herein, each inductor section L1, L2, L3, L4 includes two ports P1 and P2 to couple the inductor sections L1, L2, L3, L4 to corresponding inductor discharge circuits 726, 728, 730, 732.

Figure 39:
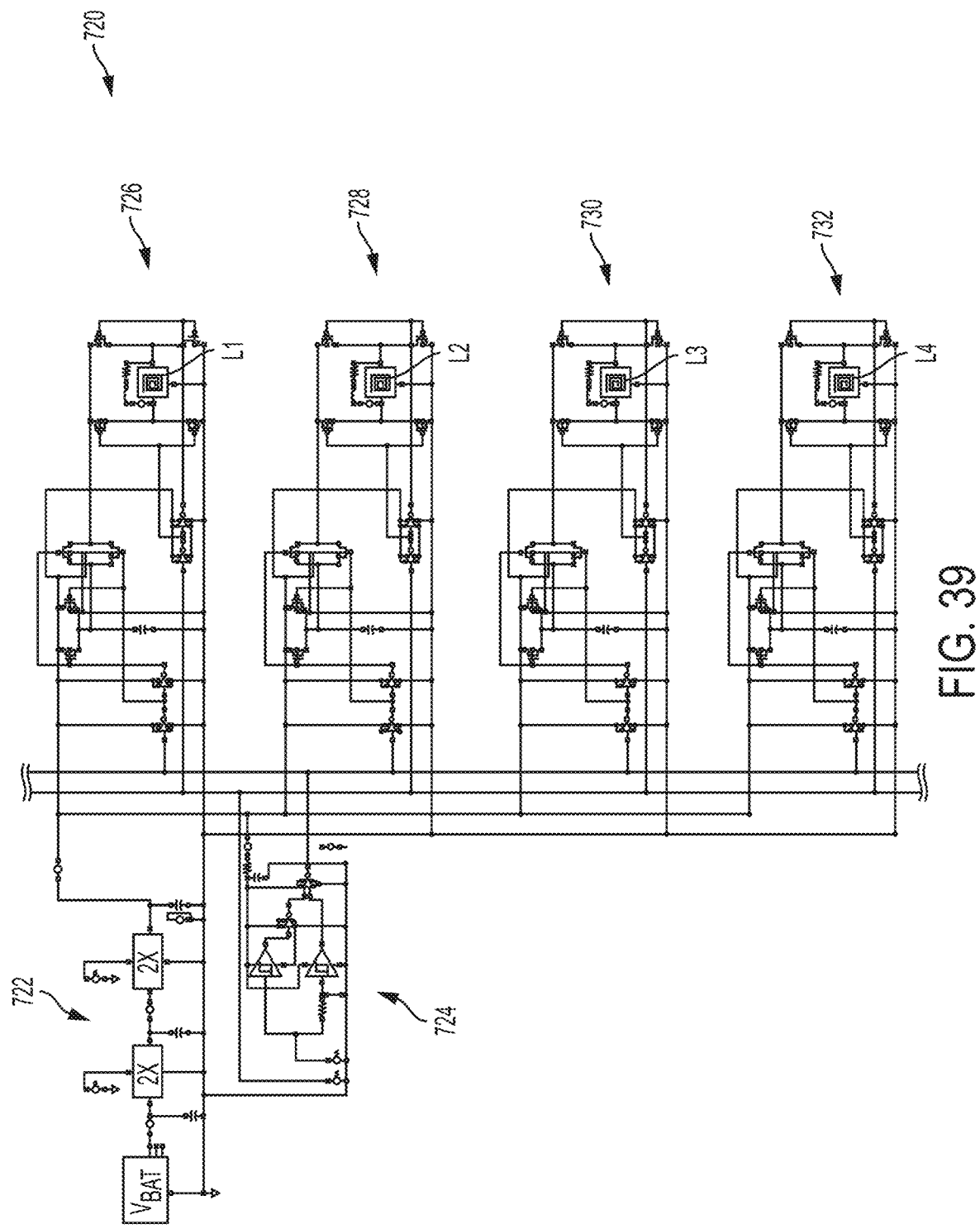
FIG. 39 is a schematic diagram of the impulse inductor driver circuit shown in FIG. 38, according to one aspect of the present disclosure.

FIG. 39 is a schematic diagram of the impulse inductor driver circuit 720 shown in FIG. 38, according to one aspect of the present disclosure. The inductor driver circuit 720 is employed to push a signal through the inductor sections L1, L2, L3, L4 provided on individual layers of a semiconductor integrated circuit. The battery voltage doubler circuit 722 quadruples the battery voltage $V_{BAT}$, which is applied to each of the inductor discharge circuit 726, 728, 730, 732. The pulse generator circuit 724 applies impulses to each of the inductor discharge circuit 726, 728, 730, 732, which drive the corresponding inductor sections L1, L2, L3, L4. Detailed descriptions of the battery voltage doubler circuit 722, the pulse generator circuit 724, and the inductor discharge circuit 726, 728, 730, 732 is provided in connection with FIGS. 40-43.

Figure 40:
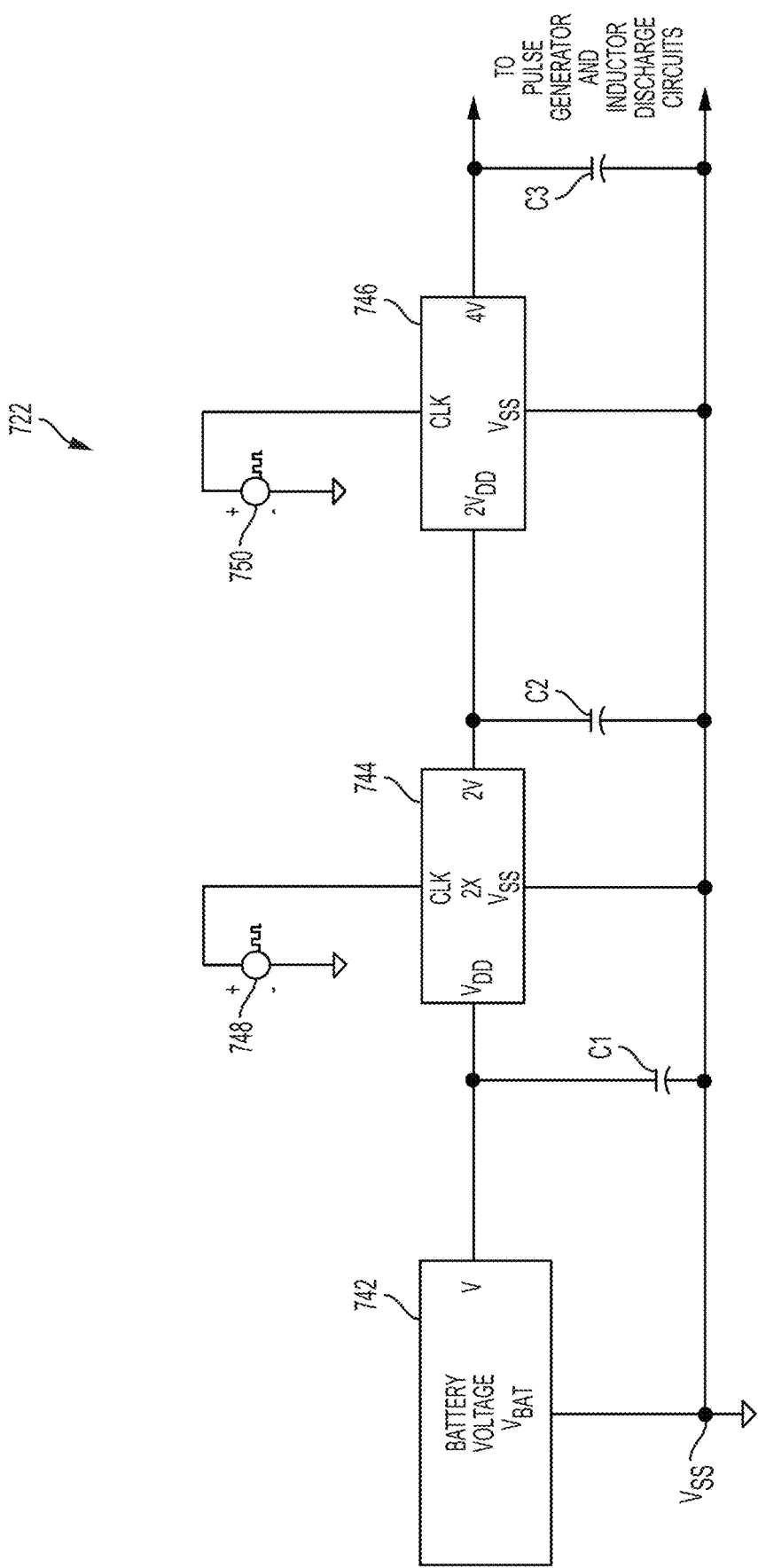
FIG. 40 is a block diagram of the battery voltage doubler circuit shown in FIGS. 38 and 39, according to one aspect of the present disclosure.

FIG. 40 is a block diagram of the battery voltage doubler circuit 722 shown in FIGS. 38 and 39, according to one aspect of the present disclosure. The battery voltage doubler circuit 722 includes a battery voltage 742 $V_{BAT}$ coupled to the input of a first voltage doubler circuit 744 and the output of the first voltage doubler circuit 744 $2*V_{BAT}$ is coupled to the input of a second voltage doubler circuit 746. The output of the second voltage doubler circuit 746 $4*V_{BAT}$ is applied to the pulse generator circuit 724 and the inductor discharge circuits 726, 728, 730, 732.

The multiplier 744, 746 may be employed where the supply voltage (from a battery for instance) is lower than the voltage required by the circuitry. MOSFET circuits are commonly the standard logic block in many integrated circuits. For this reason the diodes are often replaced by this type of transistor, but wired to function as a diode—an arrangement called a diode-wired MOSFET. Capacitors C1, C2, C3 stabilize the output voltages of the battery $V_{BAT}$, the first voltage doubler circuit 744 $2*V_{BAT}$, and the second voltage doubler circuit 746 $4V_{BAT}$.

In one aspect, each voltage doubler circuit 744, 746 may comprise a charge pump, or multiplier, comprising a cascade of diode/capacitor cells with the bottom plate of each capacitor driven by a clock pulse train supplied by clock oscillator circuits 748, 750. The circuit takes a DC input $V_{BAT}$ from the system battery 742 with the clock trains providing the switching signal. The multiplier normally requires that alternate cells are driven from clock pulses of opposite phase.

Figure 41:
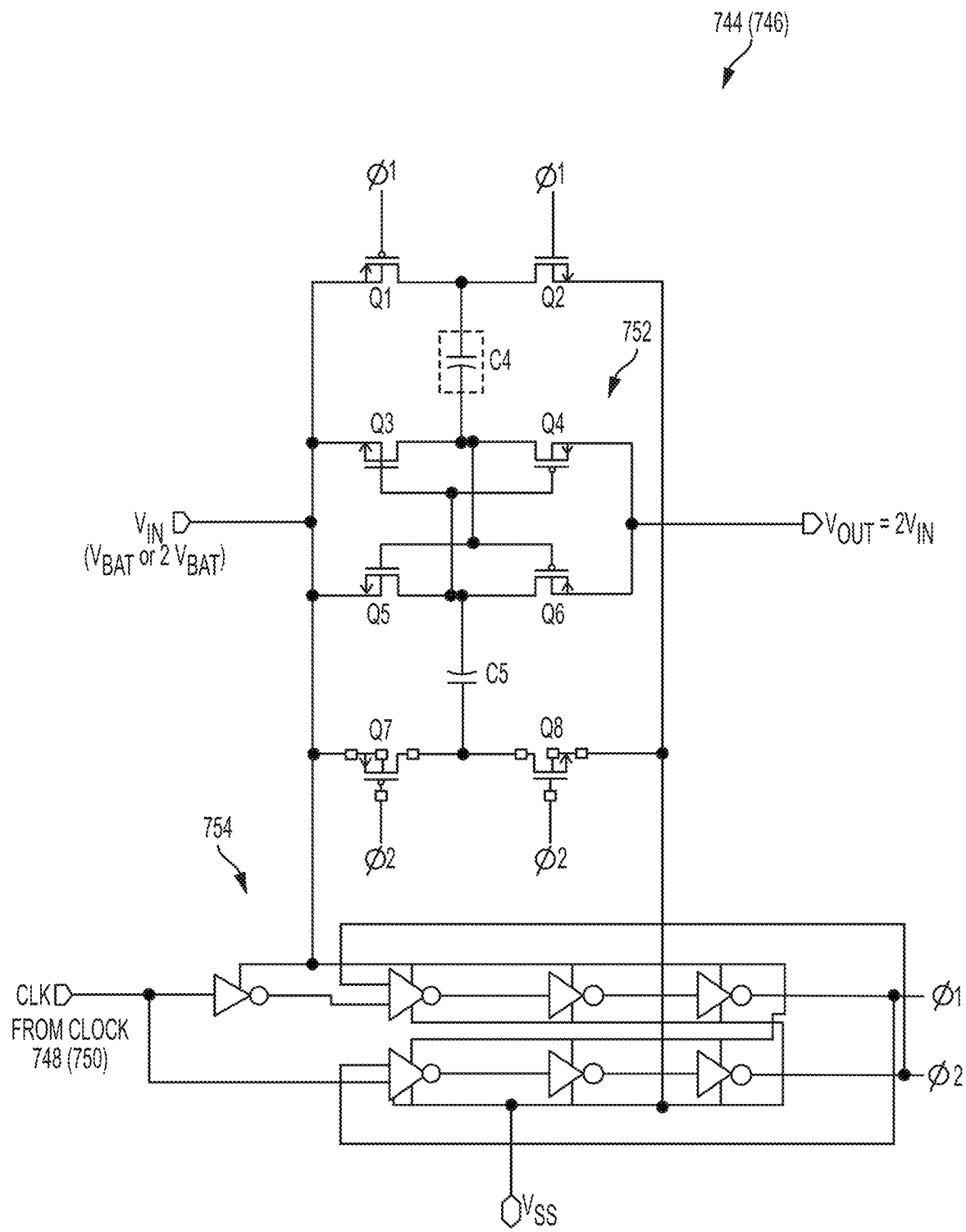
FIG. 41 is a schematic diagram of each voltage doubler circuit stage shown in FIG. 40, according to one aspect of the present disclosure.

FIG. 41 is a schematic diagram of a voltage doubler circuit 744 (746) stage shown in FIG. 40, according to one aspect of the present disclosure. The cross-coupled switched capacitor circuits continue to supply power when it has discharged to under one volt. The voltage doubler circuit 744 (746) comprises a switched capacitor stage 752 and a clock stage 754. The clock stage 754 receives a pulse train at the clock input CLK from the clock oscillator circuit 748 (750) and produces clock pulses of opposite phases φ1 and φ2. When clock φ1 is low transistors Q1 and Q4 are turned on and transistors Q2 and Q3 are turned off and the voltage on capacitor C4 is applied to the output Vout. At the same time clock φ2 is high turning off transistors Q6 and Q7 and turning on transistors Q5 and Q8 resulting in capacitor C5 being charged to Vin. When clock φ2 goes low, the voltage across capacitor C5 is pushed to twice Vin (2Vin), transistors Q6 and Q7 are turned on and transistors Q5 and Q8 are turned off, and 2Vin is applied to the output such that Vout=2Vin. On the next half cycle the roles are reversed such that clock φ1 is high and clock φ2 is low, transistors Q1 and Q4 are turned off and transistors Q2 and Q3 are turned on to charge capacitor C4 to Vin. At the same time transistors Q6 and Q7 are turned off and transistors Q5 and Q8 are turned on such that the voltage on C5, 2Vin, is applied to the output. When clock φ1 goes low, the voltage across capacitor C4 is pushed to twice Vin (2Vin), transistors Q1 and Q4 are turned on and transistors Q2 and Q3 are turned off, and 2Vin is applied to the output such that Vout=2Vin. Thus, the output Vout is supplied with 2Vin alternately from each side of the circuit.

The implementation of the voltage doubler circuit 744 (746) stage described in FIG. 41 provides low loss because there are no diode-wired MOSFETs and their associated threshold voltage problems. The circuit 744 (746) also has the advantage that the ripple frequency is doubled because there are effectively two voltage doubling circuits both supplying the output from out of phase clocks φ1, φ2.

Figure 42:
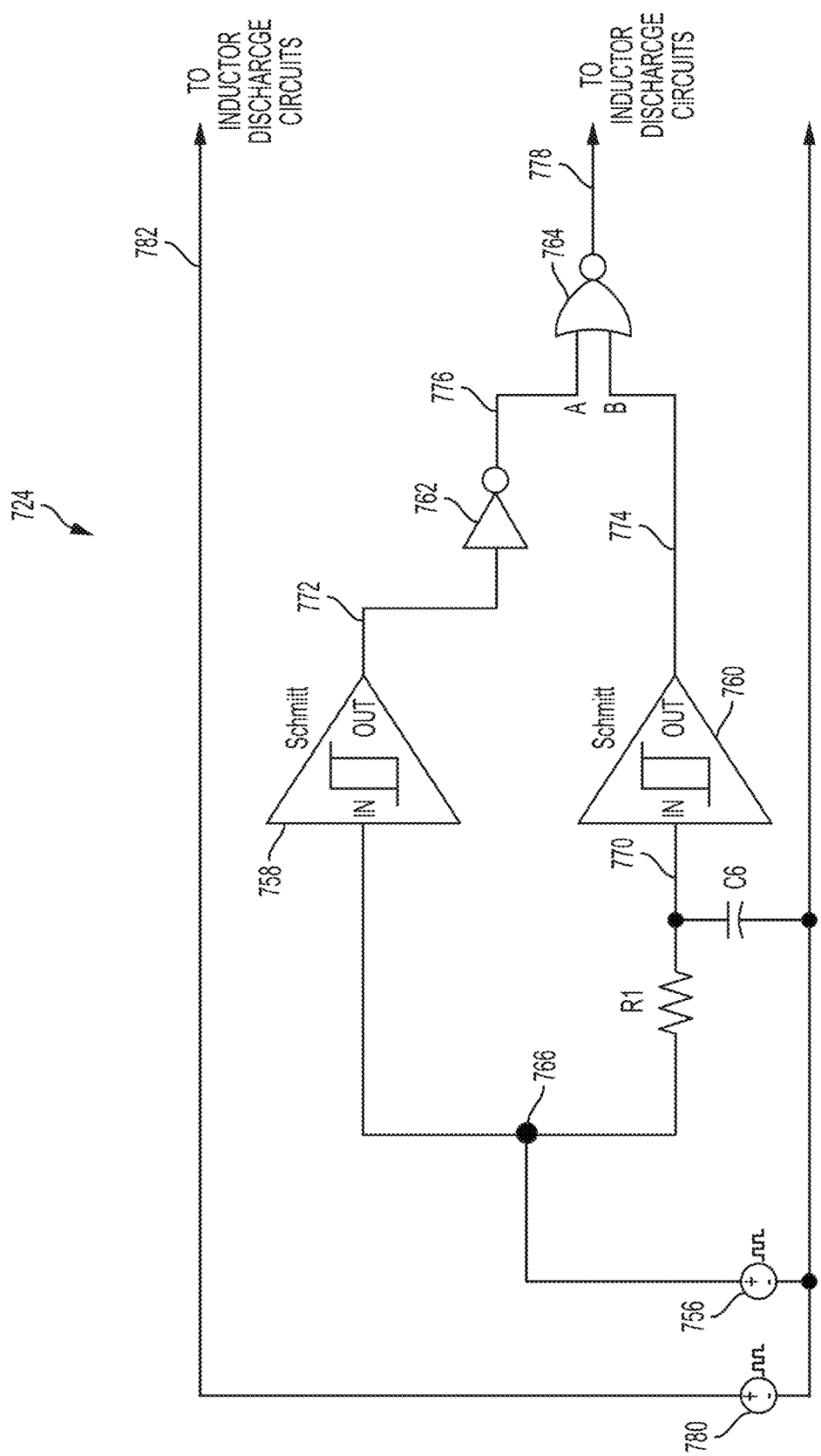
FIG. 42 is a schematic diagram of the pulse generator circuit shown in FIGS. 38 and 39, according to one aspect of the present disclosure.

FIG. 42 is a schematic diagram of the pulse generator circuit 724 shown in FIGS. 38 and 39, according to one aspect of the present disclosure. The pulse generator circuit 724 comprises first and second Schmitt triggers 758, 760, an RC circuit comprising R1 and C6 to set a time constant delay τ at the input of the second "delayed" Schmitt trigger 760, an inverter 762, and a NOR logic gate 764. In electronics, a Schmitt trigger 758, 760 is a comparator circuit with hysteresis implemented by applying positive feedback to the noninverting input of a comparator or differential amplifier. It is an active circuit which converts an analog input signal to a digital output signal. The circuit is named a "trigger" because the output retains its value until the input changes sufficiently to trigger a change. In the non-inverting configuration, when the input is higher than a chosen threshold, the output is high. When the input is below a different (lower) chosen threshold the output is low, and when the input is between the two levels the output retains its value. This dual threshold action is called hysteresis and implies that the Schmitt trigger 758, 760 possesses memory and can act as a bistable multivibrator (latch or flip-flop). There is a close relation between the two kinds of circuits: a Schmitt trigger can be converted into a latch and a latch can be converted into a Schmitt trigger.

A first oscillator 756 provides a clock train to the input 766 of the first Schmitt trigger 758 and simultaneously to the input of resistor R1 of the R1, C6 circuit. Thus, the clock signal appearing at the input 770 of the second Schmitt trigger 760 is delayed by τ set by the R1, C6 circuit. Accordingly, assuming that the first and second Schmitt triggers 758, 760 have similar internal propagation delay properties, the output 774 of the second "delayed" Schmitt trigger 760 is delayed from the output 772 of the first Schmitt trigger 758 by a time constant τ=R1*C6 seconds. The output 772 of the first "undelayed" Schmitt trigger 758 is inverted by the inverter 762 and the output 776 of the inverter 762 is applied to input A of the NOR gate 764. The output 774 of the second "delayed" Schmitt trigger 760 is applied to input B of the NOR gate 764. The output 778 of the NOR gate 764 is a series of impulses that are applied to one input of the inductor discharge circuits 726, 728, 730, 732 (FIGS. 38, 39). A second oscillator 780 provides a clock train 782, which is applied to another input of the inductor discharge circuits 726, 728, 730, 732 (FIGS. 38, 39).

Figure 43:
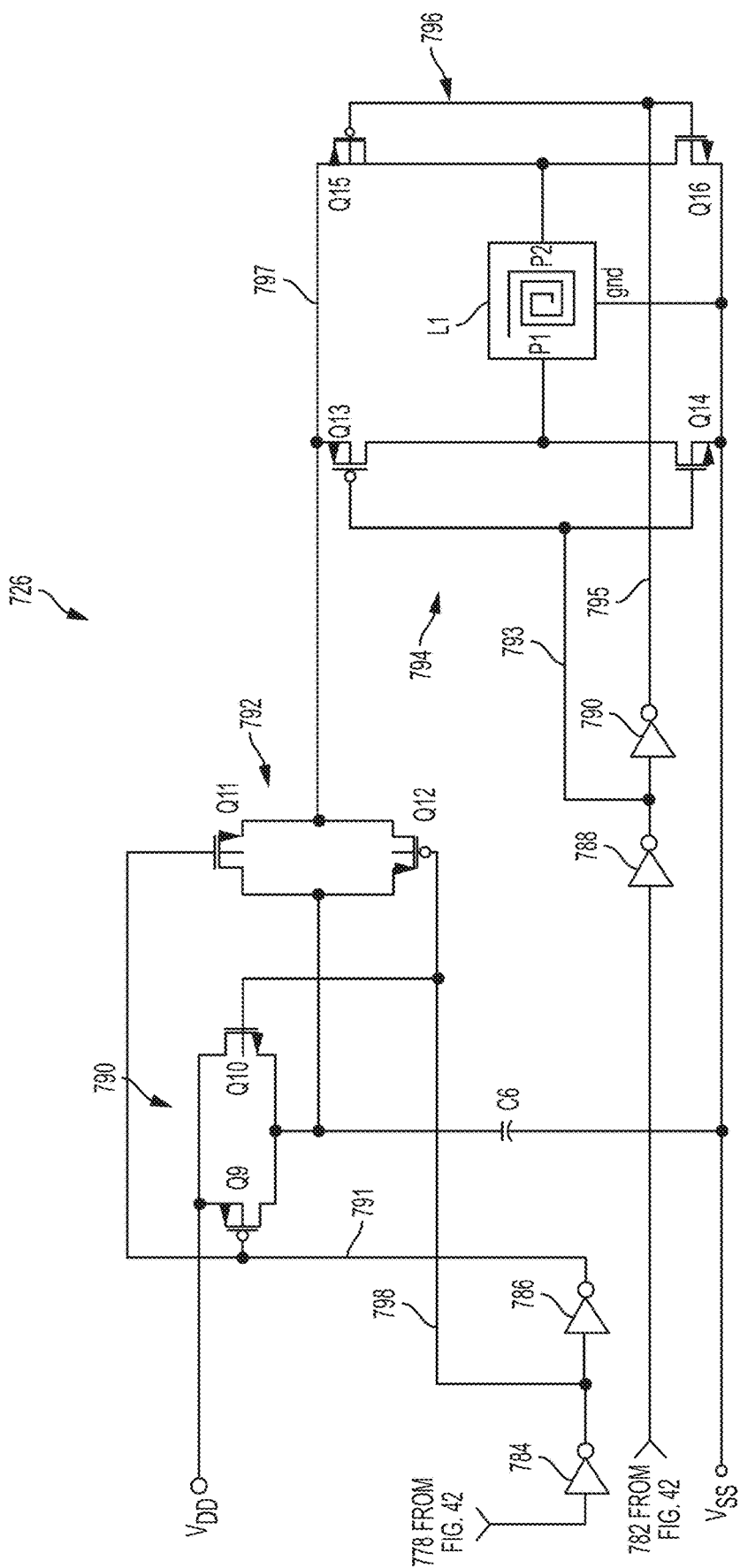
FIG. 43 is a simplified schematic diagram of an inductor discharge circuit 726 shown in FIGS. 38 and 39, according to one aspect of the present disclosure.

FIG. 43 is a simplified schematic diagram of an inductor discharge circuit 726 shown in FIGS. 38 and 39, according to one aspect of the present disclosure. As described herein, the inductor discharge circuit 726 is coupled to the pulse generator circuit 724 (FIG. 42). In this "charge pump" configuration, the inductor discharge circuit 726 is applied to one of N-layers of inductors. The inductor section L1 is connected in mono-phasic mode. As described herein, the inductor section L1 includes two ports P1 and P2 to couple the inductor section L1 to corresponding circuit structures of the inductor discharge circuit 726.

The inductor discharge circuit 726 comprises a capacitor charging circuit 790, a coupling circuit 792, and inductor section L1 charging and discharging circuits 794, 796. The inductor discharge circuit 726 receives a series of impulses from the output 778 of the NOR gate 764 (FIG. 42). The series of impulses are applied to a first inverter 784. The output 798 of the first inverter 784 is applied to the gate of transistor Q10 of the capacitor charging circuit 790, to the gate of the transistor Q12 of the coupling circuit 792, and to the input of a second inverter 786. The output 791 of the second inverter 786 is applied to the gate of transistor Q9 of the capacitor charging circuit 790 and the gate of transistor Q11 of the coupling circuit 792. When the input to the first inverter is low, transistors Q9 and Q10 are turned on and transistors Q11 and Q12 are turned off to charge the capacitor C6. When the input to the first inverter is high, transistors Q9 and Q10 are turned off and transistors Q11 and Q12 are turned on apply the voltage on the capacitor C6 to the input 797 of the discharging circuits 794, 796.

A second oscillator 780 provides a clock train 782, which is applied to a third inverter 788. The output 793 of the third inverter 788 is applied to the gates of transistors Q13 and Q14 and to the input of a fourth inverter 790. The output 795 of the fourth inverter 790 is applied to the gates of transistors Q15 and Q16 such that the transistors Q13, Q16 and transistors Q14, Q15 are alternately turned on and off. For example, when the input of the third inverter 788 is high, transistors Q13 and Q16 are turned on and transistors Q14 and Q15 are turned off. Thus port P1 the inductor section L1 is coupled to the capacitor voltage at input 797 through transistor Q13 and port P2 of the inductor section L1 is coupled to $V_{SS}$ through transistor Q16. When the input to the third inverter 788 goes low, the roles are reversed such that transistors Q14 and Q15 are turned on and transistors Q13 and Q16 are turned off. Thus port P2 of the inductor section L1 is coupled to the capacitor voltage at input 797 through transistor Q15 and is port P2 of inductor section L1 is coupled to $V_{SS}$ through transistor Q14. As the series of impulses arrive from the output 778 of NOR gate 764 (FIG. 42) and the clock train 782 from the second oscillator 780 (FIG. 42), the capacitor section L1 is alternately charged and discharged to create an electromagnetic signal.

Thus, the inductor discharge circuit 726 pumps charge into the capacitor C6 and then discharges capacitor C6 into the inductor section L1 over a very short discharge cycle relative to duty cycle to provide a transmission protocol. The operation of the other inductor discharge circuits 728, 730, 732 is similar to the inductor discharge circuit 726 and will not be repeated here for conciseness and clarity of disclosure.

Impulse Communication Protocols

In some aspects, an impulse communication protocol is defined for transmitting a signal from the ingestible identifier (e.g., ingestible identifier 104) and for being, received, detected and decoded by a receiver (e.g., any of receivers 106, 108, 110, 112, 114, 116, 118, 150, 152). Typically, the ingestible identifiers of the present disclosures are extremely small and inexpensive systems. Their cost and/or size limits the inclusion of components typically used to create better signal quality, such as adding a crystal to the circuit to precisely tune the oscillator to a known frequency. This tends to enable the receiver to know the actual frequency of the ingestible receiver to within +/−5-10% initially. Furthermore, the biogalvanic battery voltage and current output of an ingestible identifier tends to change throughout the transmission sequence. Because of the limited size, the amplitude of the signal tends to be very weak compared to any noise. Because of the very limited resources on the transmitter (ingestible identifier) side, it may be desirable to resort to just a one-way communication protocol, which necessarily prevents any acknowledgement, confirmation of syncing, or any response message from being transmitted from the receiver and received at the ingestible identifier. Furthermore, multiple ingestible identifiers may be active in a user at the same time, each transmitting similar (and possibly changing) signals that a single receiver would need to pick up before their respective battery lives run out. The system constraints herein strongly suggest that the burden for properly communicating a signal lies with the receiver, in that the receiver must be configured to account for an initially imprecise signal frequency, a possibly changing voltage and current output, a signal with a natively low signal to noise ratio, identification without any reciprocol communication, and multiples of these transmission sequences.

Aspects of the present disclosure address at least some of these issues by disclosing an impulse communication protocol that utilizes a series of electromagnetic pulses generated by the inductor in the ingestible identifier. These electromagnetic pulses may be transmitted according to one of the variations of the protocol defined herein below, and may be correspondingly received, detected, and decoded by the receiver according to the same protocol. The various examples of this impulse communication protocol may also be referred to herein as a "spike" protocol.

In general, the spike protocol may be initiated by the impulse system of the ingestible identifier accumulating charge from the battery and releasing it through the inductor in a very short period, thus producing a higher amplitude signal for a shorter duration than what would be obtained from a continuous wave. To produce this, the control circuit defines a gap between the pulses. Correspondingly, the receiver takes advantage of this by looking for a signal only where there should be spikes, ignoring the time between spikes. For example, if there are 10 spikes each of 1 µs duration in a 1000 µs period, all of the signal energy is compressed into 1% of the time. If the detector (e.g., receiver) ignores the data between pulses, then only 1% of the noise that is present during that period is actually competing w/ the signal energy. By comparison, in a typical "resonant system," the signal energy would be uniformly distributed over the entire 1000 µs and all of the noise in that period would compete with the signal energy. Thus, the spike protocol can improve the signal to noise ratio by, in this example, 100×. The SNR improvement is inversely related to the duty cycle.

In addition, the spike protocol may allow for the detection of multiple ingestible identifiers that are ingested simultaneously without interference between the signals. This is accomplished because unless two signals have exactly the same transmission frequency and phase, the pulses of a coincident signal will appear in the gaps between pulses and thus ignored.

Figure 44:
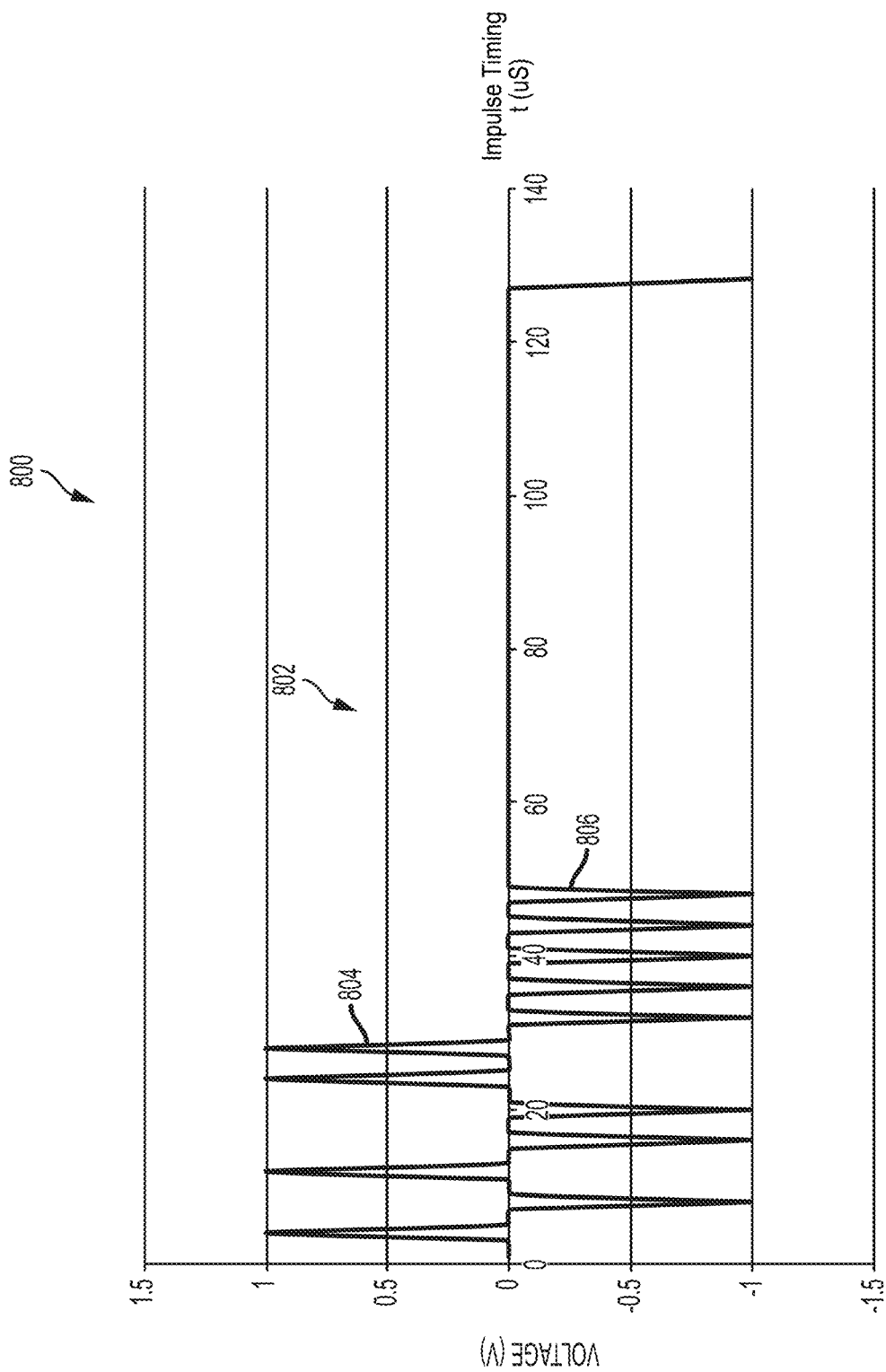
FIG. 44 is a timing and polarity diagram of an impulse communication protocol that may be generated by the impulse inductor driver circuit shown in FIGS. 38-43, according to one aspect of the present disclosure.

FIG. 44 is a timing and polarity diagram 800 according to one example of the spike protocol that may be generated by the impulse inductor driver circuit 720 shown in FIGS. 38-43, according to one aspect of the present disclosure. The vertical axis represents voltage (V) and the horizontal axis represents "impulse timing" time (µs). The impulse function 802 comprises a series of impulses 804, 806 of different polarity over a predetermined period (~130 µs) or time frame. The impulse function 802 encodes information associated with the ingestible identifier as discussed herein. The positive impulses 804 have a positive polarity (+1V) or amplitude and the negative impulses 806 have a negative polarity (−1V) or amplitude. The impulse function 802 is generated by the impulse inductor circuit 720 and is transmitted by the inductor acting as a transmission antenna. The impulse or spike protocol may be biphasic or monophasic.

As described herein, the transmission protocol is implemented by charging a capacitor C (e.g., C6, FIG. 43) and then discharging the capacitor over a very short discharge cycle relative to duty cycle into an inductor section L (e.g., L1, FIG. 43), as discussed in connection with the impulse inductor driver circuit 720 in FIGS. 38-43. The impulse protocol is a series of +/− or off/on sequences at 128 locations, for example. All the energy is put into ~13 pulses, and the noise is distributed over 128 pulses, which improves the noise per bit figure in this example. Accordingly, the spike protocol may also be referred to herein as a "sparse impulse" code. An example of the impulse protocol is described hereinbelow.

Accordingly, in one aspect, the "sparse impulse" code can be implemented as follows:

| | | |
|---|---|---|
| gaps | = | [3 3 3 3 3 3 3 3 3 3 3 3 79]; |
| impulseNoGapsMask | = | [1 −1 1 −1 −1 1 1 −1 −1 −1 −1 −1 −1]; |
| impulses | = | [ ]; % load in impulse pattern |
| for i = 1:13 | | |
| a | = | impulseNoGapsMask(i); |
| g | = | zeros(1,gaps(i)); |
| impulses | = | [impulses g a]; % variable duty cycle |
| End | | |
| code | = | [0 1 0 0 1 1 0 0 0 1 1 1 0 0 0 0 1 1 1 1 0 0 1 1]; |

Code is the data packet, it is preceded by 12 zeros (sync) and a [1 0 1 0] (preamble). The symbol definition works this way: an "impulse" (discharge of the capacitor through the coil, with polarity determined by impulseNoGapsMask) is preceded by a number of no-impulses (zeros), the number coming from "gaps."

So the "Impulse" "one" ends up as 128 zeroes followed by the following 128 chip sequence:

| | | | | | | | | | | | | | | | |
|---|---|---|---|---|---|---|---|---|---|---|---|---|---|---|---|
| 0 | 0 | 0 | 1 | 0 | 0 | 0 | −1 | 0 | 0 | 0 | 1 | 0 | 0 | 0 | −1 |
| 0 | 0 | 0 | −1 | 0 | 0 | 0 | 1 | 0 | 0 | 0 | 1 | 0 | 0 | 0 | −1 |
| 0 | 0 | 0 | −1 | 0 | 0 | 0 | −1 | 0 | 0 | 0 | −1 | 0 | 0 | 0 | −1 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | 0 |

| | | | | | | | | | | | | | | | |
|---|---|---|---|---|---|---|---|---|---|---|---|---|---|---|---|
| 0 | 0 | 0 | 0 | 0 | 0 | 0 | 0 | 0 | 0 | 0 | 0 | 0 | 0 | 0 | 0 |
| 0 | 0 | 0 | 0 | 0 | 0 | 0 | 0 | 0 | 0 | 0 | 0 | 0 | 0 | 0 | −1 |

In this definition, 128 "sub-chips," where a sub-chip is defined as either a +1 spike, a −1 spike, or no spike, make up a single chip. 64 chips make up a symbol. In this definition, there is a 1:1 correspondence between the symbol and a bit. A zero in this case is the following sequence below, followed by 128 zeroes:

| | | | | | | | | | | | | | | |
|---|---|---|---|---|---|---|---|---|---|---|---|---|---|---|
| 0 | 0 | 0 | −1 | 0 | 0 | 0 | 1 | 0 | 0 | 0 | −1 | 0 | 0 | 0 1 |
| 0 | 0 | 0 | 1 | 0 | 0 | 0 | −1 | 0 | 0 | 0 | −1 | 0 | 0 | 0 1 |
| 0 | 0 | 0 | 1 | 0 | 0 | 0 | 1 | 0 | 0 | 0 | 1 | 0 | 0 | 0 1 |
| 0 | 0 | 0 | 0 | 0 | 0 | 0 | 0 | 0 | 0 | 0 | 0 | 0 | 0 | 0 0 |
| 0 | 0 | 0 | 0 | 0 | 0 | 0 | 0 | 0 | 0 | 0 | 0 | 0 | 0 | 0 0 |
| 0 | 0 | 0 | 0 | 0 | 0 | 0 | 0 | 0 | 0 | 0 | 0 | 0 | 0 | 0 0 |
| 0 | 0 | 0 | 0 | 0 | 0 | 0 | 0 | 0 | 0 | 0 | 0 | 0 | 0 | 0 0 |
| 0 | 0 | 0 | 0 | 0 | 0 | 0 | 0 | 0 | 0 | 0 | 0 | 0 | 0 | 0 1 |

In this sequence, each chip is 1 μs, each symbol is thus 128 μs, and each bit is 64*128=8192 μs.

In one aspect, a "very sparse impulse" code may be employed. A "very sparse impulse" code is where the gap between the impulses is ~998 times the width of the impulse. This will give the ingestible identifier more time for the charge pump to develop maximum voltage on the capacitor before discharging it. Likely this aspect will not vary the gap length between impulses, except during transitions between bits.

In one aspect, the pulses may be very short. Transmission frequencies can occur at frequencies in the range of ~12.5 kHz to ~20 kHz or greater than ~24 kHz and as high as ~10 MHz, for example. The impulses are not deterministic, but they repeat over 128 pulses at a repetition rate of ~6 kHz. Battery readiness is random and battery impedance (Z) and voltage ($V_{BAT}$) may fluctuate. The pulse width and repetition rate can be adjusted based on the current condition of the battery. These types of protocols can be adapted in Internet of things type circuits.

Figure 45:
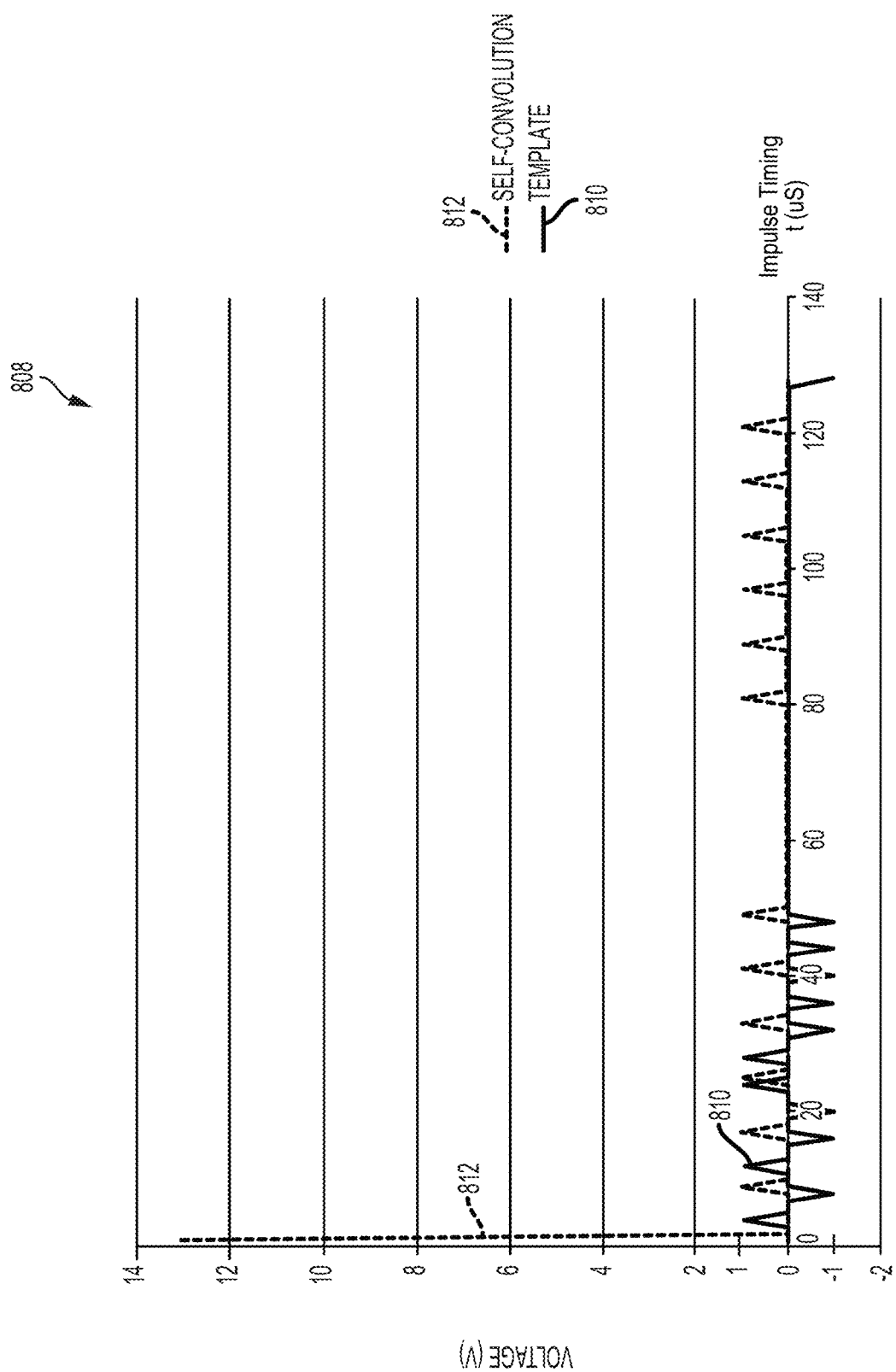
FIG. 45 is a sparse impulse template and self-convolution diagram of the impulse communication protocol shown in FIG. 44, according to one aspect of the present disclosure.

FIG. 45 is a sparse impulse template and self-convolution diagram 808 of the impulse communication protocol shown in FIG. 44, according to one aspect of the present disclosure. The vertical axis represents voltage (V) and the horizontal axis represents "impulse timing" time (μs). A template impulse function 810 (shown in solid line) is representative of the impulse function 802 shown in FIG. 44. The self-convolution of the template impulse function 810 generates a self-convolution function 812 (shown in dashed line). The self-convolution function 812 is the autocorrelation of the impulse function 802. The autocorrelation or self-convolution of the impulse function 802 is a cross-correlation of the impulse function 802 with itself at different points in time. Generally speaking, it is the similarity between observations as a function of the time lag between them. The self-convolution function 812 is a mathematical tool for finding repeating patterns, such as the presence of a periodic signal obscured by noise, or identifying the missing fundamental frequency in a signal implied by its harmonic frequencies. It can be used by a receiver to identify the transmit or broadcast frequency. Accordingly, the impulse function 802 transmitted through space is detected by a receiving antenna of a receiver. The receiver includes signal processing circuits to implement functions to identify the transmission frequency of the impulse function 802. The receiver is configured to determine the transmit frequency by employing the template impulse function 810 as well as the self-convolution function 812 (or autocorrelation) of the template impulse function 810.

Figure 46:
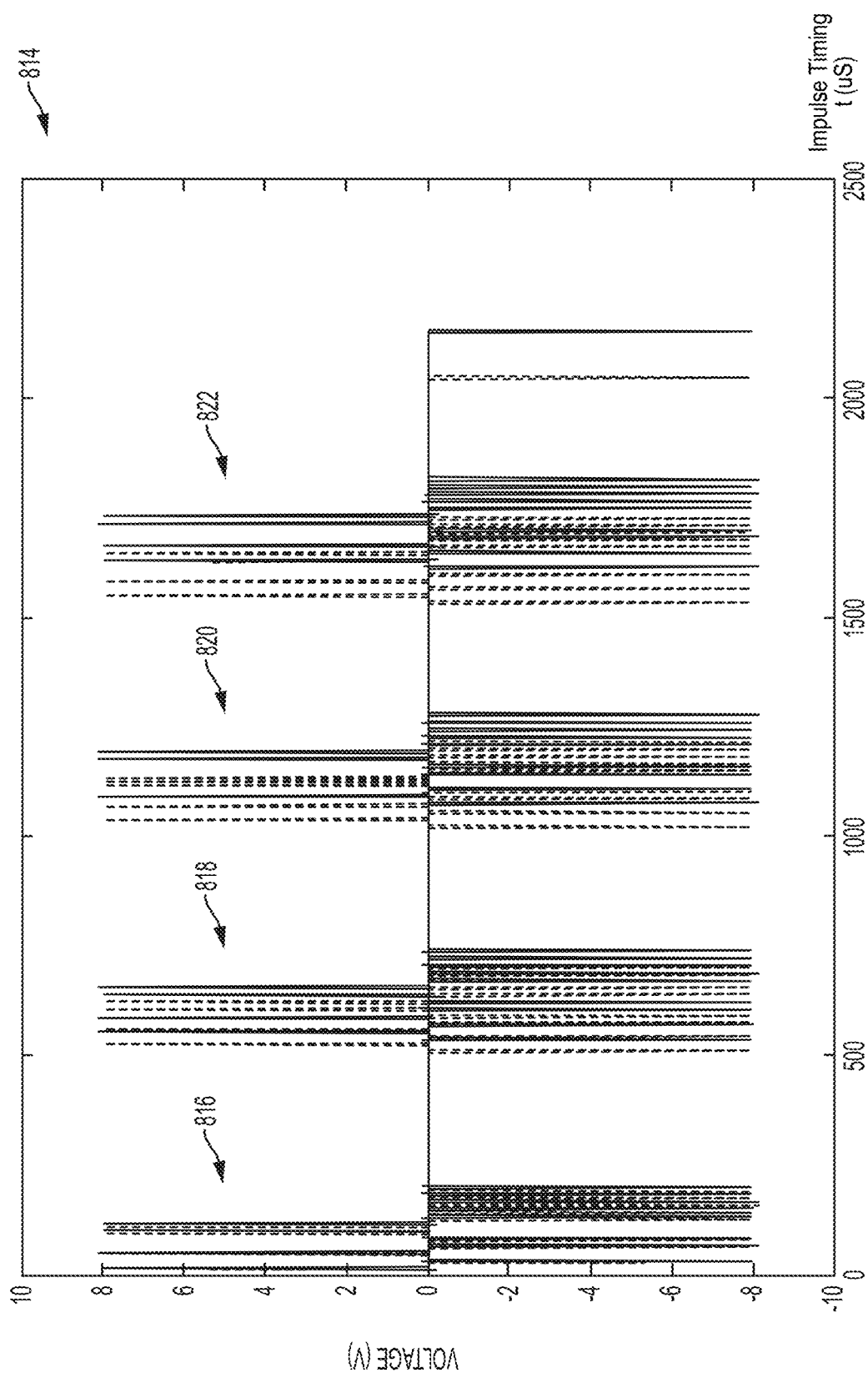
FIG. 46 is a variable template diagram that may be employed to identify the transmit frequency of the impulse function shown in FIG. 44, according to one aspect of the present disclosure.

FIG. 46 is a variable template diagram 814 that may be employed to identify the transmit frequency of the impulse function 802 shown in FIG. 44, according to one aspect of the present disclosure. The vertical axis represents voltage (V) and the horizontal axis represents "impulse timing" time (μs). The template diagram 814 shows the variable templates 816, 818, 820, 822 for the lowest (template 816) to the highest (template 822) broadcast frequencies used to transmit the impulse function 802.

According to some aspects, one definition of the spike protocol utilizes two sequences of sparse pulses, referred to herein as a "zero" chip and a "one" chip. Referring to FIG. 62, plot 1800 shows an example of the "zero" chip sequence of pulses, and plot 1810 shows an example of the "one" chip sequence of pulses. Note that the zero is different than the one, and there is a shift in phase from one to the other. For the chip definitions shown, available operations include calculating the autocorrelations and cross correlations of the chips: 0×0, 1×1, 0×1, 1×0, (0+1)×(0+1). Note that in this scheme, the (0×1) and (1×0) correlations are not as important as in other protocols that do not combine the all of the chips to determine the alignment of the starting frame. Since this protocol uses all of the available data to determine the starting point, only the combined convolution, (0+1)×(0+1) is important. Ideally, this convolution would have the maximum value at precise alignment and zero everywhere else. This particular set of chip definitions does not accomplish that, but does provide a convolution where the "side-lobes" are relatively small and, the biggest of the side lobes are of opposite polarity and conveniently located near the peak. These side lobes can also help in establishing the "best guess" alignment.

Figure 63:
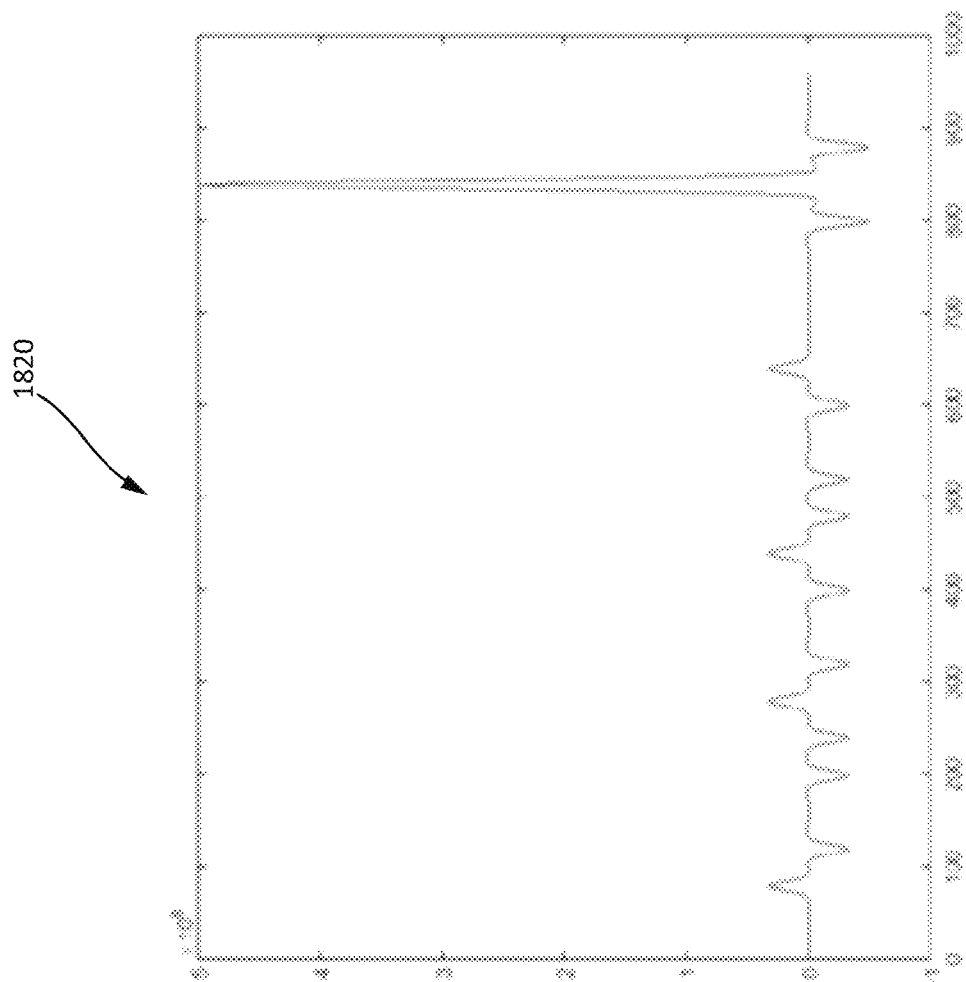
FIG. 63 shows a plot of combined (0+1) data correlated with a template, illustrating how both frequency and alignment is found: the highest peak determines both.

FIG. 63 shows a plot 1820 of combined (0+1) data correlated with a template, illustrating how both frequency and alignment is found: the highest peak determines both. This is a relatively high SNR case. It should also be noted that these two chip definitions produce the combined convolution only if there is an equal number of zeros and ones in the data packet. This is because the chip definitions do not have an equal number of up and down spikes in them.

To decode this spike protocol, the decoder module (e.g., processing in the receiver) looks for a single packet to decode. Both the frequency and start times of the two packets are unknown. It does this by looking in a window that is 1.5× the maximum packet size (since it is not known where the registration packet is within the frame, so this assures that a complete packet is obtained), and then incrementing the window by 0.5× packet distance, according to some aspects. The data from each of these thirds can be reused, so each frame actually analyzes one third of the data, keeping ⅔ of the data from the previous analysis.

In some aspects, the analog data from the ingestible identifier is digitized and stored into frames of data that are equal to the maximum packet length (lowest transmission frequency). Two of these frames are analyzed at a time, and the analysis information from each frame is stored and reused when the next frame is added.

To decode the packet, one needs to find the precise timing between these pulses, and also the starting point of the communication. Thus, the impulse pattern is designed so that if the assumed timing between pulses is correct and the assumed starting point is correct, the corresponding correlation product will be very large compared to if either is off, even by a small amount. Thus, referring back to FIG. 56, plot 1200 shows the correlation product (autocorrelation) for the best-guess starting point for a variety of impulse timing variations. Notice the broad range of impulse timing variation (0-1000 μs is the variation from nominal, actually +/−500 μs).

From here, to find the "best-guess starting point" for each of these impulse timing variations in a computationally efficient manner, the first step, for each impulse timing assumption, is to perform a "Stretch or Squeeze" process of the sampled points into a nominal (i.e., predefined reference amount) frame of a nominal number of sample points. Thus, if the time between impulses is less than nominal, the sampled points for each set of, say, 13 spikes, must be "stretched" into the number of sample points that would represent the nominal timing between spikes. On the other hand, if the time between spikes is greater than nominal, then the number of samples needed to gather all 13 spikes is greater than nominal, and the data needs to be "squeezed" into the nominal number of sample points. This "stretching and squeezing" is to be done in a way that the starting point of the communication packet is still unknown, but is preserved in the "stretched/squeezed" data. A more detailed example of performing this stretch and squeeze operation is defined below in the second example spike protocol definition.

Next: the communication packet may be, for example, 40 bits long, and each bit may be represented by, for example, 64 identical chips per symbol, and each chip may be represented by, for example, 13 spikes. Thus, this definition would need somewhat more than 40*64=2560 "frames," where each frame represents 13 spikes (and the gaps between them). More than the number of frames should be obtained because it is not known where the packet starts at this point. How much more depends somewhat on the higher level protocol: how much time between packets? Typically, a gap between packets is desired that is at least of couple of bits wide so that when the decoding process starts looking for the start of the packet, these gaps show up as blanks.

The next step in the process is to take all 2560 (in this example) frames, stack them up, and add them together (the $1^{st}$ data point of each of the 2560 frames are added together to make the $1^{st}$ data point of the summed frame, the $2^{nd}$ data points of each frame are added together to make the $2^{nd}$ data point of the summed frame, and so on). This is an example of the "stacking and summing" operation briefly alluded to earlier. This stacking and summing operation reinforces the spikes and averages out the noise.

Figure 57:
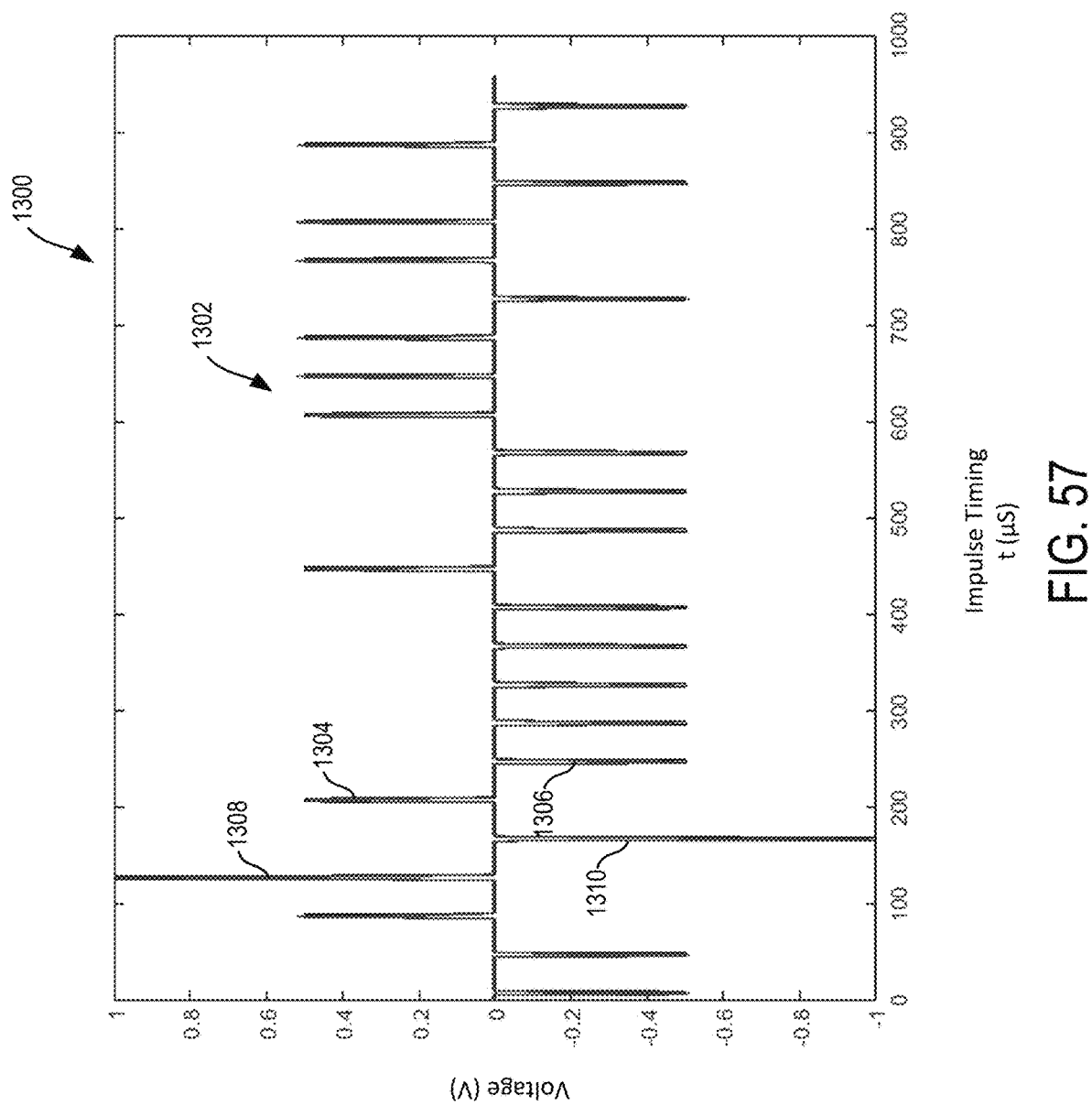
FIG. 57 is a timing and polarity diagram of an impulse communication protocol that may be generated by the impulse inductor driver circuit shown in FIGS. 38-43, according to one aspect of the present disclosure.

Thus, all of the 2560×13=33,280 spikes are represented by one frame of data of nominal size. With this frame, the starting point now needs to be determined, within the frame, for the start of each symbol and, simultaneously, the best-guess of the time between symbols. Thus, the choice of symbols for the "zero" and "one" serves two important roles: For when decoding the signal, it is useful to optimally be able to distinguish between a "one" and a "zero." This is similar to pre-existing protocols. What is new here, is that when the 26 spikes representing all of the ones and zeros of the entire transmission are combined into a single frame, they should produce a template that allows optimal identification of the starting point within the frame and the actual time between the spikes (i.e. the frequency of the transmission). FIG. 57 shows an example of such a section of symbols for "one" and "zero." The vertical axis represents voltage (V) and the horizontal axis represents "impulse timing" time (μs). The impulse function 1302 comprises a series of impulses 1304, 1306 of different polarity over a predetermined period or time frame. The impulse function 1302 encodes information associated with the ingestible identifier as discussed herein. The positive impulses 1304 have a positive polarity (+0.5V) or amplitude and the negative impulses 1306 have a negative polarity (−0.5V) or amplitude. The impulse function 1302 is generated by the impulse inductor circuit 720 and is transmitted by the inductor acting as a transmission antenna. The impulse protocol may be biphasic or monophasic.

A first pattern or series of impulses of the impulse function 1302 represent a logic 0 and a second pattern or series of impulses represents a logic 1. Two of the impulses 1308, 1310 are twice the amplitude of the other impulses 1304, 1306 because they are common to the logic 0's and the logic 1's. At the receiver side, the broadcast frequency is unknown and the time between impulses also is unknown. The receiver first identifies the broadcast frequency and then identies the bits (logic 1's and 0's) by correlating across 1000 points. The receiver then compares the received series of impulses such as the impulse function 1302 and stretches and squeezes a template until ther is match of the frequency and the starting point of a packet. Thus, the receiver looks for a specific impulse function 1302 or series of impulses and correlates across many points (e.g., 1000 points) at the correct offset. The logic 1's and 0's are orthogonal and slightly overlap, which allows the receiver to identify the frequency and polarity of the impulses.

Note that since both the symbol for "one" and the symbol for "zero" each have a spike in the $4^{th}$ and $5^{th}$ time slots, the amplitude of those spikes are double that of the rest, which are present in only one or the other. These "double peaks" thus allow one to establish the parity of the as-received signal.

Figure 58:
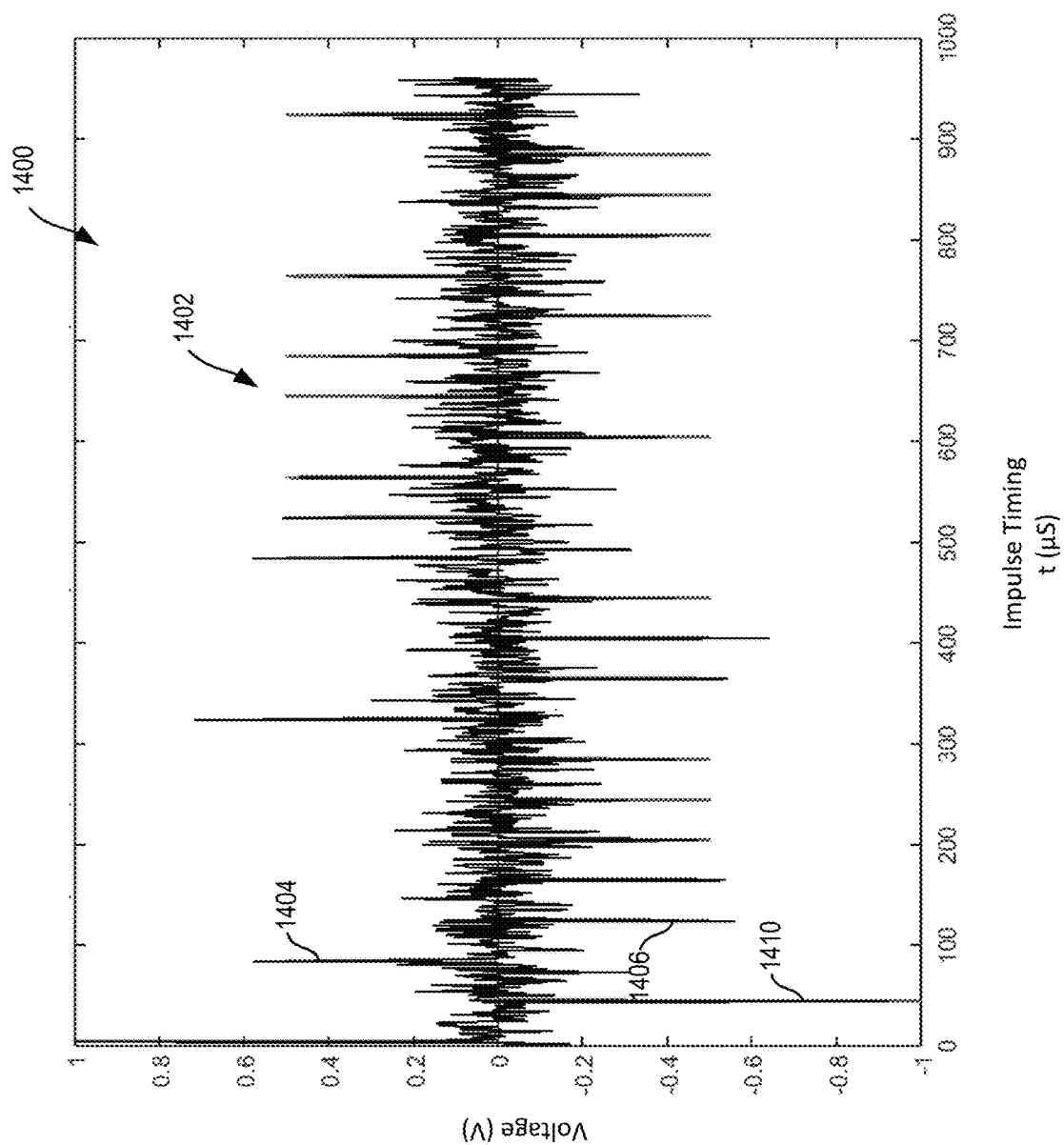
FIG. 58 is a timing and polarity diagram of an impulse communication protocol that may be received by the receiver circuits shown in FIGS. 47-53, according to one aspect of the present disclosure.
Figure 59:
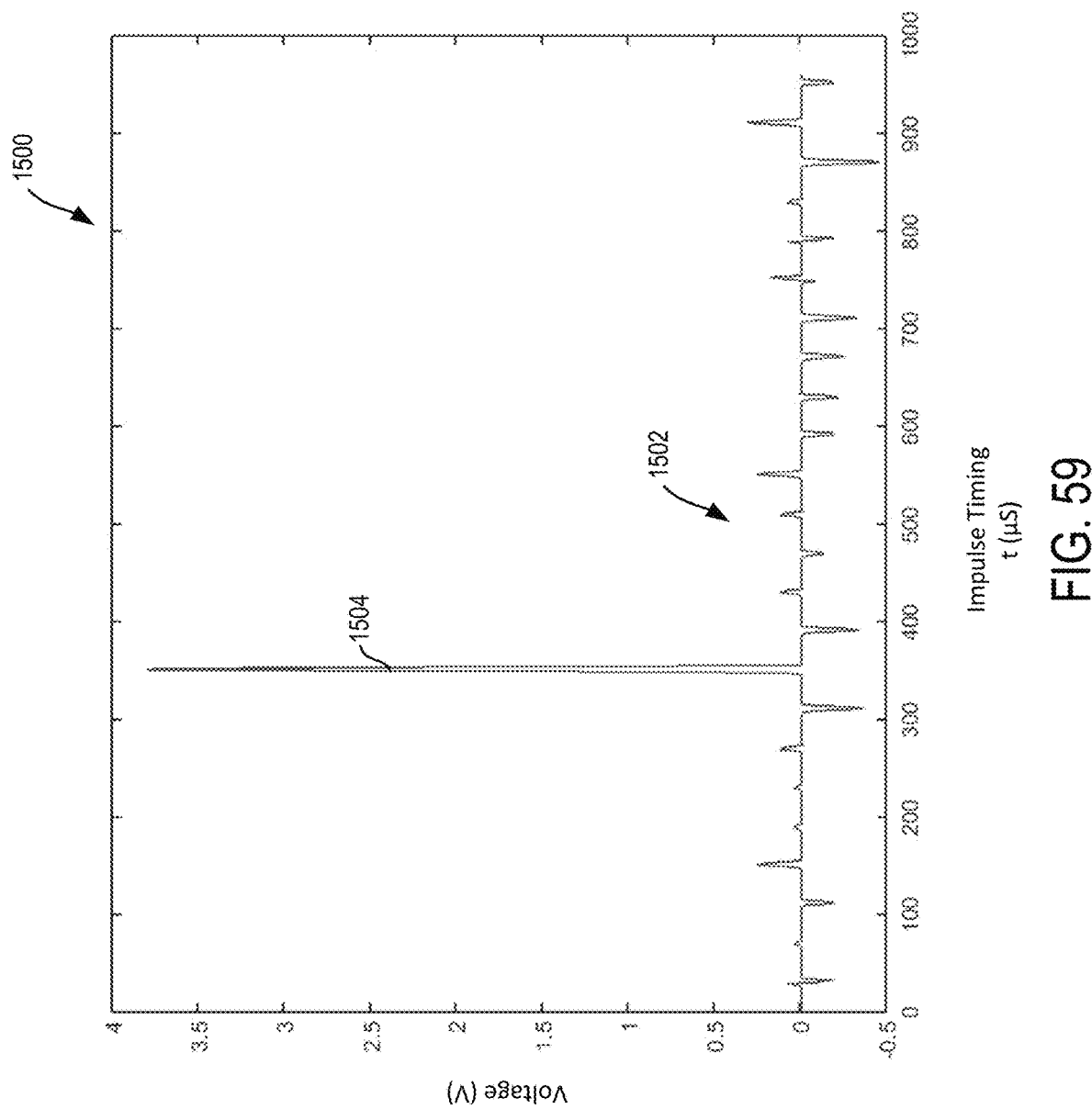
FIG. 59 is a timing and polarity diagram of an impulse communication protocol that may be received by the receiver circuits shown in FIGS. 47-53, according to one aspect of the present disclosure.

A next step is to perform a convolution operation to generate another plot based on a transformation of the data. As shown in FIG. 59, as one convolves the summed-frame data to the combined-spikes template, one finds the tallest peak when there is perfect alignment, and the "side-lobes" are much lower in amplitude. FIG. 59 is the graphical representation of a no-noise auto convolution of the summed-frame template to illustrate the relative amplitude of the side-lobes to the main lobe. The vertical axis represents voltage (V) and the horizontal axis represents "impulse timing" time (μs). The impulse function 1502 received by the receiver comprises a series of impulses 1502 of different polarity over a predetermined period or time frame. The impulse function 1502 encodes information associated with the ingestible identifier as discussed herein. The positive impulses 1404 have a positive polarity (+0.5V) or amplitude and the negative impulses 1406 have a negative polarity (−0.5V) or amplitude. The impulse function 1502 is generated by the impulse inductor circuit 720 and is transmitted by the inductor acting as a transmission antenna. The impulse protocol may be biphasic or monophasic. The reference impulse 1504 has an amplitude much higher than the series of impulses of the impulse function 1502. FIG. 58 is a graphical representation of the summed-frame for the best-guess frequency in the presence of noise whose noise maximum amplitude is 1000× higher than the maximum amplitude of each spike. This may be generated by the receiver circuits 900 (FIG. 47), 930 (FIG. 49), 950 (FIG. 50), 960 (FIG. 51), 970 (FIG. 52), 990 (FIG. 53), 1010 (FIG. 54), 1100 (FIG. 55), according to one aspect of the present disclosure. The vertical axis represents voltage (V) and the horizontal axis represents "impulse timing" time (μs). The impulse function 1402 received by the receiver comprises a series of impulses 1404, 1406 of different polarity over a predetermined period or time frame. The impulse function 1402 encodes information associated with the ingestible identifier as discussed herein. The positive impulses 1404 have a positive polarity (+0.5V) or amplitude and the negative impulses 1406 have a negative polarity (−0.5V) or amplitude. The impulse function 1402 is generated by the impulse inductor circuit 720 and is transmitted by the inductor acting as a transmission antenna. The impulse protocol may be biphasic or monophasic.

A first pattern or series of impulses of the impulse function 1402 represent a logic 0 and a second pattern or series of impulses represents a logic 1. The impulse 1410 is twice the amplitude of the other impulses 1404, 1406 because it are common to the logic 0's and the logic 1's and is the reference impulse for a new packet. At the receiver side, the broadcast frequency is unknown and the time between impulses also is unknown. The receiver first identifies the broadcast frequency and then identifies the bits (logic 1's and 0's) by correlating across 1000 points. The receiver then compares the received series of impulses such as the impulse function 1402 and stretches and squeezes a template until there is match of the frequency and the starting point of a packet. Thus, the receiver looks for a specific impulse function 1402 or series of impulses and correlates across many points (e.g., 1000 points) at the correct offset. The logic 1's and 0's are orthogonal and slightly overlap, which allows the receiver to identify the frequency and polarity of the impulses.

Figure 56:
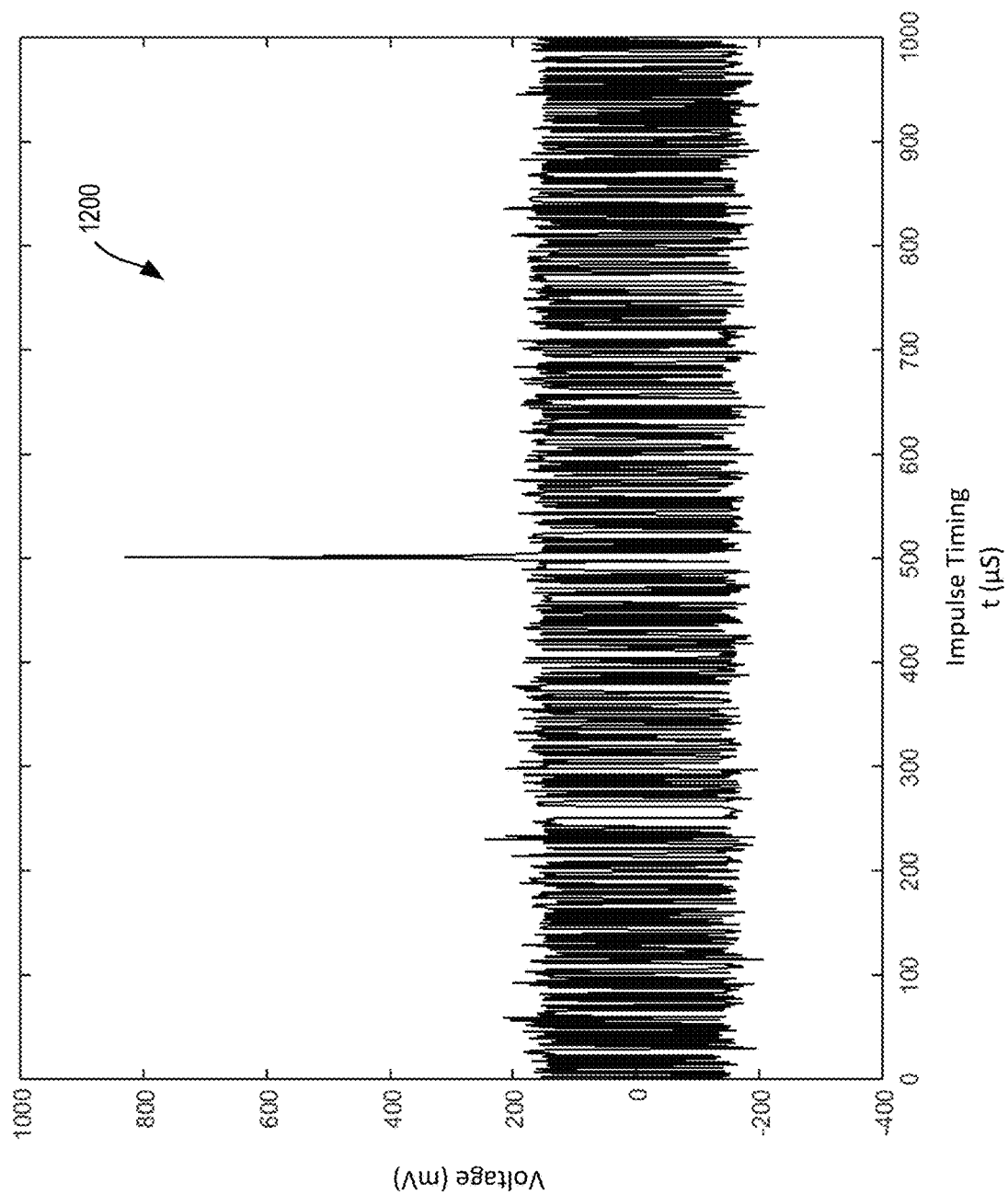
FIG. 56 is a plot of an impulse transmission spectrum according to one aspect of the present disclosure.

When this summed frame is convolved with the summed-frame template, the result was the maximum peak shown in FIG. 56. The vertical axis represents voltage (mV) and the horizontal axis represents "impulse timing" time (µs). As described herein, the transmission protocol is implemented by charging a capacitor C (e.g., C6, FIG. 43) and then discharging the capacitor over a very short discharge cycle relative to duty cycle into an inductor section L (e.g., L1, FIG. 43), as discussed in connection with the impulse inductor driver circuit 720 in FIGS. 38-43. The impulse protocol is a series of +/− or off/on sequences at 128 locations, for example. All the energy is put into a plurality of pulses, and the noise is distributed over a larger number of pulses, which improves the noise per bit figure. Accordingly, the impulse protocol is referred to herein as a "sparse impulse" code.

Going back to FIG. 56, it is clear that the frequency has been found to within the resolution of this search. To better resolve the frequency and starting point within the frame and also of the data packet within the data stream, the search process may be repeated with a finer granularity around the discovered peak, always keeping the combination with the highest correlation product. The result of this for the with-noise example is shown in FIG. 61.

Once the frequency and starting point (of the packet and within the frame) are known, in this example, 64 slices per bit are each first summed up, and then each bit-length-frame is then convolved at the appropriate starting point with the "zero" template and the "one" template. (Noting again that these templates are >75% zeros, since for this protocol, in the combined slice there is a spike every 4 µs of roughly 1 µs width—which eliminates the noise between spikes from interfering with the interpretation.) The higher value of the two declares the bit.

Figure 60:
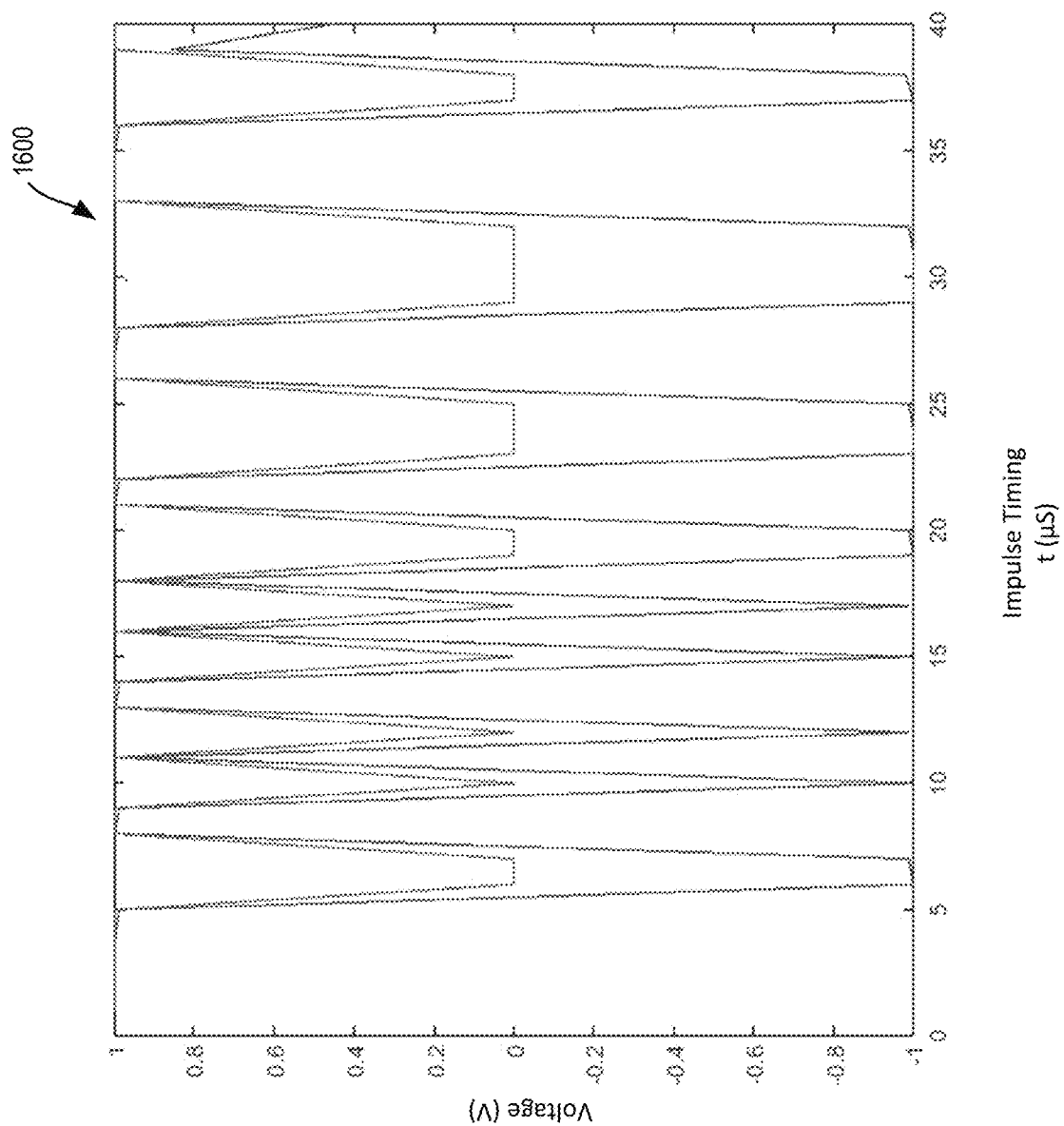
FIG. 60 is a 40 bit packet received by the receiver circuits shown in FIGS. 47-53, according to one aspect of the present disclosure.
Figure 61:
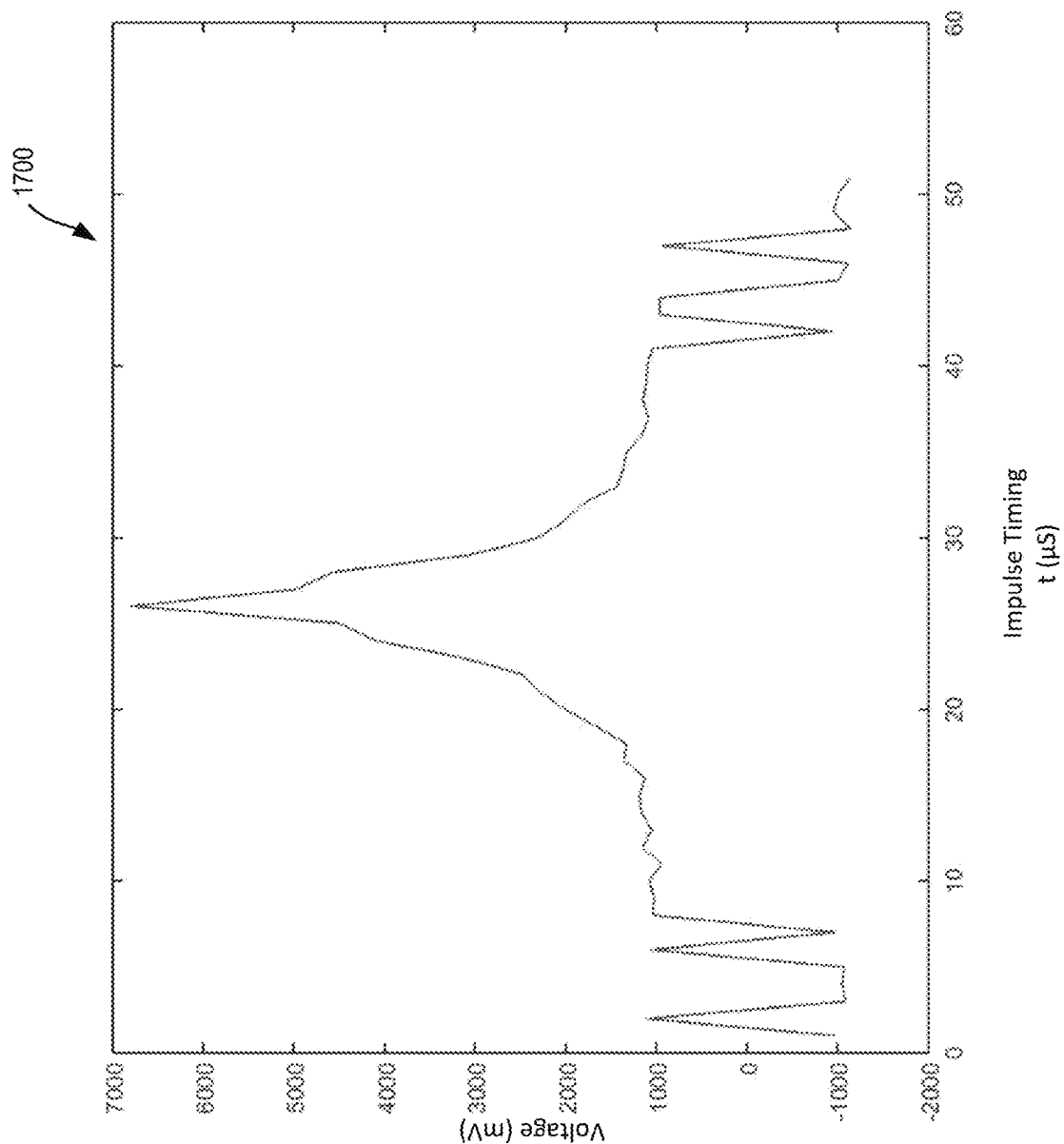
FIG. 61 is a fine spectrum of a packet received by the receiver circuits shown in FIGS. 47-53, according to one aspect of the present disclosure.

FIG. 60 shows the output of each bit-length-frame and the corresponding bit pattern of the packet using the same data as was shown in FIGS. 56, 58, and 61. Shown is a 40 bit packet 1600 received by the receiver circuits 900 (FIG. 47), 930 (FIG. 49), 950 (FIG. 50), 960 (FIG. 51), 970 (FIG. 52), 990 (FIG. 53), 1010 (FIG. 54), 1100 (FIG. 55), according to one aspect of the present disclosure. The vertical axis represents voltage (V) and the horizontal axis represents "impulse timing" time (µs). In spite of the high level of noise compared to signal amplitude, the data is clearly and easily read.

FIG. 61 is a fine spectrum of a packet 1700 received by the receiver circuits 900 (FIG. 47), 930 (FIG. 49), 950 (FIG. 50), 960 (FIG. 51), 970 (FIG. 52), 990 (FIG. 53), 1010 (FIG. 54), 1100 (FIG. 55), according to one aspect of the present disclosure. The vertical axis represents voltage (mV) and the horizontal axis represents "impulse timing" time (µs).

In another aspect, a second spike protocol definition is presented herein. Compared to the previous protocol, this second protocol definition doubles the amount of time available for the transmitter to charge up the capacitor, essentially doubling the amplitude of the transmitted spike. Second, this second protocol improves the pseudo-random code that is used to find the frequency so that the "side-lobes" are all either zero or minus one. Third, this code is designed to work equally well if the packet is all zeros, all ones, or anywhere in between. Otherwise, this second protocol definition works in a similar manner as the previous version.

In this second example spike protocol definition, two "subchips" "A" and "B" are defined that can be combined in certain ways to form the "zero" and the "one" chip. Here is an example definition:

Sub-Chip Definitions:
The "A" subchip is {1 0 −1 0 −1 0 1 0 1 0 −1 0 1 0 −1 0 1 0 1 0 1}
The "B" subchip is {0 −1 0 −1 0 −1 0 −1 0 −1 0 1 0 −1 0 1 0 −1 0 1 0 1 0}
The "zero" chip is {A B}
The "one" chip is {B A}
When decoding, the "stacking" length is len(A)=len(B)

The aforementioned sequences were selected so that when they are combined, i.e, A+B={1 −1 −1 −1 −1 −1 1 −1 1 −1 −1 1 1 −1 −1 1 1 −1 1 −1 1 1 1}

Figure 68:
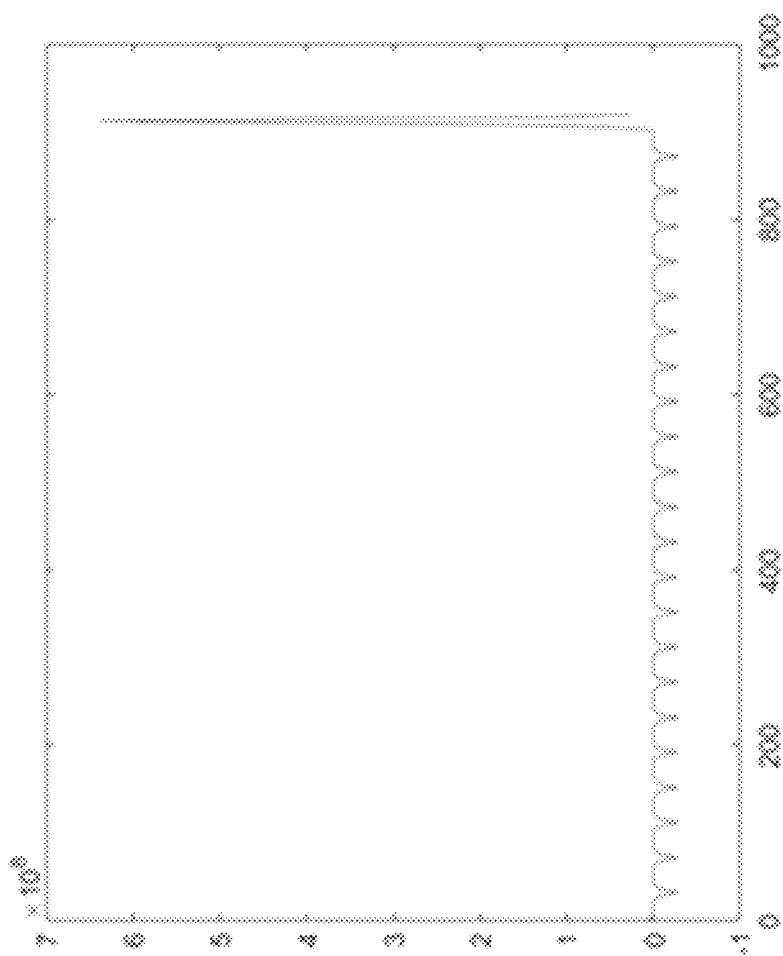
FIG. 68 shows a plot of a typical low-noise convolution for the best-match combined slice; the template convolution sum v. slice number.

{A+B}×{A+B} produces an (autocorrelation) pattern that has a central peak 23 units tall and all other side lobes=−1 (see FIG. 68). Other codes of different length many be used, as well, and aspects are not so limited. For example, at 19 units long, the code is {1 −1 −1 −1 −1 1 −1 1 −1 1 1 1 1 −1 −1 1 −1 −1 1 1}. In general, the two subchip definitions may have different patterns so long as the autocorrelation of their summation produces a pattern with a central peak equal to the length of the subchips, and the side lobes are not equal to 1.

Further in this Definition:
40 bit packet=24 bits data preceded by a 16-bit preamble:
preamble=[1 1 1 1 1 0 0 1 1 0 1 0 1 1 0 1];

In addition, 70 chips in a row makes a symbol, which is identical to the bit. (In other protocols the symbols do not have a one-to-one relationship to bits). Increasing the number of chips per symbol uses up more time (packet is longer) but if the transmitting clock is stable, then there is more power into each symbol and thus a lower bit error rate.

Further in this Definition:
12+11=23 spikes per chip
2×4=8 µs between spikes (except when transitioning from bit=1 to bit=0). When the subchip frames are stacked up, there will be 4 µs between 23 spikes.
23×2×4=184 us/chip
70 chips/bit
"A" sub-chip spikes are on 8 µs spacing starting at t=0;
"B" sub-chip spikes are on 8 µs spacing starting at t=4 µs;
12.88 ms/bit 40 bits/packet, data payload=24 bits
515.2 ms/packet FIG. 64 shows graphical representations of the the "A" subchip in plot 1830, and the "B" subchip in plot 1840. The x-axis is sample number, assuming 8 μs between spikes and sampling rate=10 MSPS).

Referring to FIG. 65, based on the aforementioned example definition of the second spike protocol, combining A and B according to the above descriptions produces the "Zero" chip =[A B], as shown in plot 1850, and the "One" chip=[B A], as shown in plot 1860.

To make a "zero" bit, 70 "zero" chips are broadcast in sequence; to make a "one" bit, 70 "one" chips are broadcast in sequence. In this way, the entire packet is broadcast. According to some current specifications of the ingestible identifier, nominally, it takes 12.88 ms to transmit each bit and 515.2 ms to transmit a packet. At a lower transmit frequency, say 5% lower, it may take 541 ms to transmit a packet, but at a higher frequency, say 5% higher, only 489 ms.

When decoding the signal, enough data is stored in a frame to be sure of capturing one packet, but not so much that the noise between packets overwhelms the signal. A few empty bits of gap between packets may be enough, particularly if the packets are synchronized to each other.

The data is then "sliced" into segments of length equal to a sub-chip. However, since the frequency of transmission is not exactly known, the exact length of a sub-chip is not known, either. The range of frequency determining the number of samples or sub-samples per slice depends upon the assumed frequency of transmission. Thus, at the nominal frequency there may be 1840 samples per sub-chip=1840 samples per slice. At a slightly lower frequency, there may be 1840.1 samples per slice, which means that every ten slices an extra sample has been "squeezed" into the slice. At a slightly higher frequency, there may be 1839.99 samples per slice, which means that every 100 slices, a sample has been "stretched." By appropriate stretching and squeezing, slices of equal length for all frequencies are obtained. These slices can then be treated equally, without worrying about how many samples and sub-samples were used to create each slice. This action is the stretch-squeeze slicing process. To accomplish stretch-squeezing efficiently, a template is made which stores an array of pointers that describes the starting point for each slice in the frame for each frequency. The term template refers to a specific and predetermined pattern of pulses (or pointers, slices, etc.) that acts as a reference to be compared against. Alternatively, depending on implementation constraints, one might use an algorithm to continuously generate each template.

The slices are then stacked up and summed. Since each slice, in this example, is 1840 samples, the $1^{st}$ sample of the $1^{st}$ slice is added to the $1^{st}$ sample of the $2^{nd}$ slice, and then $1^{st}$ sample of the $3^{rd}$ slice is added to that sum, and so forth until all first samples of all slices are summed into the $1^{st}$ sample of the combined slice. In this manner, all 1840 samples of the combined slice are produced, each a sum of all the same number of samples in each of all the slices.

Figure 66:
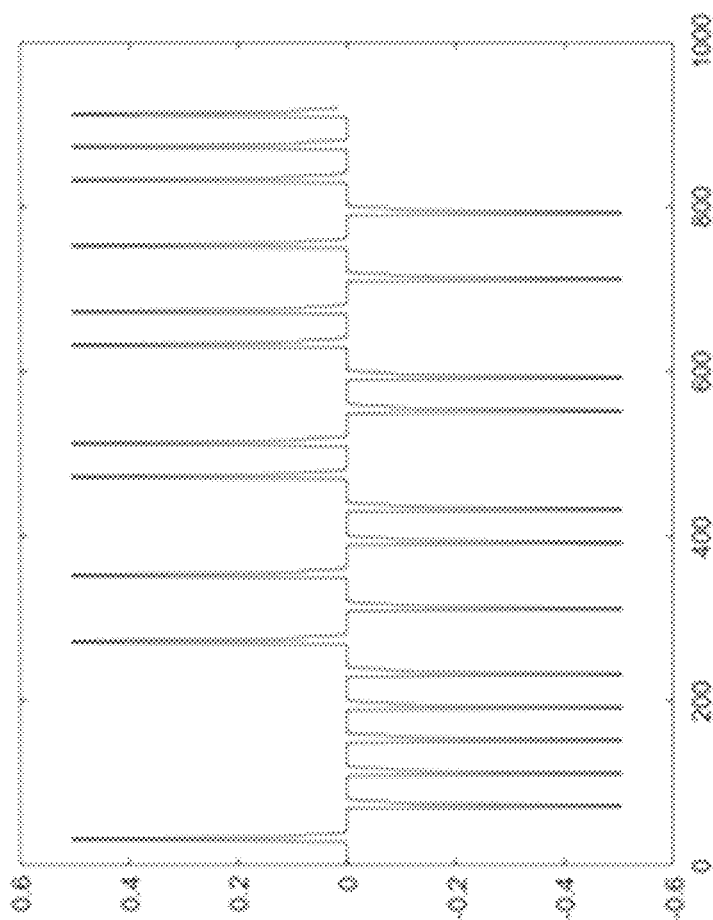
FIG. 66 is a plot showing how a combined slice may look like with SNR=5000.

With no noise, this combined slice may look like the plot shown in FIG. 66. This combined slice may have an SNR=5000.

Figure 67:
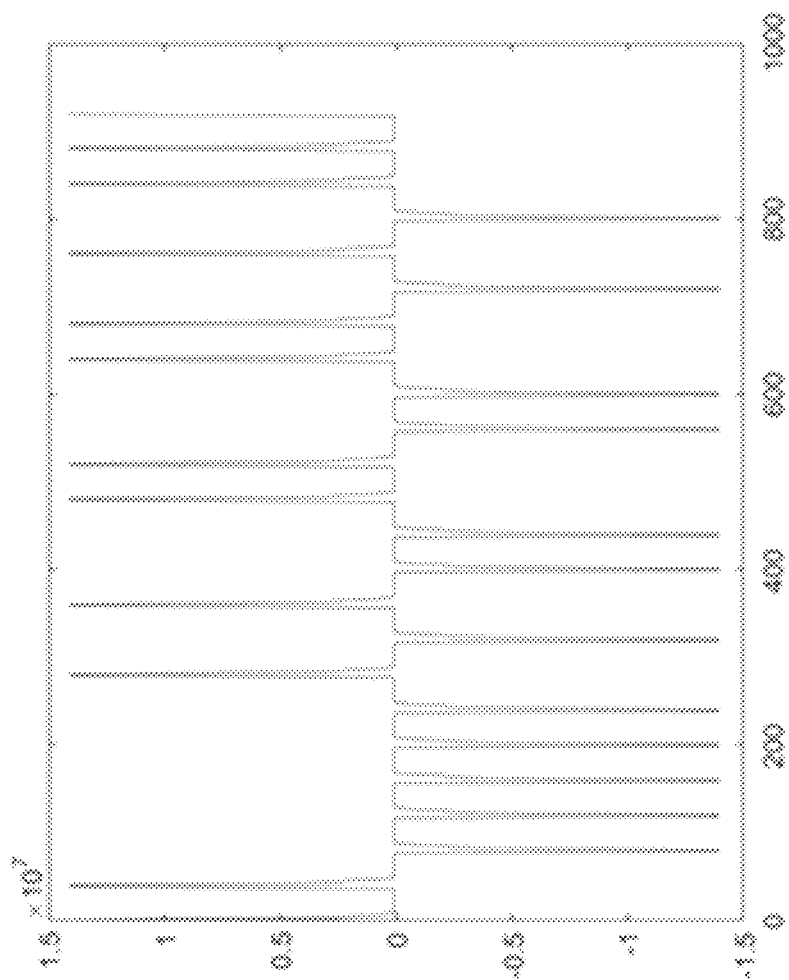
FIG. 67 shows a template plot, which is produced by summing the "A" sub-chip and the "B" sub-chip, and is used in decoding to find the correct frequency and the starting point of the packet.

Summing the "A" sub-chip and the "B" sub-chip produces the "template," which is used in decoding to find the correct frequency and the starting point of the packet. The template is shown in FIG. 67. Note that the spacing between the 23 spikes is 40 samples or 4 μs. Since there is always an equal number of A and B chips, the amplitude of sums are always nominally equal (noise will cause these amplitudes to vary in practice).

The next step is to convolve the combined slice with the template of the combined slice to find the best match starting point for each assumed frequency. A typical low-noise convolution for the best-match combined slice (matching the combined slice shown above) is shown in FIG. 68. This plot shows the template convolution sum v slice number.

Note that when the template lines up with the best-fit combined slice, the amplitude is 23. When the slice is mis-aligned by the equivalent of 4 us, the amplitude is −1. At all other misalignments, the amplitude is zero. Two values are retained for each assumed frequency: amplitude of the peak and sample number. Note that the absolute value of this correlation score is compared with the others. If the best fit score is negative, then each data point in the data set is multiplied by −1 in successive calculations.

Figure 69:
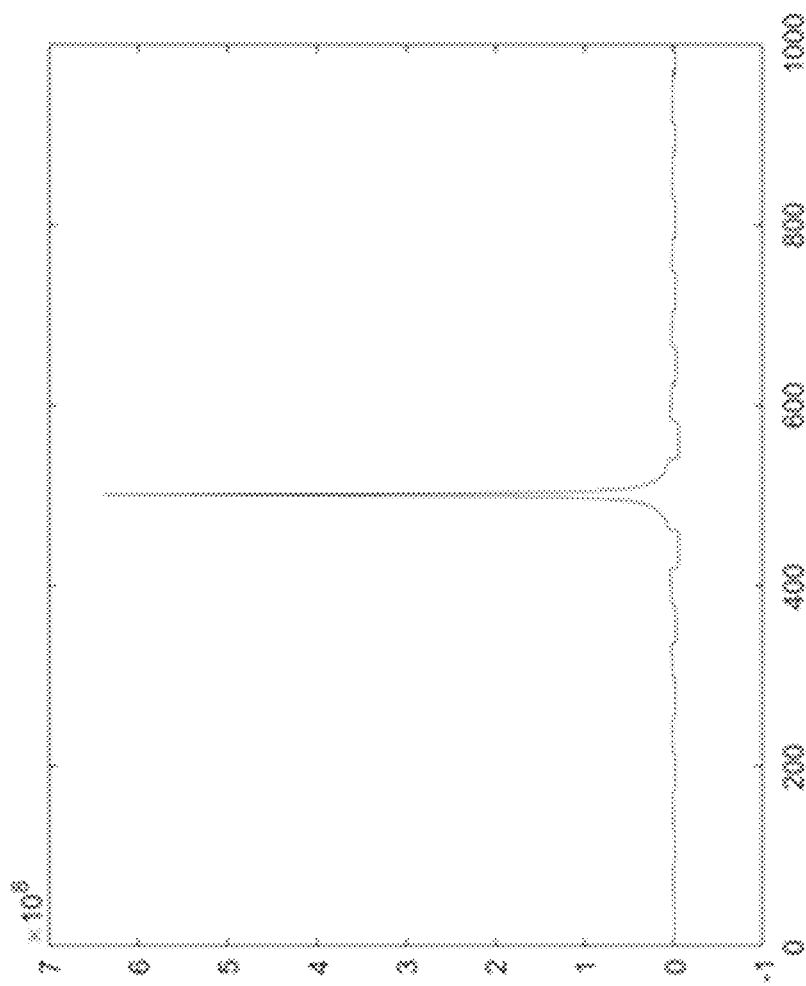
FIG. 69 shows a plot of a spectrum with SNR=5000, which is a plot of the maximum convolution values for each assumed frequency vs. the assumed frequency.

The maximum convolution value for each assumed frequency is calculated, and stored. A plot of these values versus assumed frequency is the "spectrum." Shown in FIG. 69 is the spectrum for this SNR=5000 example: (best convolution sum v "frequency")

This example shows that the frequency is near the nominal value, which would be 501. If the peak is closer to 1, then the frequency is below nominal (e.g., nominal length−1); if it is closer to 1000, then the frequency is above nominal (e.g., nominal length+1). From the highest peak we learn two things: the actual broadcast frequency and the (from the previous graph in FIG. 68) the starting index within the combined slice.

The next step is to produce (or pull from memory) the pointers for this frequency and this starting index. The pointers are a list of numbers, each representing the starting point and template for each slice.

The pointers and template are then used to generate two sub-chip scores for each slice: an "A" sub-chip score and a "B" sub-chip score.

Figure 70:
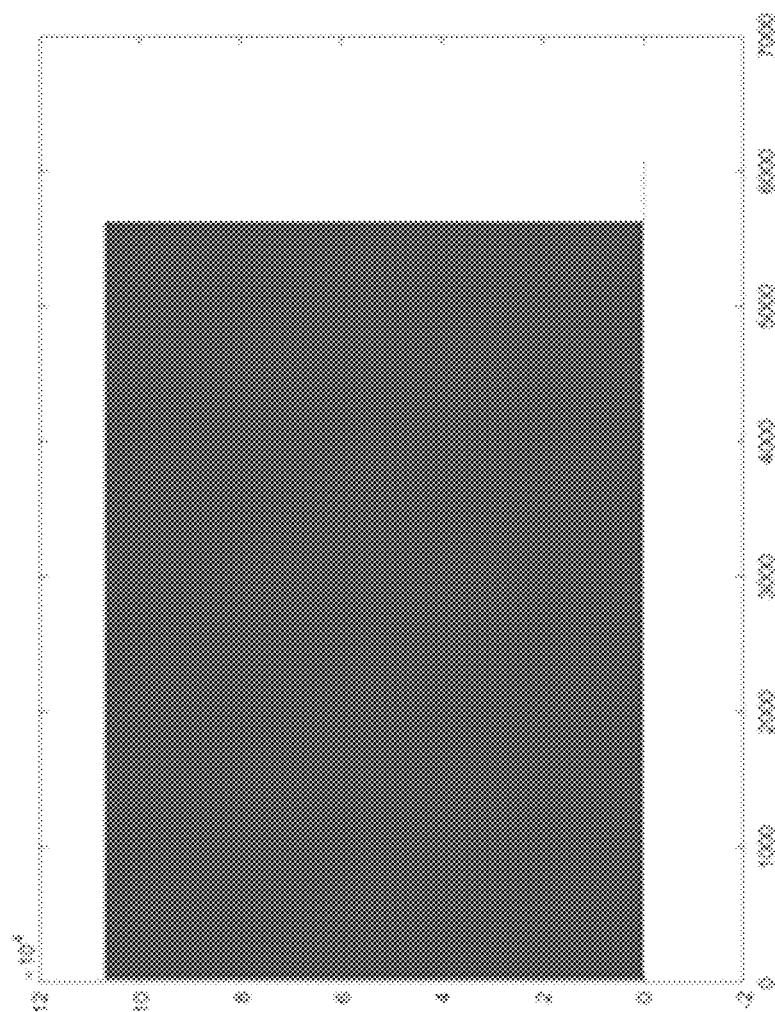
FIG. 70 shows the "A" sub chip scores for each slice for the very low noise case: (X-axis: slice number, Y-Axis: correlation value).
Figure 71:
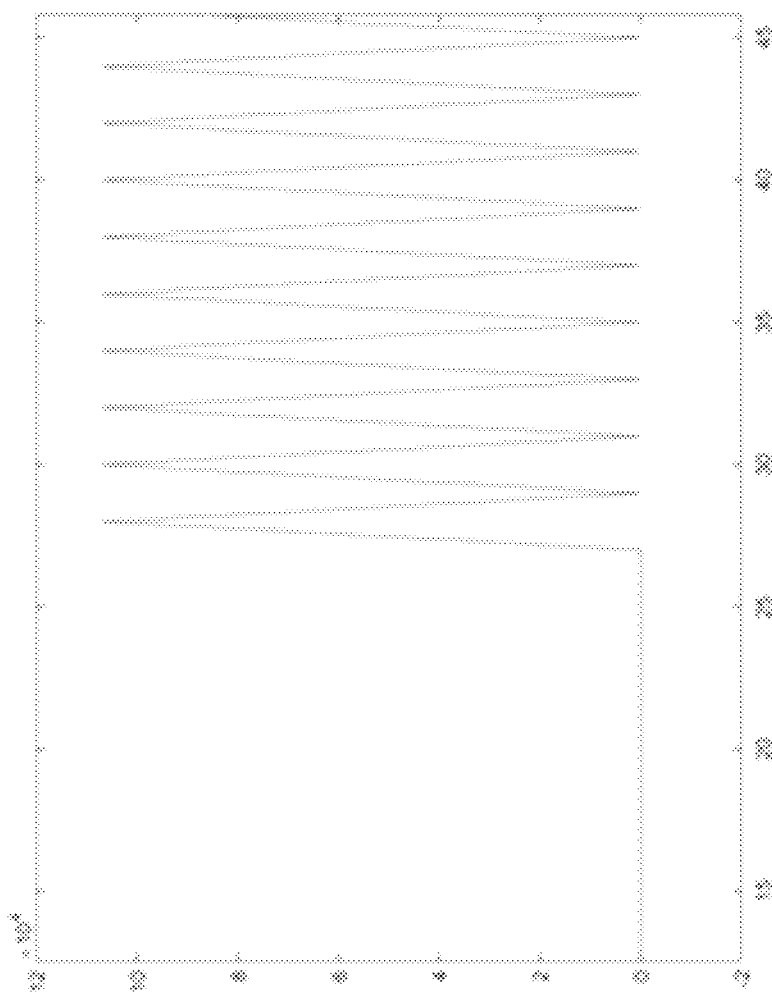
FIG. 71 shows a zoomed in view at the beginning of the packet of the A chip score: (X-axis: slice number, Y-Axis: correlation to "A template" value).

Shown in FIG. 70 are the "A" sub chip scores for each slice for the very low noise case: (X-axis: slice number, Y-Axis: correlation value). Note that since there is very little noise in this example, the beginning and end of the packet are very easy to see. Zooming in at the beginning of the packet, the A chip score is shown in FIG. 71: (X-axis: slice number, Y-Axis: correlation to "A template" value).

Figure 72:
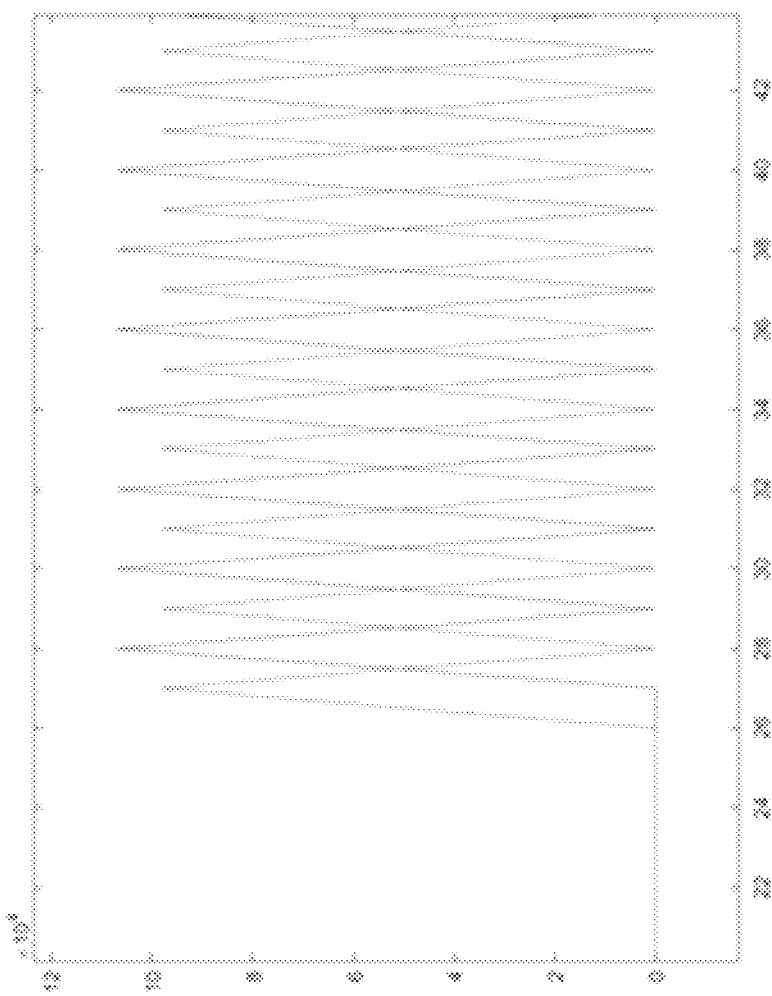
FIG. 72 shows plotting both the A sub-chip and the B sub-chip correlation values together.

Plotting both the A sub-chip and the B sub-chip correlation values together is shown in FIG. 72. It is easy to see that when the A sub-chip score is high, the B-sub-chip score is low, and vice-versa. Note that the A sub-chip score is greater than the B sub-chip score in this example. This is because there is one more spike in the A sub-chip than the B sub-chip, producing a "combined" chip (when stacked together) that is an odd number, thus allowing the all −1 side-lobes, as shown in the best-fit combined slice FIG. 68 above.

The next step is to generate, using the sub-chip scores, "zero" and "one" chip scores for each slice. Here is the formula, according to some aspects:

```
for subChipNum = 1:chipsPerFrame
   chipScores(subChipNum,1) =
subChipScores(subChipNum,1)+subChipScores(subChipNum+1,2);
   chipScores(subChipNum,2) =
subChipScores(subChipNum,2)+subChipScores(subChipNum+1,1);
end
chipScores(:,3) = chipScores(:,2)–chipScores(:,1); % Use for decoding
chipScores(:,4) = chipScores(:,2)+chipScores(:,1); % Use for finding the packet start &
finish
```

Thus, a "zero" chip is the sum of the A(n) sub-chip+B(n+1) sub-chip, while the "one" chip is the sum of the B(n) sub-chip+A(n+1) sub-chip. Note that the difference between the zero chip and the one chip scores is used for decoding, while the sum of the two is used for finding the packet starting point.

Figure 73:
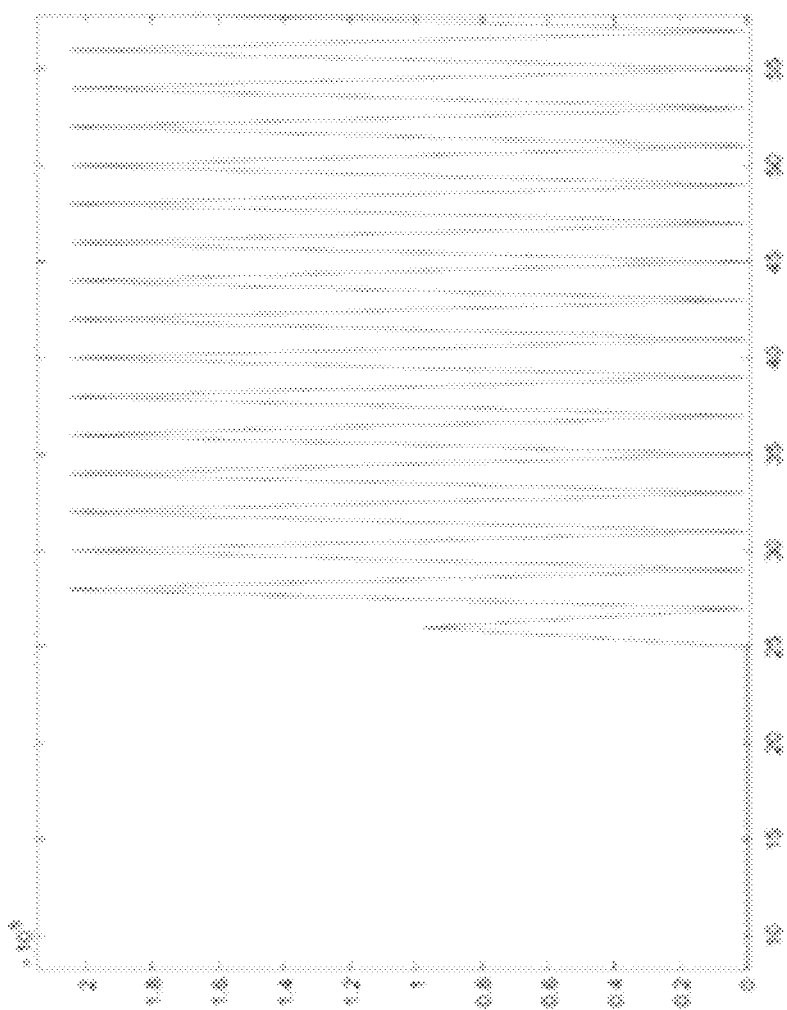
FIG. 73 shows a plot of the the "zero" chip values as a function of slice number.

FIG. 73 shows a plot of the the "zero" chip values as a function of slice number.

Figure 74:
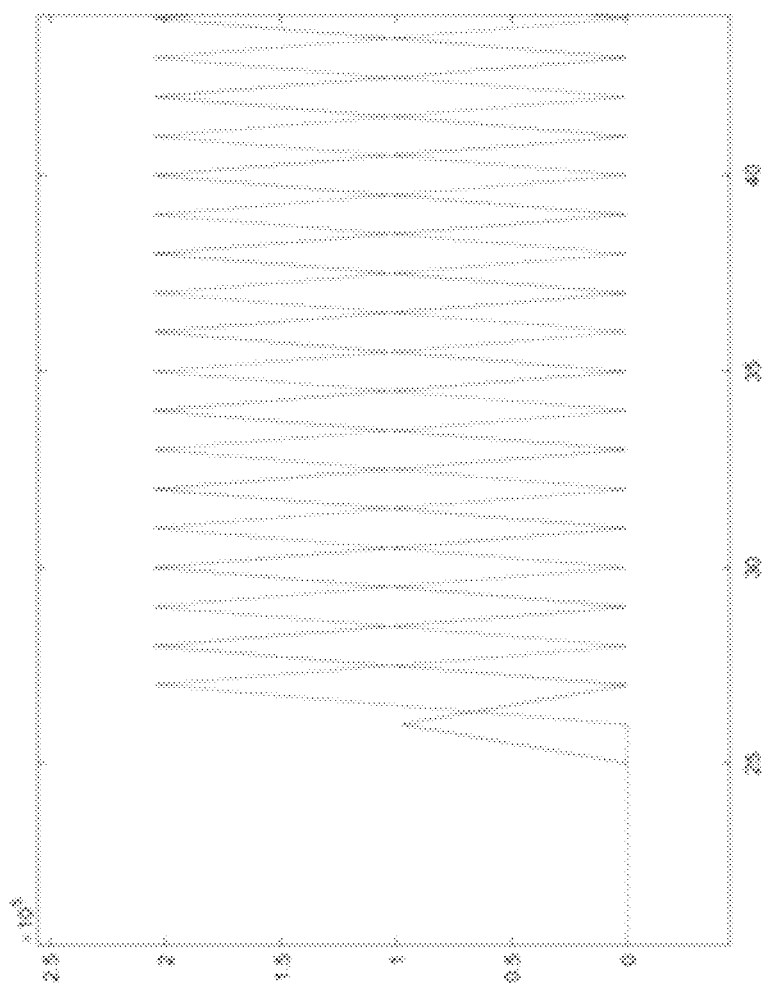
FIG. 74 shows a plot of both zero and one chip score as a function of slice number.

FIG. 74 shows a plot of both zero and one chip score as a function of slice number. Again, note that when one chip score is high, the other is low. Registration, i.e. determining the exact starting point of the packet, is critical here: if one is off by one slice, all the zero chips become ones, and vice-versa. This problem is addressed by starting the packet with a known bit sequence, the "preamble."

The next step in decoding is to calculate for each slice number two "bit scores," one summing all the zero sub-chips for each bit length of sub chips, the other summing all the one sub-chips for each bit length of one sub-chips. The MATLAB code for this is shown below as an example for how to implement this step:

```
bitLengthScores(1:chipsPerFrame-subChipsPerBit,1:2) = 0.0;
for chipNum = 1:chipsPerFrame - subChipsPerBit
   for thisChipNum = chipNum:2:chipNum+subChipsPerBit-1
bitLengthScores(chipNum,1)=bitLengthScores(chipNum,1)+chipScores(thisChipNum,3);
bitLengthScores(chipNum,2)=bitLengthScores(chipNum,2)+chipScores(thisChipNum,4);
   end
end
```

Note that two bit length scores are produced: one using the difference of the chip scores, and the second based on the sum of the chip scores. The latter becomes the packet envelope. To be sure, a frame as used herein represents a segment of data being analyzed, which should contain a packet. Thus, in a frame, the packet would be surrounded by noise.

Figure 75:
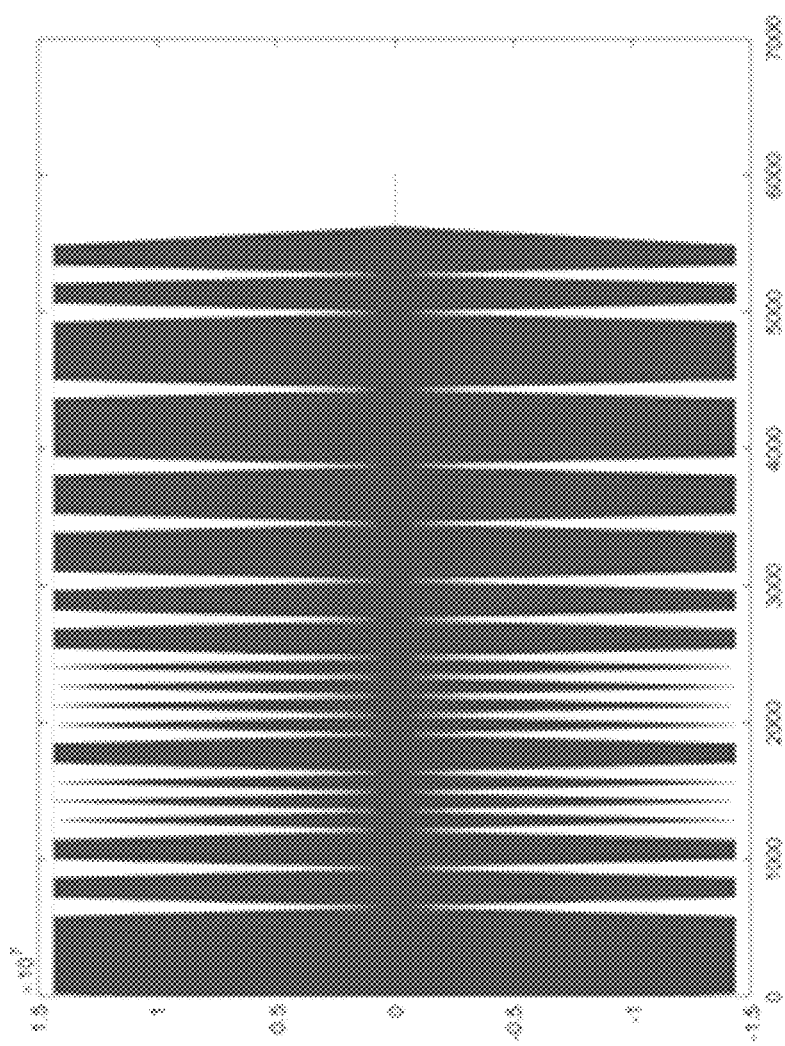
FIG. 75 shows a plot of the bit length scores v. slice number.

FIG. 75 shows a plot of the bit length scores v. slice number. Note that even though the second bit length score represents the envelope of the bit length scores used to decode the packet, the bit length score flips with each slice number. The exact starting point is found using an algorithm that rewards starting points that produce the correct preamble, while giving credit for slices that have valid bits. Thus, a combination of the first bit length score (for the preamble bits) and the second bit length score (for the data packet bits) is used to find the best-estimate of the packet.

Example MATLAB code for searching through the slices to make this calculation is shown below:

```
preamble = params.preamble*2-1;
bestSC(1:2) = 0.0;
thisPacket(1:40,1:3) = 0.0;
bestPacket(1:40,1:2) = 0.0;
```

-continued

```
for chipNum = 1:chipsPerFrame - subChipsPerPacket
   for i = 1:40
      thisPacket(i,1) = bitLengthScores(chipNum+(i-1)*subChipsPerBit,1);
      thisPacket(i,3) = bitLengthScores(chipNum+(i-1)*subChipsPerBit,2);
      if thisPacket(i,1)>0
         thisPacket(i,2)=1;
      else
         thisPacket(i,2)=0;
      end
   end
   thisPreamble = thisPacket(1:16,1).*preamble';
   thisScore = 0.0;
   factor = 1.0;
   for preambleNum = 1:16
      if thisPreamble(preambleNum) > 0
         factor = factor*1.01;
      else
         factor = 1.0;
      end
      thisScore = thisScore+factor*thisPreamble(preambleNum);
   end
   thisScore = thisScore+sum(thisPacket(17:40,3));
```

-continued

```
   if thisScore > bestSC(2)
      bestSC(1:2) = [chipNum thisScore];
      bestPacket(:,1:2) = thisPacket(:,1:2);
   end
end
bestPacket(:,1) = bestPacket(:,1)/max(bestPacket(:,1));
```

At this point, the best estimate of the packet has been determined. The preamble is checked to see if it is correct. If it is correct, then the data payload is recorded, and assumed correct. Depending on the SNR of the signal (see below), a certain number of data packets at the same or similar frequency are determined and if they match, then the data packet is assumed correct. Alternatively, if the SNR is below a certain number, a number of these bit length scores may be combined to produce a meta-bit length score that combines neighboring data packets to produce a better estimate of a single data packet.

Figure 76:
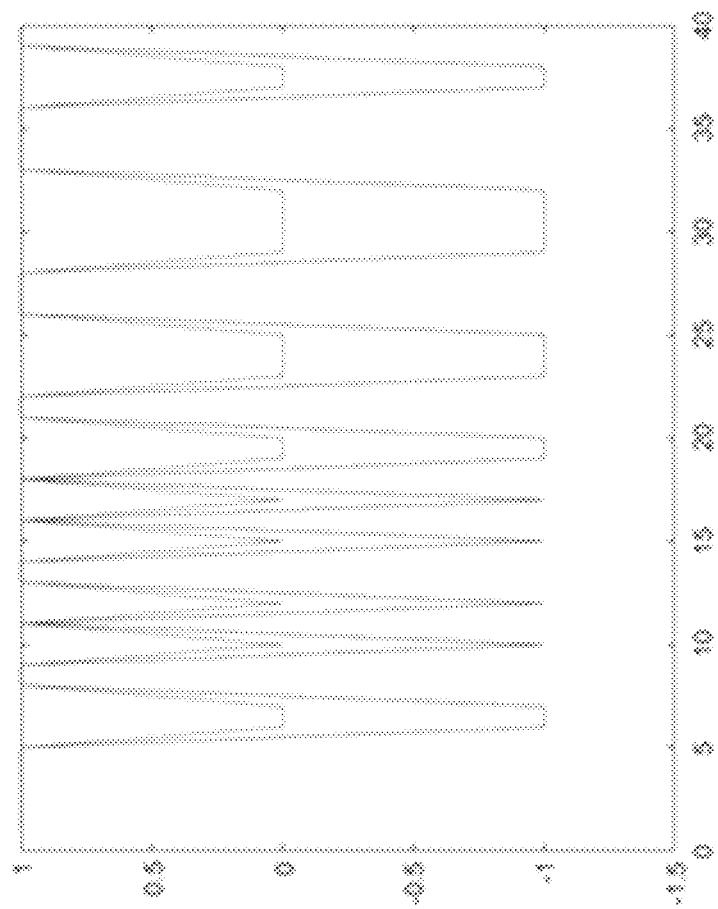
FIG. 76 shows a plot of a low noise packet, with two lines: the line that falls deeper is the bit length score and the more shallow line is the as-interpreted bit value.
Figure 77:
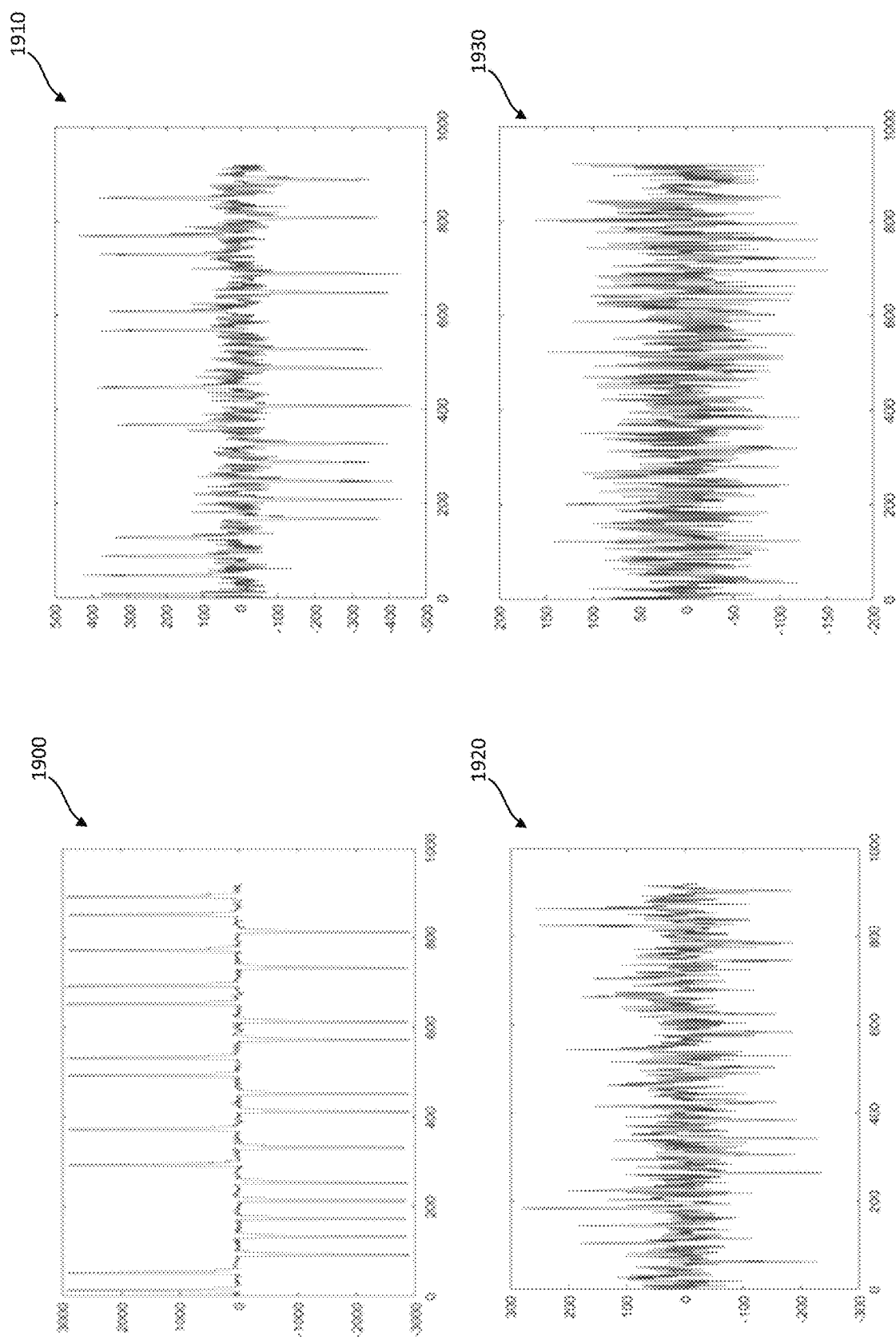
FIG. 77 shows four plots of the best-fit combined slice at different signal to noise ratios.

FIG. 76 shows a plot of the low noise packet. Two lines are shown: the line that falls deeper is the bit length score and the more shallow line is the as-interpreted bit value. Now, it can be seen how these same parameters look in the presence of various amounts of noise. In all the following examples SNR is measured to be Vmax/V noise rms, where Vmax is spike amplitude and V noise rms=sqrt(mean (noise.*noise)) (MATLAB notation). Here is the relevant MATLAB code illustrating this:
noise=2.0*rand(1,length(signal))−1.0;
noiseRMS=sqrt(mean(noise.*noise));
vMax=000.0192;
inData=1.0*signarvMax/max(signal);
log_vMaxOverVn=10.0*log(vMax/noiseRMS)
simData=inData+noise;

FIG. 77 shows four plots of the best-fit combined slice at different signal to noise ratios. Plot 1900 shows the best-fit combined slice for SNR=5 dB. Plot 1910 shows the best-fit combined slice for SNR=−15 dB. Plot 1920 shows the best-fit combined slice for SNR=−24 dB. Plot 1930 shows the best-fit combined slice for SNR=−34 dB.

The next critical parameter is produced by convolving the "best-fit-sums" to the template to determine the best-guess starting point within the combined sum.

Figure 78:
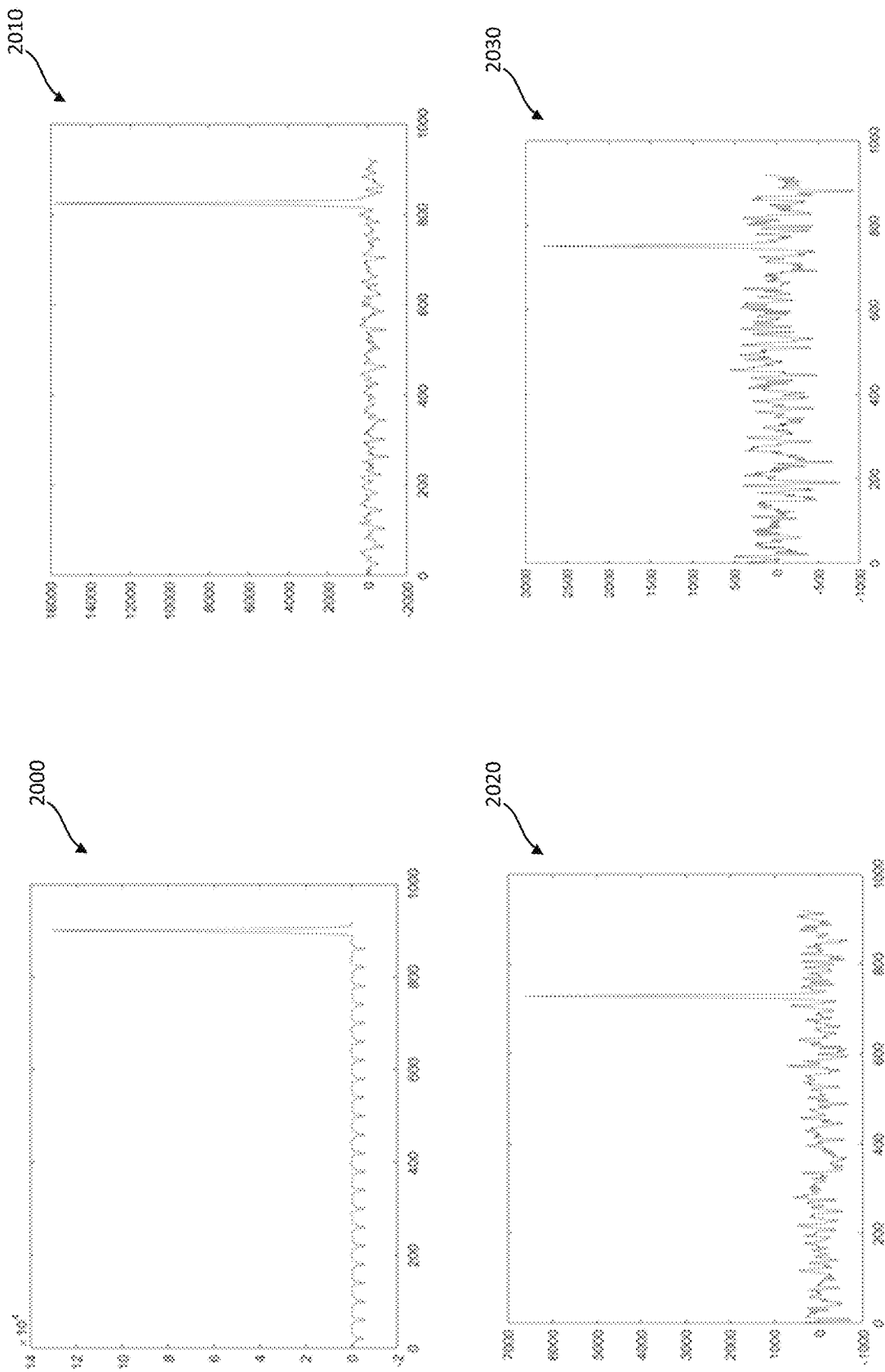
FIG. 78 shows various plots of the "bestThisSums," which is the "best-fit-sums" convolved with the "template" for various SNR.

FIG. 78 shows various plots of the "bestThisSums," which is the "best-fit-sums" convolved with the "template" for various SNR. In each case, the plot is of the "best-guess," that is, the frequency that produced the maximum peak. Plot 2000 shows this convolution of the "bestThisSums" for SNR=5 dB. Each frequency will produce a peak: the highest peak is the correct frequency (see "spectrum" for a plot of the peaks for each frequency). The location of the peak (the highest overall peak) indicates the starting index. Thus, when the frame is broken up into slices, this starting index is used to correlate the A-sub-chip and B-sub-chip templates to produce sub-chip scores for each slice. One could also say that the location of the peak decides the registration of the starting point of each sub-chip within each slice.

Plot 2010 shows the "bestThisSums" for SNR=−15 dB. Plot 2020 shows the "bestThisSums" for SNR=−24 dB. Plot 2010 shows the "bestThisSums" for SNR=−34 dB. Note that even in the −34 dB case (which represents a data set where the peak amplitude of the spikes are ~2% of the peak amplitude of the background noise), the correlation values are still easily found. In this case, the correct peak (~3000) is about three times that of the next nearest peak (~−1000).

Figure 79:
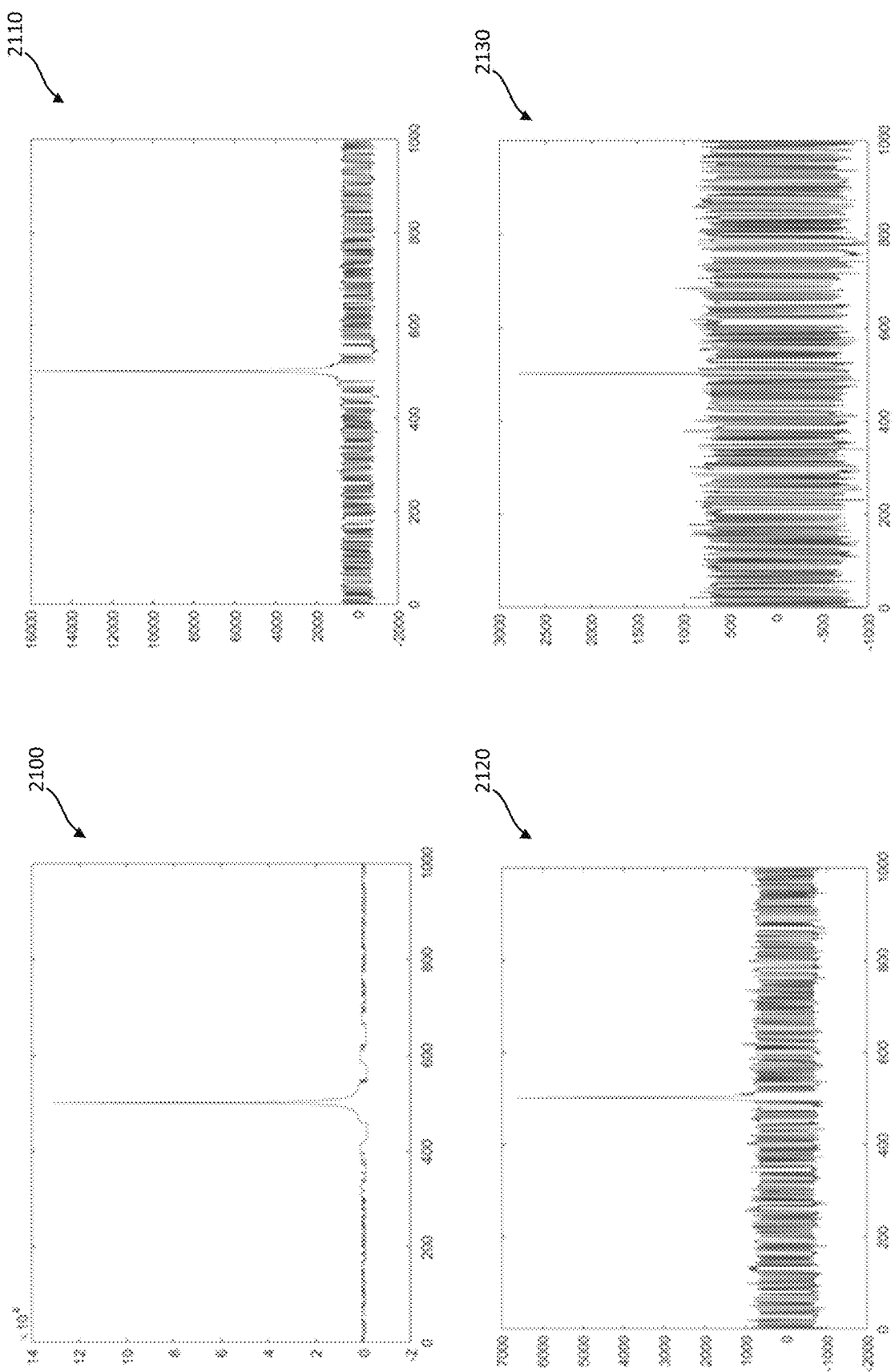
FIG. 79 shows various spectrum plots at different SNR.

Plotting the best bestThisSums values for each frequency produces something akin to a "spectrum," i.e., the best-fit correlation v frequency number. FIG. 79 shows various spectrum plots at different SNR. Plot 2100 shows the spectrum for SNR=5 dB. Plot 2110 shows the spectrum for SNR=−15 dB. Plot 2120 shows the spectrum for SNR=−24 dB. At −24 dB, the spike amplitude is ~5% of the peak noise amplitude. The ratio of best correlation peak to next best peak is ~7. Plot 2130 shows the spectrum for SNR=−34 dB. This signal is decoded with very high accuracy even at this level of noise.

Again, at the point where the detection accuracy of a single packet begins to slip significantly, the peak is ~3× that of the next biggest peak. Once this ratio dips below 4 or 5, it might be helpful to begin combining packets at both the spectrum level (to see if the peak-to-noise ratio is better than ~5) and the bit-length score level to improve decoding accuracy.

Figure 80:
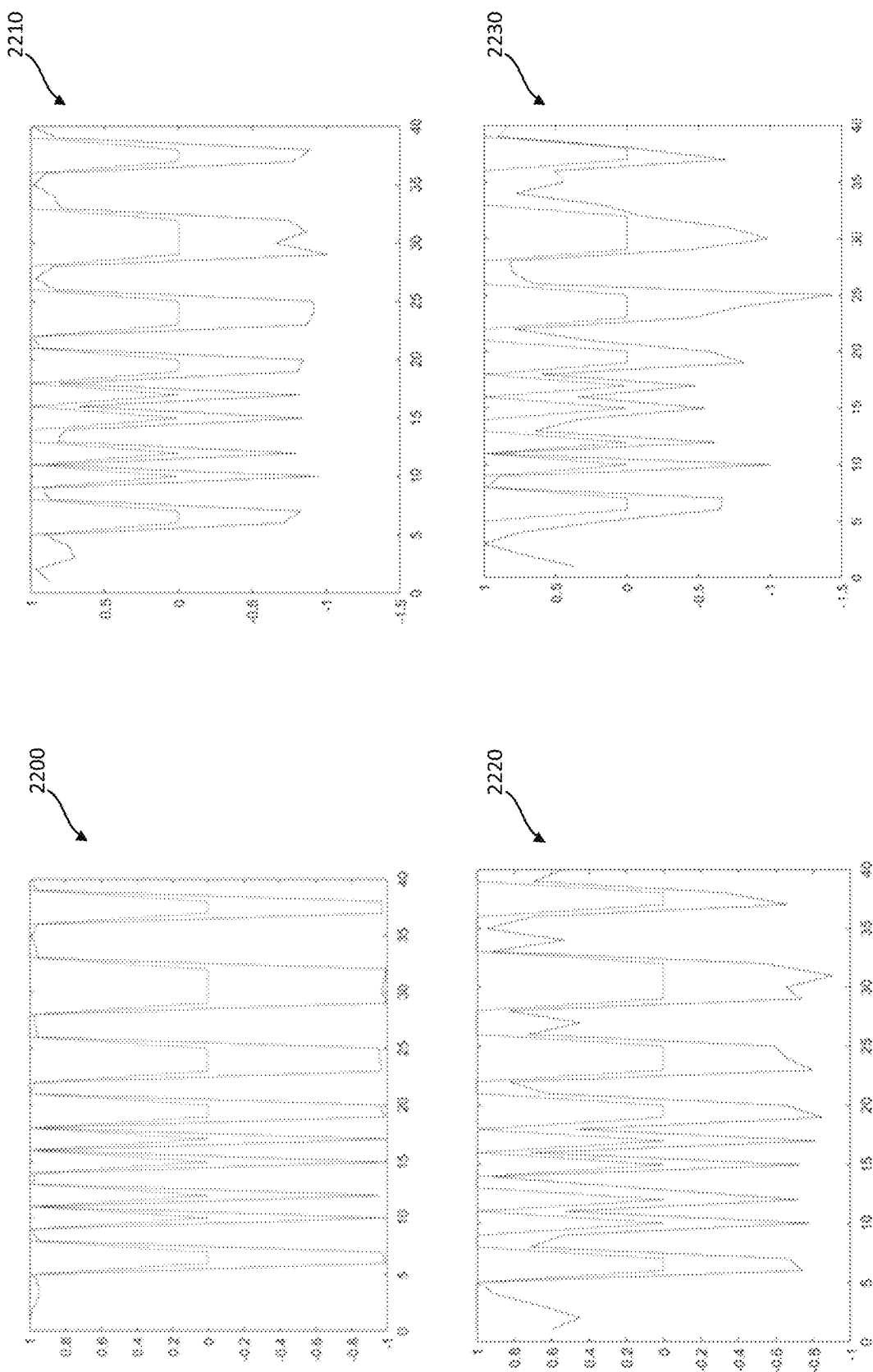
FIG. 80 shows the bit length scores used to successfully decode the packet at these various levels of SNR.

The bit length scores used to successfully decode the packet at these various levels of SNR are shown in FIG. 80. Plot 2200 shows the bit scores for SNR=5 dB. Plot 2210 shows the bit scores for SNR=−15 dB. Plot 2220 shows the bit scores for SNR=−24 dB. Plot 2230 shows the bit scores for SNR=−34 dB. Plot 2230, where SNR=−33.9 dB, corresponding to spike amplitude=1.95% of max noise amplitude, was successfully decoded. By either combining packets or using more sub chips per chip, signals comprised of smaller amplitude spikes relative to the background noise may be found and decoded.

In a third example definition of the spike protocol, rather than utilize just 2 sub-chips, N orthogonal chips, where N is the number of units predefined in each chip itself, may be utilized to be combined in a vastly greater number of ways. In this case, N=23, but other sizes may be used (e.g., N=19 or 17). In this example, compared to the first previously described protocols, this third definition increases by a factor of 23 the amount of time available for the transmitter to charge up the capacitor between discharges, vastly increasing the amplitude of the transmitted spike (given a current-limited charging system, such as on an ingestion sensor). Second, this protocol definition improves the pseudo-random code that is used to find the frequency so that the "side-lobes" are all either zero or minus one (same as in the second protocol). Third, every packet is comprised of the same 23 unique symbols, but the order of appearance of these 23 symbols determines the information. (The first spike protocol required an equal number of zeros and ones in the packet to work properly.) Otherwise, the protocol works in a similar manner as the previous revision.

Defined here are the chip definitions for this third example protocol definition:
% "A" sub-chip spikes are on 92 μs spacing starting at t=0;
% "B" sub-chip spikes are on 92 μs spacing starting at t=4 μs;
% "C" sub-chip spikes are on 92 μs spacing starting at t=8 μs;
% "W" sub-chip spikes are on 92 μs spacing starting at t=88 μs;
% 240 chips/symbol (e.g., 240 "A" chips in a row makes an "A" symbol)
% 44.16 ms/symbol
% 23 symbols/packet, data payload=2%
% 270.5 ms/packet
The "A" chip is {1 0 0 0 0 0 0 0 0 0 0 0 0 0 0 0 0 0 0 0 0 0 0}
The "B" chip is {0 −1 0 0 0 0 0 0 0 0 0 0 0 0 0 0 0 0 0 0 0 0 0}
The "C" chip is {0 0 −1 0 0 0 0 0 0 0 0 0 0 0 0 0 0 0 0 0 0 0 0}
The "D" chip is {0 0 0 −1 0 0 0 0 0 0 0 0 0 0 0 0 0 0 0 0 0 0 0}
The "E" chip is {0 0 0 0 −1 0 0 0 0 0 0 0 0 0 0 0 0 0 0 0 0 0 0}
The "F" chip is {0 0 0 0 0 −1 0 0 0 0 0 0 0 0 0 0 0 0 0 0 0 0 0}
The "G" chip is {0 0 0 0 0 0 1 0 0 0 0 0 0 0 0 0 0 0 0 0 0 0 0}
The "H" chip is {0 0 0 0 0 0 0 −1 0 0 0 0 0 0 0 0 0 0 0 0 0 0 0}
The "I" chip is {0 0 0 0 0 0 0 0 1 0 0 0 0 0 0 0 0 0 0 0 0 0 0}
The "J" chip is {0 0 0 0 0 0 0 0 0 −1 0 0 0 0 0 0 0 0 0 0 0 0 0}
The "K" chip is {0 0 0 0 0 0 0 0 0 0 −1 0 0 0 0 0 0 0 0 0 0 0 0}
The "L" chip is {0 0 0 0 0 0 0 0 0 0 0 1 0 0 0 0 0 0 0 0 0 0 0}
The "M" chip is {0 0 0 0 0 0 0 0 0 0 0 0 1 0 0 0 0 0 0 0 0 0 0}
The "N" chip is {0 0 0 0 0 0 0 0 0 0 0 0 0 −1 0 0 0 0 0 0 0 0 0}
The "O" chip is {0 0 0 0 0 0 0 0 0 0 0 0 0 0 −1 0 0 0 0 0 0 0 0}

The "P" chip is {0 0 0 0 0 0 0 0 0 0 0 0 0 0 0 1 0 0 0 0 0 0 0}

The "Q" chip is {0 0 0 0 0 0 0 0 0 0 0 0 0 0 0 0 1 0 0 0 0 0 0}

The "R" chip is {0 0 0 0 0 0 0 0 0 0 0 0 0 0 0 0 0 −1 0 0 0 0 0}

The "S" chip is {0 0 0 0 0 0 0 0 0 0 0 0 0 0 0 0 0 0 −1 0 0 0 0}

The "T" chip is {0 0 0 0 0 0 0 0 0 0 0 0 0 0 0 0 0 0 0 1 0 0 0}

The "U" chip is {0 0 0 0 0 0 0 0 0 0 0 0 0 0 0 0 0 0 0 0 1 0 0}

The "V" chip is {0 0 0 0 0 0 0 0 0 0 0 0 0 0 0 0 0 0 0 0 0 −1 0}

The "W" chip is {0 0 0 0 0 0 0 0 0 0 0 0 0 0 0 0 0 0 0 0 0 0 1}

When decoding, the "stacking" length is length(A)=length(B)= . . . =length(W)

The aforementioned sequences were selected so that when the 23 symbols are combined (240 A chips make an A symbol, 240 B chips make a B symbol, etc.), i.e,

{A+B+C+ . . . +W}={1−1−1−1−1−11−11−1−111−1−111−11−1111}

{sum(A:W)}×{sum(A:W)} produces an (autocorrelation) pattern that has a central peak 23 units tall and all other side lobes=−1 (see FIG. 68). Other codes of different length many be used, as well. For example, at 19 units long, the code is {1 −1 −1 −1 −1 1 −1 1 −1 1 1 1 1 −1 −1 1 −1 −1 1}

One of the unique features of this protocol is that the packet is composed of exactly 23 symbols, A-W. Each symbol is comprised of some sequential number of related chips. In this situation, 240 chips per symbol produces a packet whose time duration is similar to the previous protocols. Using more chips per symbol increases the amplitude of each symbol when the chips are summed up, and averages more noise, reducing its average magnitude.) The information is contained in the order in which the symbols appear. There are thus 23! (23 factorial) equals ~$10^{21}$ unique codes, roughly 70 bits of information. These "bits" are used for packet preamble, address, and data, or other purposes. For example:

preamble=A F K P T
ID: 000=BC DE GH IJ LM NO QR SU VW
ID: 001=BC DE GH IJ LM NO QR SU VVV
ID: 010=BC DE GH IJ LM NO QR SV UW
ID: 011=BC DE GH IJ LM NO QR SV WU
ID: 100=BC DE GH IJ LM NO QR SW UV
ID: 101=BC DE GH IJ LM NO QR SW VU Below are definitions for this protocol of sub-chip, chip, symbol and bits:

There are 23 sub-chips per chip (same as the number of spikes in the template). Each sub-chip is at an equally-spaced location in time for a spike to occur; a spike may be either +1 or −1.

There are 240 chips per symbol (could be more or less, as well).

There are 23 unique symbols per packet.

The relationship between symbols and bits is a bit more complicated and depends upon how many symbols, if any in each case, are used for the preamble, the address, and the data field.

For example, to deliver the above preamble and address=binary(101), the packet would be simply:
Packet={AFKPTBCDEGHIJLMNOQRSWVU}

Increasing the number of chips per symbol uses up more time (packet is longer) but if the transmitting clock is stable, then there is more power into each symbol and thus a lower bit error rate. It will be discussed how the spike slice algorithm can address frequency variations within the packet later on.

Figure 81:
FIG. 81 shows the first four "A" chips for an additional spike protocol.

FIG. 81 shows the first four "A" chips. The x-axis is sample #, assuming 92 µs between spikes and sampling rate=10 MSPS.

Figure 82:
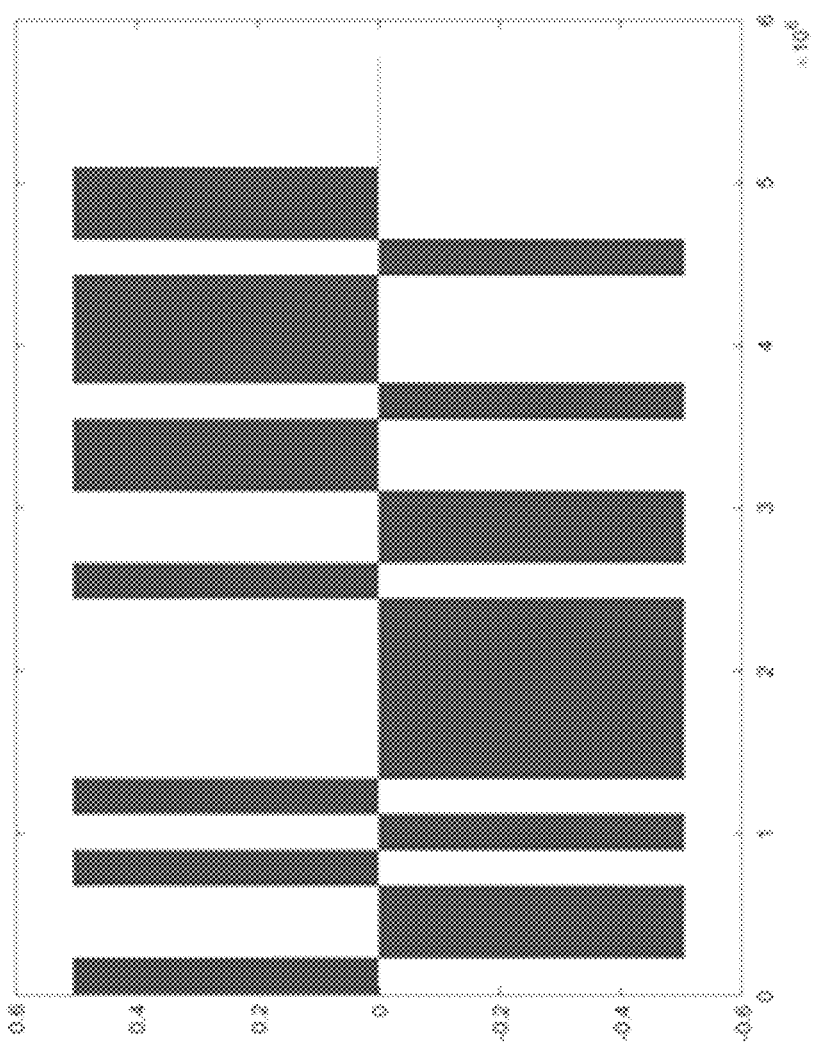
FIG. 82 shows a plot of the signal, as transmitted, assuming 240 chips per symbol.

FIG. 82 shows a plot of the signal, as transmitted, assuming 240 chips per symbol. Note in FIG. 82, the signal looks similar to the 23-bit template pattern, only that the spikes are much wider. This is because each "bit" of the 23-bit template pattern is 240 identical spikes: either all +1 or all −1.

To make an "A" symbol, 240 "A" chips are broadcast in sequence; to make a "B" symbol, 240 "B" chips are broadcast in sequence. In this way, the entire packet is broadcast. Nominally, it takes 44.16 ms to transmit each symbol and 541 ms to transmit a packet. At a lower transmit frequency, say 5% lower, it may take 568 ms to transmit a packet, but at a higher frequency, say 5% higher, only 514 ms.

When decoding the signal, enough data is stored in a frame to be sure of capturing one packet, but not so much that the noise between packets overwhelms the signal. A few empty bits of gap between packets may be enough, particularly if the packets are synchronized to each other.

The data is then "sliced" into segments of length equal to a sub-chip. However, since the frequency of transmission is not exactly known, the exact length of a sub-chip is not known, either. The range of frequency determining the # of samples or sub-samples per slice depends upon the assumed frequency of transmission. Thus, at the nominal frequency there may be 920 samples per chip=920 samples per slice. At a slightly lower frequency, there may be 920.1 samples per slice, which means that every ten slices an extra sample has been "squeezed" into the slice. At a slightly higher frequency, there may be 919.99 samples per slice, which means that every 100 slices, a sample has been "stretched". By appropriate stretching and squeezing, slices of equal length for all frequencies are obtained. These slices can then be treated equally, without worrying about how many samples and sub-samples were used to create each slice. This action is the stretch-squeeze slicing process. To accomplish stretch-squeezing efficiently, a template is made which stores an array of pointers that describes the starting point for each slice in the Frame for each frequency.

The slices are then stacked up and summed. Since each slice, in this example, is 920 samples, the $1^{st}$ sample of the $1^{st}$ slice is added to the $1^{st}$ sample of the $2^{nd}$ slice, and then $1^{st}$ sample of the $3^{rd}$ slice is added to that sum, and so forth until all first samples of all slices are summed into the $1^{st}$ sample of the combined slice. In this manner, all 920 samples of the combined slice are produced, each a sum of all the same number of samples in each of all the slices.

With no noise, this combined slice may look like what is shown in FIG. 66, showing a combined slice with SNR=5000. Note that the combined slice in Protocol 3 looks exactly the same as the combined slice in Protocol 2. In fact, if the duration of the packets were the same, and the amount of energy that was transmitted by the packets were the same, then the two combined slices would indeed be identical. The difference, is that in Protocol 3, 23*4 µs=92 µs of charge pumping occurs between each spike, whereas in Protocol 2, 2*4 µs=8 µs of charge pumping occurs between each spike. Thus, the amplitude of each spike in Protocol 3 is roughly ten times the amplitude of each spike in Protocol 2. Now, if the analog front ends in each system were "ideal" and the Analog-to-digital converter in each system was also "ideal," then, with the total available energy and the number of spikes in the combined slice fixed, there should be no difference in the combined slice from Protocol 2 and Protocol 3. But the world is not ideal, and there are likely cases where a 10× increase in amplitude of the spike means that the least-significant bit of the ADC flips often enough during a spike so that when 240 spikes are summed up for each of 23 locations in time, then a detectible set of spikes is observed. In addition, having 92 µs between spikes encourages use of an spike slice algorithm that takes advantage of this fact and eliminates the noise between these 92 µs spikes. This increases the noise contribution by nearly 99%, compared to the 75% reduction possible with the previously described protocol 2. We will explore this variation a bit later.

Summing all of the "A" through "W" chips produces the "template," which is used in decoding to find the correct frequency and the starting point of the packet. This is the same template as used in Protocol 2 (see FIG. 67).

Note that the spacing between the 23 spikes is 40 samples or 4 µs. Since there is always an equal number of A and B chips, the amplitude of sums are always nominally equal (noise will cause these amplitudes to vary in practice).

The next step is to convolve the combined slice with the template of the combined slice to find the best match starting point for each assumed frequency. A typical low-noise convolution for the best-match combined slice (matching the combined slice shown above) is shown in FIG. 68 again.

Note that when the template lines up with the best-fit combined slice, the amplitude is 23. When the slice is mis-aligned by the equivalent of 4 µs, the amplitude is −1. At all other misalignments, the amplitude is zero. Two values are retained for each assumed frequency: amplitude of the peak and sample number. Note that the absolute value of this correlation score is compared with the others. If the best fit score is negative, then each data point in the data set is multiplied by −1 in successive calculations. This process is identical to that of Protocol 2.

The maximum convolution value for each assumed frequency is calculated. A plot of these values versus assumed frequency is the "spectrum." See FIG. 69 again for a plot of the spectrum a SNR=5000 in this example.

This example shows that the frequency is near the nominal value, which would be 501. If the peak is closer to 1, then the frequency is below nominal; if it is closer to 1000, then the frequency is above nominal. From the highest peak we learn two things: the actual broadcast frequency and the (from the previous graph) the starting index within the combined slice.

The next step is to produce (or pull from memory) the pointers for this frequency and this starting index. The pointers are a list of numbers, each representing the starting point and template for each slice.

The pointers and template are then used to generate 23 chip scores for each slice: an "A" chip score through a "W" chip score. Each chip score is the correlation sum of that slice convolved with the template for that chip. Thus, the template for the "A" chip is a single spike at time sample number 1 (for example . . . ). The template for the B chip would be a single spike (i.e., expected signal received in a low-noise system from the discharged capacitor through the coil) at sample number 41 (i.e., at t=4 µs, assuming 10^6 samples per second).

Figure 83:
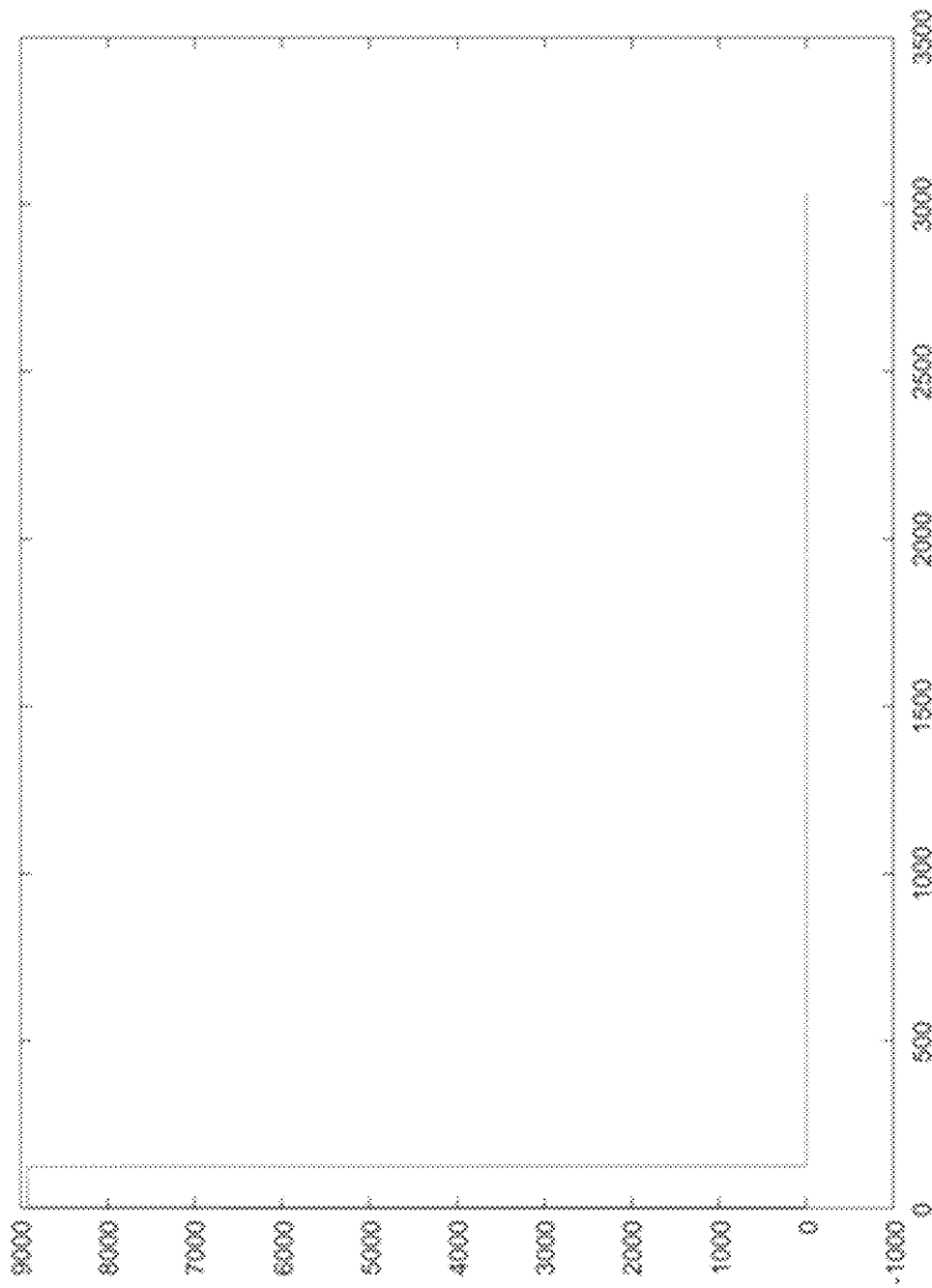
FIG. 83 shows the "A" sub chip scores for each slice for the very low noise case.

Shown in FIG. 83 are the "A" sub chip scores for each slice for the very low noise case. The X-axis represents the slice number, and the Y-Axis represents the correlation value. Note that since there is very little noise in this example, it is easy to see that the A chips all occur at the beginning of the packet.

Figure 84:
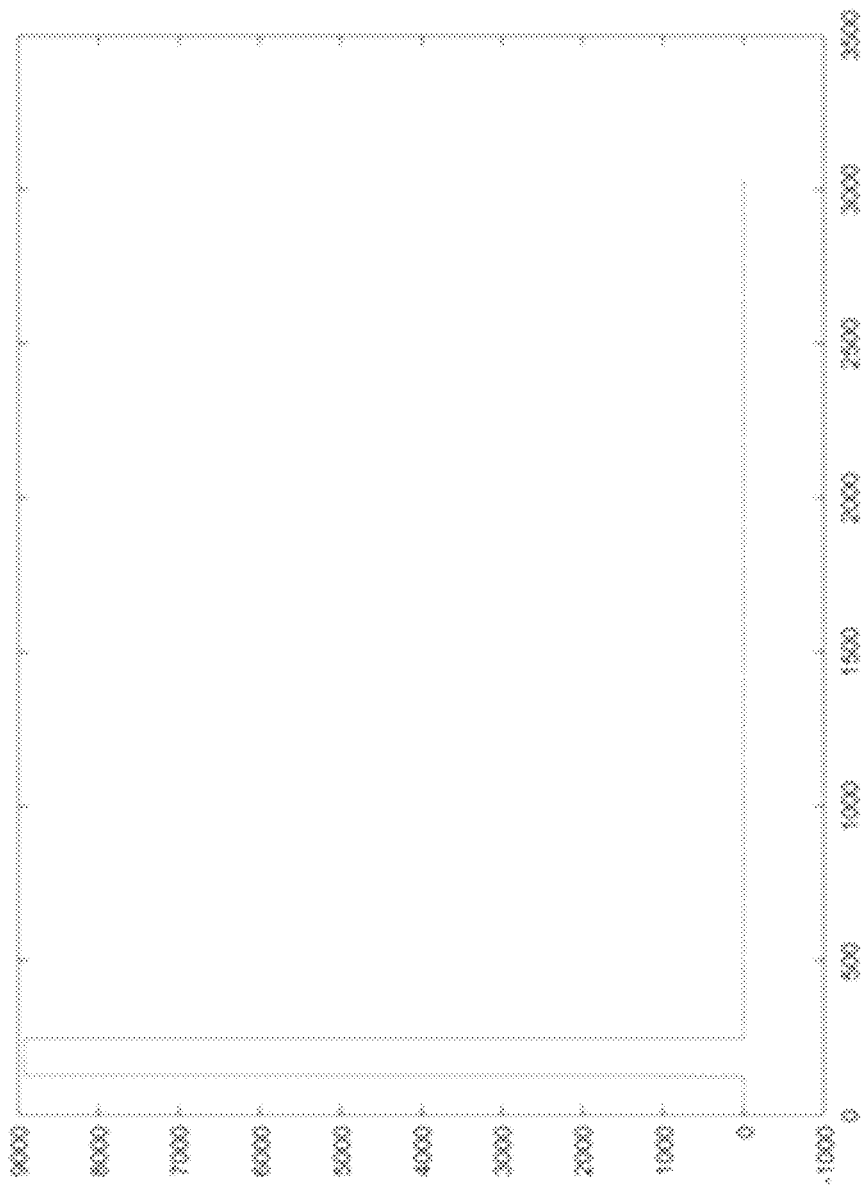
FIG. 84 shows the F chip scores for each slice for the very low noise case.

FIG. 84 shows the F chip scores for each slice for the very low noise case. Similarly, as the second symbol in the packet, the F chip scores for each slice are high when one would expect the second symbol in the packet to occur.

Figure 85:
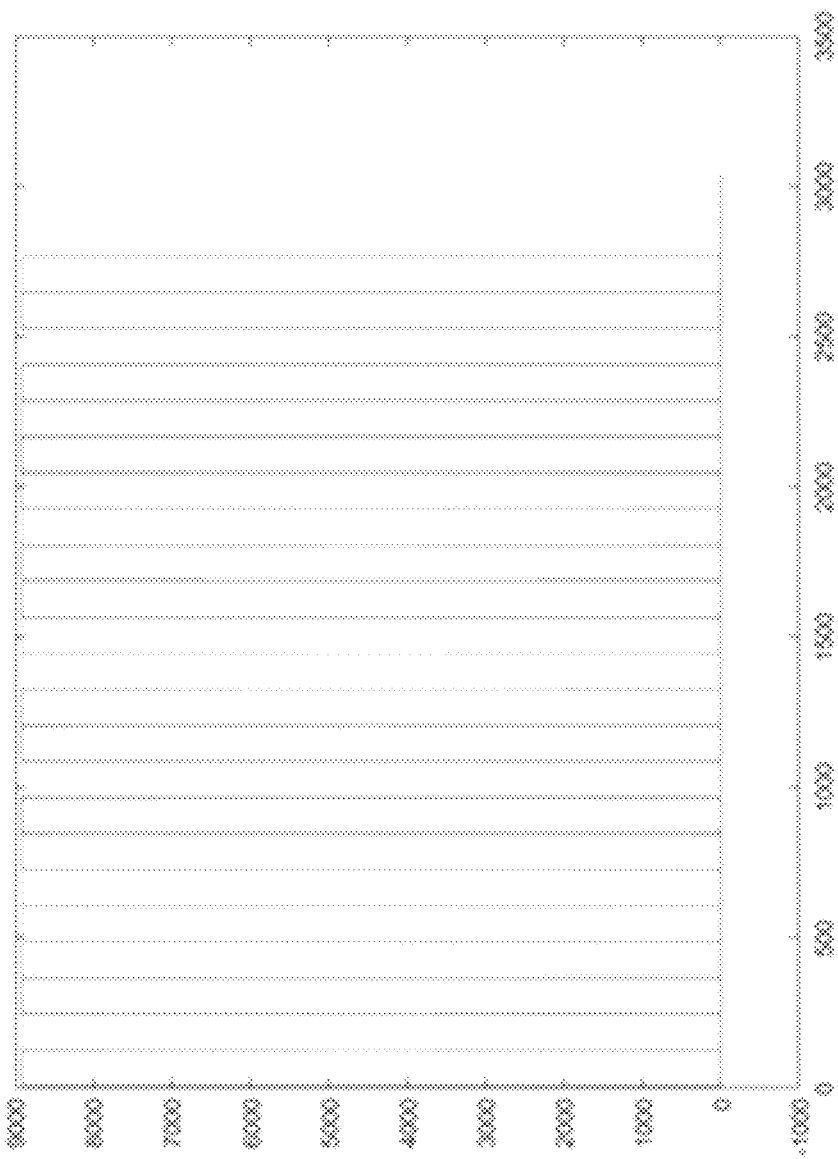
FIG. 85 shows a plot of all A through W chip scores versus slice number.

FIG. 85 shows a plot of all A through W chip scores versus slice number. It is easy to see, in the low-noise case, that the values of each symbol are about zero whenever they are not present. This is because all of the chips share the same registration, or starting point, and thus each symbol is orthogonal to each of the other symbols, given that registration. Thus, a key difference with other protocols is that all of the packet energy is used to find the frequency and in-slice registration point. For any given in-slice registration point, all of the symbols are orthogonal to each other. While it might make sense, if one desired, for example 140 bits of information, to simply repeat the 23-symbol packet in a different permutation. This would work, of course, and again all of the packet energy would be used to find the frequency, but now, relative to that packet-quantity of energy, the per symbol energy would be half. A better approach to accomplish the same objective would be to find a 25 symbol system that has a similar autocorrelation pattern. The 25 symbol packet could yield 84 bits. In this case the symbol energy/packet energy would be reduced by only 8%. Thus, each chip score has 23 numbers, each a correlation sum to a symbol for a single slice.

Ultimately, only one of these chip scores per slice will be used in the calculation of the best-guess packet. This means, that the signal in a ~1 µs period is gathered along with the noise that occurs during that 1 µs. However, the noise that occurs in the other 91 µs of each slice is completely left out. An alternative embodiment, however, might be to average all of the 23 chip scores for each slice, and subtract the average of the other chip scores from each chip score. This alternative embodiment, however, would then gather and use the noise in 22 more micro-seconds per slice. Perhaps there are certain situations where this may be an advantage.

Either way, the next step is to generate, using the chip scores, the symbol length scores for each slice. Again, there are 23 symbol scores for each slice, each representing the sum of chip scores of that slice and the next 239 slices. Here is the formula:

```
for chipNum = 1:symbolsPerFrame - chipsPerSymbol
    for thisChipNum = chipNum:chipNum+chipsPerSymbol
        for symbolNum = 1:23
            symbolLengthScores(chipNum,symbolNum) =
    symbolLengthScores(chipNum,symbolNum)...
                +chipScores(thisChipNum,symbolNum);
        end
    end
end
```

Figure 86:
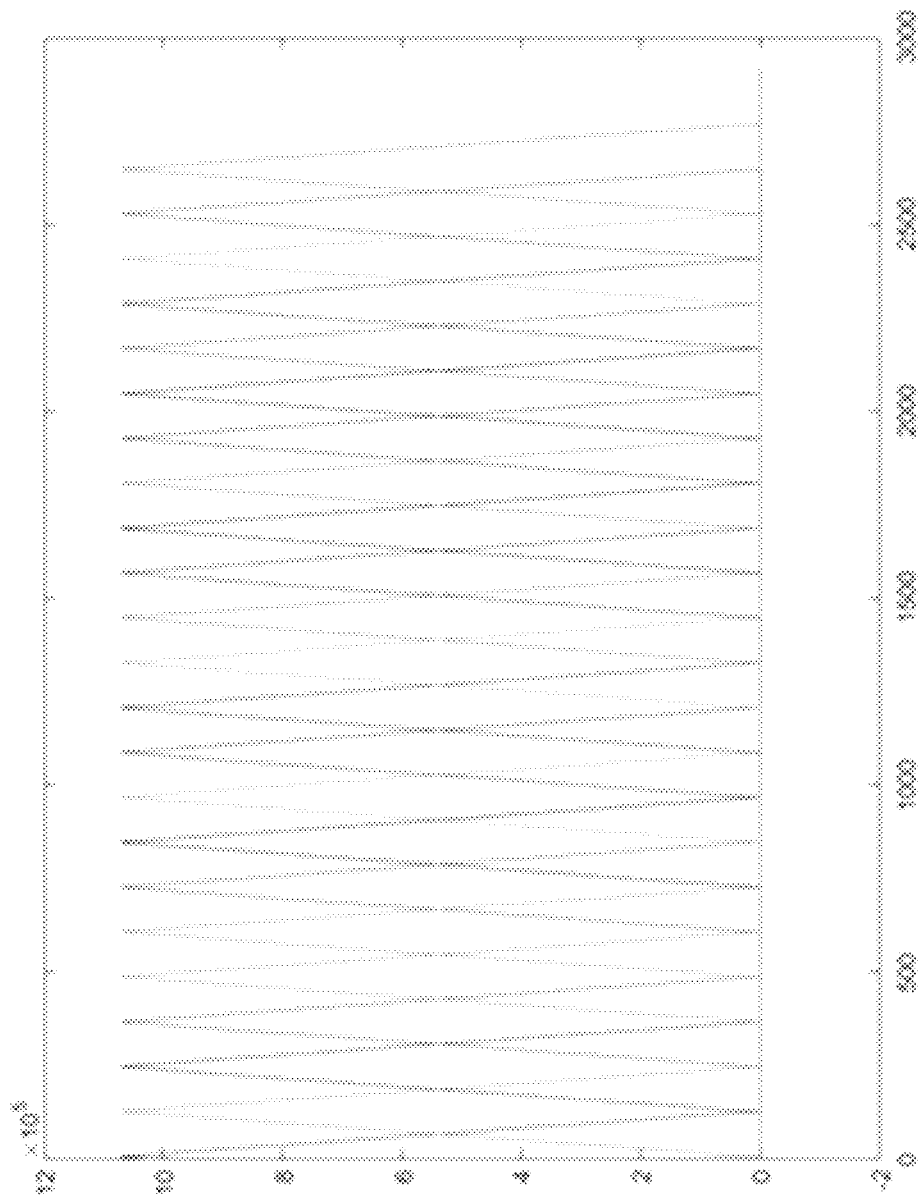
FIG. 86 shows a plot of each of the symbol length scores v slice number.

FIG. 86 shows a plot of each of the symbol length scores v slice number. At this point, the next step is to determine a packet length score for each slice. To do this, one starts by declaring the maximum symbol-length score for each slice to be that symbol. When there is little noise, this is easy: one of the symbols has a very big score, the other ones have very little scores. Then, one adds up these maximum symbol length scores from the appropriate 23 time points that define a packet, and one determines a "packet score" for each slice. As one works through all of the candidate slices for the biggest packet score, one must also check to see if the 23 chosen symbols are unique, i.e., each symbol "maximum" once and only once. As one searches through the slices for the maximum packet score, one can ignore most of those that are not the biggest on the first cut. If the slice with the greatest packet score does not identify 23 unique symbols (because of noise), then an error correction algorithm is used to find the best-guess packet with 23 unique symbols.

One way of running such an algorithm is shown below in example MATLAB code:

```
symbolLen = length(allSymbolScores);
packetSums(1:symbolLen,1:2) = 0.0;
[convolutionSums, symbolNums] = sort(allSymbolScores,1,'descend');
[thisBestSum, thisBestSymbol] = max(convolutionSums(1,1:23)); %Find the highest correlation value and locationamong all 23 x 23
while thisBestSum > 0.0
   thisLocation = round(symbolNums(1,thisBestSymbol));
   if packetSums(thisLocation,1) < 1
      packetSums(thisLocation,1:2) = [thisBestSymbol thisBestSum]; % Store thisBestSymbol in the thisLocation symbol location and its correlation score
      convolutionSums(1:symbolLen,thisBestSymbol) = 0.0; % Zero out the rest o fthe thisBestSymbol correlation scores
   else
      % IN this case, the packet location is already filled, but this symbol has not been declared.
      % Eliminate the found location for this symbol and shift the
      % values for the other locations for this symbol up.
      convolutionSums(1:symbolLen-1,thisBestSymbol) = convolutionSums(2:symbolLen,thisBestSymbol);
      symbolNums(1:symbolLen-1,thisBestSymbol) = symbolNums(2:symbolLen,thisBestSymbol);
   end
   [thisBestSum, thisBestSymbol] = max(convolutionSums(1,1:23)); %Find the highest correlation value and locationamong all 23 x 23
End
```

First, the 23 symbol scores for each of the 23 packet locations are stored in a matrix. That matrix is then sorted so that the highest symbol length scores for each location are found. The high symbol length score for all locations is found, and that symbol is declared for that location. That symbol is then removed from the competition for the other 22 locations. The next highest symbol length score among the remaining 22 locations is then found and the symbol for that location is declared and that symbol is removed from the competition for all other locations. The above algorithm is one way of accomplishing this procedure, but there are likely other more efficient ways of correcting the errors. For example, if there is a preamble, than this information may be used to find the best-guess packet and an estimate of the accuracy of the guess. Ultimately, if error correction is needed, then the packet score for that slice number will be lower. Yet, it might still be the best overall packet score.

Thus, the best estimate of the packet has been determined. Depending on the SNR of the signal, a certain number of data packets at the same or similar frequency are determined and if they match, then the data packet is assumed correct. Alternatively, if the SNR is below a certain number, a number of these bit length scores may be combined to produce a meta-symbol length score that combines neighboring data packets to produce a better estimate of a single data packet.

Figure 87:
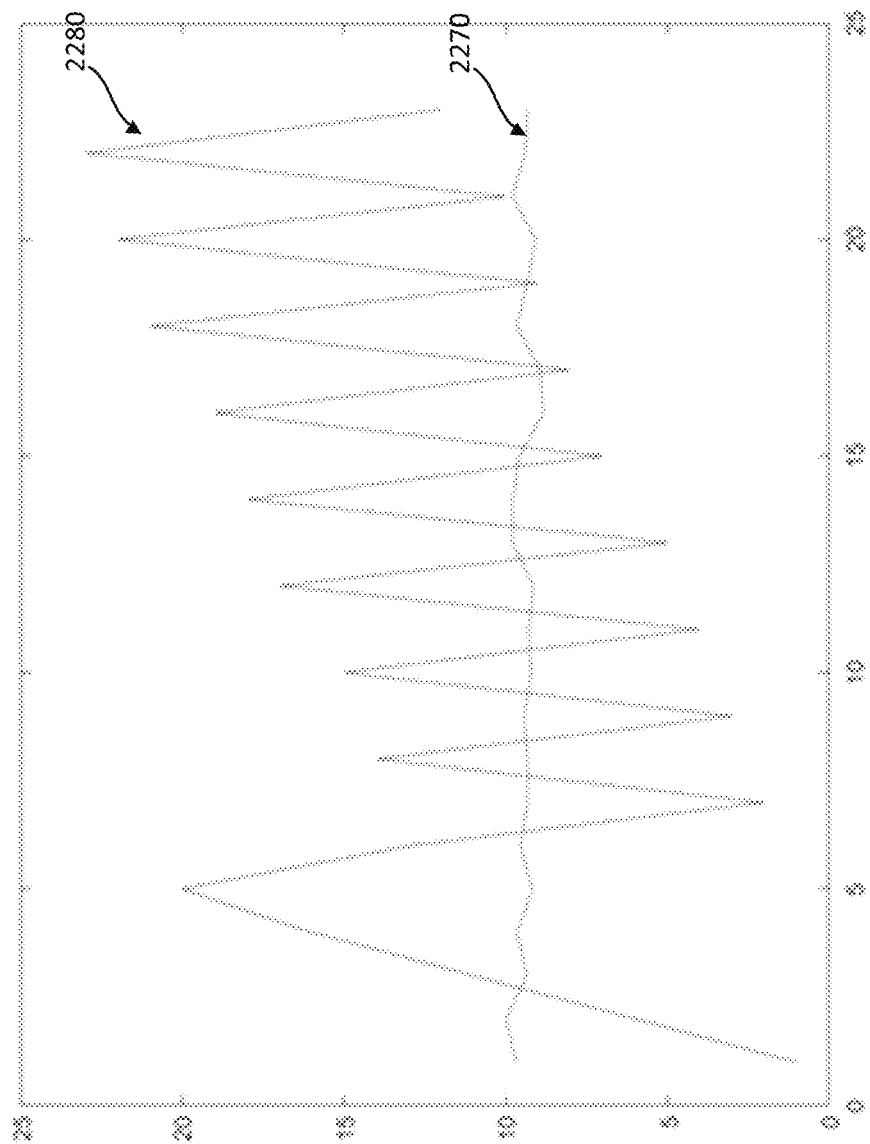
FIG. 87 is a plot showing the low noise (−5.5 dB) packet.

FIG. 87 is a plot showing the low noise (−5.5 dB) packet. Two lines are shown: the gradually changing orange line 2270 with values just below ten is the normalized bit length score at that location and the rapidly changing (blue) line 2280 with values ranging from 1 to 23 is the as-interpreted symbol value.

Figure 88:
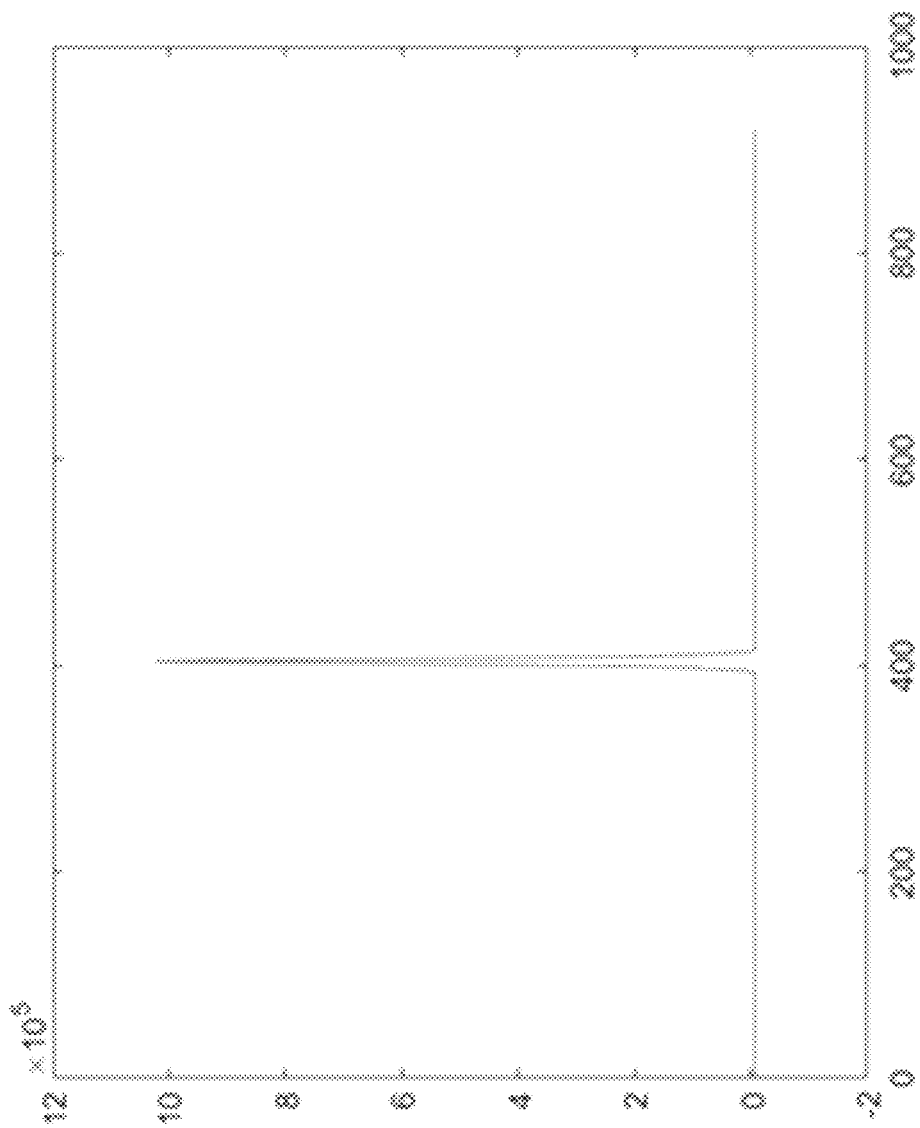
FIG. 88 shows a low-noise example of the correct frequency, showing a first combined slice of the symbol-length slice.

Now, it can be determined how these same parameters look in the presence of various amounts of noise. In all the following examples, SNR is measured to be Vmax/V noise rms, where Vmax is spike amplitude and V noise rms=sqrt (mean(noise.*noise)) (MATLAB notation). Here is the relevant MATLAB code:
noise=2.0*rand(1,length(signal))−1.0;
noiseRMS=sqrt(mean(noise.*noise));
vMax=000.0192;
inData=1.0*signarvMax/max(signal);
log_vM axOverVn=10.0*log(vMax/noiseRMS)
simData=inData+noise;

In some aspects, (and alluded to previously) an important variation to the symbol-length stretch/squeeze process is utilized. In this process, the data frame is broken up into overlapping symbol-length slices. Alternatively, the data frame is broken up into slices of length equal to 1.5 times the symbol length, and these slices increment at 0.5 times symbol length. In this case, sub-slices may be used on successive slice calculations to reduce computations. This variation guarantees that all of the energy of a single symbol will be contained in a single slice. While this process may not have much effect when finding the right frequency, it may be helpful when decoding the signal. Either way, each of these slices is then stretched or squeezed into a combined slice of nominal length (In this example, 920 samples long). A low-noise example of the correct frequency is shown in FIG. 88. Here, a first combined slice of the symbol-length slice is shown.

Note that only one peak shows up. This is because the first slice captures only a part of the first symbol and none of the second symbol. The second slice overlaps the first slice by some percentage. In this case, the percentage is 50%. The purpose of this is to ensure that one of these slices captures the majority of the symbol information and the peak may be found.

Figure 89:
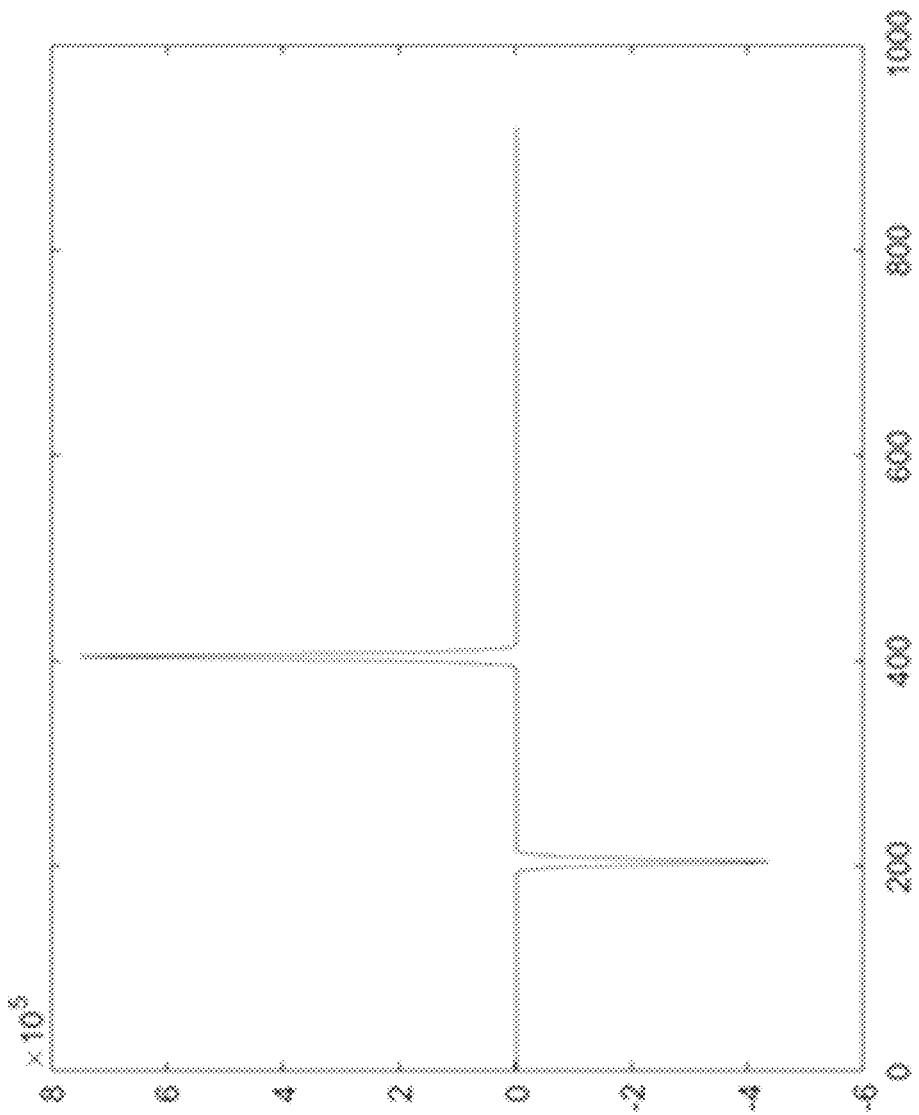
FIG. 89 shows the second combined slice sum of the symbol-length slice.

The second combined slice sum of the symbol-length slice is shown in FIG. 89. Note that the same peak that showed up in the first slice (near index=400) also shows up in the second slice. In addition, part of the next symbol (near index=200) is also seen.

FIG. 90 shows two plots of the same first slice and second slice sum, in the presence of noise, in plots 2270 and 2280, respectively. Plot 2270 shows the first slice of the symbol-length slice with SNR=7 dB. Note that this was a different set of data, and the peak shows up on a different index of this combined slice. Similarly, plot 2280 shows the second slice of the symbol-length slice, with SNR=7 dB. Note that the two peaks are visible above the background noise in this combined-slice.

Figure 91:
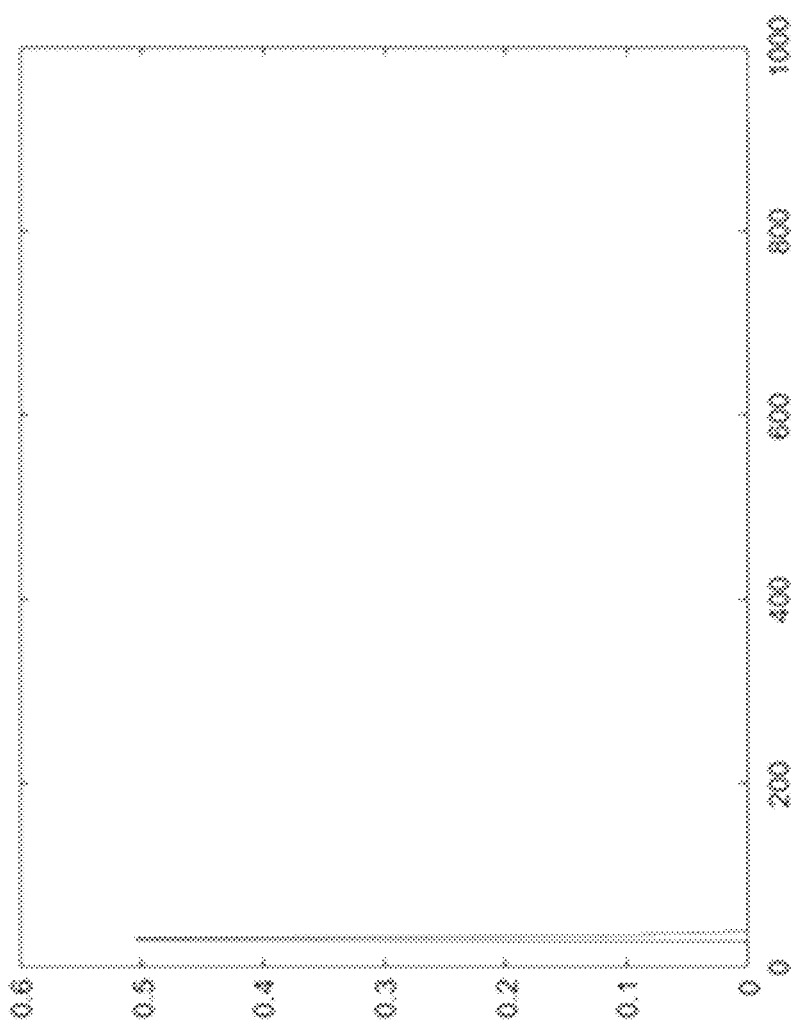
FIG. 91 shows the template used for the symbol-length slices.
Figure 92:
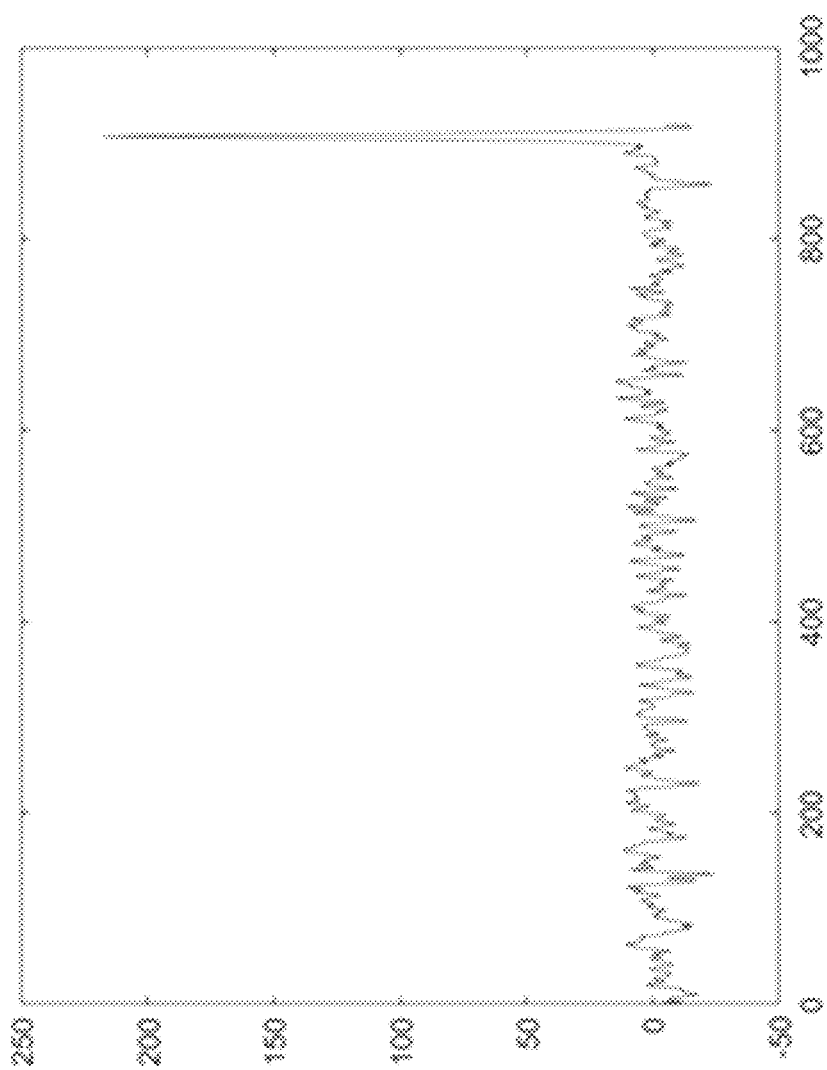
FIG. 92 illustrates the convolution of the combined slice shown in plot 2270 with the template shown in FIG. 91.

Since only one or at most two peaks in each of these symbol-length frames is expected to be shown, the template is that of a single peak, shown in FIG. 91. FIG. 91 shows the template used for the symbol-length slices. When this template is convolved with the combined slice shown in the two plots of FIG. 90, the result is as shown in FIG. 92. FIG. 92 illustrates the convolution of the combined slice shown in plot 2270 with the template shown in FIG. 91. It is analogous to the result in FIG. 68.

Figure 93:
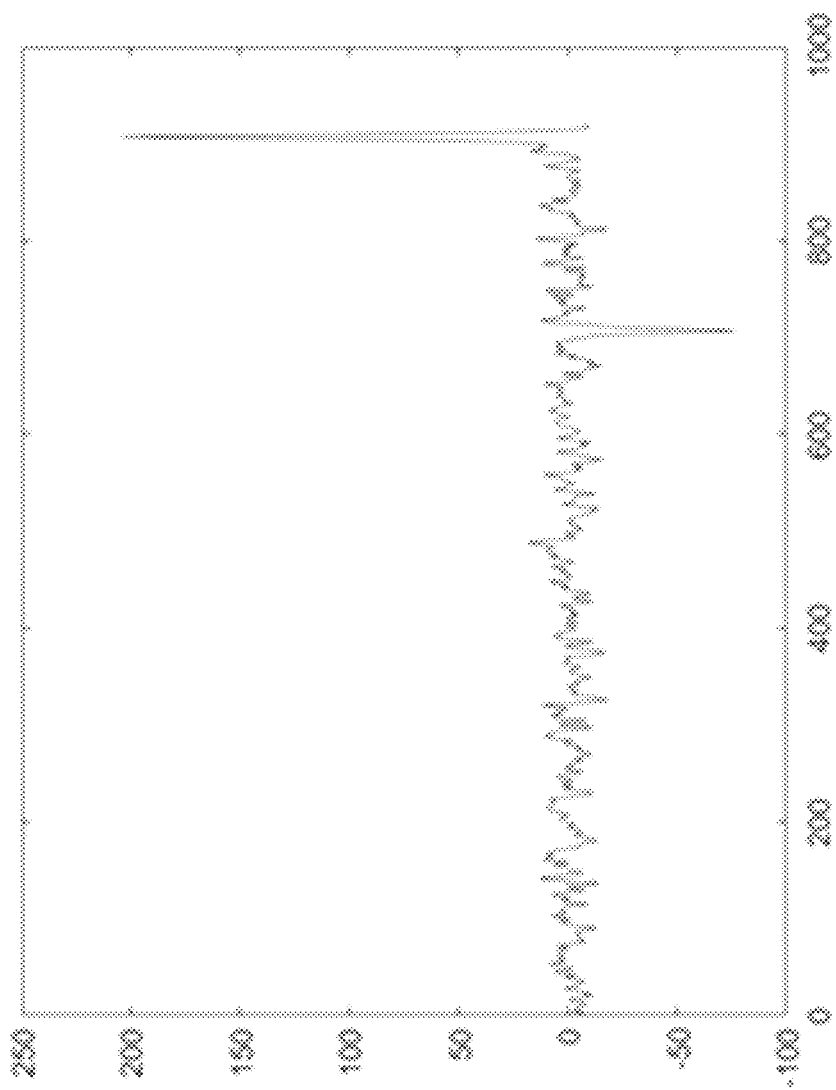
FIG. 93 shows the convolution of the combined slice shown in plot 2280 with the template shown in FIG. 91.

FIG. 93 shows the convolution of the combined slice shown in plot 2280 with the template shown in FIG. 91. It is analogous to the result in FIG. 68.

In this squeeze/stretch slice variation, two peaks are expected to be seen. These two peaks are the only information ideally to be collected, and the rest can be disregarded, which is just noise. In this way—by eliminating noise where there is no signal—the overall signal to noise of the system can be improved. In fact, by using just one of these peak values in later calculations, roughly 98% of the noise present during the transmission is eliminated from the analysis. So for each symbol-length slices:

A 1.5× symbol length of data is squeezed/stretched into a nominal-length slice (in this case 920 data points) (1.5× is used to ensure that all of each peak is in one combined slice);

The combined slice is convolved with a template that consists of a single spike.

Figure 94:
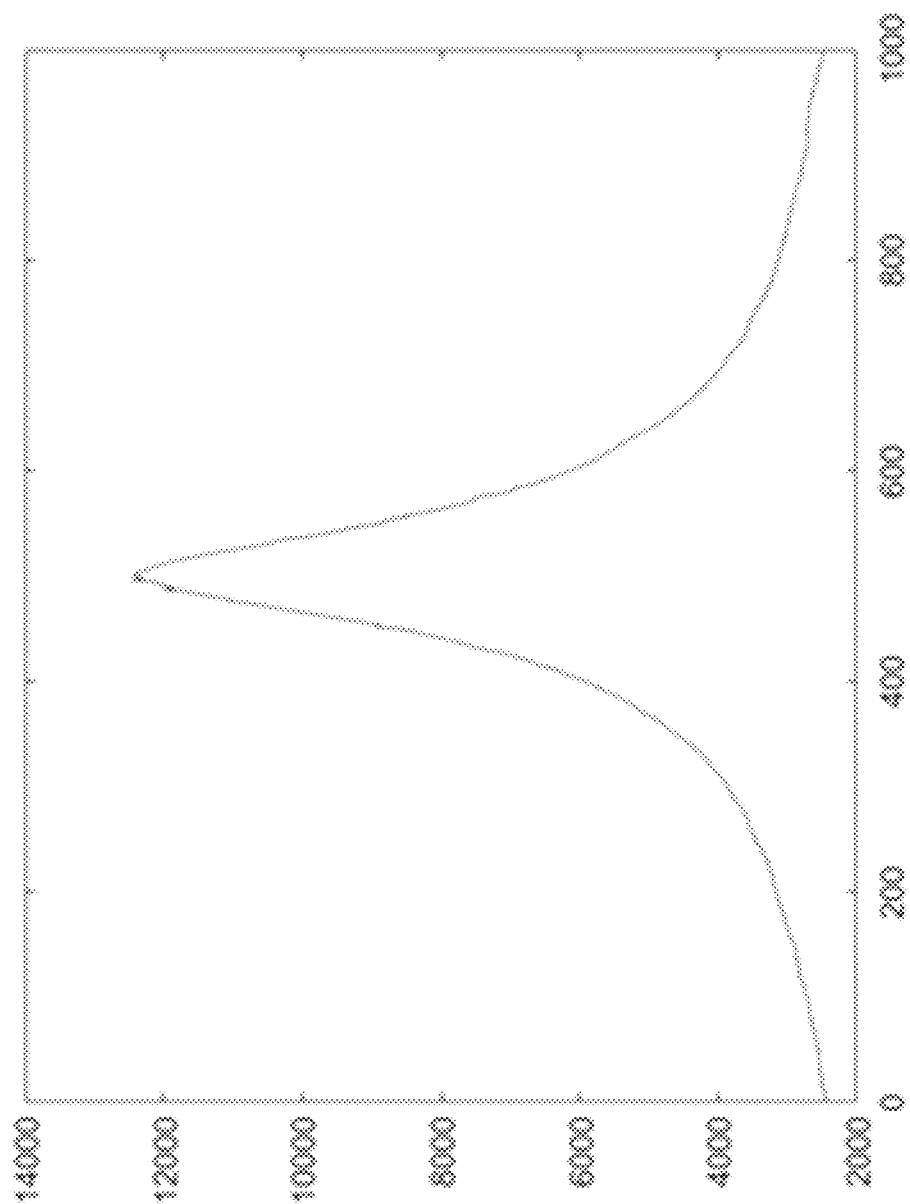
FIG. 94 shows the spectrum: the sums of the magnitudes of the two peaks for each of the symbol-length slices as a function of frequency.

The top two peaks that result from the convolution that are at least 35 μs away from each are stored in memory along with their indices (the index and magnitude are both kept). The sum of the absolute values of each of the two peaks are added to a variable called Spectrum(frequency). Thus, each of the magnitudes (absolute values) of the top two peaks in each of the symbol-length slices are added together to make the value that is compared to that of all other frequencies to find the correct frequency. These spectrum values may be plotted as a function of frequency, as shown in FIG. 94 for the same noise case. FIG. 94 shows the spectrum: the sums of the magnitudes of the two peaks for each of the symbol-length slices as a function of frequency. It is analogous to FIG. 69.

Note that compared to FIG. 69, this spectrum peak is much broader and smoother. This is because since only one symbol at a time is being analyzed, the filtering has a wider bandwidth. (Part of the smoothness is due to the fact that only magnitudes are plotted here; the earlier spectrum plots included the parity of the data set.) It lacks the specificity of the all-frame stretch/squeeze analysis with a 23 spike template. On the other hand, a great deal of noise has been eliminated from the analysis. In the 23 spike template, each spike is roughly 1 μs in width on a 4 μs spacing. In between spikes the template value is zero. Thus, in each convolution, 75% of the noise is eliminated—the spaces between the spikes in the template. In the symbol-length stretch/squeeze approach, however, the template is a single spike 1 μs wide, and is used twice. In this case, 2 μs of noise is included and 90 μs or 98% of the noise is eliminated.

Figure 95:
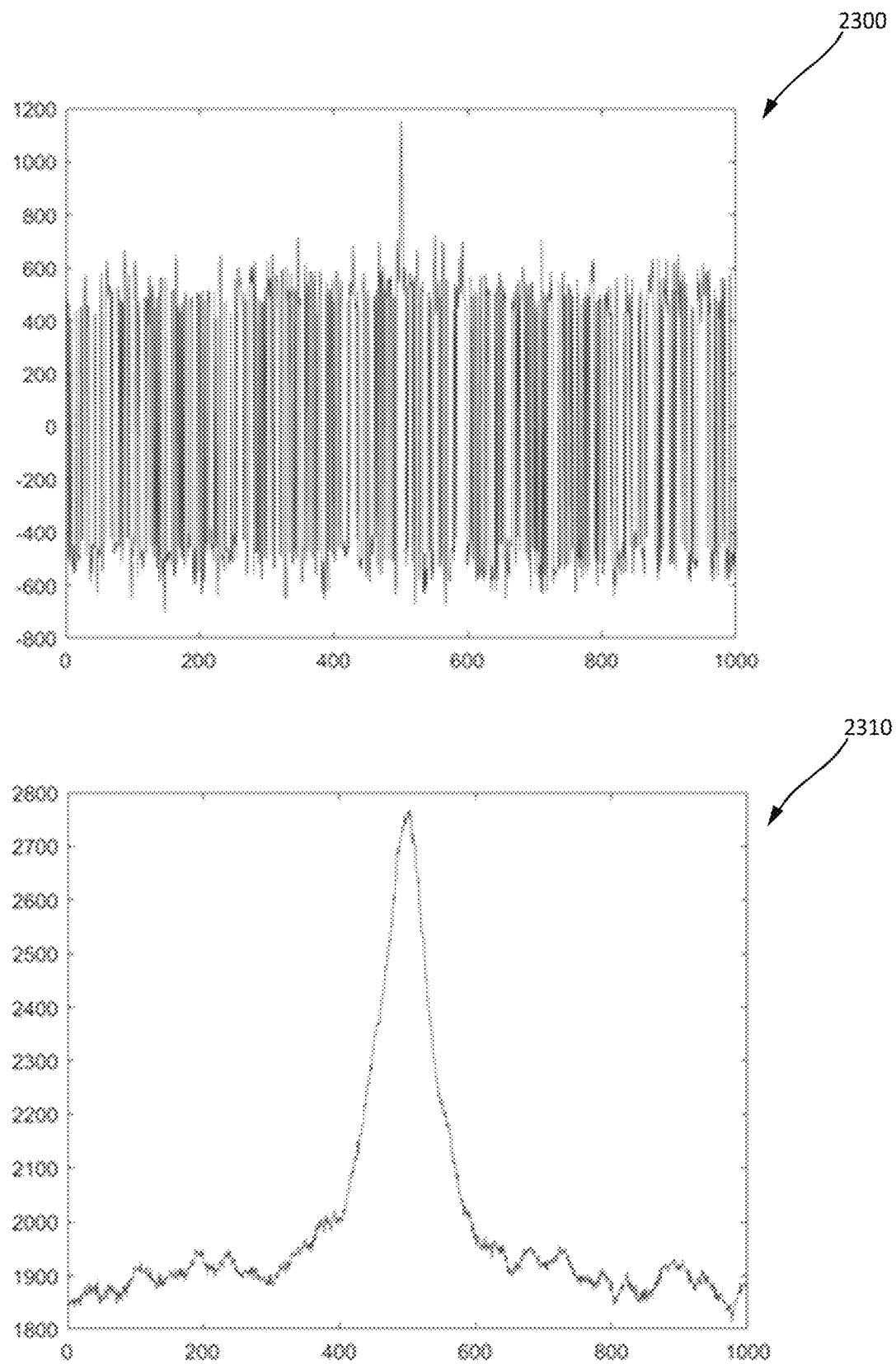
FIG. 95 shows the spectrums for both the frame-length stretch/squeeze analysis and the symbol-length stretch/squeeze analysis.

To see how this benefits the finding of the frequency when the noise level is even higher, shown in FIG. 95 are the spectrums for both the frame-length stretch/squeeze analysis and the symbol-length stretch/squeeze analysis.

Plot 2300 of FIG. 95 shows the spectrum for the frame-length slices as a function of frequency. The SNR=−10.6 dB. It was computed using the identical algorithm used to generate the plot in FIG. 69.

Plot 2310 of FIG. 95 shows the spectrum for the symbol-length slices as a function of frequency. The SNR=−10.6 dB. It was computed using the identical algorithm used to generate the plot of FIG. 94.

Note that in the above comparison, the correct answer (Index=501) is produced. It is clear, however, that the peak in plot 2330 is a smoother curve, and there is more certainty that a signal is present.

Figure 96:
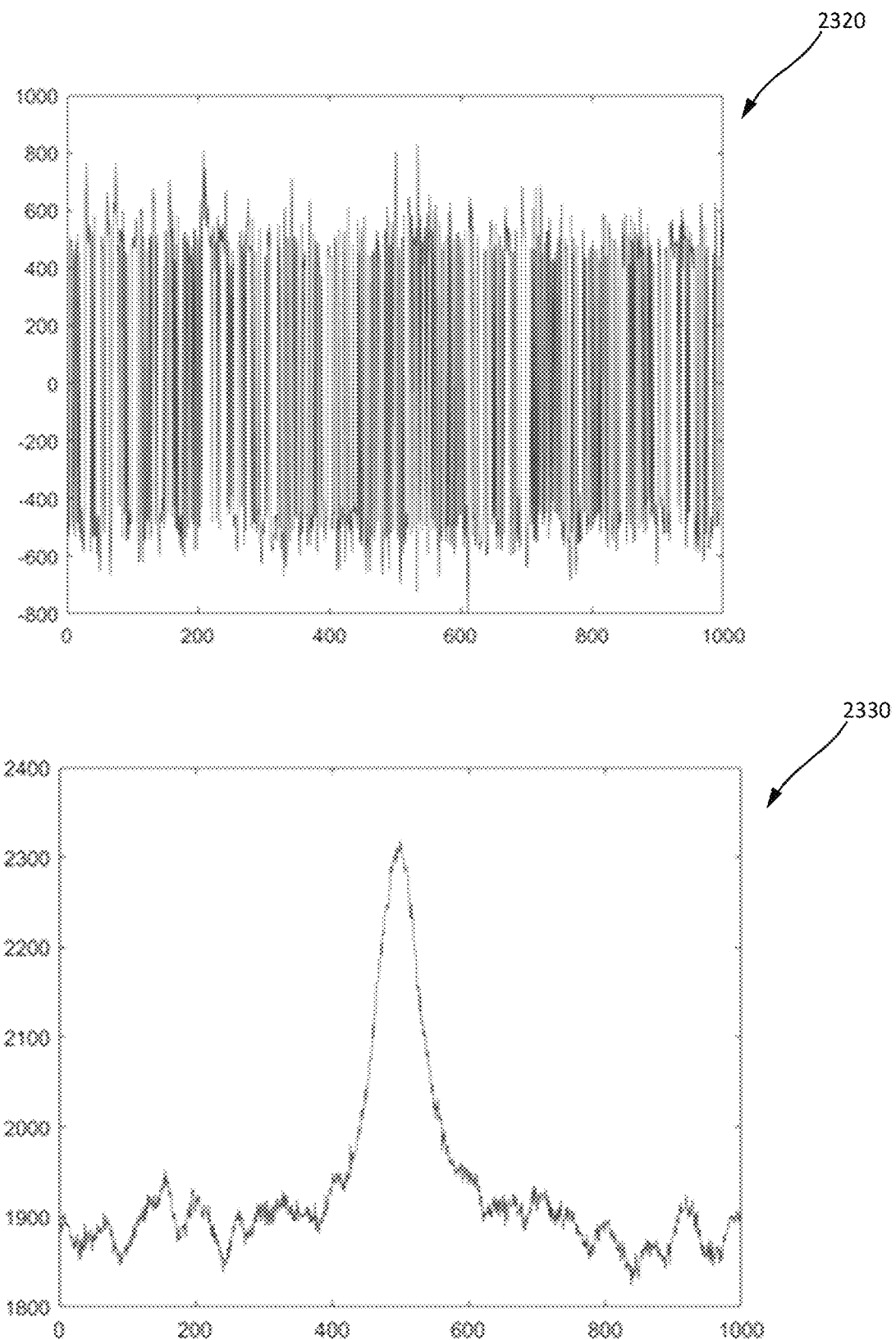
FIG. 96 shows the results from a noisier run, where the plot shows the spectrum for the frame-length slices as a function of frequency, and the SNR=−13.5 dB.

Shown in FIG. 96 are results from a noisier run. Plot 2320 shows the spectrum for the frame-length slices as a function of frequency. The SNR=−13.5 dB. It was computed using the identical algorithm used to generate the plot of FIG. 69.

Plot 2330 shows the spectrum for the symbol-length slices as a function of frequency. The SNR=−13.5 dB, but with only 120 chips per symbol. It was computed using the identical algorithm used to generate the plot of FIG. 94.

Note that in the frame length case, the correct answer (501) shows up in third place, after the peaks near indices 600 and 520. This packet was therefore not successfully decoded. The spectrum based on symbol length symbol-length slices in plot 2330, however, found the correct frequency, exactly.

Figure 97:
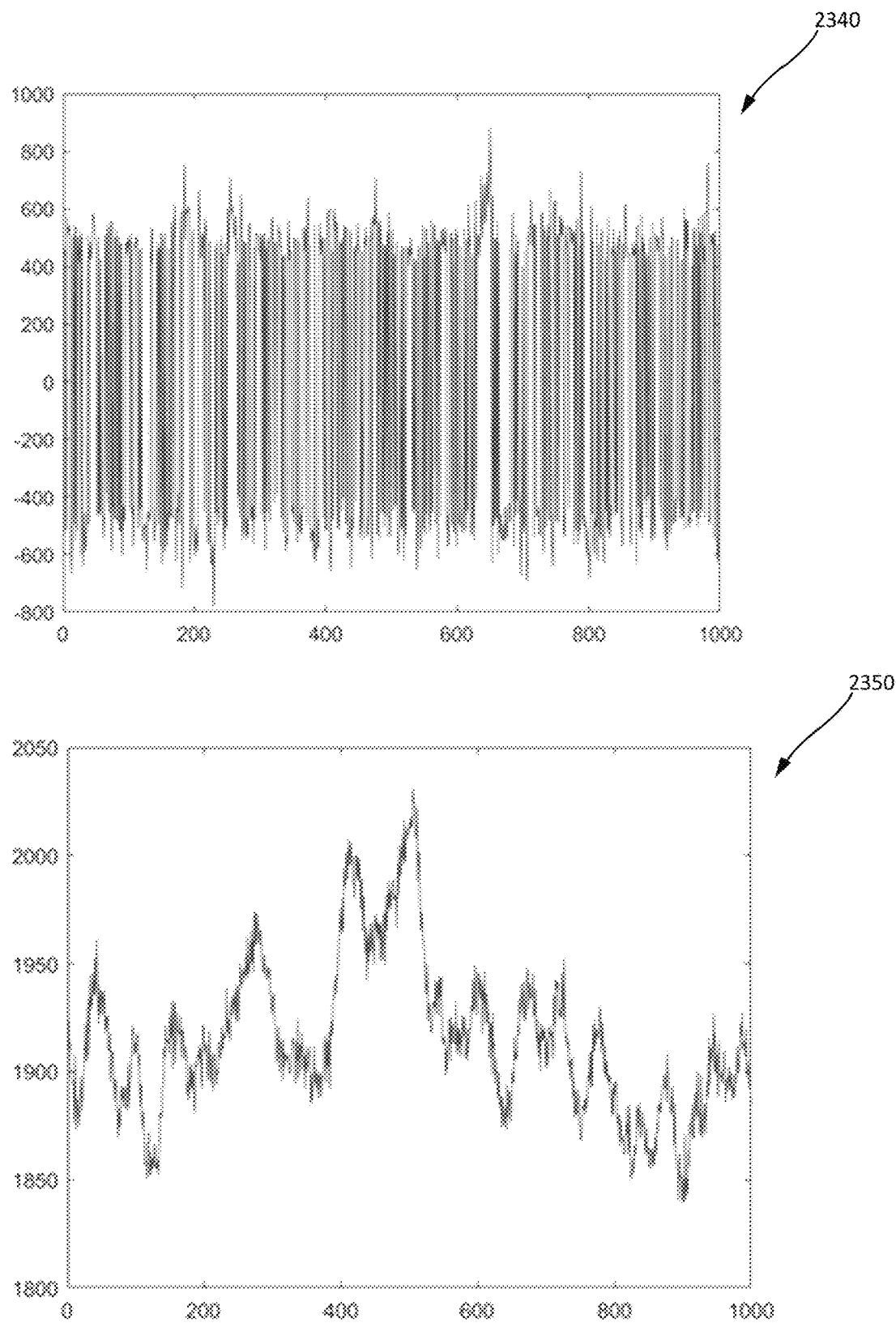
FIG. 97 shows the spectrum for the frame-length slices as a function of frequency, where the SNR=−17.5 dB, but with only 120 chips per symbol.

Referring to FIG. 97, shown in plot 2340 is the spectrum for the frame-length slices as a function of frequency. The SNR=−17.5 dB, but with only 120 chips per symbol. It was computed using the identical algorithm used to generate the plot of FIG. 69.

Plot 2350 shows the spectrum for the symbol-length slices as a function of frequency. The SNR=−17.5 dB, but with 120 chips per symbol. It was computed using the identical algorithm used to generate the plot of FIG. 94.

When the SNR was decreased further, the spectrum based on frame-length slices in plot 2340 did not come close to identifying the correct frequency. On the other hand, the spectrum based on the symbol-length slices, in plot 2350, estimated the frequency to be 505 units instead of the target 501, close enough to successfully decode the packet.

Figure 98:
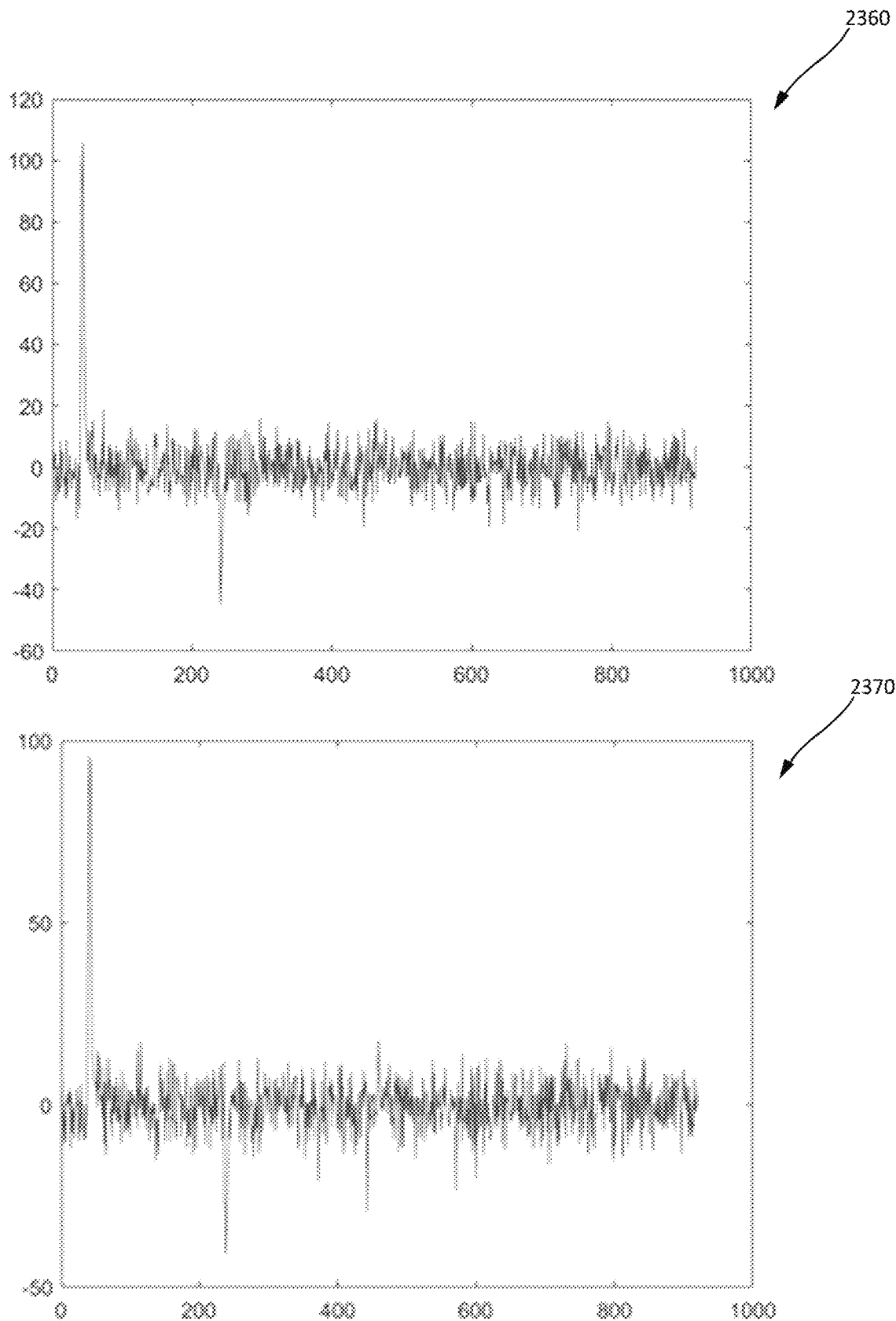
FIG. 98 is the same $2^{nd}$ slice, same data set as in plot 2280 (see FIG. 90), but at a frequency that is 10 units higher.

To see how this works at a more granular level, shown in plot 2360 of FIG. 98 is the same $2^{nd}$ slice, same data set as in plot 2280 (see FIG. 90), but at a frequency that is 10 units higher. In plot 2360, shown is the second slice of the symbol-length slice, with SNR=7 dB, but the frequency is at 511 units instead of 501. Note that most of the information contained in the spike is retained. The peak is only slightly lower.

Shown in plot 2370 is the second slice of the symbol-length slice, with SNR=7 dB, but the frequency is at 521 units instead of 501. Based on this, it can be easily seen how by spreading the spikes over more indices, the magnitude of the peak is reduced. This is barely noticeable when the search frequency is off by 10 units, but more obvious when it is off by 20 units.

Referring to FIG. 99, shown in plot 2380 is the second slice of the symbol-length slice, with SNR=7 dB, but the frequency is at 551 units instead of 501.

In plot 2390, shown is the second slice of the symbol-length slice, with SNR=7 dB, but the frequency is at 571 units instead of 501. Note that when the frequency is off by 70 units, the magnitudes of the peaks are roughly half of what they were when the frequency was exactly correct.

It should be noted here that if instead of allowing all 23 symbols to be randomly placed within the packet to produce 23! codes, it was instead insisted that the first three symbols were fixed and the others were each paired up so that spacing between two valid symbols was always the same, then a two-symbol wide slice would be dramatically more specific while retaining most of the benefits of the single-symbol wide slice shown above.

There are several benefits to this variation. For example, the idea of symbol-length slices suits itself to real-time execution: large numbers of data points are consumed and converted into a smaller number of points that may be later used to find a packet, find its frequency, and decode its information—which is the primary purposed of slices in the first place.

In this case, the packet length was 250 ms (as opposed to Protocol 2, which was ~500 ms). Longer packets imply longer symbols, which put more energy into each symbol, and thus are easier to decode. At 250 ms, each symbol was 120 (chips per symbol)*920 (samples per chip)=110,400 samples per symbol. In Protocol 2, the number was 220,800 samples per symbol (in both cases, a nominal number of samples, the exact number of samples as transmitted might be 1%, 5% or even 10% higher or lower than nominal). If it is assumed a +/−1% off of nominal frequency range may be used, say 1000 frequency buckets. For each slice, 220,800 samples can be converted into a slice that has 1000×4 data points. For more accuracy, the top 3 or top 4 peaks might be saved from each slice, increasing the information saved from 4000 points to, say, 8000 points. Nevertheless, 220,000 samples are converted into 8000 points or so, a fairly significant compression ratio.

Second, of course, is by eliminating 98% of the noise from the final analysis, the signal and frequency detection can be improved by ~6 dB, which is a significant benefit. Further variations—such as two-symbol wide slices with known separations between those two symbols, might yield further benefits.

Third, this variation is to produce a spectrum pattern that clearly indicates that an artificial signal—and not random noise—is present. This would allow, when a single packet produces enough information that it can be determined a signal is there but not enough to decode it accurately, to find and then combine successive packets carrying the same information, and combining these packets at the slice level. From a practical perspective, combining two packets, each representing five million samples using correlation between the two data sets would require a very large number of multiplications and additions and would likely not work, since one would be comparing two signals each dominated by noise. On the other hand, the slicing process eliminates 98% of the noise in each slice, and comparing 50 slices from one packet to 50 slices from another packet would yield a very good chance of aligning them properly with minimal computation required.

Fourth, symbol length slices may be useful in adjusting for variations in the transmission clock that occur during the packet broadcast (drift). When adjusting for drift, the symbol-length slice needs a clock that is stable during just the symbol length time. As long as the drift over the whole packet doesn't exceed 2 µs (in this example), the symbols retain their orthogonality.

Example Data Results from Third Spike Protocol Definition

The algorithm used to analyze the data in Protocol 3 is a variation of that described earlier. The biggest difference is the heavy reliance on the 1.5*symbol length slices to find the frequency. In this solution shown to produce strong results, this algorithm (referred to herein as Protocol 3 Symbol Slicer, or P3SS) is used in a coarse frequency mode to quickly scan the frequency for the signal, taking advantage of its broad, well-behaved spectrum. Then, a fine search using P3SS is used to find the best-guess frequency. In high noise environments, this approach is superior than using the frame-length combined slice approach because of the additional noise elimination (from 75% noise elimination to 98% noise elimination).

Of note, after the symbol slices are created (combined from 240 slices) only the index and peak values of the top two peaks (at least 35 µs apart) are kept. These are added to the other top two magnitudes for each symbol-length (or 1.5*symbolLength) slices for that frequency. The sum of these top-two magnitudes for each slice becomes that frequency's contribution to the "spectrum." All other information—all the noise appearing in the other 90 µs of sampled and convolved data—is thrown out. The resulting spectrum for the coarse frequency search at a distance of 9 inches from the detector is shown in FIG. 100.

Figure 100:
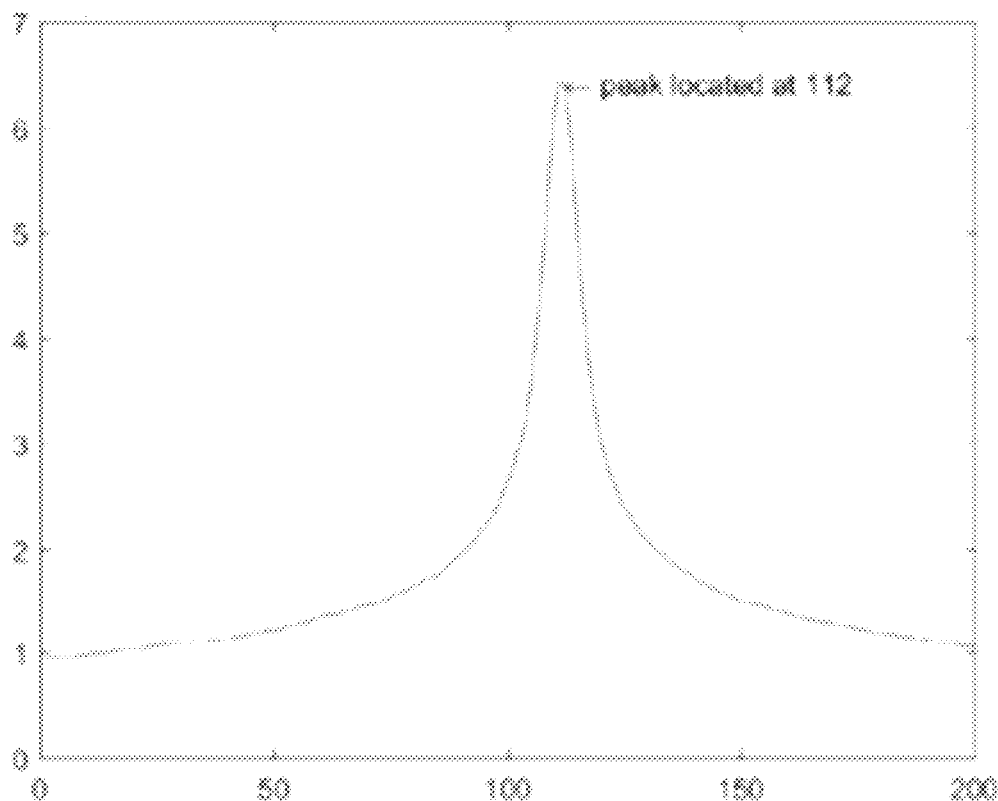
FIG. 100 shows a plot of the coarse frequency spectrum for sensor emulator at 9 inches from detector.

FIG. 100 shows a plot of the coarse frequency spectrum for sensor emulator at 9 inches from detector. The x-axis on this plot represents, at the center, a nominal number of samples per slice of 920. At X=0, there are 919 samples per slice; at X=200, there are 921 samples per slice. The resolution shown is 0.01 samples per slice. Thus the higher transmission frequency is on the left. The peak is clearly located at 112, which translates to 919+(112−1)*0.01=920.11 samples per slice.

At this point, the frame of data was trimmed to include only the packet and 3 additional symbols, one and a half on either side of the presumed packet location. This eliminates more noise from the succeeding analyses.

Using this new value as a center frequency and a resolution of 0.002 samples per slice, the P3SS analysis was run again. The Fine Spectrum that resulted is shown in FIG. 101.

Figure 101:
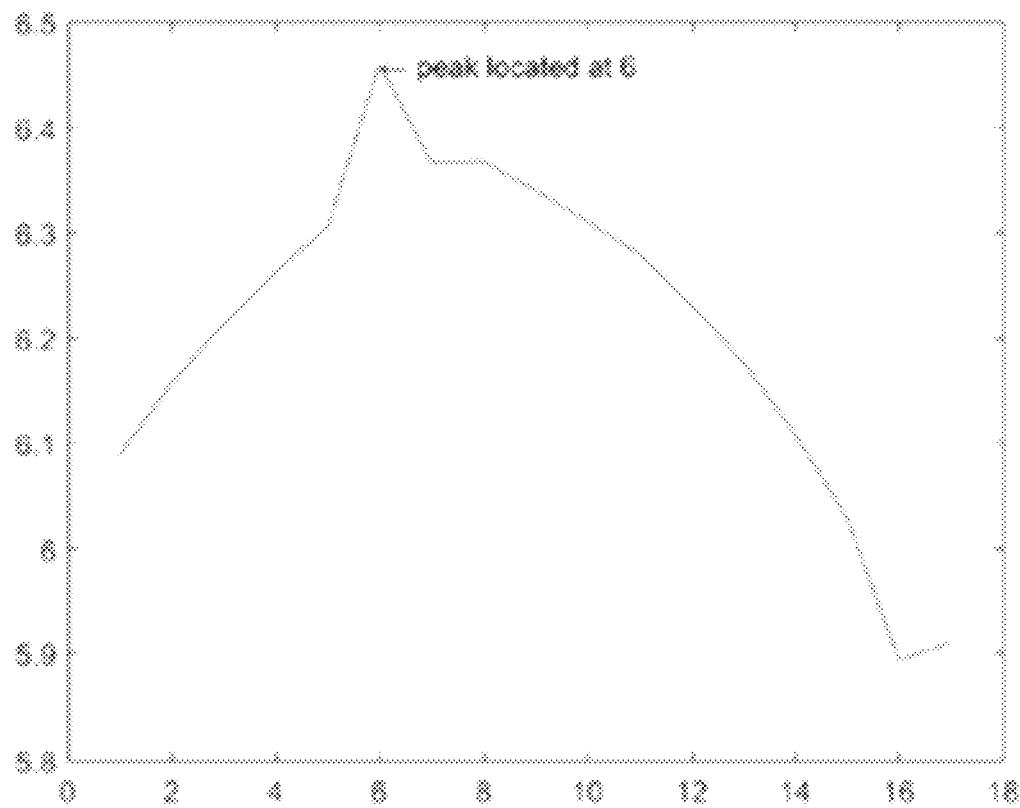
FIG. 101 shows a plot of the fine frequency spectrum for sensor emulator at 9 inches from detector.

FIG. 101 shows a plot of the fine frequency spectrum for sensor emulator at 9 inches from detector. From the Fine Spectrum, it can be seen that the peak was found at 6 units and that the final length was 920.106 samples per slice. Note that the finer resolution was extended to two coarse points on either side of the center frequency.

Figure 102:
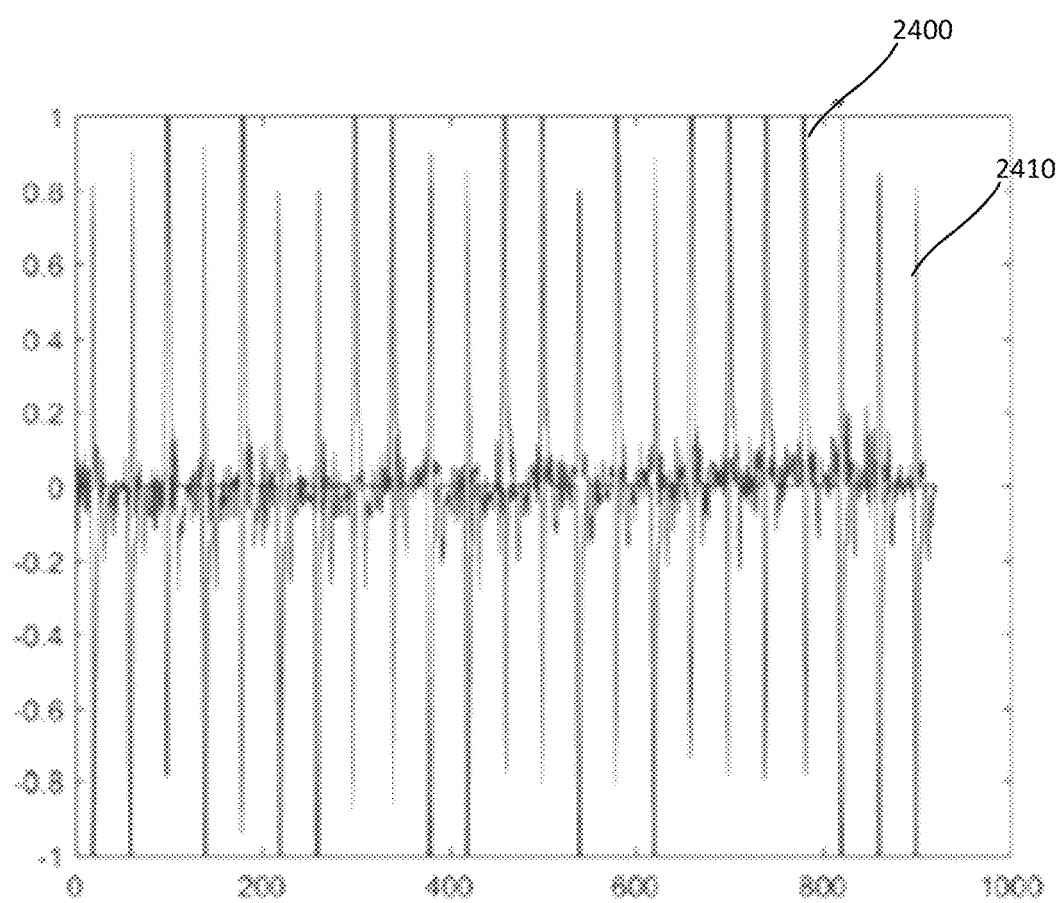
FIG. 102 shows a plot of the combined frame-length slice from the detector at 9 inches from source.

Using this as the final frequency, the full-packet-length combined slice was used to find the exact registration. FIG. 102 shows the combined slice using the center frequency found using P3SS. For example, shown in FIG. 102 are the key outputs for the ingestion sensor at a distance of 9 inches from the receiver. FIG. 102 shows a plot of the combined frame-length slice from the detector at 9 inches from source. In FIG. 102, the matching template is shown in the taller spikes (blue lines) 2400, while the combined slice data is shown in the slightly shorter spikes (red lines) 2410. Note that they have opposite parity: this information is used to adjust the parity of the incoming data to correspond with the template.

Figure 103:
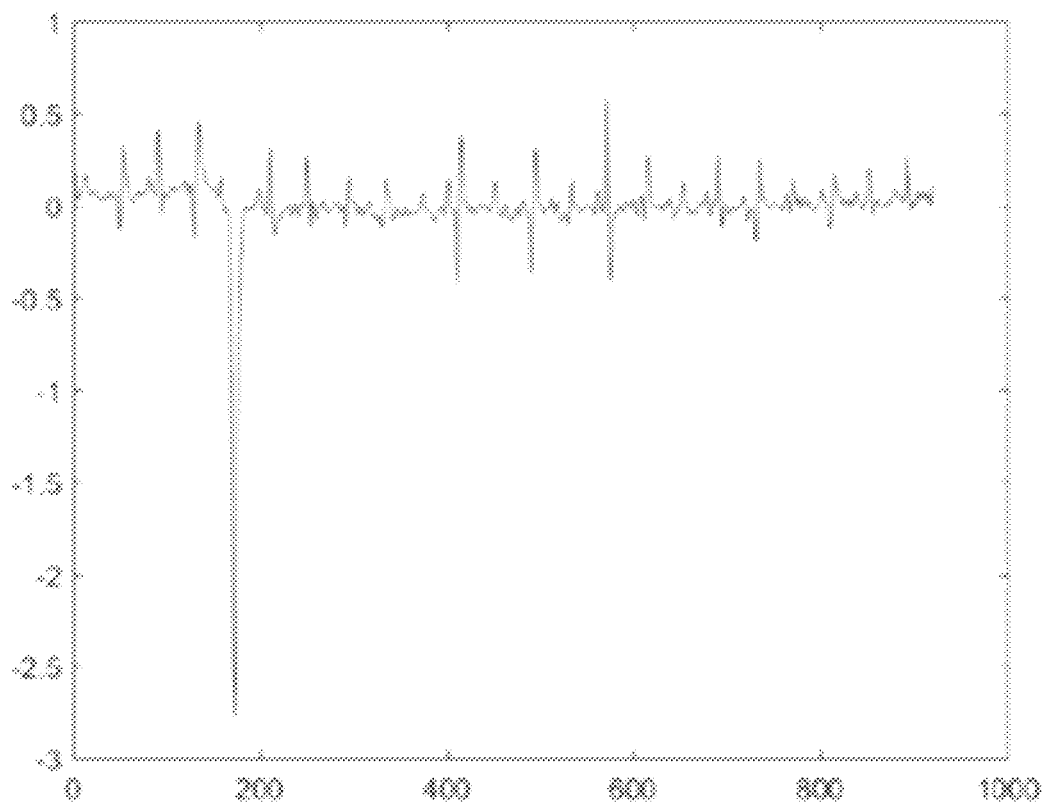
FIG. 103 is a plot showing the BestSums using data gathered at 9 inches from source.

The template is correlated with the combined slice, resulting in the "bestSums" plot shown in FIG. 103. FIG. 103 is a plot showing the BestSums using data gathered at 9 inches from source.

Figure 104:
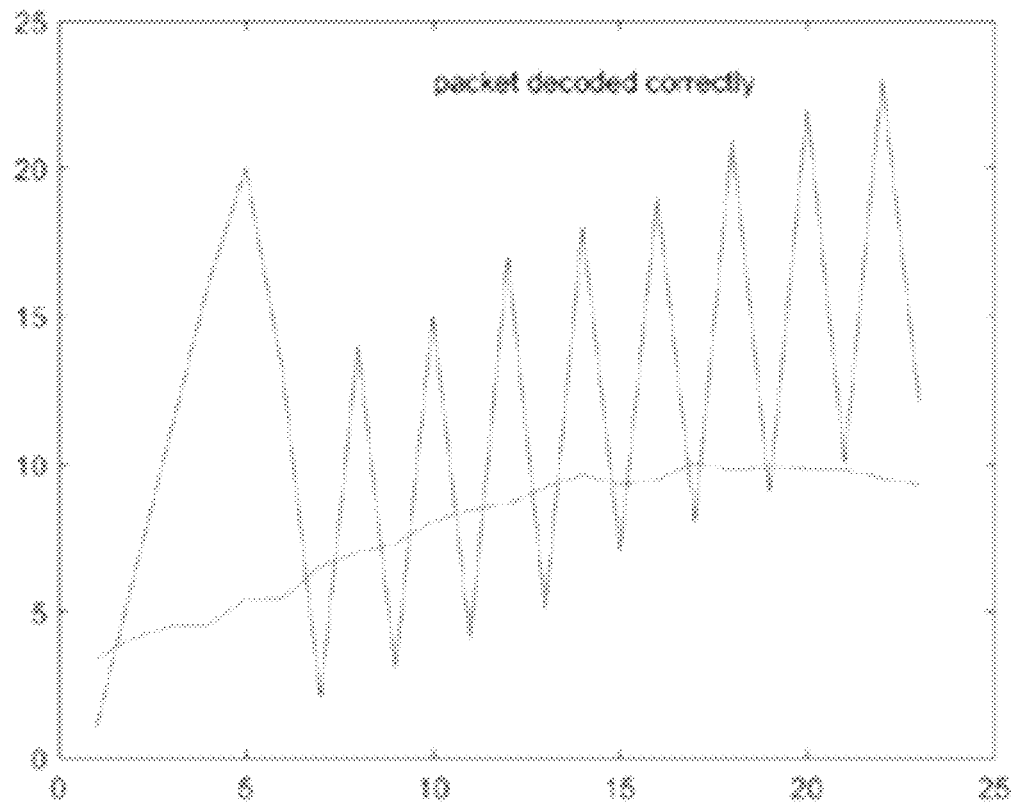
FIG. 104 is a plot showing the packet symbols and strengths using data gathered at 9 inches from source.

Using this registration index and the fine frequency from the second P3SS, the symbols were calculated and the final packet shown in FIG. 104. FIG. 104 is a plot showing the packet symbols and strengths using data gathered at 9 inches from source.

Figure 105:
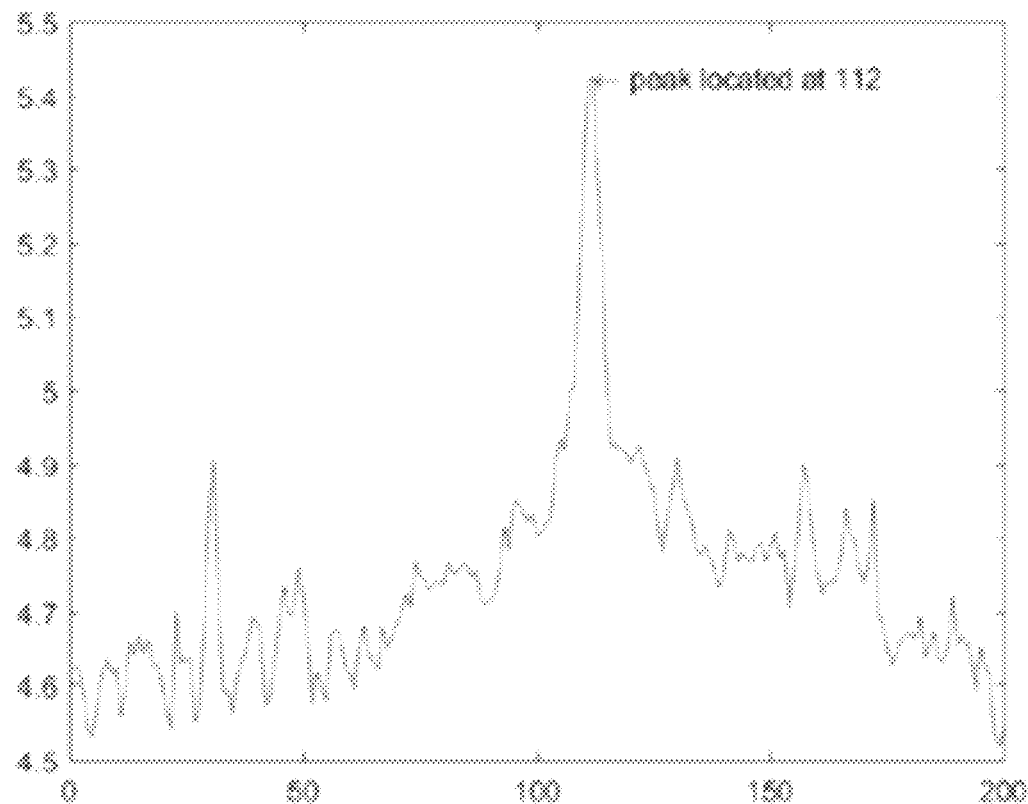
FIG. 105 is a plot showing the coarse frequency spectrum for sensor emulator at 24 inches from detector.

The same process was used at 24 inches with the following results:

FIG. 105 is a plot showing the coarse frequency spectrum for sensor emulator at 24 inches from detector.

Figure 106:
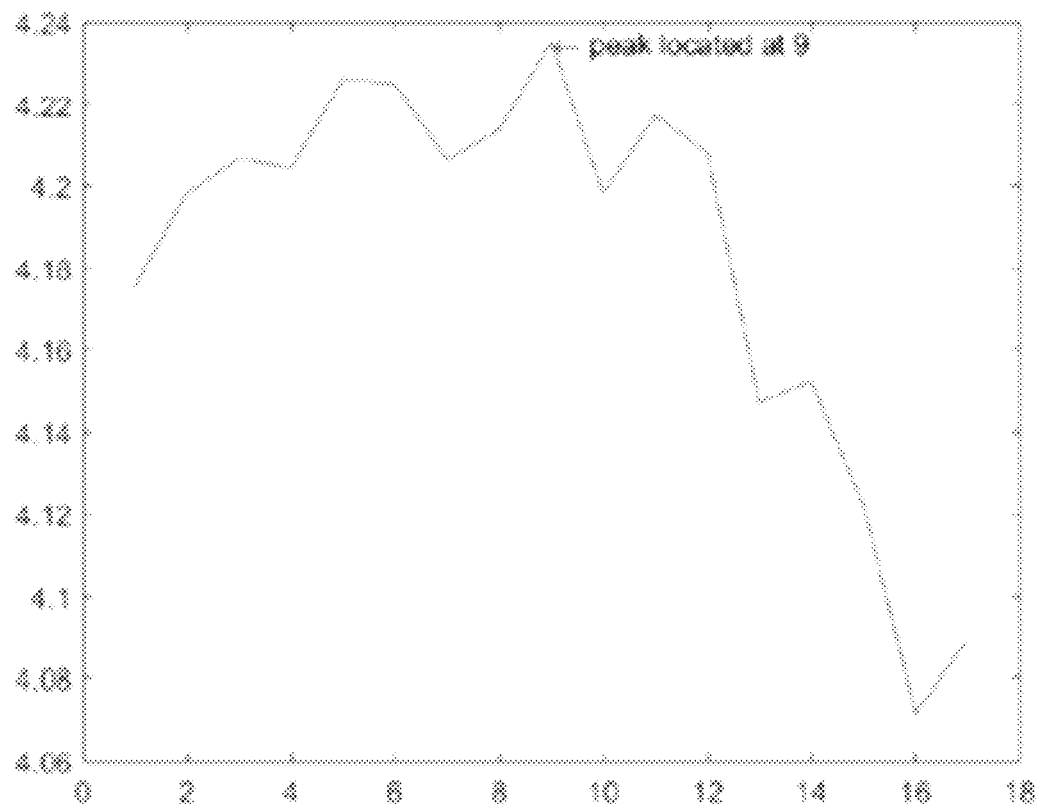
FIG. 106 shows the fine frequency spectrum P3SS2 for sensor emulator at 24 inches from detector.

Using the coarse frequency of 920.11 as the center frequency, P3SS2 (a second variation of P3SS with the adjusted coarse frequency) was run and found the finer spectrum as shown in FIG. 106. FIG. 106 shows the fine frequency spectrum P3SS2 for sensor emulator at 24 inches from detector.

Figure 107:
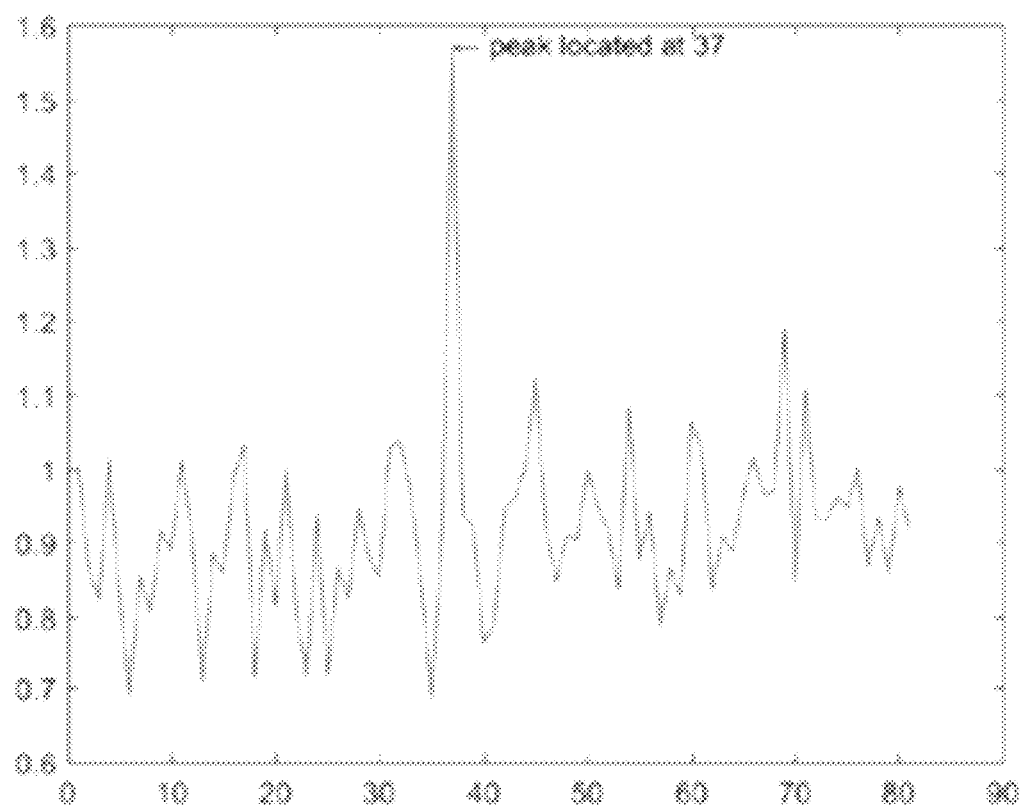
FIG. 107 shows the fine full-frame frequency spectrum for sensor emulator at 24 inches from detector.

This time P3SS2 was off by slice length of 0.004 sample points per slice, and the decoding was inaccurate. Repeating the fine search with the full frame slice technique produced the following spectrum as shown in FIG. 107. FIG. 107 shows the fine full-frame frequency spectrum for sensor emulator at 24 inches from detector.

Figure 108:
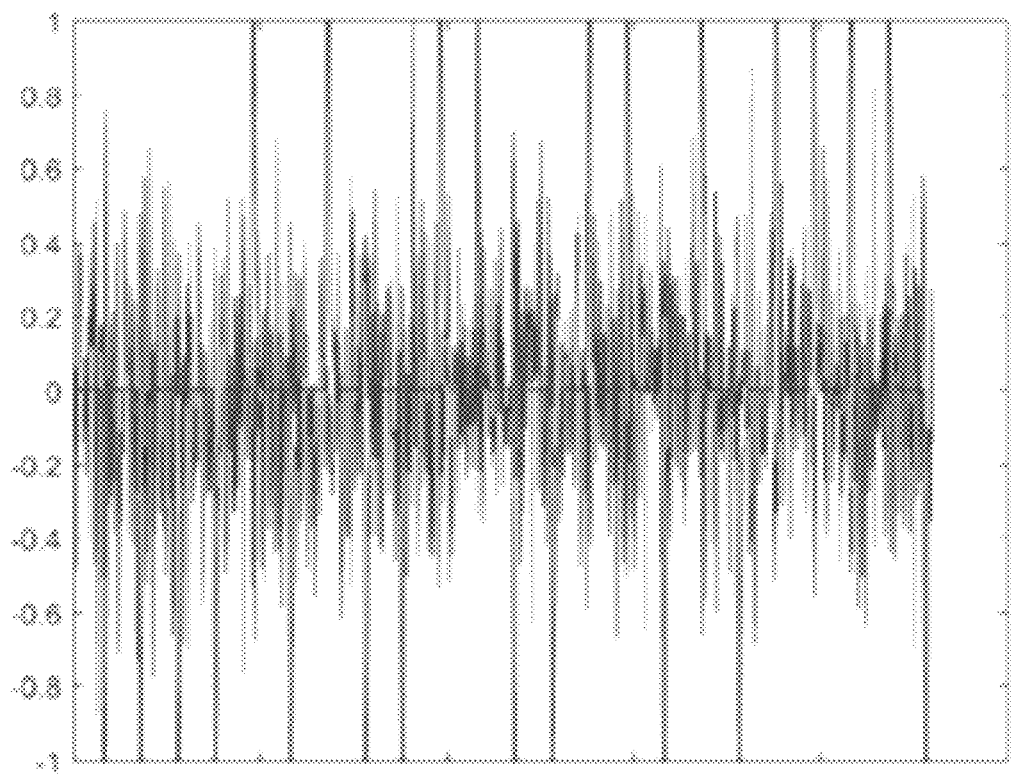
FIG. 108 shows a plot of the best combined full-frame slice along with best-fitting template for signal received 24 inches from source.

The full frame spectrum gave a better estimate of the best slice length, 920.104, and this led to a successful decoding of the packet. The intermediate sets are shown in FIG. 108. FIG. 108 shows a plot of the best combined full-frame slice along with best-fitting template for signal received 24 inches from source. Again, the taller spikes represent the template and the shorter spikes are from the full-fram slice.

Figure 109:
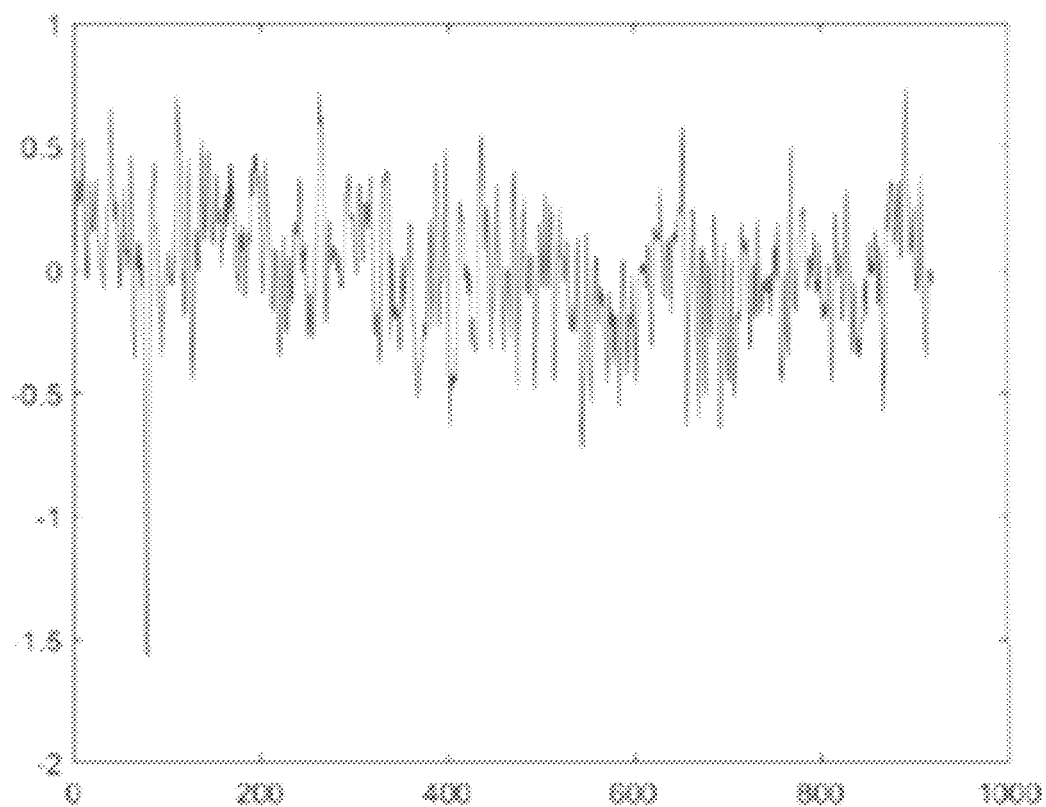
FIG. 109 is a plot showing the bestSums (result of convolution of template with combined slice) result for data gathered 24 inches from source.

FIG. 109 is a plot showing the bestSums (result of convolution of template with combined slice) result for data gathered 24 inches from source. Using the index from FIG. 109, the symbols were successfully decoded. The resulting symbols and convolution sums that went with them are shown in FIG. 110.

Figure 110:
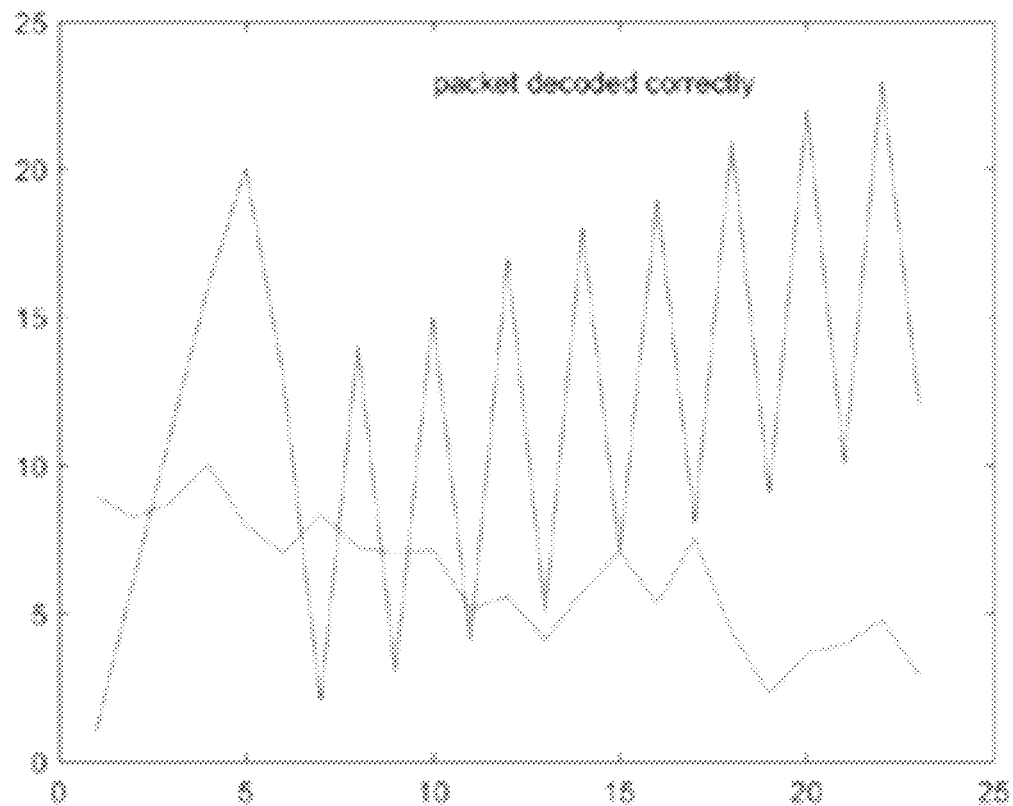
FIG. 110 is a plot showing the symbol values and packet result for data gathered 24 inches from source.

FIG. 110 is a plot showing the symbol values and packet result for data gathered 24 inches from source. These results indicate the utility of the spike warp communication protocol for ingestion sensor communication.

Figure 111:
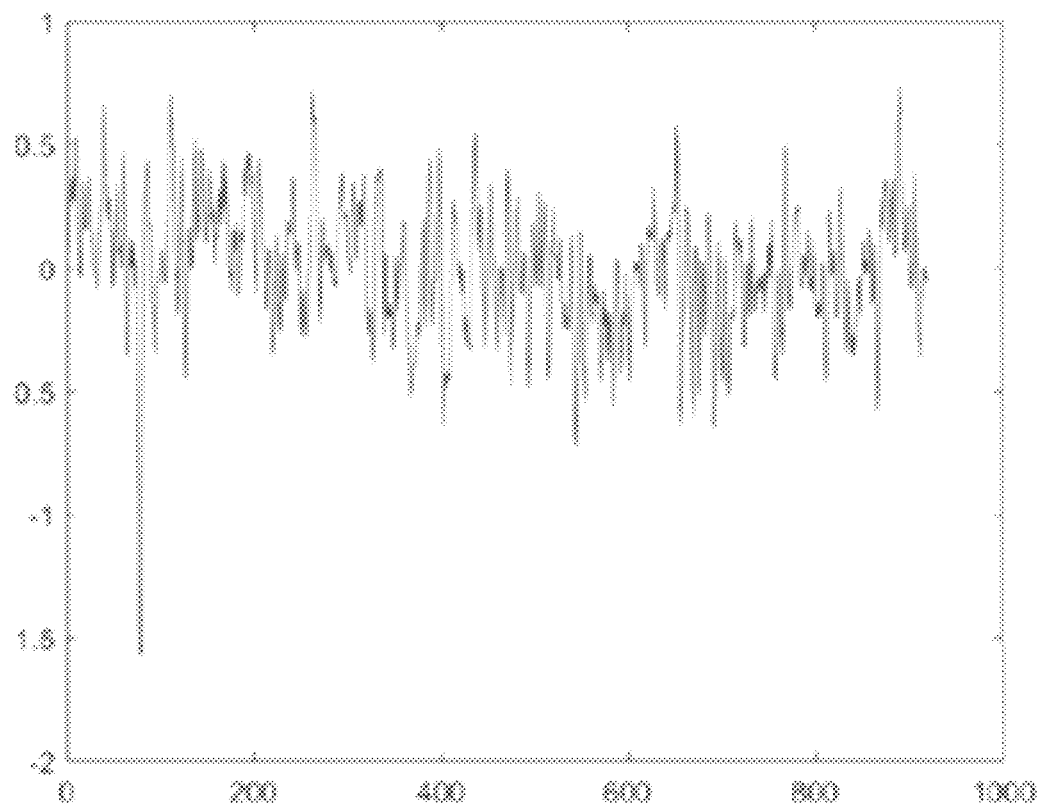
FIG. 111 is a plot showing BestSums using data gathered at 24 inches from source.

FIG. 111 is a plot showing BestSums using data gathered at 24 inches from source.

Example Receivers Utilizing Impulse Protocols

Having described the generation and transmission of the impulse "sparse impulses" function, the description now turns to various receiver circuits for receiving and decoding the signals transmitted by the impulse inductor driver circuit 720. Accordingly, FIG. 47 illustrates a voltage mode receiver 900 for detecting an electromagnetic field generated by an ingestible identifier, according to one aspect of the present disclosure. The voltage mode receiver 900 comprises a resonant circuit 902, a low noise amplifier 908 (LNA), and a receiver processor 910 comprising circuits and components for processing the received the encoded electromagnetic signal transmitted from the ingestible identifier. The resonant circuit 902 comprises a receiving inductor antenna 904 and a tuning capacitor 906 to resonate at the frequency of operation $f_0$. The receiving inductor 904 receives the electromagnetic signal in the form factor of a path with the inductor 904.

It will be appreciated that in FIGS. 44-46, the horizontal axis may not necessarily represent time, as the signal my be stretched or squeezed into a fixed number of data points. If the signal is at the nominal frequency, then the corresponding data points would correspond to time, but the units would not likely be in microseconds, but rather the unit would be scaled to whatever the duration of the chip is, which could vary, depending on the implementation.

The impulse response from the receiving inductor 904 is shown graphically in FIG. 48. The received signal over frequency (f) appears across the capacitor 906 in voltage form. The response curve 922 has the highest amplitude or energy at the operation frequency $f_0$. With reference back to FIG. 47, the voltage v signal across the tuning capacitor 906 is applied to the input of the LNA 908. The output of the LNA 908 is applied to the receiver processor 910, which processes and decodes the received signal to reproduce the data 912 transmitted by the ingestible identifier.

FIG. 49 illustrates a voltage mode receiver 930 for detecting an electromagnetic field generated by an ingestible identifier, according to one aspect of the present disclosure. The receiver 930 comprises a resonant circuit 932, a low noise amplifier 938 (LNA), a narrow band resonator or crystal filter 944, and a receiver processor 940 comprising components for processing the received encoded electromagnetic signal transmitted by the ingestible identifier. The resonant circuit 932 comprises an inductor antenna 934 and a tuning capacitor 936 to resonate at the frequency of operation $f_0$. The inductor 934 receives the electromagnetic signal in the form factor of a path with the inductor 934.

The impulse response from the receiving inductor 934 is shown graphically in FIG. 49. The received signal over frequency (f) appears across the capacitor 936 in voltage form. The response curve has the highest amplitude or energy at the operation frequency $f_0$. The voltage v signal across the tuning capacitor 936 is applied to the LNA 938. The output of the LNA 938 is applied to the resonator or crystal filter 944, which is coupled to the receiver processor 940. The receiver processor 940 processes and decodes the received signal to reproduce data 942 transmitted by the ingestible identifier.

The resonator or crystal filter 944 may comprises one or more coupled resonators or crystals to set the selectivity of the filter 944. Other types of filters that may be employed, include, without limitation, lumped inductor/capacitor (LC) filters, planar filters, coaxial filters, cavity filters, dielectric filters, electroacoustic filters, and/or waveguide filters.

The receiver processors 910, 940 may comprise analog or digital band-pass filters to filter the incoming pulses. The voltage of each pulse may be integrated over time in case the pulses are very short. Transmission frequencies can occur at a frequencies in the range of ~12.5 kHz to ~20 kHz or greater than ~24 kHz and as high as ~10 MHz, for example. Although the impulses are not deterministic, they repeat over 128 pulses at a repetition rate of ~6 kHz. Battery readiness is random and battery impedance (Z) and voltage ($V_{BAT}$) may fluctuate. The pulse width and repetition rate can be adjusted based on the current condition of the battery. These types of protocols can be adapted in Internet of things type circuits.

The receiver processors 910, 940 discussed in connection with FIGS. 47 and 49 are configured to process the received encoded electromagnetic analog signal transmitted by the ingestible identifier using a sparse impulse template and convolution technique to identify the transmit frequency. In one aspect, the receiver processors 910, 940 may comprises an analog-to-digital converter (ADC) at the front end to receive the analog sparse impulses from the amplifier circuits 908, 938. The ADC digitizes the received series of sparse impulses in the form of analog voltages and outputs a digital number that represents the amplitude of the voltage. The digital numbers output of the ADC is then applied to a processor, such as, for example, a digital signal processor (DSP) optimized for determining the transmit frequency of the sparse impulses signal and decoding the encoded sparse impulses signal to extract or reproduce the data 912, 942 transmitted by the ingestible identifier. The DSP is well suited for measuring, filtering, and/or compressing continuous the sparse impulses analog signals and performing algorithms. Alternatively, a general-purpose microprocessor also can be configured to execute digital signal processing algorithms successfully. Nevertheless, dedicated DSPs usually have better power efficiency thus they are more suitable in portable devices such as mobile phones because of power consumption constraints. DSPs often use special memory architectures that are able to fetch multiple data and/or instructions at the same time. Although DSP and general purpose microprocessors can be employed, dedicated circuits or reconfigurable circuitry such a PLDs, PGA, FPGA, ASICs, and other circuits may be employed alone or in conjunction with DSPs and general purpose microprocessors to perform the receiver functions.

Figure 50:
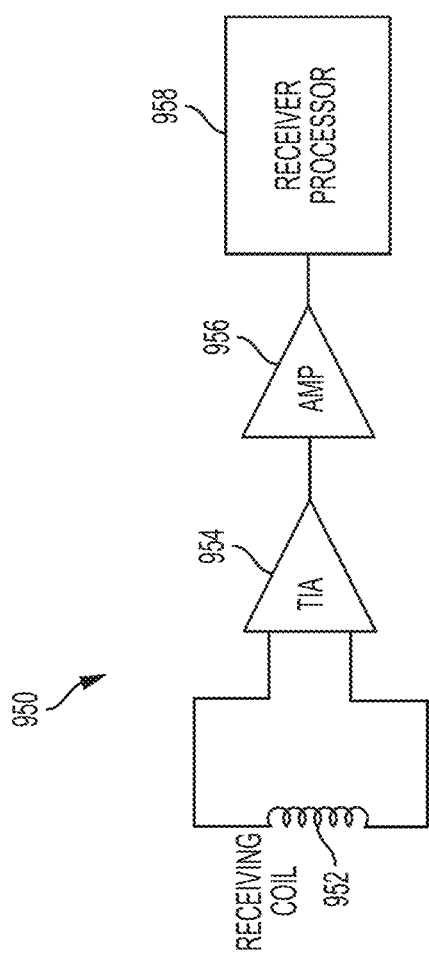
FIG. 50 illustrates a current mode receiver, according to one aspect of the present disclosure.

In addition to the voltage mode receiver circuits 900, 930 described in connection with FIGS. 47-49, multiple other receiver circuits may be employed to receive and decode the electromagnetic analog signal transmitted by the ingestible identifier. FIG. 50 illustrates a current mode receiver 950, according to one aspect of the present disclosure. The current mode receiver 950 comprises a receiving inductor 952 coupled to a transimpedance amplifier 954 (TIA), which provides low output impedance. The TIA 954 is coupled to an amplifier 956 and its output is coupled to a receiver processor 958, much like the receiver processors 910, 940 (FIGS. 47, 49). The TIA 954 is beneficial to preserve the shape of the received pulse such that the impedance of the inductor floats or is coupled through the TIA 954 and from thereon the pulse can be reconstructed from the output of the TIA 954 and is independent of any parasitic capacitance of the TIA 954.

Figure 51:
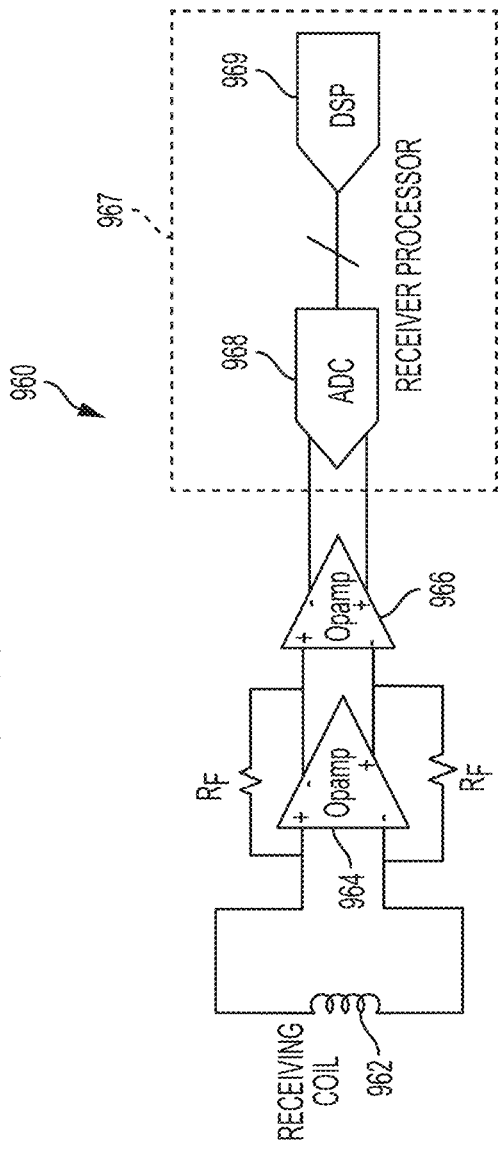
FIG. 51 illustrates another receiver circuit, according to one aspect of the present disclosure.

FIG. 51 illustrates another receiver circuit 960, according to one aspect of the present disclosure. The receiver 960 comprises a receiving inductor 962 coupled to a first amplifier 964. The output of the first amplifier 964 is coupled to a second amplifier 966. The output of the second amplifier 966 is coupled to a receiver processor 967. In the example illustrated in FIG. 51, the receiver processor 967 comprises an ADC 968 and a DSP 969 for determining the transmit frequency of the sparse impulses signal and decoding the encoded sparse impulses signal to extract or reproduce the data transmitted by the ingestible identifier. The DSP also can implemented to filter the sparse impulses analog signal and performing various algorithms.

Figure 52:
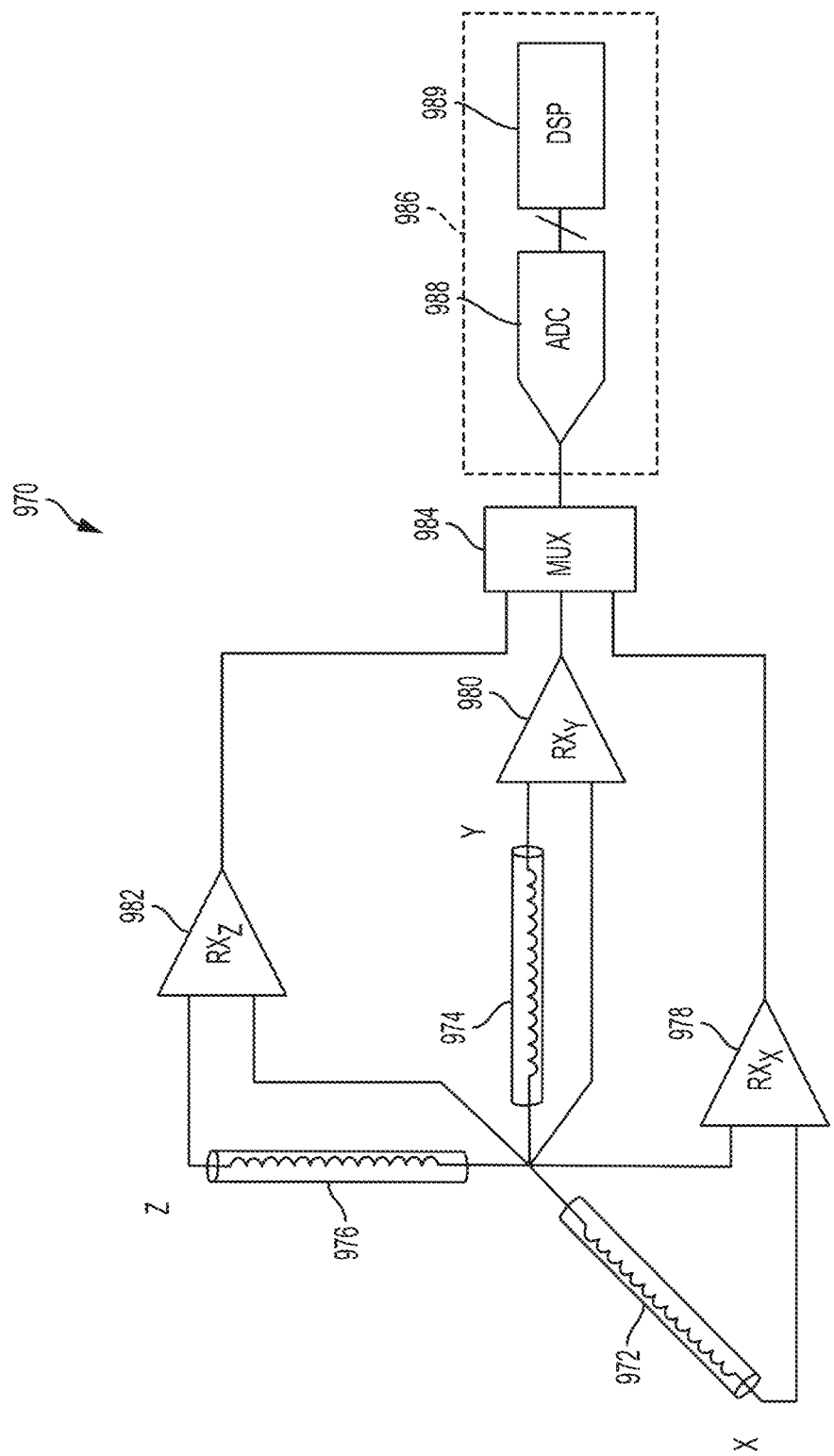
FIG. 52 illustrates a receiver configuration comprising receiving inductors orthogonally spaced relative to each other and corresponding receivers, according to one aspect of the present disclosure.

FIG. 52 illustrates a receiver configuration 970 comprising receiving inductors 972, 974, 976 orthogonally spaced relative to each other and corresponding receivers 978, 980, 982, according to one aspect of the present disclosure. The receiving inductors 972, 974, 976 have an overall elongated form factor. The receiving inductors 972, 974, 976 and the corresponding receivers 978, 980, 982 are disposed along X, Y, Z axes to mitigate dependence on the orientation of the transmitter. The outputs of the receivers 978, 980, 982 are coupled to a multiplexer 984. The output of the multiplexer 984 is coupled to a receiver processor 986 comprising an ADC 988 and a DSP 989.

Figure 53:
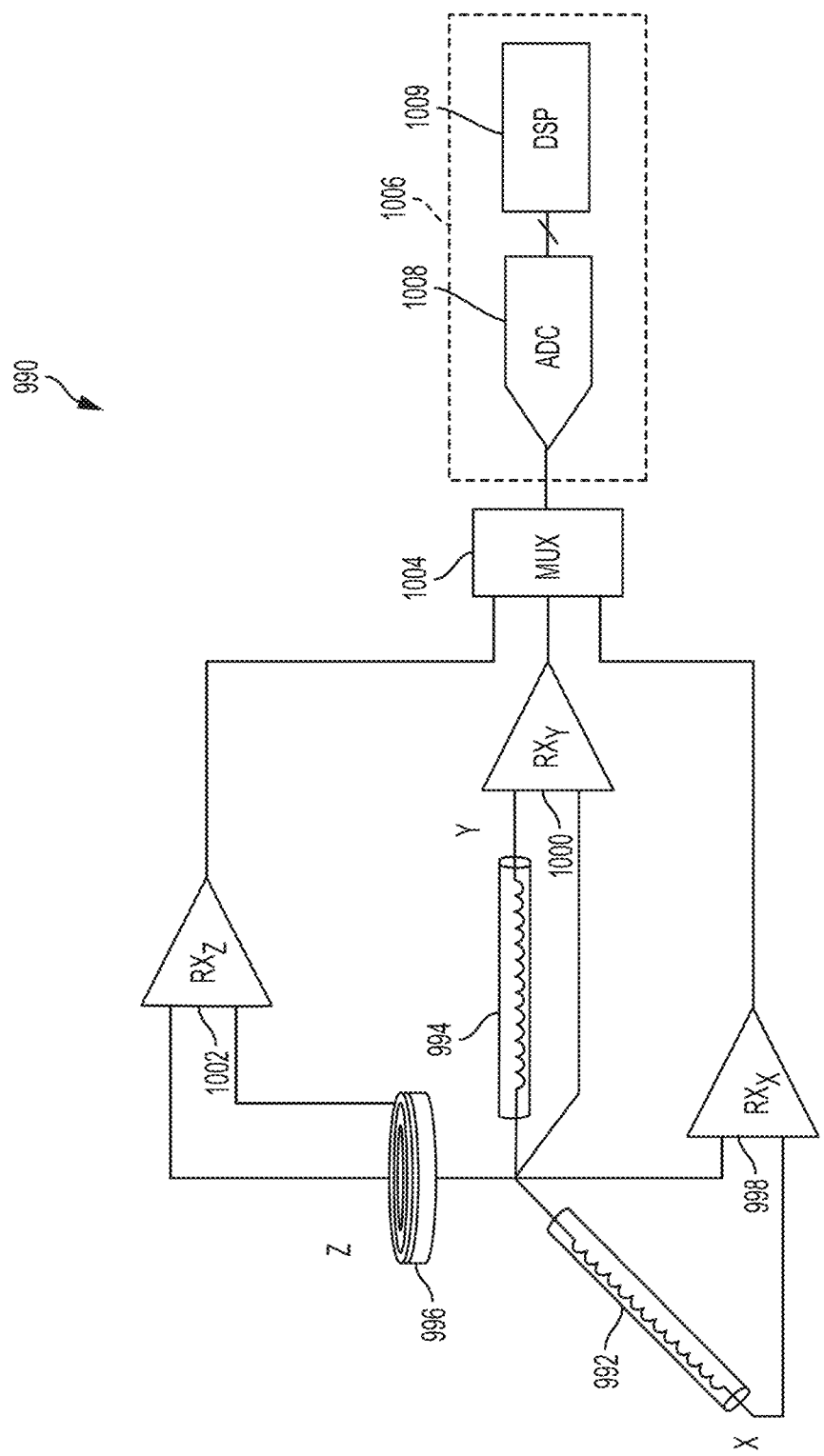
FIG. 53 illustrates a receiver configuration comprising orthogonally spaced receiving inductors and corresponding receivers, according to one aspect of the present disclosure.

FIG. 53 illustrates a receiver configuration 990 comprising orthogonally spaced receiving inductors 992, 994, 996 and corresponding receivers 998, 1000, 1002, according to one aspect of the present disclosure. Two of the receiving inductors 992, 994 have an overall elongated form factor and one of the receiving inductors 996 has an overall flat form factor. The receiving inductors 992, 994, 996 and the corresponding receivers 998, 1000, 1002 are disposed along X, Y, Z axes to mitigate dependence on the orientation of the transmitter. The outputs of the receivers 998, 1000, 1002 are coupled to a multiplexer 1004. The output of the multiplexer 1004 is coupled to a receiver processor 1006 comprising an ADC 1008 and a DSP 1009.

Figure 54:
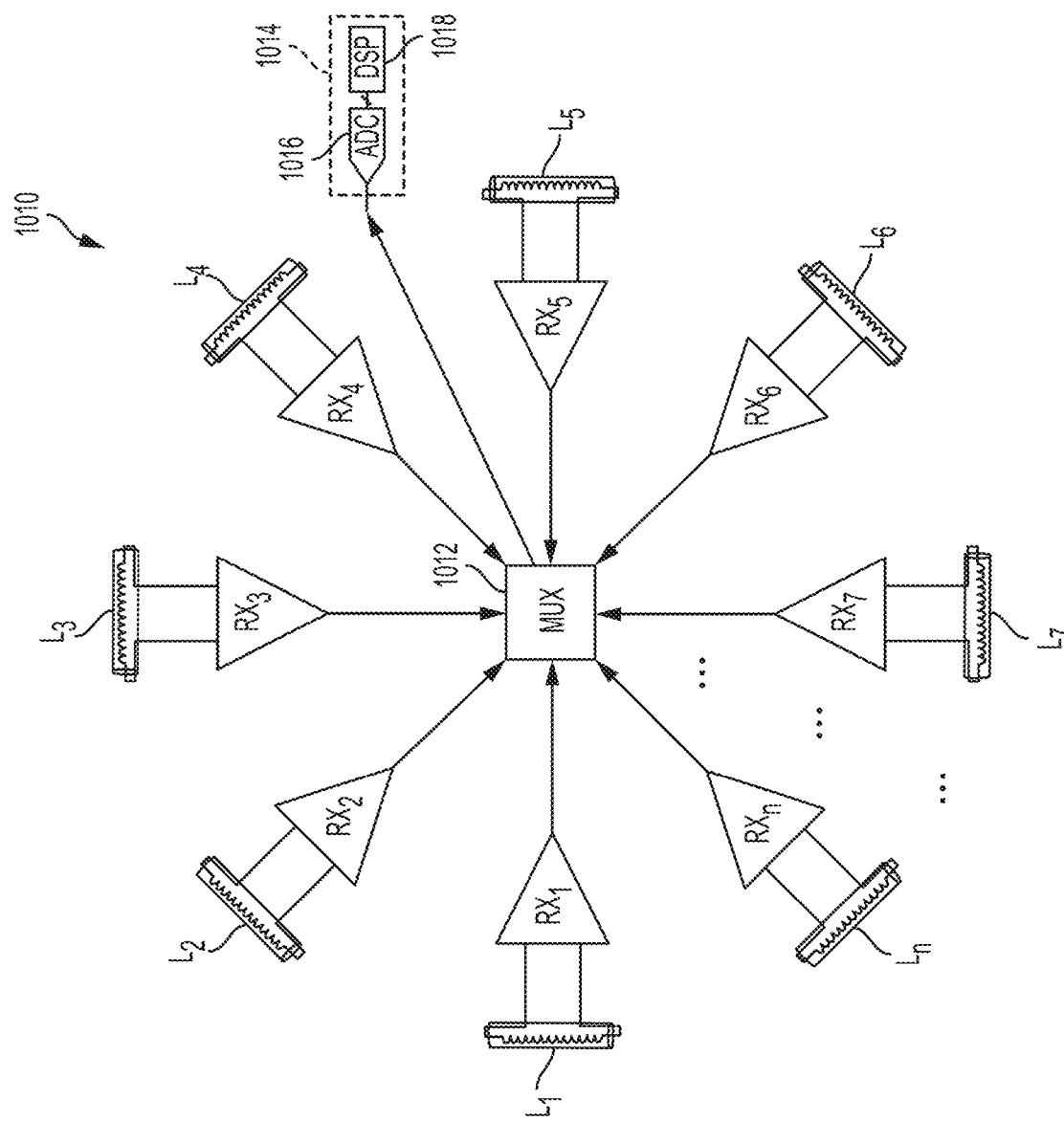
FIG. 54 illustrates a receiver configuration comprising multiple receiver inductors L1-Ln and multiple receivers $RX_1$-$RX_n$, according to one aspect of the present disclosure.

FIG. 54 illustrates a receiver configuration 1010 comprising multiple receiver inductors L1-Ln and multiple receiver amplifiers $RX_1$-$RX_n$, according to one aspect of the present disclosure. The receiver inductors L1-Ln are coupled to the inputs of the corresponding receivers $RX_1$-$RX_n$. The outputs of the receiver amplifiers $RX_1$-$RX_n$ are coupled to a multiplexer 1012. The output of the multiplexer 1012 is coupled to a receiver processor 1014. As previously discussed, the receiver processor 1014 comprises an ADC 1016 and a DSP 1018 coupled to the ADC 1016. The multiple receiver inductors L1-Ln and corresponding multiple receiver amplifiers $RX_1$-$RX_n$ improve the signal to noise ratio (SNR), orientation dependence, among others.

Figure 55:
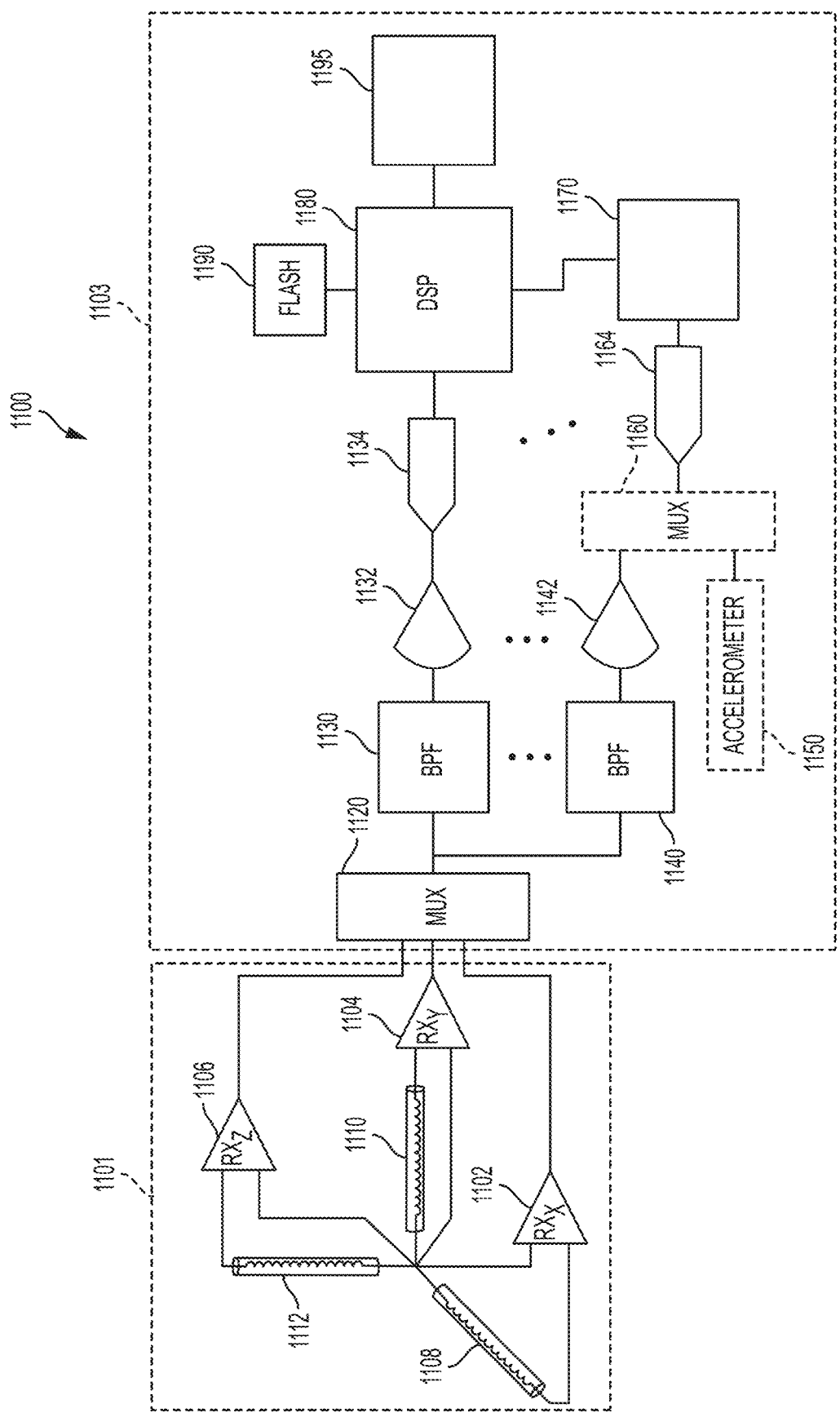
FIG. 55 illustrates a receiver circuit, according to one aspect of the present disclosure.

FIG. 55 illustrates a receiver circuit 1100, according to one aspect of the present disclosure. The receiver circuit 1100 shown in FIG. 55 comprises a front end analog circuit 1101 coupled to a receiver processor circuit 1103. The front end analog circuit 1101 comprises a receiver inductor 1108, 1110, 1112 coupled to a receiver amplifier 1102, 1104, 1106. Signals transmitted by the impulse driver circuit, such as the impulse driver circuit 720 shown in FIGS. 38 and 39 or the impulse driver circuit 726 shown in FIG. 43, are received by the receiver inductors 1108, 1110, 1112 disposed along X, Y, Z axes to mitigate dependence on the orientation of the transmitter and amplified by the corresponding receiver amplifiers 1102, 1104, 1106. As shown in FIG. 55, three receiver inductors 1108, 1110, 1112 are coupled to three corresponding receiver amplifiers 1102, 1104, 1106. The outputs of the three receiver amplifiers 1102, 1104, 1106 are multiplexed by a multiplexer 1120. In various aspects, the receiver processor 1100 may receive signals from one receiver inductor 1108, two receiver inductors 1108, 1110, or more than three receiver inductors 1108, 1110, 1112 depending on the system implementation details.

The multiplexer 1120 is electrically coupled to one or more band pass filters, As shown in FIG. 55, the multiplexer 1120 is electrically coupled to a high band pass filter 1130 and a low band pass filter 1140 to filter the broadcast frequencies used to transmit the impulse function. Additional band pass filters and amplifiers may be coupled to the multiplexer 1120 to cover frequency bands between those recited herein. The high and low frequency signal chains provide for programmable gain to cover the desired level or range. In this specific aspect, the high band pass filter 1130 passes frequencies in the band of ~500 KHz to ~1500 KHz while filtering out noise from out-of-band frequencies. This high frequency band may vary, and may include, for example, a range of ~800 KHz to ~1200 KHz, and in some aspects frequencies of ~1000 KHz. The passing frequencies are then amplified by an amplifier 1132 before being converted into a digital signal by an analog-to-digital converter 1134 (ADC) for input into a high power processor 1180 (shown as a DSP) which is electrically coupled to the high frequency signal chain.

A low band pass filter 1140 is shown passing lower frequencies in the range of ~50 KHz to ~150 KHz while filtering out-of-band frequencies. The frequency band may vary, and may include, for example, frequencies in the range of ~80 KHz to ~120 KHz, and in some aspects frequencies of ~100 KHz. The passing frequency signals are amplified by an amplifier 1142. Also shown is an accelerometer 1150 electrically coupled to second multiplexer 1160. A multiplexer 1160 multiplexes the signals from the accelerometer with the amplified signals from the amplifier 1142. The multiplexed signals are then converted to digital signals by an ADC 1164 which is also electrically coupled to the low power processor 1170.

In one aspect, optionally, an accelerometer 1150 may be multiplexed with the output of the amplifier 1142 by a multiplexer 1160. A digital accelerometer (such as one manufactured by Analog Devices), may be implemented in place of the accelerometer 1150. Various advantages may be achieved by using a digital accelerometer. For example, because the signals the digital accelerometer would produce signals already in digital format, the digital accelerometer 1150 could bypass the ADC 1164 and electrically couple to a low power microcontroller 1170, in which case the multiplexer 1160 would no longer be required. Also, the digital signal may be configured to turn itself on when detecting motion, further conserving power. In addition, continuous step counting may be implemented. The digital accelerometer may include a FIFO buffer to help control the flow of data sent to the low power processor 1170. For instance, data may be buffered in the FIFO until full, at which time the processor may be triggered to turn awaken from an idle state and receive the data.

The low power processor 1170 may be, for example, an MSP430 microcontroller from Texas Instruments. The low power processor 1170 of the receiver 1100 maintains the idle state, which as stated earlier, requires minimal current draw, e.g., ~10 µA or less, or ~1 µA or less.

The high power processor 1180 may be, for example, a VC5509 digital signal process from Texas Instruments. The high power processor 1180 performs the signal processing actions during the active state. These actions, as stated earlier, require larger amounts of current than the idle state, e.g., currents of 30 µA or more, such as 50 µA or more, and may include, for example, actions such as scanning for conductively transmitted signals, processing conductively transmitted signals when received, obtaining and/or processing physiologic data, etc.

The receiver 1100 may include a hardware accelerator component to process data signals. The hardware accelerator component may be implemented instead of, for example, a DSP. Being a more specialized computation unit, it performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or very long instruction word (VLIW) assembly language. In the course of use, their functions may be accessed by calls to function libraries.

The hardware accelerator (HWA) component comprises an HWA input block to receive an input signal that is to be processed and instructions for processing the input signal; and, an HWA processing block to process the input signal according to the received instructions and to generate a resulting output signal. The resulting output signal may be transmitted as needed by an HWA output block.

Also shown in FIG. 55 is a flash memory 1190 electrically coupled to the high power processor 1180. In one aspect, the flash memory 1190 may be electrically coupled to the low power processor 1170, which may provide for better power efficiency.

A wireless communication element 1195 is shown electrically coupled to the high power processor 1180 and may include, for example, a BLUETOOTH™ wireless communication transceiver. In one aspect, the wireless communication element 1195 is electrically coupled to the high power processor 1180. In another aspect, the wireless communication element 1195 is electrically coupled to the high power processor 1180 and the low power processor 1170. Furthermore, the wireless communication element 1195 may be implemented to have its own power supply so that it may be turned on and off independently from other components of the receiver, e.g., by a microprocessor.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While various details have been set forth in the foregoing description, it will be appreciated that the various aspects of the electromagnetic sensing and detection of ingestible event markers may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one aspect," or "an aspect" means that a particular feature, structure, or characteristic described in connection with the aspect is included in at least one aspect. Thus, appearances of the phrases "in one aspect," "in an aspect," "in one aspect," or "in an aspect" in various places throughout the specification are not necessarily all referring to the same aspect. Furthermore, the particular features, structures or characteristics may be combined in any suitable manner in one or more aspects.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

Some or all of the various aspects described herein may generally comprise technologies for electromagnetic sensing and detection of ingestible identifiers according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various aspects of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one aspect, several portions of the subject matter described herein may be implemented via Application Specific Integrated Circuits (ASICs), Field Programmable Gate Arrays (FPGAs), digital signal processors (DSPs), or other integrated formats.

Those skilled in the art will recognize, however, that some aspects of the aspects disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative aspect of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various aspects have been described herein, many modifications, variations, substitutions, changes, and equivalents to those aspects may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed aspects. The following claims are intended to cover all such modification and variations.

In summary, numerous benefits have been described which result from employing the concepts described herein. The foregoing description of the one or more aspects has been presented for purposes of illustration and description. It is not intended to be exhaustive or limiting to the precise form disclosed. Modifications or variations are possible in light of the above teachings. The one or more aspects were chosen and described in order to illustrate principles and practical application to thereby enable one of ordinary skill in the art to utilize the various aspects and with various modifications as are suited to the particular use contemplated. It is intended that the claims submitted herewith define the overall scope.

Various aspects of the subject matter described herein are set out in the following numbered clauses:

1. An electronic device comprising: a control device; a driver circuit coupled to the control device, the driver circuit configured to alter conductance; a partial power source coupled to the control device, the partial power source is configured to provide a voltage potential difference to the control device and the driver circuit as a result of the partial power source being in contact with a conductive fluid, the partial power source comprising: a first material electrically coupled to the control device; and a second material electrically coupled to the control device and electrically isolated from the first material; an inductor coupled to the driver circuit, wherein the driver circuit is configured to develop a current through the inductor, and wherein a magnitude of the current developed through the inductor is varied to produce an encoded signal that is remotely detectable by a receiver.

2. The electronic device of clause 1, wherein the driver circuit comprises a single ended driver circuit.

3. The electronic device of clause 1, wherein the driver circuit comprises a push-pull H-bridge driver circuit.

4. The electronic device of clause 1, wherein the driver circuit comprises: cross-coupled transistors; and a capacitor coupled between drains of the cross-coupled transistors; wherein the inductor is coupled between the drains of the cross-coupled transistors.

5. The electronic device of clause 1, further comprising: a battery voltage doubler circuit; a pulse generator circuit coupled to the battery voltage doubler circuit; and an inductor discharge circuit coupled to the pulse generator circuit.

6. The electronic device of clause 5, wherein the battery voltage doubler circuit comprises: a switched capacitor stage comprising first and second switched capacitors, wherein the switched capacitor stage receives an input voltage and outputs an output voltage having a magnitude of twice the input voltage; and a clock stage; wherein the clock stage receives a pulse train and produces clock pulses of opposite phases, wherein the clock pulses of opposite phases cause the first and second capacitors to alternately charge to a voltage equal to twice the input voltage.

7. The electronic circuit of clause 5, wherein the pulse generator circuit comprises: first and second trigger circuits; an RC timing circuit comprising a resistor R and a capacitor C to set a time constant delay $\tau$ at the input of the second delayed trigger circuit; an inverter coupled to the output of the first undelayed trigger circuit; and a logic gate having a first input coupled to an output of the inverter, a second input coupled to an output of the second trigger circuit, and an output coupled to the inductor trigger circuit; a first oscillator coupled to the input of the first trigger circuit and coupled to the RC timing circuit; and a second oscillator coupled to the inductor trigger circuit.

8. The electronic circuit of clause 5, wherein the inductor discharge circuit comprises: a capacitor charging circuit; a coupling circuit; and charging and discharging circuits for charging and discharging the inductor.

9. The electronic circuit of clause 1, wherein the driver circuit is configured to implement an impulse communication protocol.

10. The electronic device of clause 1, wherein the first and second materials are selected to provide the voltage potential difference as a result of the first and second materials being in contact with the conductive fluid.

11. The electronic device of clause 1, comprising an electronic switch, wherein the electronic switch comprises first and second terminals and a control terminal, and wherein the control terminal is operatively coupled to the driver circuit, the first terminal is coupled to the inductor, and the second terminal is coupled to the second material, and wherein the inductor is coupled between the first material and the first terminal of the electronic switch, wherein the driver circuit is configured to alter the conductance of the electronic switch between the first and second materials such that the current (i)s developed through the inductor.

12. The electronic device of clause 1, wherein the inductor comprises at least two inductive elements formed on separate insulating substructures of a semiconductor integrated circuit.

13. The electronic device of clause 12, wherein the at least two inductive elements are coupled through a via formed between the separate insulating substructures.

14. A receiver circuit, comprising: a resonant circuit; a low noise voltage amplifier coupled to the resonant circuit; and a receiver processor circuit coupled to an output of the low noise voltage amplifier, the receiver processor configured to receive an analog signal representative of an impulse communication signal, convert the analog signal to a digital signal, and decode the digital signal to reproduce data transmitted as the impulse communication signal.

15. The receiver of clause 14, further comprising a narrow band resonator coupled between the low noise amplifier and the receiver processor circuit.

16. A receiver circuit, comprising: a receiving inductor; a transimpedance amplifier coupled to the receiving coil; an amplifier coupled to an output of the transimpedance amplifier; and a receiver processor circuit coupled to an output of the amplifier, the receiver processor configured to receive an analog signal representative of an impulse communication signal, convert the analog signal to a digital signal, and decode the digital signal to reproduce data transmitted as the impulse communication signal.

17. The receiver circuit of clause 16, wherein the receiver processor comprises: an analog-to-digital converter (ADC); and a digital signal processor coupled to an output of the ADC.

18. The receiver of clause 16, comprising: at least three receiving inductors orthogonally spaced relative to each other; at least three amplifiers coupled to corresponding orthogonally spaced inductors; a multiplexer to receiver outputs of the at least three amplifiers; an analog-to-digital converter (ADC) coupled to an output of the multiplexer; and a digital signal processor coupled to an output of the ADC.

19. The receiver of clause 18, wherein at least one of the three inductors has an overall elongated form factor.

20. The receiver of clause 18, wherein at least one of the three inductors has an overall flat form factor.

21. The receiver of clause 16, comprising: a plurality of band pass filters coupled to the output of the multiplexer, wherein each band pass filter is tuned to a different frequency band; a plurality of amplifiers coupled to the corresponding plurality of band pass filters; a plurality of analog-to-digital converters (ADCs) having inputs coupled to outputs of the band pass filters and having outputs coupled to the digital signal processor.

22. The receiver of clause 21, further comprising a wireless communication element.

23. The receiver of clause 16, comprising: a plurality of receiving inductors; a plurality of corresponding amplifiers coupled to plurality of inductors; a multiplexer to receiver outputs of the plurality of amplifiers; an analog-to-digital converter (ADC) coupled to an output of the multiplexer; and a digital signal processor coupled to an output of the ADC.

24. The receiver of clause 23, wherein the plurality of receiving inductors is arranged in a circular pattern.

The invention claimed is:

1. A receiver circuit, comprising:
a receiving inductor;
a transimpedance amplifier coupled to the receiving inductor;
an amplifier coupled to an output of the transimpedance amplifier; and
a receiver processor coupled to an output of the amplifier, the receiver processor configured to:
receive an analog signal representative of an impulse communication signal, the impulse communication signal comprising an impulse pattern with a predefined impulse timing that comprises predefined gaps between a series of pulses;
convert the analog signal to a digital signal;
decode the digital signal to reproduce data transmitted as the impulse communication signal; and
decode the impulse communication signal by identifying the impulse timing of the impulse communication signal, wherein identifying the impulse timing comprises:
  receiving samples of the impulse communication signal;
  stretching or squeezing the samples of the impulse communication signal into frames, wherein each frame is comprised of a predefined number of effective samples;
  stacking and summing the frames to form summed frame data;
  convolving the summed frame data to a template; and
  determining the impulse timing based on the convolution of the summed frame data to the template.

2. The receiver circuit of claim 1, wherein the receiver processor comprises:
an analog-to-digital converter (ADC); and
a digital signal processor coupled to an output of the ADC.

3. The receiver circuit of claim 1, further comprising:
at least three receiving inductors orthogonally spaced relative to each other;
at least three amplifiers coupled to the corresponding orthogonally spaced inductors;
a multiplexer to receive outputs of the at least three amplifiers;
an analog-to-digital converter (ADC) coupled to an output of the multiplexer; and
a digital signal processor coupled to an output of the ADC.

4. The receiver circuit of claim 3, wherein at least one of the three inductors has an overall elongated form factor.

5. The receiver circuit of claim 3, wherein at least one of the three inductors has an overall flat form factor.

6. The receiver circuit of claim 3, further comprising:
a plurality of band pass filters coupled to the output of the multiplexer, wherein each band pass filter among the plurality of band pass filters is tuned to a different frequency band;
a plurality of amplifiers each coupled to each of the corresponding band pass filters among the plurality of band pass filters;
a plurality of analog-to-digital converters (ADCs) each having an input coupled to an output of each of the corresponding band pass filters and each having an output coupled to the digital signal processor.

7. The receiver circuit of claim 6, further comprising a wireless communication element.

8. The receiver circuit of claim 1, further comprising:
a plurality of receiving inductors;
a plurality of corresponding amplifiers each coupled to each of the plurality of inductors;
a multiplexer to receive outputs of the plurality of amplifiers;
an analog-to-digital converter (ADC) coupled to an output of the multiplexer; and
a digital signal processor coupled to an output of the ADC.

9. The receiver circuit of claim 8, wherein the plurality of receiving inductors is arranged in a circular pattern.

10. The receiver circuit of claim 1, wherein symbols are created by varying an order of sub-chips and each symbol produces the same template when the frames are stacked and summed.

11. The receiver circuit of claim 10, wherein a packet of data is created with a number of symbols communicated in sequence.

12. The receiver circuit of claim 10, wherein each symbol has the same effective length as a frame.

13. The receiver circuit of claim 10, wherein an autocorrelation of the template has a peak equal to a number of spikes in the template and all other side lobes are either zero or −1.

14. The receiver circuit of claim 13, wherein the number of sub-chips equals the number of spikes in the template.

15. The receiver circuit of claim 13, wherein data is encoded by an order in which the sub-chips appear in the packet.

16. The receiver circuit of claim 13, wherein all sub-chips are used in a packet.

17. The receiver circuit of claim 13, wherein there is exactly one spike per sub-chip.

* * * * *